US009131648B2

(12) United States Patent
Lewis et al.

(10) Patent No.: US 9,131,648 B2
(45) Date of Patent: Sep. 15, 2015

(54) **GENES ENCODING CHAVICOL/EUGENOL SYNTHASE FROM THE CREOSOTE BUSH *LARREA TRIDENTATA***

(75) Inventors: Norman G. Lewis, Pullman, WA (US); Laurence B. Davin, Pullman, WA (US); Sung-Jin Kim, Pullman, WA (US); Daniel Giddings Vassão, Pullman, WA (US); Ann M. Patten, Pullman, WA (US); Dietmar Eichinger, Schwetzingen (DE)

(73) Assignee: Washington State University, Pullman, WA (US)

( * ) Notice: Subject to any disclaimer, the term of this patent is extended or adjusted under 35 U.S.C. 154(b) by 991 days.

(21) Appl. No.: 12/307,343

(22) PCT Filed: May 29, 2007

(86) PCT No.: PCT/US2007/069911
§ 371 (c)(1),
(2), (4) Date: Apr. 2, 2009

(87) PCT Pub. No.: WO2008/005631
PCT Pub. Date: Jan. 10, 2008

(65) Prior Publication Data

US 2010/0031398 A1 Feb. 4, 2010

Related U.S. Application Data

(60) Provisional application No. 60/819,120, filed on Jul. 7, 2006.

(51) Int. Cl.

| | |
|---|---|
| ***C12N 15/00*** | (2006.01) |
| ***C12N 15/82*** | (2006.01) |
| ***C12N 5/04*** | (2006.01) |
| ***C12N 5/10*** | (2006.01) |
| ***C12N 15/87*** | (2006.01) |
| ***A01H 5/02*** | (2006.01) |
| ***C12N 9/02*** | (2006.01) |
| ***C12P 7/22*** | (2006.01) |

(52) U.S. Cl.
CPC ................ *A01H 5/02* (2013.01); *C12N 9/0004* (2013.01); *C12N 15/8243* (2013.01); *C12P 7/22* (2013.01); *Y02E 50/17* (2013.01)

(58) Field of Classification Search
USPC ........................................................ 800/284
See application file for complete search history.

(56) References Cited

U.S. PATENT DOCUMENTS

| | | | | |
|---|---|---|---|---|
| 4,904,465 | A | 2/1990 | Maillefer | |
| 4,959,314 | A | 9/1990 | Mark | |
| 5,017,388 | A | 5/1991 | Rabenhorst | |
| 5,514,758 | A | 5/1996 | Muller | |
| 5,530,194 | A | 6/1996 | Knauf | |
| 5,565,552 | A | 10/1996 | Magda | |
| 5,567,810 | A | 10/1996 | Weis | |
| 5,574,142 | A | 11/1996 | Meyer | |
| 5,585,481 | A | 12/1996 | Arnold | |
| 5,587,371 | A | 12/1996 | Sessler | |
| 5,597,696 | A | 1/1997 | Linn | |
| 5,958,773 | A | 9/1999 | Monia | |
| 5,981,839 | A | 11/1999 | Knauf | |
| 6,506,559 | B1 | 1/2003 | Fire | |
| 6,703,229 | B2 | 3/2004 | Kasahara | |
| 2004/0031072 | A1 | 2/2004 | La Rosa | |
| 2008/0148432 | A1 * | 6/2008 | Abad | 800/279 |

FOREIGN PATENT DOCUMENTS

| | | |
|---|---|---|
| GB | 2416769 | 2/2006 |
| GB | 2416770 | 2/2006 |
| JP | 2200192 | 8/1990 |
| WO | WO 01/12824 | 2/2001 |

(Continued)

OTHER PUBLICATIONS

Gross et al., Biosynthesis of estragole and t-anethole in bitter fennel (*Foeniculum vulgare* Mill. var. vulgare) chemotypes. Changes in SAM: phenylpropene O-methyltransferase activities during development, 163 Plant Science, 1047-1053 (2002)).*
Vassão et al. (A pinoresinol-lariciresinol reductase homologue from the creosote bush (*Larrea tridentata*) catalyzes the efficient in vitro conversion of p-coumaryl/coniferyl alcohol esters into the allylphenols chavicol/eugenol, but not the propenylphenols p-anol/isoeugenol, 465 Archives of Biochemistry and Biophysics, 209-218 at Abstract (2007); o.*
Cho et al., "(+)-Larreatricin hydroxylase, an enantio-specific polyphenol oxidase from the creosote bush (*Larrea tridentata*)," The Proceedings of the National Academy of Sciences, 2003, pp. 10641-10646, vol. 19.
Database, UniProt [Online], Oct. 1, 2000, "Sub Name: Full = Phenylcoumaran benzylic ether reductase homolog Fi2," XP002600255, retrieved from EBI accession No. UNIPROT: Q9M527, Database accession No. Q9M527, *compound*.

(Continued)

*Primary Examiner* — Brent T Page
(74) *Attorney, Agent, or Firm* — Lee & Hayes, PLLC; C. Rachal Winger; Rachel A. Haller

(57) ABSTRACT

Particular aspects provide novel methods for redirecting carbon allocation in plants or cell culture from lignification to inherently more useful and tractable materials, and to facilitate the generation of, e.g., biofuels from the remaining plant ro culture biomass. Particular aspects provided novel methods for converting monolignols into allyl/propenyl phenols, and for chavicol/eugenol formation or production. Additional aspects relate to the discovery of novel chavicol/eugenol synthases that convert p-coumaryl/coniferyl alcohol esters into chavicol/eugenol, and to novel compositions (e.g., novel proteins and nucleic acids encoding same), and novel methods using same for producing or forming chavicol/eugenol and other derivatives in cell culture and/or genetically modified plants, and for re-engineering the composition of plant biomass. Particular aspects provide novel methods for generation in culture or in planta of liquid/combustible allyl/propenyl phenols, and these phenolic products are utilized for (non-ethanol) biofuel/bioenergy purposes, while the remaining plant biomass facilitates the generation of other biofuels.

36 Claims, 33 Drawing Sheets

(56) References Cited

FOREIGN PATENT DOCUMENTS

| | | |
|---|---|---|
| WO | WO0149833 | 7/2001 |
| WO | WO 2008/005631 | 1/2008 |

OTHER PUBLICATIONS

Database, UniProt [Online], Oct. 1, 2000, "Sub Name: Full = Phenylcoumaran benzylic ether reductase homolog Fil," XP002600254, retrieved from EBI accession No. UNIPROT: Q9M528, Database accession No. Q9M528, *compound*.

Davin et al., "Dirigent phenoxy radical coupling: advances and challenges," Current Opinion in Biotechnology, 2005, pp. 398-406, vol. 16.

Gang et al., "Evolution of Plant Defense Mechanisms," The Journal of Biological Chemistry, 1999, pp. 7516-7527, vol. 274.

Koeduka et al., "Eugenol and isoeugenol, characteristic aromatic constituents of spices, are biosynthesized via reduction of a coniferyl alcohol ester," The Proceedings of the National Academy of Sciences, 2006, pp. 10128-10133, vol. 103.

Vassao et al., "A pinoresinol-lariciresinol reductase homologue from the creosote bush (*Larrea tridentata*) catalyzes the efficient in vitro conversion of p-coumaryl/coniferyl alcohol esters into the allyphenols chavicol/eugenol, but not the propenyolphenols p-anol/isoeugenol," Archives of Biochemistry and Biophysics, 2007, pp. 209-218, vol. 465.

U.S. Appl. No. 60/819,120, filed Jul. 7, 2006, Lewis.

Baucher, et al., "Lignin: Genetic Engineering and Impact on Pulping", Crit. Rev. Biochem. Mol. Biol., 2003, vol. 38 (4), pp. 305-350.

Moinuddin, et al., "Synthesis and Chiral HPLC Analysis of the Dibenzyltetrahydrofuran Lignans, Larreatricins, 8'-Epi-Larreatricins, 3,3'-Didemethoxy-verrucosins and Meso-3,3'-Didemethoxynectandrin B in the Creosote Bush (*Larrea tridentata*): Evidence for Regiospecific Control of Coupling", Org. Biomol. Chem., 2003, vol. 1 (13), pp. 2307-2313.

Office Action dated Dec. 10, 2014 in European Application No. 07797855.9.

Office Action dated Jul. 9, 2013 in European Application No. 07797855.9.

Search Report & Written Opinion dated Apr. 24, 2009 in PCT Application No. PCT/US2007/069911.

Office Action dated Sep. 27, 2010 in European Application No. 07797855.9.

Sticklen, "Plant Genetic Engineering to Improve Biomass Characteristics for Biofuels", Curr. Opin. Biotechnol., 2006, vol. 17 (3), pp. 315-319.

* cited by examiner

FIG. 1

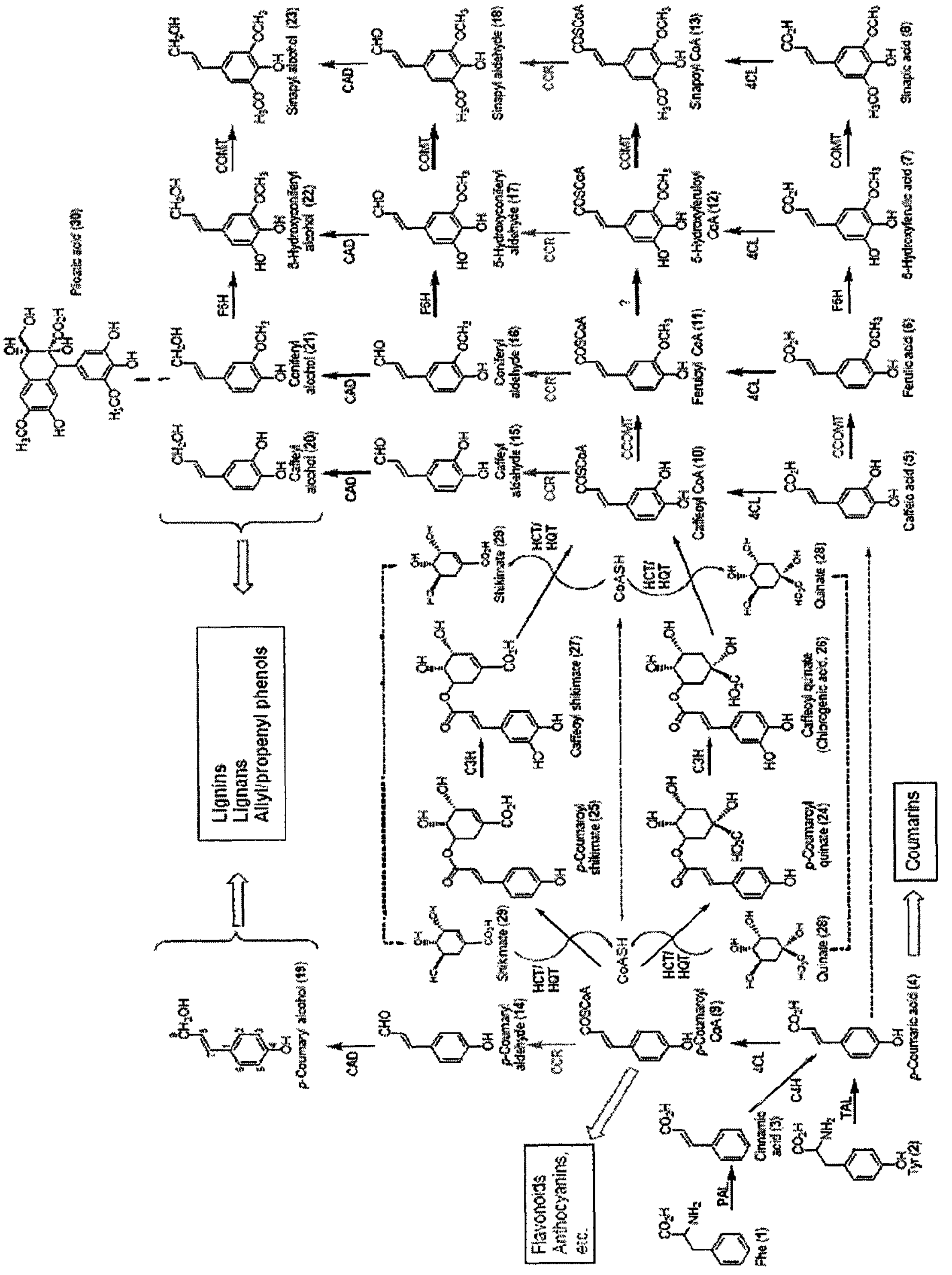

Phe (1)
Tyr (2)
Cinnamic acid (3)
p-Coumaric acid (4)
Caffeic acid (5)
Ferulic acid (6)
5-Hydroxyferulic acid (7)
Sinapic acid (8)
p-Coumaroyl CoA (9)
Caffeoyl CoA (10)
Feruloyl CoA (11)
5-Hydroxyferuloyl CoA (12)
Sinapoyl CoA (13)
p-Coumaryl aldehyde (14)
Caffeyl aldehyde (15)
Coniferyl aldehyde (16)
5-Hydroxyconiferyl aldehyde (17)
Sinapyl aldehyde (18)
p-Coumaryl alcohol (19)
Caffeyl alcohol (20)
Coniferyl alcohol (21)
5-Hydroxyconiferyl alcohol (22)
Sinapyl alcohol (23)
p-Coumaroyl quinate (24)
p-Coumaroyl shikimate (25)
Caffeoyl quinate (Chlorogenic acid, 26)
Caffeoyl shikimate (27)
Quinate (28)
Shikimate (29)

FIG. 2
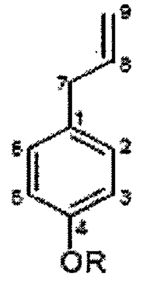
R = H, Chavicol (31)
R = $CH_3$, Methylchavicol (Estragole, 32)
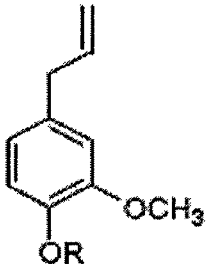
R = H, Eugenol (33)
R = $CH_3$, Methyleugenol (34)
R = Ac, Eugenyl acetate (35)
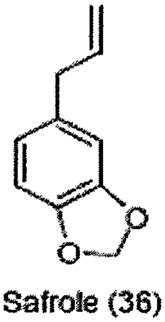
Safrole (36)
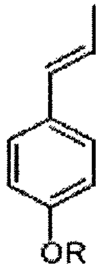
R = H, Anol (37)
R = $CH_3$, Anethole (38)
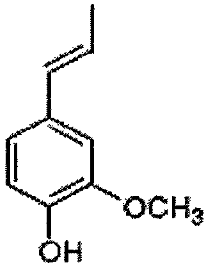
Isoeugenol (39)
FIG. 3
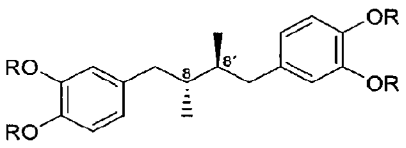
R = H, NDGA (40)
R = $CH_3$, tetra-O-methyl NDGA (41)
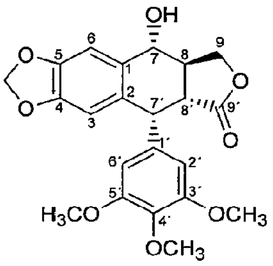
Podophyllotoxin (42)
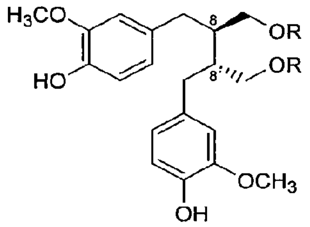
R = H, Secoisolariciresinol (43)
R = Glc, Secoisolariciresinol diglucoside (44)

FIG. 4A, 4B, and 4C
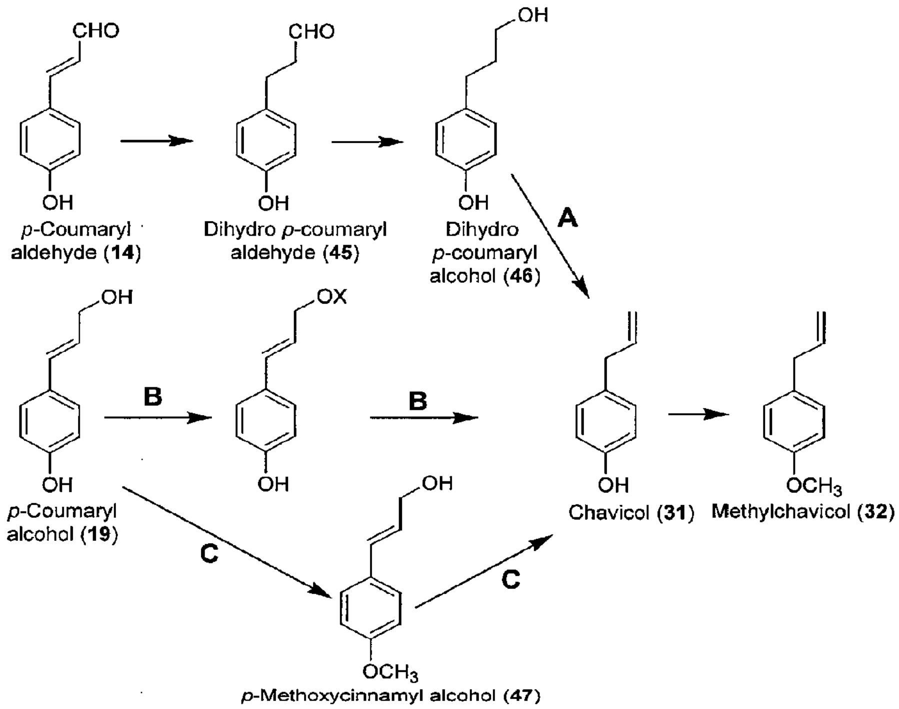
*p*-Coumaryl aldehyde (14)
Dihydro *p*-coumaryl aldehyde (45)
Dihydro *p*-coumaryl alcohol (46)
*p*-Coumaryl alcohol (19)
Chavicol (31)
Methylchavicol (32)
*p*-Methoxycinnamyl alcohol (47)
FIG. 5
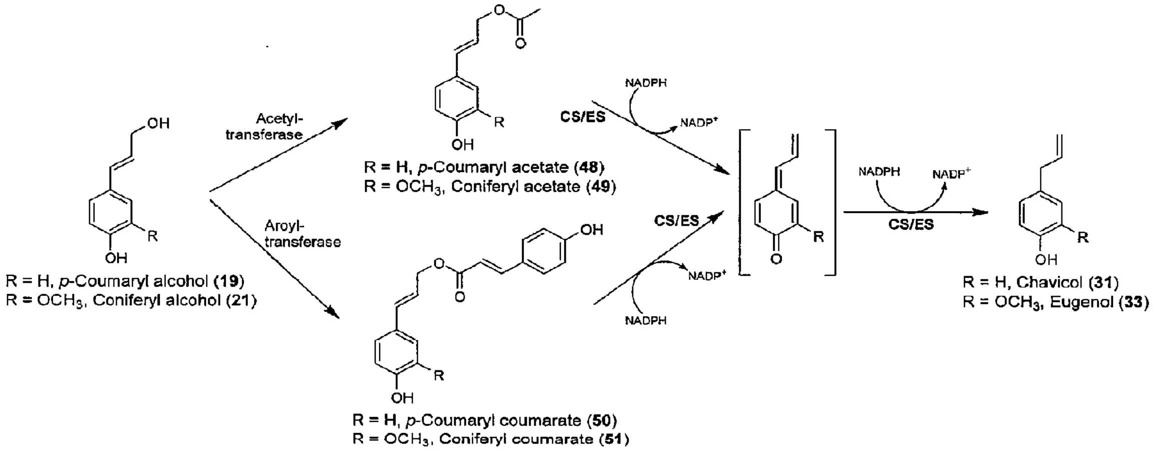
R = H, *p*-Coumaryl alcohol (19)
R = $OCH_3$, Coniferyl alcohol (21)
R = H, *p*-Coumaryl acetate (48)
R = $OCH_3$, Coniferyl acetate (49)
R = H, *p*-Coumaryl coumarate (50)
R = $OCH_3$, Coniferyl coumarate (51)
R = H, Chavicol (31)
R = $OCH_3$, Eugenol (33)

A

(*Z*)-/(*E*)-Hinokiresinol (52/53)

*p*-Coumaryl coumarate (50)

B

*p*-Coumaryl ester

R = $CH_3$ (48), (50), etc.

*p*-Anol (37)

Chavicol (31)

FIG. 7A

```
PLRh_Lt1    1 ---MAQKSKILIIGGTGYLGKFVVEASAKAGRPTFALVRESTV-SDPVKGKLIANFKNLG
PLRh_Lt2    1 ---MAQKSKILIIGGTGYLGKSLVEASAKAGHPTFALVRESTV-FHHVKGKLVKNFKDLG
Lt_PLR13    1 ----MCKSKVLIVGGTGYLGKRLVKASLALGHETYVLHRAEIG-VDIEKVQMLLSFKEQG
PLR_Fi1     1 ----MGKSKVLIIGGTGYLGRRLVKASLAQGHETYILHRPEIG-VDIDKVEMLISFKMQG
ObEGS1      1 MEENGMKSKILIFGGTGYIGNHMVKGSLKLGHPTYVFTRPN------SSKTTLLDEFQSLG
PhIGS1      1 --MTTGKGKILILGATGYLGKYMVKASISLGHPTYAYVMPLKKNSDDSKLQLLKEFESLG

PLRh_Lt1   57 VNILHGDLNDHESLVKAIKKVDVVISTVG-----NFQIADQVKIIAAIKAAGNVKRFFPS
PLRh_Lt2   57 VNLVHGDINDHDSLLKAIKQVDVVFSTLG-----HHHIGDQHKVIAAIKEAGNVKRYFPS
Lt_PLR13   56 ATLVPGSFADHQSLVNAVKLVDVVICAISGVHIRSHHILLQLKLVDAIKEAGNVKRFLPS
PLR_Fi1    56 AHLVSGSFKDFNSLVEAVKLVDVVISAISGVHIRSHQILLQLKLVEAIKEAGNVKRFLPS
ObEGS1     56 AILVKGELDEHEKLVELMKKVDVVISALAFP-----QILDQFKILEAIKVAGNIKRFLPS
PhIGS1     59 VTIFYGELSEHDKLVAVFKEVDIVISTLAVP-----QYLEQLKVIEAIKEAGNIKRFVPS

PLRh_Lt1  112 EFGNDVDRTH--AVEPAKSTFEMKAQLRRTIEAEGIPYTYVSSNFFAGYFLPVLGQVGVT
PLRh_Lt2  112 EFGNDVDRSH--AVDPVKSAYRTKAQIRRAIEAEGIPHTYVSCNFFAGYFLPTLVQLEVT
Lt_PLR13  116 EFGTDPARMEN-AMEPGRVTFDDKMVVRKAIQDAGIPYTYVSANCFAGYFLGGLCQPGSI
PLR_Fi1   116 EFGMDPAKFMDTAMEPGKVTLDEKMVVRKAIEKAGIPFTYVSANCFAGYFLGGLCQFGKI
ObEGS1    111 DFGVEEDRIN--ALPPFEALIERKRMIRRAIEEANIPYTYVSANCFASYFINYLLRP---
PhIGS1    114 EFGNEVDRVR--ALPRFQAVLDNKKKIRRATEAAGIPFTFVSANSLTAYFVDYLLHP---

PLRh_Lt1  170 APPRDKVTILGDGNQKAVFNKEDDIGTYTIKAADDPRTLNKILYIRPPKNTYSMNELVAL
PLRh_Lt2  170 APPRDKVTILGDGNKKAIFNKEDDIATYAIKAVDDPRTLNKTSYIRTPKNTYTMNELVAL
Lt_PLR13  175 IPSTEHVLLLGDGTKKAIYVDEHDIAMYTIKAIDDPRTLNKTVYIRPPVNILSQLEVVKI
PLR_Fi1   176 LPSRDFVIIHGDGNKKAIYNNEDDIATYAIKTINDPRTLNKTLYISPPKNILSQREVVQT
ObEGS1    166 YDPKDEITVYGTGEAKFAMNYEQDIGLYTIKVATDPRALNRVVIYRPSTNIITQLELISR
PhIGS1    169 RQKSEQVTIYGSGDAKAVLNYEEDVAAYTIKAADDPRAANRVLIIKPPKNIVSQLDLVSS

PLRh_Lt1  230 WEKKIGKTLEKTYVPEEQLLKNIQEAEIPWNVVLAINISVFVKGDHTNFAIKPSFGVEAS
PLRh_Lt2  230 WEKKIGKSLEKIYVPEEQILKNIQESPFSTQVMLSINISVFVKGDQTNFDIDPSFGVEAT
Lt_PLR13  235 WEKLIGKELQKTSISKEDFLESMKGQNYAEQVGLTHYYHVCYEGCLANFEIGEEG-VEAT
PLR_Fi1   236 WEKLIGKELQKITLSKEDFLASVKEQEYAQQVGLSHYHDVNYQGCLTSFEIGDE--EEAS
ObEGS1    226 WEKKIGKKFKKIHVPEEEIVALTKELPEPENIPIAILHCLFIDGATMSYDFKEN-DVEAS
PhIGS1    229 WEKTTGSTLKMTHISEQEIIKLSESINFPENIHASILHNIFIAGAQLSFELTQDHDLEAS

PLRh_Lt1  290 ELYPDVKYTTVEEYLSQFV----------------     (SEQ ID NO:2)
PLRh_Lt2  290 ELYPDVNYTTVEEYLDQFV----------------     (SEQ ID NO:4)
Lt_PLR13  294 QLYPELKYVTVEQYMKRYL----------------     (SEQ ID NO:6)
PLR_Fi1   294 KLYPEVKYTSVEEYLKRYV----------------     (SEQ ID NO:8)
ObEGS1    285 TLYPEIKTTTLDELLDIFVHDPPPPASAAF-----     (SEQ ID NO:10)
PhIGS1    289 ELYPNYNYTSVDEYLKICLVNPPKPKLATYAQPST     (SEQ ID NO:12)
```

FIG. 7B

```
PLRh_Lt1    1 ----------ATGGCACAGAAGAGCAAGATTTTGATCATTGGAGGCACTGGCTATATTGG
PLRh_Lt2    1 ----------ATGGCGCAGAAGAGCAAGATTTTGATCATTGGAGGCACTGGCTACATTGG
Lt_PLR13    1 ----------ATGTG---CAAGAGCAAAGTACTAATTGTTGGAGGAACTGGATACTTGGG
PLR_Fi1     1 ----------ATGGG---AAAAAGCAAAGTTTTGATCATTGGGGGTACAGGGTACTTAGG
ObEGS1      1 ATGGAGGAAAATGGGAT-GAAAAGCAACATTTTAATATTTGGAGGGACAGGTTACATTGG
PhIGS1      1 ----ATGACTACTGG---GAAGGGAAAAATATTGATTCTTGGAGCAACTGGTTATCTTGG

PLRh_Lt1   51 CAAATTCGTTGTTGAAGCAAGCGCTAAGGCTGGCCGTCCTACCTTTGCATTAGTTAGA--
PLRh_Lt2   51 CAAATCCATTGTCGAAGCAAGCGCCAAGGCTGGCCATCCGACCTTTGCATTGGTTAGA--
Lt_PLR13   48 AAACACGTTGGTGAAGGCAAGTTTAGCTCTAGGACATGAAACATATGTTCTTCATAGG--
PLR_Fi1    48 GAGCAGATTGGTTAAGGCAAGTTTAGCTCAAGGTCATGAAACATACATTCTGCATAGG--
ObEGS1     60 AAATCACATGGTGAAAGGAAGCCTCAAATTAGGGCACCCAACTTATGTTT---TCAC---
PhIGS1     54 AAAATATATGGTGAAAGCCAGTATTTCTTTGGGACATCCAACGTATGCCTATGTCATGCC

PLRh_Lt1  109 ---GAAAGCACTGTTTCTGACCCTGTTAAAGGAAAGCTTATTGCAAACTTCAAGAATTTG
PLRh_Lt2  109 ---GAAAGCACCGTCTTTCATCACGTTAAGGGAAAACTTGTTAAGAATTTCAAGCATTTA
Lt_PLR13  106 ---GCAGAGATTGGTGTTGATATTGAGAAAGTGCAAATGTTACTGTCATTTAAGGAGCAA
PLR_Fi1   106 ---CCTGAAATTGCTGTTGATATTGATAAAGTTGAAATGCTAATATCATTTAAAATGCAA
ObEGS1    114 ----AAGG-------CCTAATTCCTCCAAGACAACCCTTCTTGATGAGTTCCAATCCTTG
PhIGS1    114 ATTGAAGAAG--AACTCTGATGATTCTAAGCTTCAGCTTCTCAAGGAATTTGAGTCCTTG

PLRh_Lt1  166 GGTGTCAATATTCTCCATGGAGATCTCAATGATCAC-GAGAGCTTAGTGAAGGCAATTAA
PLRh_Lt2  166 GGCGTCAATCTTGTCCATGGCGACATTAATGATCAT-GATAGCTTGCTAAAGGCAATTAA
Lt_PLR13  163 GGAGCTACTCTAGTGCCTGGCTCTTTTGCTGATCATCAA-AGTCTTGTTAATGCTGTTAA
PLR_Fi1   163 GGAGCTCATCTTGTATCTGGTTCTTTCAAGGATT-TCAACAGTCTGGTCGAGGCTGTCAA
ObEGS1    163 GGTGCCATCATAGTCAAGGGAGAGTTGGATGAGCAT-GAGAAACTAGTTGAGTTGATGAA
PhIGS1    172 GGAGTAACTATATTTTATGGAGAGCTTAGTGAACAT-GATAAACTTGTTGCAGTGTTTAA

PLRh_Lt1  225 GAAGGTGGATGTGGT---------CATTTCTA-----CAG-TACGCAACTTTCACATAGC
PLRh_Lt2  225 GCAAGTGGATGTGGT---------GTTTTCTA-----CGC-TTGGTCACCATCATATAGG
Lt_PLR13  222 GCTGGTTGATGTTGTTATATGTGCAATTTCTCGTGTCCATATTAGAAGCCATCATATATT
PLR_Fi1   222 GCTCGTAGACGTAGTAATCAGCGCCATTTCTCGTGTTCATATTCGAAGCCATCAAATTCT
ObEGS1    222 GAAAGTTGATGTTGT---------CATATCTG-----CAC-TTGCATTCCCACAAATTCT
PhIGS1    231 AGAGCTTGATATTGT---------GATATCTA-----CTT-TAGCAGTGCCTCAATATCT

PLRh_Lt1  270 TGATCAAGTCAAGATTATTGCTGCTATCAAAGCGGCTGGAAATGTCAAGAGATTTTTCCC
PLRh_Lt2  270 TGACCAACACAAAGTTATTGCTGCTATCAAAGAGGCTGGTAATGTCAAGCGATATTTTCC
Lt_PLR13  282 ACTTCAACTCAAGCTAGTTGATGCAATCAAAGAGGCTGGCAATGTCAAGAGATTTTTCCC
PLR_Fi1   282 TCTTCAACTCAAGCTTGTTGAAGCTATTAAAGAGGCTGGAAATGTCAAGAGATTTTTACC
ObEGS1    267 TGATCAGTTCAAGATCTTGGAGGCCATCAAGGTTGCTGGCAATATTAAGAGCTTTCTACC
PhIGS1    276 TGAACAACTCAAGCTGATTGAGGCCATCAAAGAAGCTGGTAACATTAAGAGCTTTGTTCC

PLRh_Lt1  330 TTCAGAATTTGGAAACGACGTTGACCGA---ACCCAT---GCTGTGGAACCAGCAAAATC
PLRh_Lt2  330 TTCCGAATTCGGCAATGATGTGGATCGA---TCCCAT---GCTGTGGATCCCGTAAAATC
Lt_PLR13  342 GTCTGAGTTTGGCACAGACCCTGCAAGA---ATGGAGAATGCAATGGAACCTGGAAGAGT
PLR_Fi1   342 ATCTGAGTTTGGAATGGATCCTGCAAAATTTATGGATACGGCCATGGAACCCGGAAAGGT
ObEGS1    327 GTCGGATTTTGGCGTCGAGGAGGACAGA---ATAAAC---GCATTGCCGCCGTTCGAAGC
PhIGS1    336 TTCTGAATTTGGCAATGAAGTGGATAGC---GTAAGA---GCGTTACCACGTTTCCAAGC
```

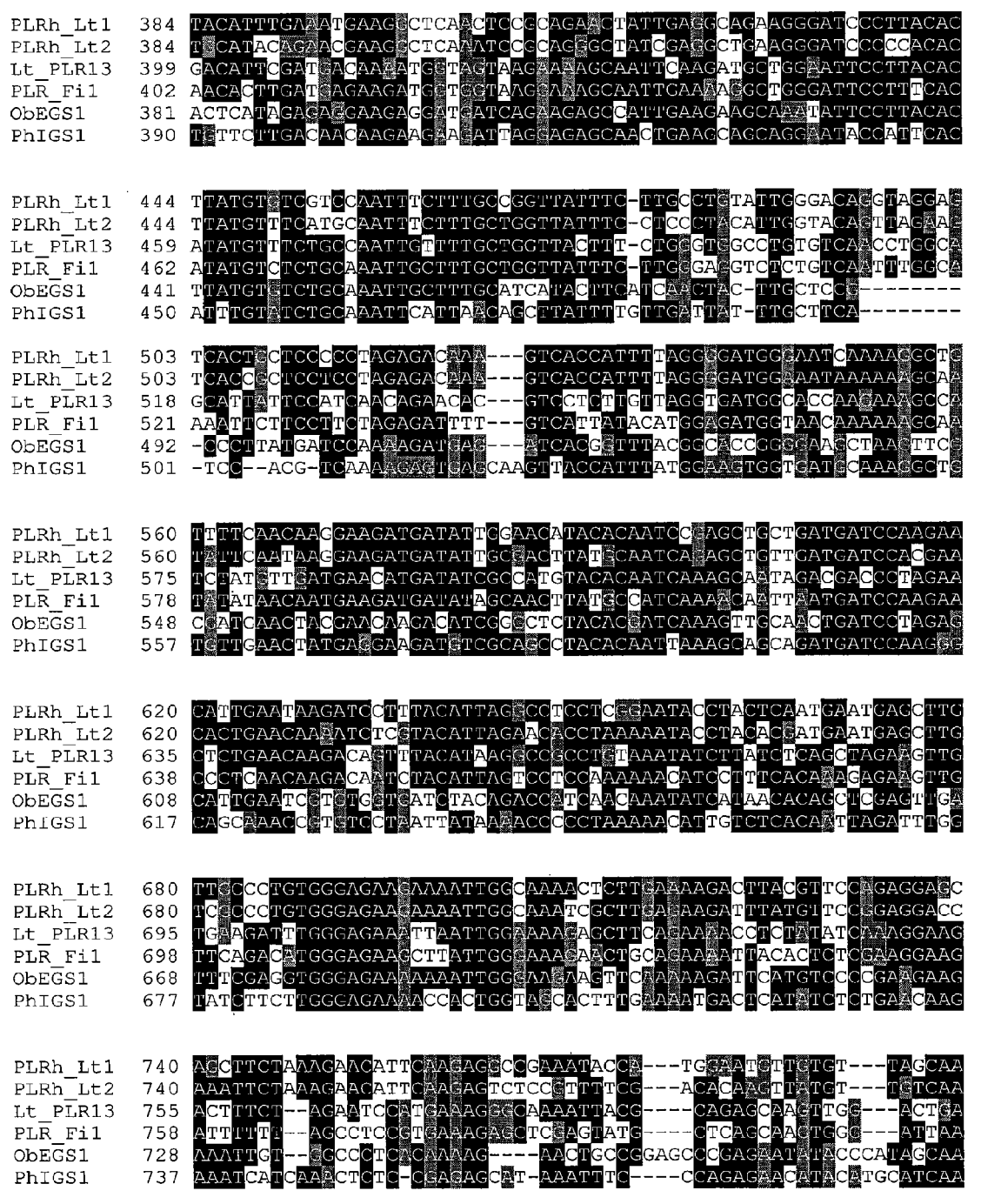

```
PLRh_Lt1  384 TACATTTGAAATGAAGGCTCAACTCCGCAGAACTATTGAGGCAGAAGGGATCCCTTACAC
PLRh_Lt2  384 TGCATACAGAACGAAGGCTCAAATCCGCAGGGCTATCGAGGCTGAAGGGATCCCCCACAC
Lt_PLR13  399 GACATTCGATGACAAAATGCTAGTAAGAAAAGCAATTCAAGATGCTGGAATTCCTTACAC
PLR_Fi1   402 AACACTTGATGAGAAGATGCTGGTAAGGAAAGCAATTCAAAAGGCTGGGATTCCTTTCAC
ObEGS1    381 ACTCATAGAGAGGAAGAGGATGATCAGAAGAGCCATTGAAGAAGCAAATATTCCTTACAC
PhIGS1    390 TGTTCTTGACAACAAGAAGAAGATTAGGAGAGCAACTGAAGCAGCAGGAATACCATTCAC

PLRh_Lt1  444 TTATGTGTCGTCCAATTTCTTTGCCGGTTATTTC-TTGCCTGTATTGGGACAGGTAGGAG
PLRh_Lt2  444 TTATGTTTCATGCAATTTCTTTGCTGGTTATTTC-CTCCCTACATTGGTACAGTTAGGAG
Lt_PLR13  459 ATATGTTTCTGCCAATTGTTTTGCTGGTTACTTT-CTGGGTGGCCTGTGTCAACCTGGCA
PLR_Fi1   462 ATATGTCTCTGCAAATTGCTTTGCTGGTTATTTC-TTGGGAGGTCTCTGTCAATTTGGCA
ObEGS1    441 TTATGTGTCTGCAAATTGCTTTGCATCATACTTGATCAACTAC-TTGCTCCG--------
PhIGS1    450 ATTTGTATCTGCAAATTCATTAACAGCTTATTTTGTTGATTAT-TTGCTTCA--------

PLRh_Lt1  503 TCACTGCTCCCCCTAGAGACAAA---GTCACCATTTTAGGGGATGGGAATCAAAAGGCTG
PLRh_Lt2  503 TCACCGCTCCTCCTAGAGACAAA---GTCACCATTTTAGGGGATGGAAATAAAAAAGCAA
Lt_PLR13  518 GCATTATTCCATGAACAGAACAC---GTCCTCTTGTTAGGTGATGGCACCAAGAAAGCCA
PLR_Fi1   521 AAATTCTTCCTTCTAGAGATTTT---GTCATTATACATGGAGATGGTAACAAAAAAGCAA
ObEGS1    492 -CCCTTATGATCCAAAAGATGAG---ATCACGGTTTACGGCACCGGGAAGCTAAGTTCG
PhIGS1    501 -TCC--ACG-TCAAAAGAGTGAGCAAGTTACCATTTATGGAAGTGGTGATGCAAAGGCTG

PLRh_Lt1  560 TTTTCAACAAGGAAGATGATATTGGAACATACACAATCCGAGCTGCTGATGATCCAAGAA
PLRh_Lt2  560 TATTCAATAAGGAAGATGATATTGCGACTTATGCAATCAGAGCTGTTGATGATCCACGAA
Lt_PLR13  575 TCTATGTTGATGAACATGATATCGCCATGTACACAATCAAAGCAATAGACGACCCTAGAA
PLR_Fi1   578 TATATAACAATGAAGATGATATAGCAACTTATGCCATCAAAACAATTAATGATCCAAGAA
ObEGS1    548 CGATCAACTACGAACAAGACATCGGCCTCTACACGATCAAAGTTGCAACTGATCCTAGAG
PhIGS1    557 TGTTGAACTATGACGAAGATGTCGCAGCCTACACAATTAAAGCAGCAGATGATCCAAGGG

PLRh_Lt1  620 CATTGAATAAGATCCTTTACATTAGGCCTCCTCGGAATACCTACTCAATGAATGAGCTTG
PLRh_Lt2  620 CACTGAACAAAATCTCGTACATTAGAACACCTAAAAATACCTACACGATGAATGAGCTTG
Lt_PLR13  635 CTCTGAACAAGACAGTTTACATAAGGCCGCCTGTAAATATCTTATCTCAGCTAGAAGTTG
PLR_Fi1   638 CCCTCAACAAGACAATCTACATTAGTCCTCCAAAAAACATCCTTTCACAAAGAGAAGTTG
ObEGS1    608 CATTGAATCCTGTGGCTGATCTACAGACCATCAACAAATATCATAACACAGCTCGAGTTGA
PhIGS1    617 CAGCAAACCGTGTCCTAATTATAAAACCCCCTAAAAACATTGTCTCACAATTAGATTTGG

PLRh_Lt1  680 TTGCCCTGTGGGAGAAGAAAATTGGCAAAACTCTTGAAAAGACTTACGTTCCAGAGGAGC
PLRh_Lt2  680 TCGCCCTGTGGGAGAACAAAATTGGCAAATCGCTTGACAAGATTTATGTTCCGGAGGACC
Lt_PLR13  695 TGAAGATTTGGGAGAAATTAATTGGAAAACAGCTTCAGAAAACCTCTATATCAAAGGAAG
PLR_Fi1   698 TTCAGACATGGGAGAAGCTTATTGGCAAAGAACTGCAGAAAATTACACTCTCGAAGGAAG
ObEGS1    668 TTTCGAGGTGGGAGAAAAAAATTGGCAAGAAGTTCAAAAAGATTCATGTCCCCGAAGAAG
PhIGS1    677 TATCTTCTTGGCAGAAAACCACTGGTAGCACTTTGAAAATGACTCATATCTCTGAACAAG

PLRh_Lt1  740 AGCTTCTAAAGAACATTCAAGAGGCCGAAATACCA---TGGAATGTTGTGT---TAGCAA
PLRh_Lt2  740 AAATTCTAAAGAACATTCAAGAGTCTCCGTTTTCG---ACACAAGTTATGT---TGTCAA
Lt_PLR13  755 ACTTTCT--AGAATCCATGAAAGGCAAAATTACG----CAGAGCAAGTTGG---ACTGA
PLR_Fi1   758 ATTTTTT--AGCCTCCGTGAAAGAGCTCGAGTATG----CTCAGCAACTGGG---ATTAA
ObEGS1    728 AAATTGT--GGCCCTCACAAAAG----AACTGCCGGAGCCCGAGAATATACCCATAGCAA
PhIGS1    737 AAATCATCAAACTCTC-CGAGAGCAT-AAATTTC----CCAGAGAACATACATGCATCAA
```

FIG. 7B (Cont'd)

```
PLRh_Lt1   794 TCAACCATTCCGTCTTTG--TA-AAGGGTGATCATACCAACTTCGCGATCAAACCATCTT
PLRh_Lt2   794 TCAATCATTCCGTCTTTG--TA-AAGGGTGATCAAACCAACTTCGACATTGATCCGTCTT
Lt_PLR13   806 CACATTACTATCACGTTTGTTATGAGGGATGTCTTGCAAACTTTGAAATTG---GAGAAG
PLR_Fi1    809 GCCATTATCATGATGTCAACTATCAGGGATGCCTTACGACTTTTCAGATAG---GACATG
ObEGS1     782 TCCTTCACTGTCTCTTCA--TA-GACGGAGCGACGATGAGTTATGATTTCA---AGGAGA
PhIGS1     791 TCCTACACAATATATTCA--TA-GCAGGAGCCCAACTAAGCTTTGAACTTACACAGGATC

PLRh_Lt1   851 TCGGCGTCGAGGCCTCCGAGCTTTATCCCGATGTCAAGTATACCACTGTTGAGGAGTACC
PLRh_Lt2   851 TCGGTGTGGAGGCTACCGAGCTTTATCCTGATGTCAACTATACCACCCTTGAACACTATC
Lt_PLR13   863 AAGGAGTAGAAGCTACTCAACTATATCCAGAAATTAAGTACGTAACAGTCGAGCAATACA
PLR_Fi1    866 AAGAAG---AGGCATCTAAACTTTATCCAGAGGTTAAGTATACCAGTGTGGAAGAGTACC
ObEGS1     836 ACGATGTGGAGGCTTCAACTCTGTATCCAGAGTTGAAGTTCACCACGATCGATGAGCTCC
PhIGS1     848 ATGACTTGGAAGCATCAGAGCTCTATCCTAATTACAACTACACCTCTGTTGATGAATATC

PLRh_Lt1   911 TTAGT----------------------------------CAGTTTG--------------
PLRh_Lt2   911 TTGAT----------------------------------CAATTCG--------------
Lt_PLR13   923 TGAAG----------------------------------CGTTATT--------------
PLR_Fi1    923 TCAAG----------------------------------CGTTACG--------------
ObEGS1     896 TCGACATTTTCGTGCACGATCCTCCACCGCCGGCTTCAGCAGCAT---------------
PhIGS1     908 TCAAAATTTGTCTGGTTAACCCTCCGAAGCCAAAATTGGCAACTTATGCCCAACCATCCA

PLRh_Lt1   923 TTTAA      (SEQ ID NO:1)
PLRh_Lt2   923 TTTAA      (SEQ ID NO:3)
Lt_PLR13   935 TATAA      (SEQ ID NO:5)
PLR_Fi1    935 TGTAG      (SEQ ID NO:7)
ObEGS1     941 TTTAA      (SEQ ID NO:9)
PhIGS1     968 CTTAA      (SEQ ID NO:11)
```

Pinoresinol (54)

Lariciresinol (55)

Secoisolariciresinol (43)

B

Dehydrodiconiferyl alcohol (56)

Isodihydrodehydrodiconiferyl alcohol (57)

FIG. 11A and 11B
A
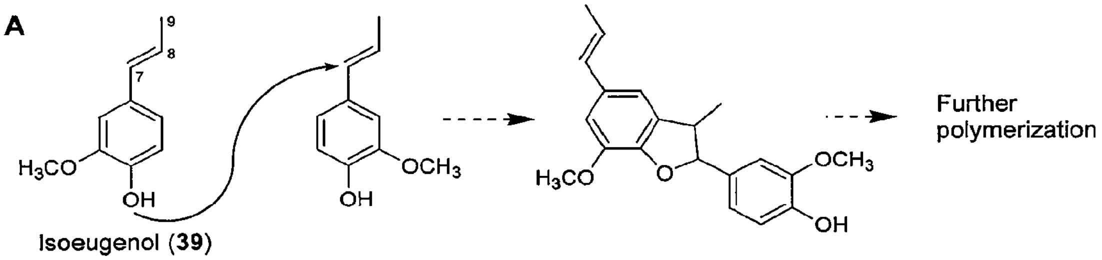
Isoeugenol (39)
B
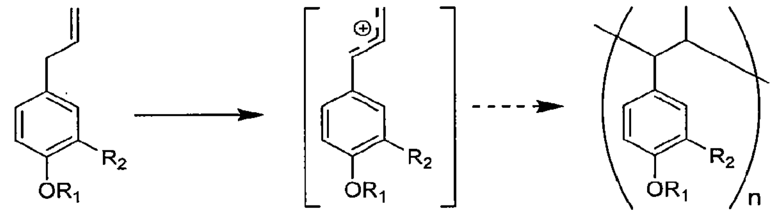
$R_1 = CH_3$, $R_2$ = H, Methylchavicol (32)
$R_1$ = H, $R_2 = OCH_3$, Eugenol (33)
FIG. 12
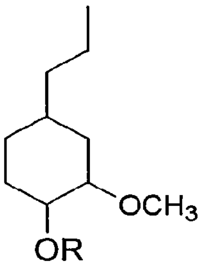
R = H, 2-Methoxy-4-propyl-cyclohexanol (58)
R = $CH_3$, 1,2-Dimethoxy-4-propyl-cyclohexane (59)
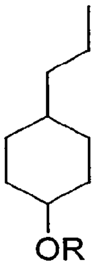
R = H, 4-Propyl-cyclohexanol (60)
R = $CH_3$, 1-Methoxy-4-propyl-cyclohexane (61)

*p*-Anol (37)

Phe (1)

Larreatricin (62)

3,3′-dihydroxylarreatricin (63)

Nordihydroguaiaretic acid (NDGA, 40)

FIG. 14

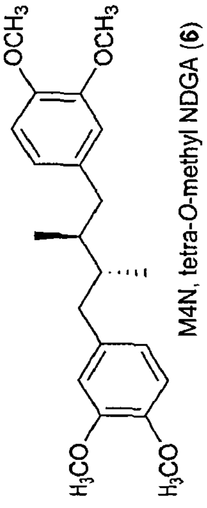

M4N, tetra-O-methyl NDGA (6)

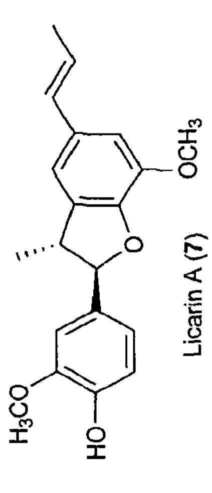

Licarin A (7)

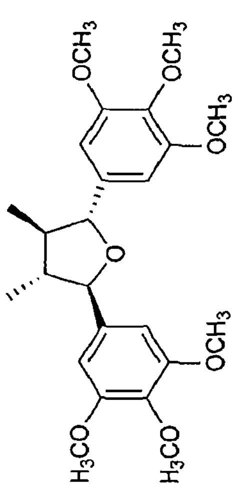

(−)-Grandisin (8)

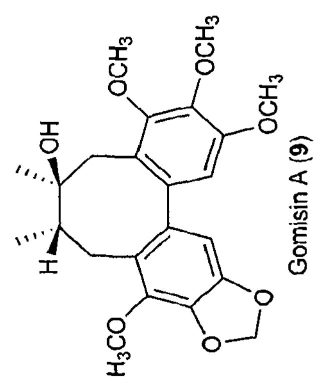

Gomisin A (9)

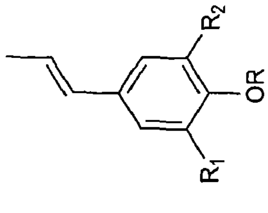

R=$R_1$=$R_2$=H, *p*-Anol (2)
R=$R_1$=H, $R_2$=$OCH_3$, Isoeugenol (10)
R=H, $R_1$=$R_2$=$OCH_3$, 5-Methoxyisoeugenol (11)
R=$CH_3$, $R_1$=$R_2$=H, Anethole (12)

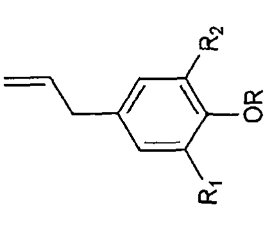

R=$R_1$=$R_2$=H, Chavicol (13)
R=$R_1$=H, $R_2$=$OCH_3$, Eugenol (14)
R=H, $R_1$=$R_2$=$OCH_3$, 5-Methoxyeugenol (15)
R=$CH_3$, $R_1$=$R_2$=H, Methylchavicol (16)

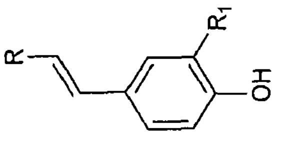

R=OH, $R_1$=H, *p*-Coumaryl alcohol (17)
R=OH, $R_1$=$OCH_3$, Coniferyl alcohol (18)
R=COOH, $R_1$=H, *p*-Coumaric acid (19)

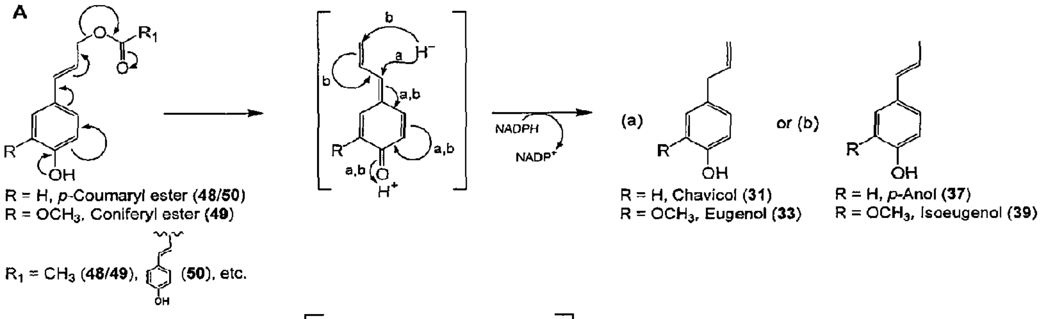

R = H, *p*-Coumaryl ester (48/50)
R = $OCH_3$, Coniferyl ester (49)

$R_1$ = $CH_3$ (48/49), (50), etc.

R = H, Chavicol (31)
R = $OCH_3$, Eugenol (33)

R = H, *p*-Anol (37)
R = $OCH_3$, Isoeugenol (39)

B

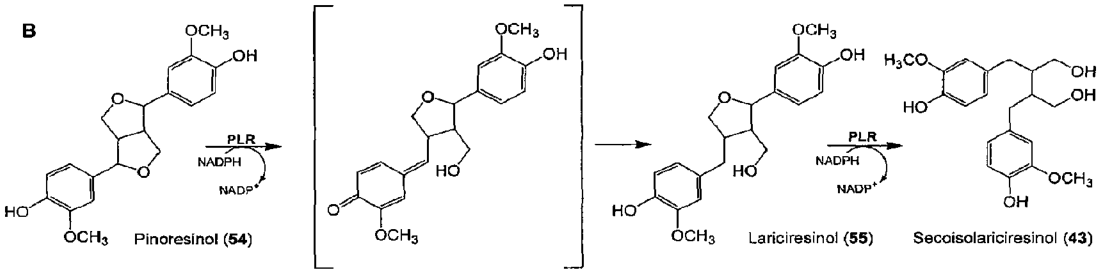

Pinoresinol (54) Lariciresinol (55) Secoisolariciresinol (43)

C

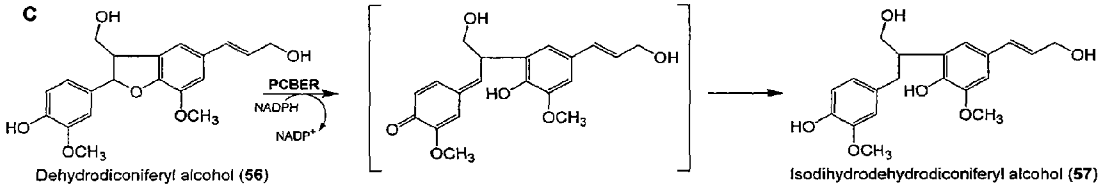

Dehydrodiconiferyl alcohol (56)

Isodihydrodehydrodiconiferyl alcohol (57)

D

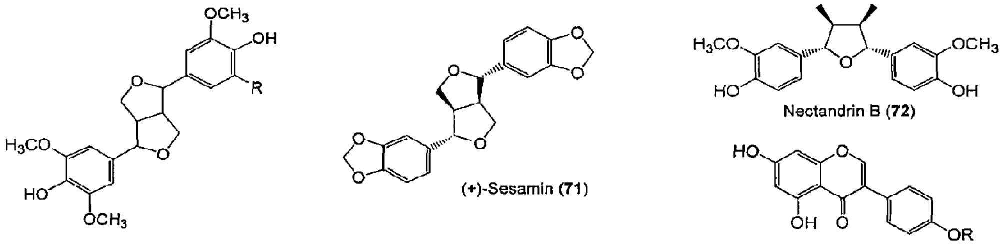

Nectandrin B (72)

(+)-Sesamin (71)

R = H, Medioresinol (69)
R = $OCH_3$, Syringaresinol (70)

R = H, Genistein (73)
R = $CH_3$, Biochanin A (74)

FIG. 17A and 17B
A
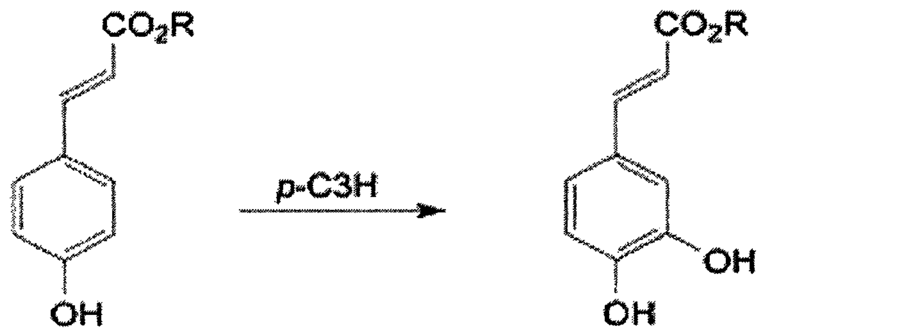
R = shikimate, *p*-coumaroyl shikimate
(R = H, *p*-coumaric acid)
R = shikimate, caffeoyl shikimate
B
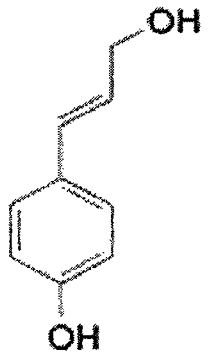
*p*-Coumaryl alcohol
(*p*-hydroxyphenyl, H)
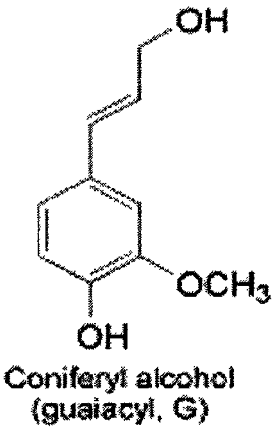
Coniferyl alcohol
(guaiacyl, G)
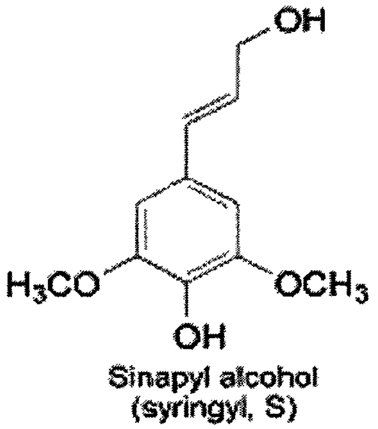
Sinapyl alcohol
(syringyl, S)

FIG. 25
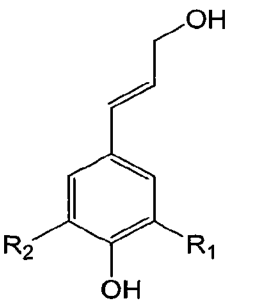
1 $R_1 = R_2 = H$
2 $R_1 = OH, R_2 = H$
3 $R_1 = OMe, R_2 = H$
4 $R_1 = OMe, R_2 = OH$
5 $R_1 = R_2 = OMe$
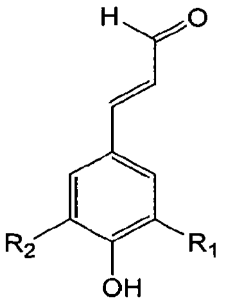
6 $R_1 = R_2 = H$
7 $R_1 = OH, R_2 = H$
8 $R_1 = OMe, R_2 = H$
9 $R_1 = OMe, R_2 = OH$
10 $R_1 = R_2 = OMe$
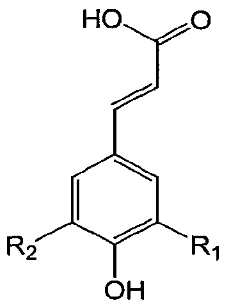
11 $R_1 = R_2 = H$
12 $R_1 = OH, R_2 = H$
13 $R_1 = OMe, R_2 = H$
14 $R_1 = OMe, R_2 = OH$
15 $R_1 = R_2 = OMe$
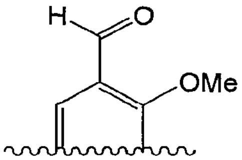
16
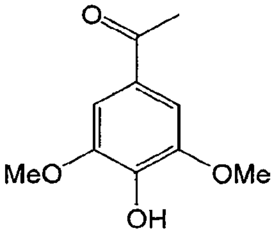
17
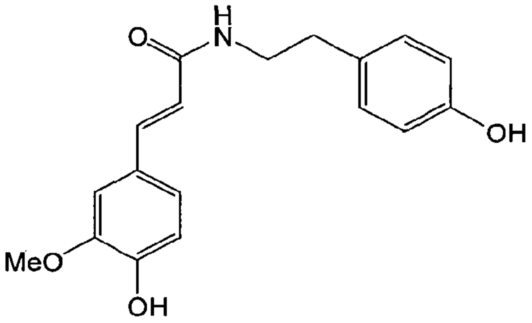
18
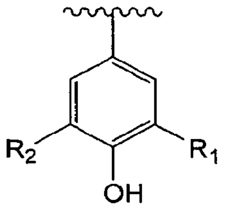
***p*-Hydroxyphenyl unit** (H unit) $R_1 = R_2 = H$
Guaiacyl unit (G unit) $R_1 = OMe, R_2 = H$
Syringyl unit (S unit) $R_1 = R_2 = OMe$ FIG. 26C, 26D, and 26E
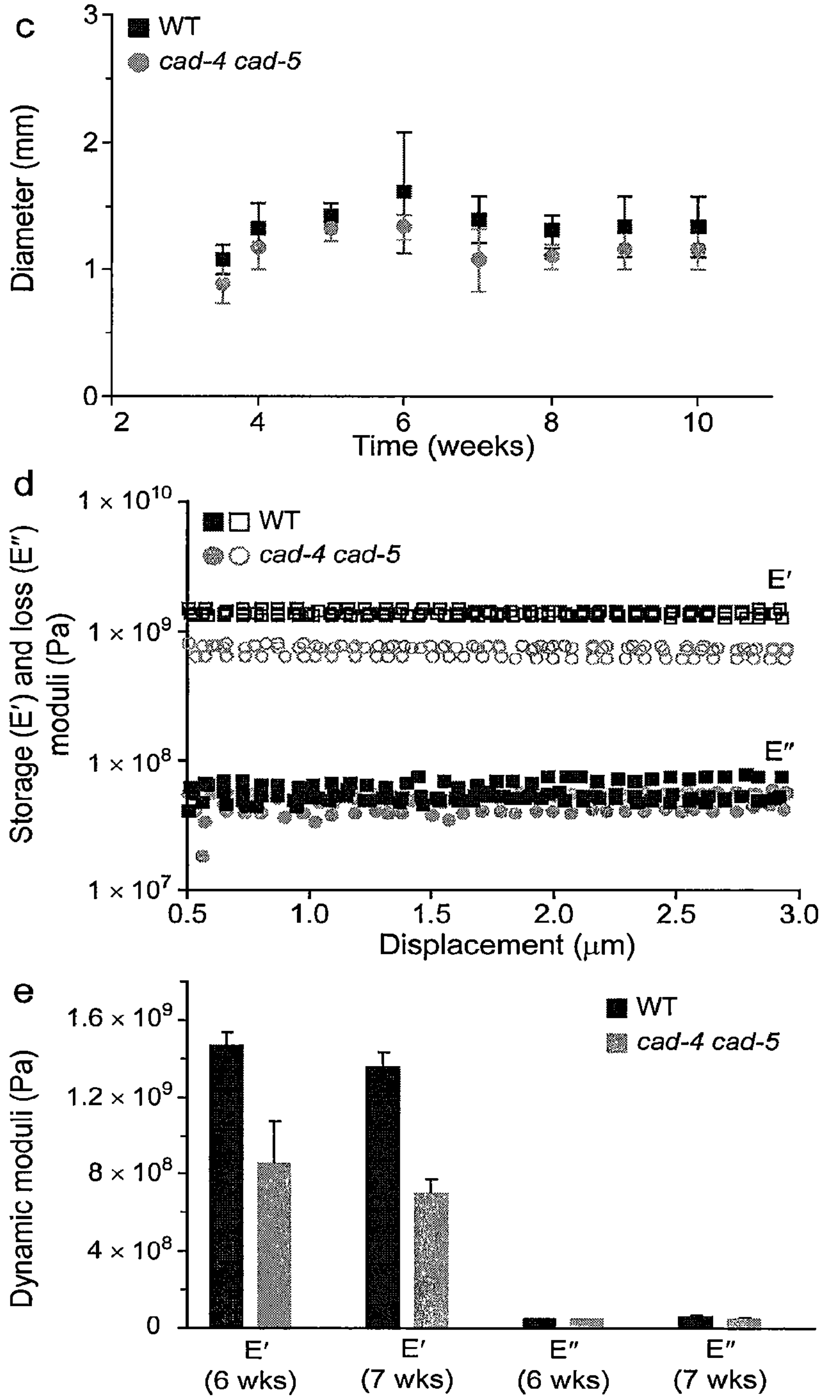

I: 8-aryl ether (8-O-4′)

II: resinol (8-8′)

III: phenylcoumaran (8-5′)

IV: dibenzodioxocin (5′-5″/8-O-4″, 7-O-4′)

V: (E)-cinnamyl alcohol

VI: cinnamyl aldehyde

VII: benzaldehyde

VIII: aldehydic 8-aryl ether (8-O-4?)

a) p-coumaryl (H) unit: $R_1 = R_2 = H$
b) guaiacyl (G) unit: $R_1 = OMe$, $R_2 = H$
c) syringyl (S) unit: $R_1 = R_2 = OMe$ FIG. 32
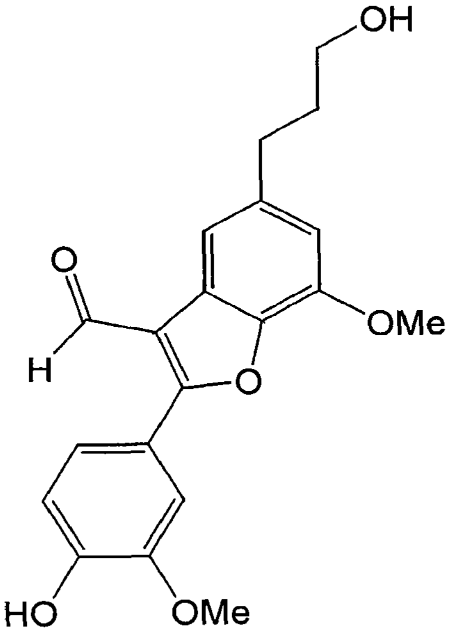
79
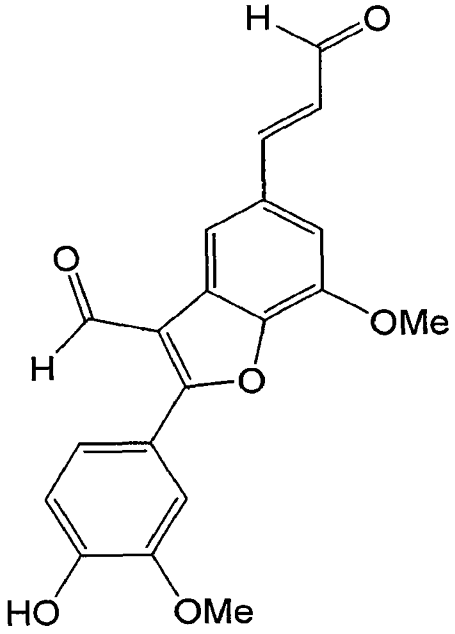
80

SEQUENCE LISTING

```
<160> NUMBER OF SEQ ID NOS: 22

<210> SEQ ID NO 1
<211> LENGTH: 927
<212> TYPE: DNA
<213> ORGANISM: Larrea tridentate

<400> SEQUENCE: 1

atggcacaga agagcaagat tttgatcatt ggaggcactg gctatattgg caaattcgtt      60
```

-continued

```
gttgaagcaa gcgctaaggc tggccgtcct acctttgcat tagttagaga aagcactgtt    120

tctgaccctg ttaaaggaaa gcttattgca aacttcaaga atttgggtgt caatattctc    180

catggagatc tcaatgatca cgagagctta gtgaaggcaa ttaagaaggt ggatgtggtc    240

atttctacag taggcaactt tcagatagct gatcaagtca agattattgc tgctatcaaa    300

gcggctggaa atgtcaagag atttttccct tcagaatttg gaaacgacgt tgaccgaacc    360

catgctgtgg aaccagcaaa atctacattt gaaatgaagg ctcaactccg cagaactatt    420

gaggcagaag ggatccctta cacttatgtg tcgtccaatt tctttgccgg ttatttcttg    480

cctgtattgg gacaggtagg agtcactgct ccccctagag acaaagtcac cattttaggg    540

gatgggaatc aaaaggctgt tttcaacaag gaagatgata ttggaacata cacaatccga    600

gctgctgatg atccaagaac attgaataag atcctttaca ttaggcctcc tcggaatacc    660

tactcaatga atgagcttgt tgccctgtgg gagaagaaaa ttggcaaaac tcttgaaaag    720

acttacgttc cagaggagca gcttctaaag aacattcaag aggccgaaat accatggaat    780

gttgtgttag caatcaacca ttccgtcttt gtaaagggtg atcataccaa cttcgcgatc    840

aaaccatctt tcggcgtcga ggcctccgag ctttatcccg atgtcaagta taccactgtt    900

gaggagtacc ttagtcagtt tgtttaa                                        927
```

<210> SEQ ID NO 2
<211> LENGTH: 308
<212> TYPE: PRT
<213> ORGANISM: Larrea tridentate

<400> SEQUENCE: 2

```
Met Ala Gln Lys Ser Lys Ile Leu Ile Ile Gly Gly Thr Gly Tyr Ile
 1               5                  10                  15

Gly Lys Phe Val Val Glu Ala Ser Ala Lys Ala Gly Arg Pro Thr Phe
            20                  25                  30

Ala Leu Val Arg Glu Ser Thr Val Ser Asp Pro Val Lys Gly Lys Leu
        35                  40                  45

Ile Ala Asn Phe Lys Asn Leu Gly Val Asn Ile Leu His Gly Asp Leu
    50                  55                  60

Asn Asp His Glu Ser Leu Val Lys Ala Ile Lys Lys Val Asp Val Val
65                  70                  75                  80

Ile Ser Thr Val Gly Asn Phe Gln Ile Ala Asp Gln Val Lys Ile Ile
                85                  90                  95

Ala Ala Ile Lys Ala Ala Gly Asn Val Lys Arg Phe Phe Pro Ser Glu
            100                 105                 110

Phe Gly Asn Asp Val Asp Arg Thr His Ala Val Glu Pro Ala Lys Ser
        115                 120                 125

Thr Phe Glu Met Lys Ala Gln Leu Arg Arg Thr Ile Glu Ala Glu Gly
    130                 135                 140

Ile Pro Tyr Thr Tyr Val Ser Ser Asn Phe Phe Ala Gly Tyr Phe Leu
145                 150                 155                 160

Pro Val Leu Gly Gln Val Gly Val Thr Ala Pro Pro Arg Asp Lys Val
                165                 170                 175

Thr Ile Leu Gly Asp Gly Asn Gln Lys Ala Val Phe Asn Lys Glu Asp
            180                 185                 190

Asp Ile Gly Thr Tyr Thr Ile Arg Ala Ala Asp Asp Pro Arg Thr Leu
        195                 200                 205

Asn Lys Ile Leu Tyr Ile Arg Pro Pro Arg Asn Thr Tyr Ser Met Asn
    210                 215                 220
```

```
Glu Leu Val Ala Leu Trp Glu Lys Lys Ile Gly Lys Thr Leu Glu Lys
225                 230                 235                 240

Thr Tyr Val Pro Glu Glu Gln Leu Leu Lys Asn Ile Gln Glu Ala Glu
                245                 250                 255

Ile Pro Trp Asn Val Val Leu Ala Ile Asn His Ser Val Phe Val Lys
            260                 265                 270

Gly Asp His Thr Asn Phe Ala Ile Lys Pro Ser Phe Gly Val Glu Ala
        275                 280                 285

Ser Glu Leu Tyr Pro Asp Val Lys Tyr Thr Thr Val Glu Glu Tyr Leu
    290                 295                 300

Ser Gln Phe Val
305


<210> SEQ ID NO 3
<211> LENGTH: 927
<212> TYPE: DNA
<213> ORGANISM: Larrea tridentate

<400> SEQUENCE: 3

atggcgcaga agagcaagat tttgatcatt ggaggcactg gctacattgg caaatccatt      60

gtcgaagcaa gcgccaaggc tggccatccg acctttgcat tggttagaga aagcaccgtc     120

tttcatcacg ttaagggaaa acttgttaag aatttcaagg atttaggcgt caatcttgtc     180

catggggaca ttaatgatca tgatagcttg ctaaaggcaa ttaagcaagt ggatgtggtg     240

ttttctacgc ttggtcacca tcatataggt gaccaacaca aagttattgc tgctatcaaa     300

gaggctggta atgtcaagcg atattttcct tccgaattcg gcaatgatgt ggatcgatcc     360

catgctgtgg atcccgtaaa atctgcatac agaacgaagg ctcaaatccg cagggctatc     420

gaggctgaag ggatccccca cacttatgtt tcatgcaatt tctttgctgg ttatttcctc     480

cctacattgg tacagttaga agtcaccgct cctcctagag acaaagtcac cattttaggg     540

gatggaaata aaaaagcaat attcaataag gaagatgata ttgcgactta tgcaatcaga     600

gctgttgatg atccacgaac actgaacaaa atctcgtaca ttagaacacc taaaaatacc     660

tacacgatga atgagcttgt cgccctgtgg gagaagaaaa ttggcaaatc gcttgagaag     720

atttatgttc cggaggacca aattctaaag aacattcaag agtctccgtt ttcgacacaa     780

gttatgttgt caatcaatca ttccgtcttt gtaaagggtg atcaaaccaa cttcgacatt     840

gatccgtctt tcggtgtgga ggctaccgag ctttatcctg atgtcaacta taccaccgtt     900

gaagagtatc ttgatcaatt cgtttaa                                          927


<210> SEQ ID NO 4
<211> LENGTH: 308
<212> TYPE: PRT
<213> ORGANISM: Larrea tridentate

<400> SEQUENCE: 4

Met Ala Gln Lys Ser Lys Ile Leu Ile Ile Gly Gly Thr Gly Tyr Ile
 1               5                  10                  15

Gly Lys Ser Ile Val Glu Ala Ser Ala Lys Ala Gly His Pro Thr Phe
            20                  25                  30

Ala Leu Val Arg Glu Ser Thr Val Phe His His Val Lys Gly Lys Leu
        35                  40                  45

Val Lys Asn Phe Lys Asp Leu Gly Val Asn Leu Val His Gly Asp Ile
    50                  55                  60
```

-continued

Asn Asp His Asp Ser Leu Leu Lys Ala Ile Lys Gln Val Asp Val Val
65 70 75 80

Phe Ser Thr Leu Gly His His His Ile Gly Asp Gln His Lys Val Ile
85 90 95

Ala Ala Ile Lys Glu Ala Gly Asn Val Lys Arg Tyr Phe Pro Ser Glu
100 105 110

Phe Gly Asn Asp Val Asp Arg Ser His Ala Val Asp Pro Val Lys Ser
115 120 125

Ala Tyr Arg Thr Lys Ala Gln Ile Arg Arg Ala Ile Glu Ala Glu Gly
130 135 140

Ile Pro His Thr Tyr Val Ser Cys Asn Phe Phe Ala Gly Tyr Phe Leu
145 150 155 160

Pro Thr Leu Val Gln Leu Glu Val Thr Ala Pro Pro Arg Asp Lys Val
165 170 175

Thr Ile Leu Gly Asp Gly Asn Lys Lys Ala Ile Phe Asn Lys Glu Asp
180 185 190

Asp Ile Ala Thr Tyr Ala Ile Arg Ala Val Asp Asp Pro Arg Thr Leu
195 200 205

Asn Lys Ile Ser Tyr Ile Arg Thr Pro Lys Asn Thr Tyr Thr Met Asn
210 215 220

Glu Leu Val Ala Leu Trp Glu Lys Lys Ile Gly Lys Ser Leu Glu Lys
225 230 235 240

Ile Tyr Val Pro Glu Asp Gln Ile Leu Lys Asn Ile Gln Glu Ser Pro
245 250 255

Phe Ser Thr Gln Val Met Leu Ser Ile Asn His Ser Val Phe Val Lys
260 265 270

Gly Asp Gln Thr Asn Phe Asp Ile Asp Pro Ser Phe Gly Val Glu Ala
275 280 285

Thr Glu Leu Tyr Pro Asp Val Asn Tyr Thr Thr Val Glu Glu Tyr Leu
290 295 300

Asp Gln Phe Val
305

<210> SEQ ID NO 5
<211> LENGTH: 939
<212> TYPE: DNA
<213> ORGANISM: Larrea tridentate

<400> SEQUENCE: 5
atgtgcaaga gcaaagtact aattgttgga ggaactggat acttgggaaa gaggttggtg 60
aaggcaagtt tagctctagg acatgaaaca tatgttcttc atagggcaga gattggtgtt 120
gatattgaga aagtgcaaat gttactgtca tttaaggagc aaggagctac tctagtgcct 180
ggctcttttg ctgatcatca aagtcttgtt aatgctgtta agctggttga tgttgttata 240
tgtgcaattt ctggtgtcca tattagaagc catcatatat tacttcaact caagctagtt 300
gatgcaatca aagaggctgg gaatgtcaag agatttttgc cgtctgagtt tggcacagac 360
cctgcaagaa tggagaatgc aatggaacct ggaagagtga cattcgatga caaaatggta 420
gtaagaaaag caattcaaga tgctggaatt ccttacacat atgtttctgc caattgtttt 480
gctggttact ttctgggtgg cctgtgtcaa cctggcagca ttattccatc aacagaacac 540
gtcctcttgt taggtgatgg caccaagaaa gccatctatg ttgatgaaca tgatatcgcc 600
atgtacacaa tcaaagcaat agacgaccct agaactctga acaagacagt ttacataagg 660
ccgcctgtaa atatcttatc tcagctagaa gttgtgaaga tttgggagaa attaattgga 720
aaagagcttc agaaaacctc tatatcaaag gaagactttc tagaatccat gaaagggcaa 780
aattacgcag agcaagttgg actgacacat tactatcacg tttgttatga gggatgtctt 840
gcaaactttg aaattggaga agaaggagta gaagctactc aactatatcc agaaattaag 900
tacgtaacag tcgagcaata catgaagcgt tatttataa 939

<210> SEQ ID NO 6
<211> LENGTH: 312
<212> TYPE: PRT
<213> ORGANISM: Larrea tridentate

<400> SEQUENCE: 6

Met Cys Lys Ser Lys Val Leu Ile Val Gly Gly Thr Gly Tyr Leu Gly
1 5 10 15

Lys Arg Leu Val Lys Ala Ser Leu Ala Leu Gly His Glu Thr Tyr Val
20 25 30

Leu His Arg Ala Glu Ile Gly Val Asp Ile Glu Lys Val Gln Met Leu
35 40 45

Leu Ser Phe Lys Glu Gln Gly Ala Thr Leu Val Pro Gly Ser Phe Ala
50 55 60

Asp His Gln Ser Leu Val Asn Ala Val Lys Leu Val Asp Val Val Ile
65 70 75 80

Cys Ala Ile Ser Gly Val His Ile Arg Ser His His Ile Leu Leu Gln
85 90 95

Leu Lys Leu Val Asp Ala Ile Lys Glu Ala Gly Asn Val Lys Arg Phe
100 105 110

Leu Pro Ser Glu Phe Gly Thr Asp Pro Ala Arg Met Glu Asn Ala Met
115 120 125

Glu Pro Gly Arg Val Thr Phe Asp Asp Lys Met Val Val Arg Lys Ala
130 135 140

Ile Gln Asp Ala Gly Ile Pro Tyr Thr Tyr Val Ser Ala Asn Cys Phe
145 150 155 160

Ala Gly Tyr Phe Leu Gly Gly Leu Cys Gln Pro Gly Ser Ile Ile Pro
165 170 175

Ser Thr Glu His Val Leu Leu Leu Gly Asp Gly Thr Lys Lys Ala Ile
180 185 190

Tyr Val Asp Glu His Asp Ile Ala Met Tyr Thr Ile Lys Ala Ile Asp
195 200 205

Asp Pro Arg Thr Leu Asn Lys Thr Val Tyr Ile Arg Pro Pro Val Asn
210 215 220

Ile Leu Ser Gln Leu Glu Val Val Lys Ile Trp Glu Lys Leu Ile Gly
225 230 235 240

Lys Glu Leu Gln Lys Thr Ser Ile Ser Lys Glu Asp Phe Leu Glu Ser
245 250 255

Met Lys Gly Gln Asn Tyr Ala Glu Gln Val Gly Leu Thr His Tyr Tyr
260 265 270

His Val Cys Tyr Glu Gly Cys Leu Ala Asn Phe Glu Ile Gly Glu Glu
275 280 285

Gly Val Glu Ala Thr Gln Leu Tyr Pro Glu Ile Lys Tyr Val Thr Val
290 295 300

Glu Gln Tyr Met Lys Arg Tyr Leu
305 310

<210> SEQ ID NO 7

<211> LENGTH: 939
<212> TYPE: DNA
<213> ORGANISM: Forsythia x intermedia

<400> SEQUENCE: 7

```
atgggaaaaa gcaaagtttt gatcattggg ggtacagggt acttagggag gagattggtt      60

aaggcaagtt tagctcaagg tcatgaaaca tacattctgc ataggcctga aattggtgtt     120

gatattgata aagttgaaat gctaatatca tttaaaatgc aaggagctca tcttgtatct     180

ggttctttca aggatttcaa cagtctggtc gaggctgtca agctcgtaga cgtagtaatc     240

agcgccattt ctggtgttca tattcgaagc catcaaattc ttcttcaact caagcttgtt     300

gaagctatta aagaggctgg aaatgtcaag agatttttac catctgagtt tggaatggat     360

cctgcaaaat ttatggatac ggccatggaa cccggaaagg taacacttga tgagaagatg     420

gtggtaagga aagcaattga aaaggctggg attcctttca catatgtctc tgcaaattgc     480

tttgctggtt atttcttggg aggtctctgt caatttggca aaattcttcc ttctagagat     540

tttgtcatta tacatggaga tggtaacaaa aaagcaatat ataacaatga agatgatata     600

gcaacttatg ccatcaaaac aattaatgat ccaagaaccc tcaacaagac aatctacatt     660

agtcctccaa aaaacatcct ttcacaaaga gaagttgttc agacatggga gaagcttatt     720

gggaaagaac tgcagaaaat tacactctcg aaggaagatt ttttagcctc cgtgaaagag     780

ctcgagtatg ctcagcaagt gggattaagc cattatcatg atgtcaacta tcagggatgc     840

cttacgagtt ttgagatagg agatgaagaa gaggcatcta aactttatcc agaggttaag     900

tataccagtg tggaagagta cctcaagcgt tacgtgtag                            939
```

<210> SEQ ID NO 8
<211> LENGTH: 312
<212> TYPE: PRT
<213> ORGANISM: Forsythia x intermedia

<400> SEQUENCE: 8

```
Met Gly Lys Ser Lys Val Leu Ile Ile Gly Gly Thr Gly Tyr Leu Gly
1               5                   10                  15

Arg Arg Leu Val Lys Ala Ser Leu Ala Gln Gly His Glu Thr Tyr Ile
            20                  25                  30

Leu His Arg Pro Glu Ile Gly Val Asp Ile Asp Lys Val Glu Met Leu
        35                  40                  45

Ile Ser Phe Lys Met Gln Gly Ala His Leu Val Ser Gly Ser Phe Lys
    50                  55                  60

Asp Phe Asn Ser Leu Val Glu Ala Val Lys Leu Val Asp Val Val Ile
65                  70                  75                  80

Ser Ala Ile Ser Gly Val His Ile Arg Ser His Gln Ile Leu Leu Gln
                85                  90                  95

Leu Lys Leu Val Glu Ala Ile Lys Glu Ala Gly Asn Val Lys Arg Phe
            100                 105                 110

Leu Pro Ser Glu Phe Gly Met Asp Pro Ala Lys Phe Met Asp Thr Ala
        115                 120                 125

Met Glu Pro Gly Lys Val Thr Leu Asp Glu Lys Met Val Val Arg Lys
    130                 135                 140

Ala Ile Glu Lys Ala Gly Ile Pro Phe Thr Tyr Val Ser Ala Asn Cys
145                 150                 155                 160

Phe Ala Gly Tyr Phe Leu Gly Gly Leu Cys Gln Phe Gly Lys Ile Leu
                165                 170                 175
```

-continued

```
Pro Ser Arg Asp Phe Val Ile Ile His Gly Asp Gly Asn Lys Lys Ala
            180                 185                 190

Ile Tyr Asn Asn Glu Asp Asp Ile Ala Thr Tyr Ala Ile Lys Thr Ile
        195                 200                 205

Asn Asp Pro Arg Thr Leu Asn Lys Thr Ile Tyr Ile Ser Pro Pro Lys
    210                 215                 220

Asn Ile Leu Ser Gln Arg Glu Val Val Gln Thr Trp Glu Lys Leu Ile
225                 230                 235                 240

Gly Lys Glu Leu Gln Lys Ile Thr Leu Ser Lys Glu Asp Phe Leu Ala
                245                 250                 255

Ser Val Lys Glu Leu Glu Tyr Ala Gln Gln Val Gly Leu Ser His Tyr
            260                 265                 270

His Asp Val Asn Tyr Gln Gly Cys Leu Thr Ser Phe Glu Ile Gly Asp
        275                 280                 285

Glu Glu Glu Ala Ser Lys Leu Tyr Pro Glu Val Lys Tyr Thr Ser Val
    290                 295                 300

Glu Glu Tyr Leu Lys Arg Tyr Val
305                 310
```

<210> SEQ ID NO 9
<211> LENGTH: 945
<212> TYPE: DNA
<213> ORGANISM: Ocimum basilicum

<400> SEQUENCE: 9

```
atggaggaaa atgggatgaa aagcaagatt ttaatatttg gagggacagg ttacattgga      60

aatcacatgg tgaaaggaag cctcaaatta gggcacccaa cttatgtttt cacaaggcct     120

aattcctcca agacaaccct tcttgatgag ttccaatcct tgggtgccat catagtcaag     180

ggagagttgg atgagcatga gaaactagtt gagttgatga agaaagttga tgttgtcata     240

tctgcacttg cattcccaca aattcttgat cagttcaaga tcttggaggc catcaaggtt     300

gctgggaata ttaagaggtt tctaccgtcg gattttgggg tcgaggagga cagaataaac     360

gcattgccgc cgttcgaagc actcatagag aggaagagga tgatcagaag agccattgaa     420

gaagcaaata ttccttacac ttatgtgtct gcaaattgct ttgcatcata cttcatcaac     480

tacttgctcc gcccttatga tccaaaagat gagatcacgg tttacggcac cggggaagct     540

aagttcgcga tgaactacga acaagacatc gggctctaca cgatcaaagt tgcaactgat     600

cctagagcat tgaatcgtgt ggtgatctac agaccatcaa caaatatcat aacacagctc     660

gagttgattt cgaggtggga gaaaaaaatt gggaagaagt tcaaaaagat tcatgtcccc     720

gaagaagaaa ttgtggccct cacaaaagaa ctgccggagc ccgagaatat acccatagca     780

atccttcact gtctcttcat agacggagcg acgatgagtt atgatttcaa ggagaacgat     840

gtggaggctt caactctgta tccagagttg aagttcacca cgatcgatga gctcctcgac     900

attttcgtgc acgatcctcc accgccggct tcagcagcat tttaa                     945
```

<210> SEQ ID NO 10
<211> LENGTH: 314
<212> TYPE: PRT
<213> ORGANISM: Ocimum basilicum

<400> SEQUENCE: 10

```
Met Glu Glu Asn Gly Met Lys Ser Lys Ile Leu Ile Phe Gly Gly Thr
 1               5                  10                  15

Gly Tyr Ile Gly Asn His Met Val Lys Gly Ser Leu Lys Leu Gly His
```

```
            20                  25                  30

Pro Thr Tyr Val Phe Thr Arg Pro Asn Ser Ser Lys Thr Thr Leu Leu
        35                  40                  45

Asp Glu Phe Gln Ser Leu Gly Ala Ile Ile Val Lys Gly Glu Leu Asp
    50                  55                  60

Glu His Glu Lys Leu Val Glu Leu Met Lys Lys Val Asp Val Val Ile
65                  70                  75                  80

Ser Ala Leu Ala Phe Pro Gln Ile Leu Asp Gln Phe Lys Ile Leu Glu
                85                  90                  95

Ala Ile Lys Val Ala Gly Asn Ile Lys Arg Phe Leu Pro Ser Asp Phe
            100                 105                 110

Gly Val Glu Glu Asp Arg Ile Asn Ala Leu Pro Pro Phe Glu Ala Leu
        115                 120                 125

Ile Glu Arg Lys Arg Met Ile Arg Arg Ala Ile Glu Glu Ala Asn Ile
    130                 135                 140

Pro Tyr Thr Tyr Val Ser Ala Asn Cys Phe Ala Ser Tyr Phe Ile Asn
145                 150                 155                 160

Tyr Leu Leu Arg Pro Tyr Asp Pro Lys Asp Glu Ile Thr Val Tyr Gly
                165                 170                 175

Thr Gly Glu Ala Lys Phe Ala Met Asn Tyr Glu Gln Asp Ile Gly Leu
            180                 185                 190

Tyr Thr Ile Lys Val Ala Thr Asp Pro Arg Ala Leu Asn Arg Val Val
        195                 200                 205

Ile Tyr Arg Pro Ser Thr Asn Ile Ile Thr Gln Leu Glu Leu Ile Ser
    210                 215                 220

Arg Trp Glu Lys Lys Ile Gly Lys Lys Phe Lys Lys Ile His Val Pro
225                 230                 235                 240

Glu Glu Glu Ile Val Ala Leu Thr Lys Glu Leu Pro Glu Pro Glu Asn
                245                 250                 255

Ile Pro Ile Ala Ile Leu His Cys Leu Phe Ile Asp Gly Ala Thr Met
            260                 265                 270

Ser Tyr Asp Phe Lys Glu Asn Asp Val Glu Ala Ser Thr Leu Tyr Pro
        275                 280                 285

Glu Leu Lys Phe Thr Thr Ile Asp Glu Leu Leu Asp Ile Phe Val His
    290                 295                 300

Asp Pro Pro Pro Pro Ala Ser Ala Ala Phe
305                 310


<210> SEQ ID NO 11
<211> LENGTH: 972
<212> TYPE: DNA
<213> ORGANISM: Petunia x hybrida

<400> SEQUENCE: 11

atgactactg ggaagggaaa aatattgatt cttggagcaa ctggttatct tggaaaatat      60

atggtgaaag ccagtatttc tttgggacat ccaacgtatg cctatgtcat gccattgaag     120

aagaactctg atgattctaa gcttcagctt ctcaaggaat ttgagtcctt gggagtaact     180

atattttatg gagagcttag tgaacatgat aaacttgttg cagtgtttaa agaggttgat     240

attgtgatat ctactttagc agtgcctcaa tatcttgaac aactcaaggt gattgaggcc     300

atcaaagaag ctggtaacat taagaggttt gttccttctg aatttgggaa tgaagtggat     360

agggtaagag cgttaccacg tttccaagct gttcttgaca acaagaagaa gattaggaga     420

gcaactgaag cagcaggaat accattcaca tttgtatctg caaattcatt aacagcttat     480
```

```
tttgttgatt atttgcttca tccacgtcaa aagagtgagc aagttaccat ttatggaagt    540

ggtgatgcaa aggctgtgtt gaactatgag gaagatgtcg cagcctacac aattaaagca    600

gcagatgatc caagggcagc aaaccgtgtc ctaattataa aacccoctaa aaacattgtc    660

tcacaattag atttggtatc ttcttgggag aaaaccactg gtagcacttt gaaaatgact    720

catatctctg aacaagaaat catcaaactc tccgagagca taaatttccc agagaacata    780

catgcatcaa tcctacacaa tatattcata gcaggagccc aactaagctt tgaacttaca    840

caggatcatg acttggaagc atcagagctc tatcctaatt acaactacac ctctgttgat    900

gaatatctca aatttgtct ggttaaccct ccgaagccaa aattggcaac ttatgcccaa    960

ccatccactt aa                                                        972
```

<210> SEQ ID NO 12
<211> LENGTH: 323
<212> TYPE: PRT
<213> ORGANISM: Petunia x hybrida

<400> SEQUENCE: 12

```
Met Thr Thr Gly Lys Gly Lys Ile Leu Ile Leu Gly Ala Thr Gly Tyr
 1               5                  10                  15

Leu Gly Lys Tyr Met Val Lys Ala Ser Ile Ser Leu Gly His Pro Thr
            20                  25                  30

Tyr Ala Tyr Val Met Pro Leu Lys Lys Asn Ser Asp Asp Ser Lys Leu
        35                  40                  45

Gln Leu Leu Lys Glu Phe Glu Ser Leu Gly Val Thr Ile Phe Tyr Gly
    50                  55                  60

Glu Leu Ser Glu His Asp Lys Leu Val Ala Val Phe Lys Glu Val Asp
65                  70                  75                  80

Ile Val Ile Ser Thr Leu Ala Val Pro Gln Tyr Leu Glu Gln Leu Lys
                85                  90                  95

Val Ile Glu Ala Ile Lys Glu Ala Gly Asn Ile Lys Arg Phe Val Pro
            100                 105                 110

Ser Glu Phe Gly Asn Glu Val Asp Arg Val Arg Ala Leu Pro Arg Phe
        115                 120                 125

Gln Ala Val Leu Asp Asn Lys Lys Lys Ile Arg Arg Ala Thr Glu Ala
    130                 135                 140

Ala Gly Ile Pro Phe Thr Phe Val Ser Ala Asn Ser Leu Thr Ala Tyr
145                 150                 155                 160

Phe Val Asp Tyr Leu Leu His Pro Arg Gln Lys Ser Glu Gln Val Thr
                165                 170                 175

Ile Tyr Gly Ser Gly Asp Ala Lys Ala Val Leu Asn Tyr Glu Glu Asp
            180                 185                 190

Val Ala Ala Tyr Thr Ile Lys Ala Ala Asp Asp Pro Arg Ala Ala Asn
        195                 200                 205

Arg Val Leu Ile Ile Lys Pro Pro Lys Asn Ile Val Ser Gln Leu Asp
    210                 215                 220

Leu Val Ser Ser Trp Glu Lys Thr Thr Gly Ser Thr Leu Lys Met Thr
225                 230                 235                 240

His Ile Ser Glu Gln Glu Ile Ile Lys Leu Ser Glu Ser Ile Asn Phe
                245                 250                 255

Pro Glu Asn Ile His Ala Ser Ile Leu His Asn Ile Phe Ile Ala Gly
            260                 265                 270

Ala Gln Leu Ser Phe Glu Leu Thr Gln Asp His Asp Leu Glu Ala Ser
```

-continued 275 280 285

Glu Leu Tyr Pro Asn Tyr Asn Tyr Thr Ser Val Asp Glu Tyr Leu Lys
290 295 300

Ile Cys Leu Val Asn Pro Pro Lys Pro Lys Leu Ala Thr Tyr Ala Gln
305 310 315 320

Pro Ser Thr

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide

<400> SEQUENCE: 13
ctacatttga aatggcggct caactccgca g 31

<210> SEQ ID NO 14
<211> LENGTH: 31
<212> TYPE: DNA
<213> ORGANISM: Artificial Sequence
<220> FEATURE:
<223> OTHER INFORMATION: Oligonucleotide

<400> SEQUENCE: 14
ctgcggagtt gagccgccat ttcaaatgta g 31

<210> SEQ ID NO 15
<211> LENGTH: 23
<212> TYPE: DNA
<213> ORGANISM: Artificial Sequence
<220> FEATURE:
<223> OTHER INFORMATION: Oligonucleotide

<400> SEQUENCE: 15
gggctggcaa gccacgtttg gtg 23

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide

<400> SEQUENCE: 16
ccgggagctg catgtgtcag agg 23

<210> SEQ ID NO 17
<211> LENGTH: 927
<212> TYPE: DNA
<213> ORGANISM: Larrea tridentate

<400> SEQUENCE: 17
atggcgcaga agagcaagat tttgatcatt ggaggcactg gctacattgg caaatccatt 60
gtcgaagcaa gcgccaaggc tggccatcct acctttgcat tggttagaga aagcaccgtc 120
tttcatcacg ttaagggaaa acttgttaag aatttcaagg atttaggcgt caatcttgtc 180
catggggaca ttaatgatca tgagagcttg ctaaaggcaa ttaagcaagt ggatgtggtg 240
ttttctacgc ttggtcacca tcatataggt gaccaacaca aagttattgc tgctatcaaa 300
gaggctggta atgtcaagcg atattttcct tccgaattcg gcaatgatgt ggatcgatcc 360
catgctgtgg atcccgtaaa atctgcatac agaatgaagg ctcaaatccg cagggctatc 420

```
gaggctgaag ggatccccca cacttatgtt tcatgcaatt tctttgctgg ttatttcctc    480

cctacattgg tacagttaga agtcaccgct cctcctagag acaaagtcac cattttaggg    540

gatggaaata aaaaagcaat attcaataag gaagatgata ttgcgactta tgcaatcaga    600

gctgttgatg atccacgaac actgaacaaa atcttgtaca ttagaacacc taaaaatacc    660

tacacgatga atgagcttgt cgccctgtgg gagaagaaaa ttggcaaatc gcttgagaag    720

atttatgctc cggaggacca aattctaaag aacattcaag agtctccgtt ttcgacacaa    780

gttatgttgt caatcaatca ttccgtcttt gtaaagggtg atcaaaccaa cttcgacatt    840

gatctgtctt tcggtgtgga ggctaccgag ctttatcctg atgtcaacta taccaccgtt    900

gaagagtatc ttgatcaatt cgtttaa                                        927
```

<210> SEQ ID NO 18
<211> LENGTH: 308
<212> TYPE: PRT
<213> ORGANISM: Larrea tridentate

<400> SEQUENCE: 18

```
Met Ala Gln Lys Ser Lys Ile Leu Ile Ile Gly Gly Thr Gly Tyr Ile
 1               5                  10                  15

Gly Lys Ser Ile Val Glu Ala Ser Ala Lys Ala Gly His Pro Thr Phe
            20                  25                  30

Ala Leu Val Arg Glu Ser Thr Val Phe His His Val Lys Gly Lys Leu
        35                  40                  45

Val Lys Asn Phe Lys Asp Leu Gly Val Asn Leu Val His Gly Asp Ile
    50                  55                  60

Asn Asp His Glu Ser Leu Leu Lys Ala Ile Lys Gln Val Asp Val Val
65                  70                  75                  80

Phe Ser Thr Leu Gly His His His Ile Gly Asp Gln His Lys Val Ile
                85                  90                  95

Ala Ala Ile Lys Glu Ala Gly Asn Val Lys Arg Tyr Phe Pro Ser Glu
            100                 105                 110

Phe Gly Asn Asp Val Asp Arg Ser His Ala Val Asp Pro Val Lys Ser
        115                 120                 125

Ala Tyr Arg Met Lys Ala Gln Ile Arg Arg Ala Ile Glu Ala Glu Gly
    130                 135                 140

Ile Pro His Thr Tyr Val Ser Cys Asn Phe Phe Ala Gly Tyr Phe Leu
145                 150                 155                 160

Pro Thr Leu Val Gln Leu Glu Val Thr Ala Pro Pro Arg Asp Lys Val
                165                 170                 175

Thr Ile Leu Gly Asp Gly Asn Lys Lys Ala Ile Phe Asn Lys Glu Asp
            180                 185                 190

Asp Ile Ala Thr Tyr Ala Ile Arg Ala Val Asp Asp Pro Arg Thr Leu
        195                 200                 205

Asn Lys Ile Leu Tyr Ile Arg Thr Pro Lys Asn Thr Tyr Thr Met Asn
    210                 215                 220

Glu Leu Val Ala Leu Trp Glu Lys Lys Ile Gly Lys Ser Leu Glu Lys
225                 230                 235                 240

Ile Tyr Ala Pro Glu Asp Gln Ile Leu Lys Asn Ile Gln Glu Ser Pro
                245                 250                 255

Phe Ser Thr Gln Val Met Leu Ser Ile Asn His Ser Val Phe Val Lys
            260                 265                 270

Gly Asp Gln Thr Asn Phe Asp Ile Asp Leu Ser Phe Gly Val Glu Ala
```

```
        275                 280                 285

Thr Glu Leu Tyr Pro Asp Val Asn Tyr Thr Thr Val Glu Glu Tyr Leu
    290                 295                 300

Asp Gln Phe Val
305
```

<210> SEQ ID NO 19
<211> LENGTH: 927
<212> TYPE: DNA
<213> ORGANISM: Larrea tridentate

<400> SEQUENCE: 19

```
atggcgcaga agagcaagat tttgatcatt ggaggcactg gctacattgg caaatccatt      60

gtcgaagcaa gcgccaaggc tggccatccg acctttgcat tggttagaga aagcaccgtc     120

tttcatcacg ttaagggaaa acttgttaag aatttcaagg atttaggcgt caatcttgtc     180

catggggaca ttaatgatca tgagagcttg ctaaaggcaa ttaagcaagt ggatgtggtg     240

ttttctacgc ttggtcacca tcatataggt gaccaacaca aagttattgc tgctatcaaa     300

gaggctggta atgtcaagcg atattttcct tctgaattcg gcaatgatgt ggatcgatcc     360

catgctgtgg atcccgtaaa atctgcatac agaacgaagg ctcaaatccg cagggctatc     420

gaggctgaag ggatccccca cacttatgtt tcatgcaatt tctttgctgg ttatttcctc     480

cctacattgg tacagttaga agtcaccgct cctcctagag acaaagtcac cattttaggg     540

gatggaaata aaaaagcaat attcaataag gaagatgata ttgcgactta tgcaatcaga     600

gctgttgatg atccacgaac actgaacaaa atcttgtaca ttagaacacc taaaaatacc     660

tacacgatga atgagcttgt cgccctgtgg gagaagaaaa ttggcaaatc gcttgagaag     720

atttatgtcc cggaggacca aattctaaag aacattcaag agtctccgtt ttcgacacaa     780

gttatgttgt caatcaatca ttccgtcttt gtaaagggtg atcaaaccaa cttcgacatt     840

gatccgtctt tcggtgtgga ggctaccgag ctttatcctg atgtcaacta taccaccgtt     900

gaagagtatc ttgatcaatt cgtttaa                                         927
```

<210> SEQ ID NO 20
<211> LENGTH: 308
<212> TYPE: PRT
<213> ORGANISM: Larrea tridentate

<400> SEQUENCE: 20

```
Met Ala Gln Lys Ser Lys Ile Leu Ile Ile Gly Gly Thr Gly Tyr Ile
 1               5                  10                  15

Gly Lys Ser Ile Val Glu Ala Ser Ala Lys Ala Gly His Pro Thr Phe
            20                  25                  30

Ala Leu Val Arg Glu Ser Thr Val Phe His His Val Lys Gly Lys Leu
        35                  40                  45

Val Lys Asn Phe Lys Asp Leu Gly Val Asn Leu Val His Gly Asp Ile
    50                  55                  60

Asn Asp His Glu Ser Leu Leu Lys Ala Ile Lys Gln Val Asp Val Val
65                  70                  75                  80

Phe Ser Thr Leu Gly His His His Ile Gly Asp Gln His Lys Val Ile
                85                  90                  95

Ala Ala Ile Lys Glu Ala Gly Asn Val Lys Arg Tyr Phe Pro Ser Glu
            100                 105                 110

Phe Gly Asn Asp Val Asp Arg Ser His Ala Val Asp Pro Val Lys Ser
        115                 120                 125
```

```
Ala Tyr Arg Thr Lys Ala Gln Ile Arg Arg Ala Ile Glu Ala Glu Gly
    130                 135                 140

Ile Pro His Thr Tyr Val Ser Cys Asn Phe Phe Ala Gly Tyr Phe Leu
145                 150                 155                 160

Pro Thr Leu Val Gln Leu Glu Val Thr Ala Pro Pro Arg Asp Lys Val
                165                 170                 175

Thr Ile Leu Gly Asp Gly Asn Lys Lys Ala Ile Phe Asn Lys Glu Asp
            180                 185                 190

Asp Ile Ala Thr Tyr Ala Ile Arg Ala Val Asp Asp Pro Arg Thr Leu
        195                 200                 205

Asn Lys Ile Leu Tyr Ile Arg Thr Pro Lys Asn Thr Tyr Thr Met Asn
    210                 215                 220

Glu Leu Val Ala Leu Trp Glu Lys Lys Ile Gly Lys Ser Leu Glu Lys
225                 230                 235                 240

Ile Tyr Val Pro Glu Asp Gln Ile Leu Lys Asn Ile Gln Glu Ser Pro
                245                 250                 255

Phe Ser Thr Gln Val Met Leu Ser Ile Asn His Ser Val Phe Val Lys
            260                 265                 270

Gly Asp Gln Thr Asn Phe Asp Ile Asp Pro Ser Phe Gly Val Glu Ala
        275                 280                 285

Thr Glu Leu Tyr Pro Asp Val Asn Tyr Thr Thr Val Glu Glu Tyr Leu
    290                 295                 300

Asp Gln Phe Val
305
```

<210> SEQ ID NO 21
<211> LENGTH: 927
<212> TYPE: DNA
<213> ORGANISM: Larrea tridentate

<400> SEQUENCE: 21

```
atggcgcaga agagcaagat tttgatcatt ggaggcactg gctacattgg caaatccatt     60

gtcgaagcaa gcgccaaggc cggccatcct acctttgcat tggttagaga aagcaccgtc    120

tttcatcacg ttaagggaaa acttgttaag aatttcaagg atttaggcgt caatcttgtc    180

catggggaca ttaatgatca tgagagcttg ctaaaggcaa ttaagcaagt ggatgtggtg    240

ttttctacgc ttggtcacca tcatataggt gaccaacaca aagttattgc tgctatcaaa    300

gaggctggta atgtcaagcg atattttcct tccgaattcg gcaatgatgt ggatcgatcc    360

catgctgtgg atcccgtaaa atctgcatac agaacgaagg ctcaaatccg cagggctatc    420

gaggctgaag ggatccccca cacttatgtt tcatgcaatt tctttgctgg ttatttcctc    480

cctacattgg tacagttaga agtcaccgct cctcctagag acaaagtcac cattttaggg    540

gatggaaata aaaaagcaat attcaataag gaagatgata tcgcgactta tgcaatcaga    600

gctgttgatg atccacgaac actgaacaaa atcttgtaca ttagaacacc taaaaatacc    660

tacacgatga atgagcttgt cgccctgtgg gagaagaaaa ttggcaaatc gcttgagaag    720

atttatgttc cggaggacca aattctaaag aacattcaag agtctccgtt ttcgacacaa    780

gttatgttgt caatcaatca ttccgtcttt gtaaagggtg atcaaaccaa cttcgacatt    840

gatctgtctt tcggtgtgga ggctaccgag ctttatcctg atgtcaacta taccaccgtt    900

gaagagtatc ttgatcaatt cgtttaa                                        927
```

<210> SEQ ID NO 22

-continued

```
<211> LENGTH: 308
<212> TYPE: PRT
<213> ORGANISM: Larrea tridentate

<400> SEQUENCE: 22

Met Ala Gln Lys Ser Lys Ile Leu Ile Ile Gly Gly Thr Gly Tyr Ile
 1               5                  10                  15

Gly Lys Ser Ile Val Glu Ala Ser Ala Lys Ala Gly His Pro Thr Phe
            20                  25                  30

Ala Leu Val Arg Glu Ser Thr Val Phe His His Val Lys Gly Lys Leu
        35                  40                  45

Val Lys Asn Phe Lys Asp Leu Gly Val Asn Leu Val His Gly Asp Ile
    50                  55                  60

Asn Asp His Glu Ser Leu Leu Lys Ala Ile Lys Gln Val Asp Val Val
65                  70                  75                  80

Phe Ser Thr Leu Gly His His His Ile Gly Asp Gln His Lys Val Ile
                85                  90                  95

Ala Ala Ile Lys Glu Ala Gly Asn Val Lys Arg Tyr Phe Pro Ser Glu
            100                 105                 110

Phe Gly Asn Asp Val Asp Arg Ser His Ala Val Asp Pro Val Lys Ser
        115                 120                 125

Ala Tyr Arg Thr Lys Ala Gln Ile Arg Arg Ala Ile Glu Ala Glu Gly
    130                 135                 140

Ile Pro His Thr Tyr Val Ser Cys Asn Phe Phe Ala Gly Tyr Phe Leu
145                 150                 155                 160

Pro Thr Leu Val Gln Leu Glu Val Thr Ala Pro Pro Arg Asp Lys Val
                165                 170                 175

Thr Ile Leu Gly Asp Gly Asn Lys Lys Ala Ile Phe Asn Lys Glu Asp
            180                 185                 190

Asp Ile Ala Thr Tyr Ala Ile Arg Ala Val Asp Asp Pro Arg Thr Leu
        195                 200                 205

Asn Lys Ile Leu Tyr Ile Arg Thr Pro Lys Asn Thr Tyr Thr Met Asn
    210                 215                 220

Glu Leu Val Ala Leu Trp Glu Lys Lys Ile Gly Lys Ser Leu Glu Lys
225                 230                 235                 240

Ile Tyr Val Pro Glu Asp Gln Ile Leu Lys Asn Ile Gln Glu Ser Pro
                245                 250                 255

Phe Ser Thr Gln Val Met Leu Ser Ile Asn His Ser Val Phe Val Lys
            260                 265                 270

Gly Asp Gln Thr Asn Phe Asp Ile Asp Leu Ser Phe Gly Val Glu Ala
        275                 280                 285

Thr Glu Leu Tyr Pro Asp Val Asn Tyr Thr Thr Val Glu Glu Tyr Leu
    290                 295                 300

Asp Gln Phe Val
305
```

GENES ENCODING CHAVICOL/EUGENOL SYNTHASE FROM THE CREOSOTE BUSH *LARREA TRIDENTATA*

CROSS-REFERENCE TO RELATED APPLICATIONS

This application is the United States national phase of International Patent Application No. PCT/US2007/069911, filed May 29, 2007, which claims the benefit of priority to U.S. Provisional Patent Application Ser. No. 60/819,120, filed Jul 7, 2006, which is incorporated herein by reference in its entirety.

STATEMENT REGARDING FEDERAL SUPPORT

Particular aspects of this invention were supported by National Science Foundation Grants MCB 04-1729 and Department of Energy Grant DE-FG-0397ER20259, National Institute of General Medical Sciences grant 5-R01-GM-066173-02, NSF grant MCB-0417291, and the United States Government has certain rights.

FIELD OF THE INVENTION

Particular aspects relate generally to the discovery of a novel metabolic process for converting monolignols into allyl/propenyl phenols, and more particularly relate to chavicol/eugenol formation or production and to the discovery of a novel chavicol/eugenol synthase that converts p-coumaryl/coniferyl alcohol esters into chavicol/eugenol, and further relates to novel compositions and methods e.g., novel proteins and nucleic acids encoding same, and novel methods for using same for producing or forming chavicol/eugenol in cell culture and/or genetically modified plants, and for re-engineering the composition of plant biomass.

BACKGROUND

Humanity currently faces enormous political and scientific challenges in identifying and securing stable future sources of renewable energy in an environmentally acceptable and sustainable manner (e.g., leading to so-called biofuels/bioenergy). Similar concerns and considerations also apply to the continued future supply of other key petrochemical intermediates, such as monomers needed for sufficient levels of industrial polymer production (e.g., polystyrenes, polyethylenes, etc.) as well as for stable sources of key specialty chemicals (e.g., flavor and fragrance chemicals, which at present are produced in regions of varying political stability, and which can also be subject to seasonal (climatic) variations; such factors often result in unpredictable market prices for these commodities). This is not a new scientific problem, but rather reflects one that has been difficult to solve over a period spanning more than three decades, until now again brought to the forefront by the most recent biofuels/bioenergy crisis. Today, about 12% of all the petroleum resources are used for non-fuel/non-energy purposes, this including polymer and other specialty chemical applications.

The so-called 'lignin problem' or challenge. To date, the difficulties in plant biomass utilization have centered on the recalcitrance of the various lignocellulosic matrices present in (woody) plants; namely, the so-called 'lignin problem' or challenge. Lignins are monolignol-derived polymeric end-products of the phenylpropanoid pathway (originating from the amino acids phenylalanine and tyrosine). From a structural perspective, the lignins, Nature's second most abundant organic substances after cellulose, are amorphous plant cell wall polymers that make up ca 20-30% of all plant stem biomass.[10,11] More specifically, vascular plant species have differing lignin contents, with values ranging from ~30% in conifers (softwoods) to lower amounts (~20-25%) in hardwoods (such as poplar) and herbaceous plant species, to even smaller levels in various primitive plant species. The physiological roles of lignins are to engender structural support to the vascular apparatus, thereby enabling such organisms to stand upright, as well as providing conduits for water and nutrient transport, and to provide physical barriers against opportunistic pathogens. Particular actual (i.e., minimal) lignin contents and/or compositions may be needed for a particular plant to avoid any deleterious effects for growth/development/stem structural integrity, etc. In general, lignins represent a formidable technical challenge, particularly due to their intractable nature, for improved plant biomass utilization, e.g., when considering the use of woody biomass for bioethanol production, as well as for wood, pulp and paper manufacture.

More specifically, there are two major scientific hurdles that have not been technically overcome for the facile utilization of this and other plant renewable resources, both of which involve the polymeric lignins.

The first results from their intractable nature, since lignin removal has long been a limitation in the processing of wood for both pulp/paper manufacture and for forage digestibility by ruminants. This is largely due to the lack of isolated enzymes and/or proteins that can efficiently degrade lignin macromolecules, in contrast to reports in the nineteen-eighties that indicated this problem had been solved.[3-6] That is, nearly twenty years ago, it was reported that several productive routes for lignin removal from wood had both been discovered and attained via utilization of lignin-degrading enzymes in fungi/bacteria, and where three candidates ultimately emerged (lignin peroxidase, manganese peroxidase and laccase). However, this "lignin peroxidase" or "ligninase"[6] was only assayed initially with an aqueous acetone extract of spruce wood,[3] which does not actually extract the lignins from wood. Twenty years later, none of these enzymes are (routinely) utilized in biotechnological applications for lignin removal/separation, and their roles in enzymatic lignin biodegradation are still in question, as we had noted earlier.[7] Today, more than 50 million tons of lignin-derived substances are generated annually as by-products of pulp/paper manufacture within the USA alone.[8] Other possibilities now being considered are the putative true lignin depolymerases that target specific inter-unit linkages in lignin macromolecules.[9]

The second technological hurdle is that lignins cannot readily be converted into either ethanol and/or other liquid/gaseous fuels using currently available fermentation processes. Indeed, the polymeric lignins themselves are a formidable physical barrier to an efficient fermentation of carbohydrate biomass for ethanol generation, and thus their presence represents a critical problem in making these technologies more economical.

There is therefore, an urgent need in the art for highly creative and sound technological solutions for renewable (plant) resource utilization.

There is therefore, a pronounced need in the art for an approach whereby the carbon allocated towards lignification is redirected, to provide for inherently more useful and/or more easily tractable materials, and to facilitate the generation of, for example, biofuels from the remaining plant biomass.

SUMMARY OF ASPECTS OF THE INVENTION

Aspects of the present invention provide highly creative and sound technological solutions for renewable (plant)

resource utilization. Particular aspects provide a novel approach whereby the carbon allocated towards lignification is redirected, to provide for inherently more useful and/or more easily tractable materials, and to facilitate the generation of, for example, biofuels from the remaining plant biomass. Particular aspects provide a novel methods for generation in planta of liquid/combustible allyl/propenyl phenols, such as eugenol and chavicol. In additional aspects, these phenolic products are utilized for (non-ethanol) biofuel/bioenergy purposes, while the remaining plant biomass facilitates the generation of, for example, other biofuels.

Particular aspects of the present invention relate generally to the discovery of a novel metabolic process for converting monolignols into allyl/propenyl phenols, and more particularly relate to chavicol/eugenol formation or production in cell culture and/or genetically modified plants.

Certain aspects provide novel chavicol/eugenol synthase proteins that convert monolignols such as p-coumaryl/coniferyl alcohol esters into allyl/propenyl phenols such as chavicol/eugenol.

Additional aspects provide novel nucleic acids (e.g., genes, cDNAs, RNA) encoding the novel chavicol/eugenol synthase proteins.

Yet additional aspects provide genetically modified cultured cells (e.g., plant cells) and plants comprising one or more nucleic acids (e.g., genes, cDNAs, RNA) encoding the novel chavicol/eugenol synthase proteins.

Further aspects provide novel methods using the chavicol/eugenol synthase proteins and/or the encoding nucleic acids and for producing or forming chavicol/eugenol, or increasing the amount thereof, in cell culture and/or in genetically modified plants.

Yet further aspects provide novel methods using the chavicol/eugenol synthase proteins and/or the encoding nucleic acids for re-engineering the biomass composition of genetically engineered cells and plants.

Additional aspects provide novel methods using the chavicol/eugenol synthase proteins and/or the encoding nucleic acids for improved plant biomass utilization (e.g., in view of biomass utilization for bioethanol production, as well as for wood, pulp, and paper manufacture, etc.) by re-engineering the biomass composition of genetically engineered cells and plants.

Additional aspects provide novel methods using the chavicol/eugenol synthase proteins and/or the encoding nucleic acids for re-engineering the amount and/or composition of lignins of genetically engineered cells and plants. In preferred embodiments, the amount of lignins is reduced relative to wild type (WT; normal cell or plant counterparts).

Further aspects provide novel methods using the chavicol/eugenol synthase proteins and/or the encoding nucleic acids for altering/re-engineering the dynamic modulus of genetically engineered cells and/or plants relative to WT by re-engineering the amount and/or composition of lignins of the cells and/or plants. In preferred embodiments, the dynamic modulus is reduced with reduction in the amount of lignins in the cells and/or plants.

Yet further aspects provide novel methods using the chavicol/eugenol synthase proteins and/or the encoding nucleic acids for altering/re-engineering the formation of 'reaction tissue' of genetically engineered cells and/or plants relative to WT by re-engineering the amount and/or composition of lignins of the cells and/or plants. In preferred embodiments, the amount and/or composition of reaction tissue is increased and/or altered with reduction in the amount of lignins in the cells and/or plants.

Additional aspects provide novel methods using the chavicol/eugenol synthase proteins and/or the encoding nucleic acids for altering/re-engineering the antimicrobial/analgesic/plant defense properties of genetically engineered cells and/or plants relative to WT by re-engineering the amount and/or composition of lignins of the cells and/or plants. In preferred embodiments, the amount and/or composition of antimicrobial/analgesic/plant defense properties is increased and/or altered with reduction in the amount of lignins in the cells and/or plants.

Yet additional aspects provide novel methods using the chavicol/eugenol synthase proteins and/or the encoding nucleic acids for altering/re-engineering the flavor/fragrance properties of genetically engineered cells and/or plants relative to WT by re-engineering the amount and/or composition of lignins of the cells and/or plants. In preferred embodiments, the amount and/or composition of flavor/fragrance properties is increased, and/or altered, or decreased with reduction in the amount of lignins in the cells and/or plants.

Yet additional aspects provide novel methods of using the genetically engineered cells and/or plants comprising the inventive chavicol/eugenol synthase proteins and/or the inventive encoding nucleic acids for production of chavicol/eugenol for use in making antibacterials/plant defense/analgesics, polymer building blocks and in biofuel/bioenergy production.

Accordingly, novel compositions, methods and sources of chavicol and/or eugenol are provided, and the compositions and compounds so produced have novel properties. Particular aspects provide novel and facile methods for redirecting carbon flow in plants from, e.g., lignin synthesis, to the synthesis of liquid, highly combustible, monomers for potential application as either flavoring agents, biofuels/bioenergy and/or building blocks for polymer applications (e.g., based on styrene chemistry).

BRIEF DESCRIPTION OF THE DRAWINGS

FIG. 1 shows, according to exemplary aspects of the present invention, the current view of the phenylpropanoid pathway (the biosynthetic pathway of monolignols). 4CL, hydroxycinnamoyl CoA ligases; C3H, p-coumarate 3-hydroxylase; C4H, cinnamate 4-hydroxylase; CAD, cinnamyl alcohol dehydrogenases; CCOMT, hydroxycinnamoyl CoA O-methyltransferases; CCR, cinnamoyl-CoA oxidoreductases; COMT, caffeic acid O-methyltransferase; F5H, ferulate 5-hydroxylase; HCT/HQT, hydroxycinnamoyl shikimate/quinate transferase; PAL, phenylalanine ammonia lyase; TAL, tyrosine ammonia lyase. The phenylpropanoid pathway entry point is generally considered to be the amino acid phenylalanine (1, Phe), through action of phenylalanine ammonia lyase (PAL, EC 4.3.1.5) forming trans-cinnamic acid (3), but PAL does not appear to serve as a major carbon allocation regulator.

FIG. 2 shows, according to exemplary aspects of the present invention, known phenylpropanoid pathway monomeric metabolites (selected allylphenols and propenylphenols), namely the liquid allyl/propenyl phenols, chavicol (31), eugenol (33), and their analogues (32, 34-39).

FIG. 3 shows, according to exemplary aspects of the present invention, the lignan nor-dihydroguaiaretic acid (40, NDGA) and its synthetic derivative (41) as well as podophyllotoxin (47) and its precursors (43, 44).

FIGS. 4A, B and C show, according to exemplary aspects of the present invention, hypothetical biosynthetic pathways from p-coumaryl alcohol (19) to chavicol (31) and methylchavicol (32), of which pathway B was demonstrated to occur. Shown are three potential mechanisms for the conversion of 19 into 32 included either reduction of the monolignol side-chain (i.e., saturation) followed by dehydration (FIG. 4A), methylation of the phenolic moiety preceding further side-chain modification (FIG. 4C), and/or activation of the terminal (C-9) oxygenated functionality prior to side-chain double bond reduction (FIG. 4B).

FIG. 5 shows, according to exemplary aspects of the present invention, the biosynthetic pathway to chavicol (31) and eugenol (33) from the corresponding monolignols, p-coumaryl (19) and coniferyl (21) alcohols. CS—chavicol synthase; ES—eugenol synthase. The figure shows a novel metabolic process converting monolignols (such asp-coumaryl (19) and coniferyl (21) alcohols) into allyl/propenyl phenols (chavicol (31) and eugenol (33), respectively), with two enzymes being implicated in their formation in planta.

FIG. 7 shows, according to exemplary aspects of the present invention, amino acid alignment of basil (*Ocimum basilicum*) chavicol/eugenol synthase (ObEGS1), *Petunia hybrida* isoeugenol synthase (PhIGS1), and PIP reductases from *Medicago sativa* (MsIFR), *Thuja plicata* (TpPLR), *Pinus taeda* (PtPCBER), *Forsythia intermedia* (FiPLR) and *Larrea tridentata* (LtCES1). The Figure shows a novel pinoresinol-lariciresinol reductase homologue from the creosote bush (*Larrea tridentata*) catalyzing the efficient in vitro conversion of p-coumaryl/coniferyl alcohol esters (48-51) into chavicol/eugenol (31/33), but not p-anol/isoeugenol (37/39). Various novel PLR/CS/ES homologue from *L. tridentata* (e.g., LtCES1) (SEQ ID NOS:1 and 2) were isolated and based on sequence homology, and characterized as described herein.

FIGS. 11A and B show, according to exemplary aspects of the present invention, polymerization of A. isoeugenol (39) via furanocoumaran intermediacy, and B. methylchavicol (32) and eugenol (33) through rearrangement prior to polymerization, and shows that for isoeugenol, the phenolic oxygen moiety also participates in the polymerization reactions, thereby increasing the structural complexity of the resulting polymer(s) so formed (FIG. 11A). Additionally, allylphenols such as methylchavicol (32) and eugenol (33) can form mixed polymers, resulting from the partial rearrangement of the side-chain double bond upon carbocation formation prior to attachment to the polymer chain (FIG. 11*b*).

FIG. 12 shows cyclohexane derivatives (58-61) formed upon catalytic hydrogenation of the corresponding allyl/propenyl phenols.

FIG. 14 shows naturally occurring 9,9'-deoxygenated lignans licarin A (64), (−)-grandisin (65), gomisin A (66), the semisynthetic tetra-O-methylated NDGA derivative M4N (41), allyl/propenyl phenols p-anol (37), isoeugenol (39), 5-methoxyisoeugenol (68), anethole (38), chavicol (31), eugenol (33), 5-methoxyeugenol (67) and methylchavicol (32), as well as the phenylpropanoid metabolites p-coumaryl alcohol (19), coniferyl alcohol (21) and p-coumaric acid (4).

FIG. 15 shows proposed mechanisms for enzymatic catalyses performed by (A) allyl/propenyl phenol synthases such as (a) LtCES1, ObEGS1 and (b) PhIGS1; (B) PLR and (C) PCBER. (D) Medioresinol (69) and syringaresinol (70), additional PLR substrates, as well as sesamin (71), which does not undergo PLR-catalyzed reduction (Kim et al. Manuscript in preparation); nectandrin B (72), genistein (73) and biochanin A (74), which do not serve as substrates for LtPLRh1 (LtCES1)-catalyzed reduction.

FIGS. 17A and B show, according to exemplary aspects of the present invention, (A) p-C3H biochemical reaction. (B) Lignin monomers and aromatic nuclei (H, G, S) depictions.

FIG. 25 shows, according to exemplary aspects of the present invention, phenylpropanoid pathway intermediates. p-hydroxycinnamyl alcohols 19-23 (monolignols), p-hydroxycinnamaldehydes 14, 16, p-hydroxycinnamic acids 4-8, the putative 2-methoxybenzaldehyde "lignin" substructure (76), and the acetosyringone 77 and feruloyl tyramine (78) "lignin" substructures, as well as aromatic ring (H, G, S) units.

FIGS. 26*a-e* show, according to exemplary aspects of the present invention, *Arabidopsis thaliana* wild type (ecotype Wassilewskija) and CAD double mutant visible phenotypes, growth/development parameters, and tensile modulus data. a) Phenotypical differences between WT and double mutant plants at 4 wks growth/development, b) stem lengths, c) basal stem diameters at different growth/developmental stages, and d) DMA strain scans of 6 and 7 week old plants; analyses were performed in triplicate at room temperature and at a frequency of 0.5 Hz, and e) comparison of tensile storage and loss moduli of 6 and 7 week old plants. E'=storage and E"=loss moduli.

FIG. 32 shows, according to exemplary aspects of the present invention, lignan 79 isolated from *Salvia miltiorrhiza* and synthetic lignan 80.

DETAILED DESCRIPTION OF EXEMPLARY ASPECTS

Figure 6A:
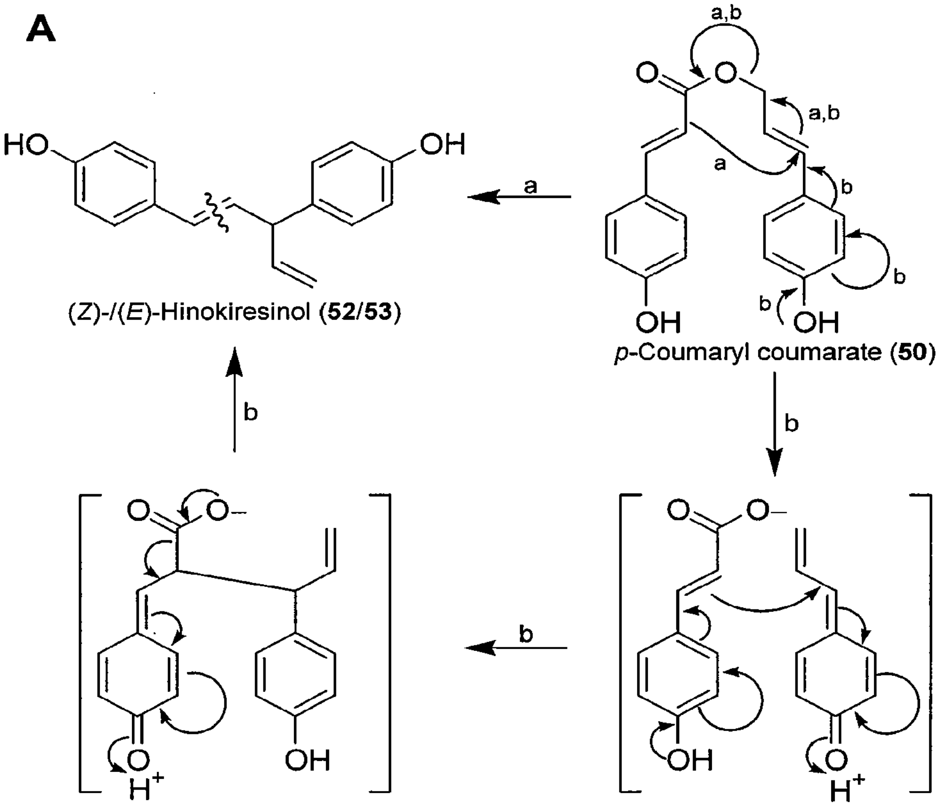
FIGS. 6A and B show, according to exemplary aspects of the present invention, potential mechanisms whereby the departing carboxylate (as $C0_2$) facilitates formation of the final C8-C7' bond, without any additional cofactors, can be envisaged (FIG. 6A). It is also possible to propose potential mechanisms where p-coumaryl coumarate (50) (or other p-coumaryl alcohol esters, e.g., p-coumaryl acetate (48)) generates, through the addition of an incoming hydride, chavicol (31) and/or its regioisomer p-anol (37) (FIG. 6B). The figure shows possible mechanisms for conversion of p-coumaryl alcohol esters (48, 50) into (A) hinokiresinol (52/53), (B) chavicol (31) and p-anol (37). A. (a) Concerted, or (b) through intermediacy of a quinone methide; B. (c) and (d) formation of a quinone methide intermediate through displacement of the (interchangeable) ester leaving group, with subsequent reduction by hydride [from NAD(P)H] and re-aromatization to form either (c) chavicol (31) and/or (d) p-anol (37). The reactions in (B) may also proceed through direct displacement, without intermediacy of the quinone methide, by an incoming hydride at carbons 7 or 9 to form chavicol (31) or p-anol (37), respectively (not shown) (Modified from Vassão et al.)

Particular aspects of the present invention relate to new developments in the enzymology and molecular biology of plant phenylpropanoids, and therefore offer numerous opportunities to re-engineer the composition and/or properties of plant biomass. According to particular aspects, two main targets of such modifications are: the optimized production of valuable compounds; and reductions in the levels of less desirable products (e.g., the structural biopolymeric lignins). In particular aspects, for example, the amounts of lignin biopolymers in (woody) species are reduced, with carbon flow concurrently redirected towards production of related non-polymeric phenylpropanoids, such as the more valuable allyl/propenyl phenols (e.g., eugenol, chavicol).

As described above, lignins are monolignol-derived polymeric end-products of the phenylpropanoid pathway (originating from the amino acids phenylalanine (1) and tyrosine (2)), and represent a formidable technical challenge, particularly due to their intractable nature, for improved plant biomass utilization, e.g., when considering the use of woody biomass for bioethanol production, as well as for wood, pulp and paper manufacture. Other species-specific outcomes of the phenylpropanoid pathway, however, include metabolites such as lignans, flavonoids and allyl/propenyl phenols.

According to preferred aspects of the present invention, applicants' discovery of the biochemical pathway resulting in the production of the more valuable liquid allyl/propenyl phenols (e.g., eugenol (33), chavicol (31), methylchavicol (32), and anethole (38)), which are, for example, important components of plant spice aromas and flavors, provide a substantially useful approach and method to re-engineer cell and plant metabolism in new directions. According to particular aspects, these compounds are synthesized from monolignols in two consecutive enzymatic reactions, (i) acylation of the terminal (C-9) oxygen of the monolignol forming an ester, and (ii) regiospecific, NAD(P)H-dependent reduction of the phenylpropanoid side chain with displacement of the carboxylate ester as leaving group. According to additional aspects, the proteins involved in the latter step are homologous to well-characterized phenylpropanoid reductases (pinoresinol-lariciresinol, isoflavone, phenylcoumaran-benzylic ether and leucoanthocyanidin reductases), with similar catalytic mechanisms being operative. In preferred aspects, the proteins (and corresponding genes) involved in these transformations have been isolated and characterized, and provide methods of re-engineering plants to redirect (e.g., partially redirect) carbon flow from lignin (or lignans) into these liquid volatile compounds in oilseeds, leafy or heartwood-forming tissues, or woody stems.

In further aspects, the proteins (and/or corresponding genes) involved in these transformations provide methods of re-engineering plants to facilitate wood processing in pulp/paper industries and offer sources of renewable plant-derived biofuels, intermediate chemicals in polymer industries, or specialty chemicals in perfume and flavor industries.

Summary of Working Examples

Example 1 herein discloses novel chavicol/eugenol synthases that were isolated from *Larrea tridentata*. The creosote bush (*Larrea tridentata*) accumulates a complex mixture of 8-8' regiospecifically linked lignans, of which the potent antioxidant nordihydroguaiaretic acid (NDGA, 40) is the most abundant. Its tetra-O-methyl derivative (M4N, 41) is showing considerable promise in the treatment of the refractory (hard-to-treat) cancers of the head and neck. NDGA (40) and related 9,9'-deoxygenated lignans are thought to be formed by dimerization of allyl/propenyl phenols, phenylpropanoid compounds that lack C-9 oxygenation, thus differentiating them from the more common monolignol-derived lignans. In applicants' ongoing studies dedicated towards elucidating the biochemical pathway to NDGA (40) and its congeners, six pinoresinol-lariciresinol reductase homologues ("PLRh") (nucleic acid SEQ ID NOS:1, 3, 5, 17, 19 and 21 and polypeptide SEQ ID NOS:2, 4, 6, 18, 20 and 22, respectively) were isolated from *L. tridentata*, with protein obtained in recombinant form. According to aspects of the present invention all three of these enzymes catalyze the conversion of p-coumaryl (48/50) and coniferyl alcohol (49) esters into the corresponding allylphenols, chavicol (31) and eugenol (33). Of these three PLRh_Lt proteins, one of these homolouges (PLRh_Lt1) (nucleic acid SEQ ID NO:1; polypeptide SEQ ID NO:2) was analyzed in greatest detail, and this protein efficiently catalyzes the conversion of p-coumaryl (48/50) and coniferyl (49) alcohol esters into the corresponding allylphenols, chavicol (31) and eugenol (b), and neither of their propenylphenol regioisomers, p-anol (37) and isoeugenol (39), are formed during this enzyme reaction.

Example 2 herein discloses data relating to reaction tissue formation in alfalfa, *Medicago sativa* L. (Fabaceae), wild type and p-coumarate-3-hydroxylase down-regulated lines and their stem tensile modulus properties. The discovery of reaction tissue in the forage crop alfalfa (*Medicago sativa* L.) is described, which to applicants' knowledge, has not hitherto been established as occurring in herbaceous perennials. It was first observed during an investigation of a transgenic alfalfa line reduced in overall lignin content, but was also formed in the wild type line as well. The transgenic alfalfa line, obtained through standard down-regulation of the gene encoding p-coumarate-3-hydroxylase (pC3H), was reduced in lignin content by circa 64%, as expected from our previous metabolic flux analyses (Anterola et al., 2002). Comparison of the pC3H down-regulated (pC3H-I) and WT lines established several differences, however, when employing microscopy analyses and biomechanical testing of various (internodal) alfalfa branch sections. Relative to WT, the pC3H-I line: (a) apparently more rapidly formed reaction tissue containing gelatinous fibers with adjacent thick-walled fibers (presumed to be 'intermediate' tissue) during development and in greater amount; (b) had an increased volume of xylem tissue, and (c) had comparable tensile dynamic modulus properties. These findings thus establish the (limited) ability of this perennial angiosperm to form (inducible) reaction tissue, in a manner somewhat analogous to that of woody arborescent angiosperms. Finally, with the recent rapidly growing interest in lignocellulosic materials for biofuels (e.g., bioethanol), the potential of effectuating reductions in lignin amounts in (woody) angiosperms with increased formation of reaction (tension wood) tissue is discussed. This is because the latter tissues are often viewed as a deleterious trait for many agronomic/forestry applications, e.g. due to the difficulties experienced in their subsequent processing for many industrial/commercial applications.

Thus, in Example 2, applicants disclose that formation of reaction (tension) tissue occurs in wild type (WT) alfalfa (designated WT C-1) and whose amounts have also apparently increased in the pC3H down-regulated line (e.g. pC3H-I), as did the overall xylem volume. Yet, in spite of the greatly reduced lignin content (~64%), there were apparently no significant differences between both lines in terms of material strength properties (i.e. as shown by tensile dynamic modulus testing) of young developing alfalfa branches. It is thus proposed that formation of reaction tissue may be increased in alfalfa and other angiosperms when the overall vasculature is weakened through reducing lignin content(s). This can then serve as a compensatory mechanism in order to attempt to maintain needed biophysical/biomechanical properties of the overall vasculature, which would otherwise be weakened.

Example 3 herein discloses particular exemplary applications of Applicants inventive compositions and methods to provide chavicol/eugenol for biofuels/intermediate chemicals). The Example relates to advances made by Applicants and which result in formation of two well-known molecules: chavicol (31) and eugenol (33). Both substances have historically been used as flavor/fragrance components from Tanzania, Madagascar and Indonesia; however, the biochemical/biotechnological manipulations disclosed herein provide for the diversion of monolignols from lignin/lignan formation in plant species to instead diverting these compounds for use, for example, in biodiesel or polymer production (plastic replacement), i.e., in addition to their current roles in human nutrition and medicine. The present inventive methods could be applied, for example, either in oilseed-bearing plants (e.g., canola) or in heartwood-forming tissues of trees (e.g., western red cedar) used for lumber and pulp/paper products. In the latter, heartwood formation is generally accompanied by a massive deposition of non-structural low molecular weight molecules, such as the lignan, plicatic acid, which, in western red cedar can be ~20% of the overall dry weight of the stem. These processes (oilseed and heartwood formation/deposition of metabolites), as well as judicial modification of lignin content and composition, thus offer the potential to rationally optimize plant feedstocks for biofuel/bioenergy either directly in specific crops or indirectly as part of wood processing for pulp/paper, specialty chemicals, etc.

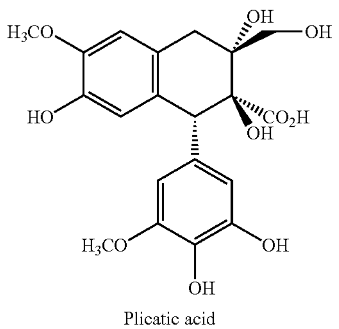

Plicatic acid

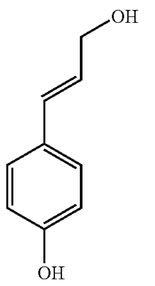

p-Coumaryl alcohol

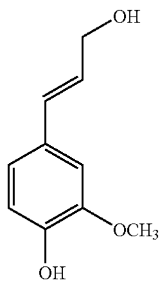

Coniferyl alcohol

-continued

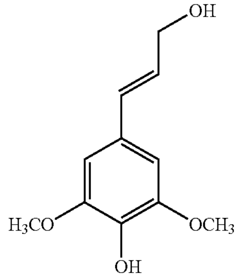

Sinapyl alcohol

Presently, a new pathway utilizing monolignols has been discovered, which applicants consider has extraordinarily promising potential for either biofuels, intermediate chemicals or as an improved and stable source of the spice (chavicol (31) and eugenol (33)) components. For example, eugenol (33) is widely used in medical and dental applications due to its biocidal and analgesic properties. In the pathway to these two allylphenols, the monolignol precursors are first biochemically activated (via ester formation) and then subsequently converted into the highly combustible liquid fuels, the aromatic hydrocarbons, chavicol and eugenol (FIG. 5). Importantly, the protein involved, chavicol/eugenol synthase (CS/ES), is a homologue of Applicants' PLR/PCBER proteins, whose encoding cDNA hybridizes under the same conditions as for PLR. According to particular aspects of the present invention, this discovery provides novel methods for diverting monolignol flow away from lignin biopolymer formation, or from heartwood lignan accumulation/deposition, to that engendering formation of the potential product liquid fuels/intermediate chemicals of interest. In additional aspects, this strategy enhances oilseed production as well, both in relative amounts of bioproduct/biofuels and their calorific value. In further aspects, these products (chavicol/eugenol) would be removed, leaving the remaining (lignin-reduced) biomass able to be more efficiently fermented for ethanol production.

Preferably, two genes encoding respective proteins are used to provide proteins that can: (i) acylate monolignol precursors to afford the corresponding acylated derivatives (e.g., the acylating transferase family from *Taxus brevifolia;* Chau, et al., *Arch Biochem Biophys* 430:237-246, 2004.), and (ii) convert the latter into liquid biofuel/intermediate chemicals (e.g., using the presently disclosed CS/ES). Alternatively, the monolignols can be chemically acylated, followed by conversion by CS/ES.

Example 4 herein discloses that plant cell walls are enfeebled when attempting to preserve native lignin configuration with poly-p-hydroxycinnamaldehydes: evolutionary implications. This Example relates to the effects of disruption of lignin macromolecular configuration and stem vascular integrity through CAD mutations. With such mutations, template polymerization was attempted but aborted at an early stage of cell-wall phenolic deposition when p-hydroxycinnamaldehydes were employed as substrates. More specifically, the lignin deficient double mutant of cinnamyl alcohol dehydrogenase (CAD, cad-4, cad-S or cad-c, cad-d) in *Arabidopsis thaliana* (Sibout et al., 2005), was comprehensively examined for effects on disruption of native lignin macromolecular configuration; the two genes encode the catalytically most active CAD's for monolignol/lignin formation (Kim et al., 2004 *Proc. Natl. Acad. Sci., USA.* 101:1455-1460). The inflorescence stems of the double mutant presented a prostrate phenotype with dynamic modulus properties greatly reduced relative to that of the wild type (WT) line due to severe reductions in macromolecular lignin content. Interestingly, initially the overall pattern of phenolic deposition in the mutant was apparently very similar to WT, indicative of comparable assembly processes attempting to be duplicated. However, shortly into the stage involving (monomer cleavable) 8-O-4' linkage formation, deposition was aborted. At this final stage, the double mutant had retained a very limited ability to biosynthesize monolignols as evidenced by cleavage and release of ca 4% of the monolignol-derived moieties relative to the lignin of the WT line. In addition, while small amounts of cleavable p-hydroxycinnamaldehyde-derived moieties were released, the overall frequency of (monomer cleavable) 8-O-4' inter-unit linkages closely approximated that of WT for the equivalent level of lignin deposition, in spite of the differences in monomer composition. Additionally, 8-5' linked inter-unit structures were clearly evident, albeit as fully aromatized phenylcoumaran-like substructures. The data are interpreted as a small amount of p-hydroxycinnamaldehydes being utilized in highly restricted attempts to preserve native lignin configuration, i.e. through very limited monomer degeneracy during template polymerization which would otherwise afford lignins proper in the cell wall from their precursor monolignols. The defects introduced (e.g. in the vascular integrity) provide important insight as to why p-hydroxycinnamaldehydes never evolved as lignin precursors in the 350,000 or so extant vascular plant species. Prior to investigating lignin primary structure proper, it is instructive to initially define the fundamental characteristics of the biopolymer(s) being formed, such as inter-unit frequency and lignin content, in order to design approaches to determine overall sequences of linkages.

Lignin Formation and Manipulation:

Outcomes of the phenylpropanoid ($C_6C_3$) pathway include not only the lignins in woody/non-woody vascular plants but also, to varying extents, lignans, flavonoids, coumarins, anthocyanins, as well as allyl and propenyl phenols in different species.

Biosynthesis of monolignols. The phenylpropanoid pathway (FIG. 1) entry point is generally considered to be the amino acid phenylalanine (1, Phe), through action of phenylalanine ammonia lyase (PAL, EC 4.3.1.5) forming trans-cinnamic acid (3). Although initially regarded as a rate-determining reaction in the pathway, PAL does not seem to serve as a major carbon allocation regulator, with flux apparently being determined by the availability of Phe (1) and by downstream enzymes in the pathway, especially C4H/C3H.

According to particular aspects of the present invention, there are compelling reasons to identify novel ways to more effectively either utilize the lignin biopolymers or to manipulate the amounts or forms of carbon allocated to the lignin-forming pathway, e.g. to produce more desirable bioproducts in commercially cultivated plant species. Indeed, a number of biotechnological manipulations of both lignin contents and compositions in various plant species have already been carried out (i.e., various transgenic/mutant lines have been successfully obtained using standard transformation procedures (see Anterola & Lewis, Trends in lignin modification: A comprehensive analysis of the effects of genetic manipulations/mutations on lignification and vascular integrity, *Phytochemistry,* 61:221-294, 2002, for examples and references therein). Generally, the effects of drastically reducing lignin contents in both woody and non-woody vascular plants result in a significant impairment/weakening of the vascular apparatus, e.g., collapsed vessels, etc. Such defects potentially lead to severe drawbacks in growing biotechnologically modified plant lines commercially, as this can lead to, for example, premature lodging, weakening of plant stems, dwarfing, etc., during growth/development. These examples underscore the importance of the extent to which lignin compositions/contents are manipulated, and illustrate the importance of particular novel methods disclosed herein, for providing partial reduction in lignin levels to avoid introducing structural defects prohibiting field applications of the resulting plant cultivars in, for example, bioethanol/biofuel/bioproduct generation. According to additional aspects, the inventive compositions and methods provide for partial reduction in lignin levels to avoid a weakened vascular apparatus that may result in plants more susceptible to opportunistic pathogens. Therefore, according to preferred aspects, a judicious balance is maintained in growing vascular plants for commercial purposes and in reducing/modifying lignin contents/compositions. According to particular aspects of the present invention using the inventive compositions and methods described herein, lignin contents are partially reduced to preclude or at least lessen the extent of drawbacks associated with drastically reducing lignin contents.

According to additional aspects, there are novel and alternative biotechnological opportunities to produce renewable energy biofuels and specialty bioproducts. That is, there are other metabolic outcomes of the phenylpropanoid pathway from its entry point phenylalanine (1) (depending upon the species) that can include, for example, differential formation of coumarins, lignans and flavonoids, as well as allyl/propenyl phenols (see FIG. 1). In particular, allylphenols and propenylphenols, which differ in the position of their side-chain double bonds, include the high-value liquids eugenol (33), methyl chavicol ((32), and anethole (38) (FIG. 2). These natural products account for much of the aroma present in specialty "essential oils" of various plant species, such as cloves, tarragon and anise, respectively, and are thought to be produced in planta mainly for defense against insects and parasites, as well as for attraction of pollinators. In addition, most of these compounds are liquid at room temperature, and their relatively low degree of oxygenation grants them with high heats of combustion. According to particular aspects, these are more desirable characteristics when considering their possible utilization as fuels. Notably, lignins and most lignans, as well as the allyl/propenyl phenols, are all derived from the same monolignol precursors; thus, as disclosed herein, an approach whereby the latter are differentially utilized could impact the production/accumulation of these diverse classes of compounds.

Therefore, according to particular aspects of the present invention, biotechnological manipulations of this pathway are not only be directed towards simply reducing lignin levels, but also to retarget carbon towards related metabolic pathways, e.g., through redirection of metabolic (carbon) flux to the production of related phenolic compounds in the main repositories for plant organic carbon storage. The latter could include either oilseed-bearing structures (e.g., flax (*Linum usitatissimum*) seed, or heartwood-forming tissues of trees, e.g., western red cedar (*Thuja plicata*)). It is these "repositories" that are largely used as plant renewable resources, whether as sources of (vegetable) oils or for lumber/pulp/paper products. In addition to the structural lignins, heartwood formation is often accompanied by massive deposition of non-structural low molecular weight molecules, such as the monolignol-derived lignan plicatic acid (30, see FIG. 1 for structure) and its congeners in western red cedar, whose amounts can be ~20% of the overall dry weight. In particular embodiments, rational optimization/modification of plant biomass is accomplished directly for either biofuel/bioenergy/bioproduct generation in specific crops, or indirectly as part of (heart)wood processing for pulp/paper, specialty chemicals, etc.

For example, recent studies (VASSÃO, et al., *Org. Biomol. Chem.,* 4:2733-2744, 2006; and KOEDUKA, et al., *Proc. Natl. Acad. Sci., USA,* 103:10128-10133, 2006.) have described the formation of some quite well-known phenylpropanoid pathway monomeric metabolites, namely the liquid allyl/propenyl phenols, chavicol (31), eugenol (33), and their analogues (32, 34-39) (FIG. 2). Historically, such allyl/propenyl phenols have commonly been used throughout the world mainly as flavor/fragrance components present in spices, especially cloves, with those being largely imported from Tanzania, Madagascar and Indonesia. Such material sources are imported simply because it is in those countries where the plant species accumulating these more unusual metabolites are cultivated. According to particular aspects, these biochemical/biotechnological processes provide a method of diversion of monolignols from either lignin and/or lignan formation in more commonly utilized woody/non-woody plant species of, for example, North America, to afford instead the liquid allyl/propenyl phenol monomers.

Biosynthesis of Allyl and Propenyl Phenols and Related Phenylpropanpoid Moieties:

According to particular aspects, besides lignin, specialized plant metabolism can utilize monolignols in the formation of lignans (phenylpropanoid dimers) as well as allyl- and propenyl-phenols. Allylphenols differ from propenylphenols in their side-chain double bond position, with the former having terminal (C-8-C-9) desaturation and the latter having the chemically more stable internal (C-7-C-8) double bond. Several biochemical hypotheses had been created in the art to explain their distinctive lack of a C-9 oxygenated functionality but experimental support for any was lacking.

The present applicants' interest in the allyl/propenyl phenols first began with studies directed to elucidating the biochemical pathway(s) to the lignan nor-dihydroguaiaretic acid (40, NDGA, FIG. 3) and its congeners, these being abundant metabolites in the creosote bush (*Larrea tridentata*). These lignans, however, lack oxygenated carbon 9,9' functionalities that are present in most lignan classes (e.g., podophyllotoxin (41), secoisolariciresinol (42)) (FIG. 3), as well as in the polymeric lignins and monomeric phenylpropanoids (e.g., monolignols 19-23) in the vast majority of plant species. Based on previous radiolabeling/stable isotope labeling studies, it was presumed that the unusual "loss" of the oxygenated functionality occurred at the monomer stage, i.e., allyl and/or propenyl phenols could be serving as the precursors/substrates for dimerization to form these less common lignans. In this regard, the biosynthetic pathways to the allyl/propenyl phenols had not been elucidated in any organism and, in particular, the precise precursor (substrate) undergoing deoxygenation represented both a long-standing question and a biochemical mystery (Anonica, et al., *J. Chem. Soc., Chem. Commun.,* 1108-1109, 1971; Klischies, et al., *J. Chem. Soc., Chem. Commun.,* 479-880, 1975; Manitto, et al., *J. Chem. Soc., Perkin Trans.* 1, 1974, 1727-1731; Manitto et al., *Tetrahedron Lett.,* 15:1567-1568, 1974; and Senanayake, et al., *Cinnamomum zeylanicum, Phytochemistry,* 16:2032-2033, 1977).

Basil (*Ocimum basilicum*, Thai variety) was selected by the present Applicants as a suitable study system since it accumulates the simplest allylphenol, methylchavicol (32); based on various radiolabeling studies, it was shown that the latter was derived from the corresponding monolignol, p-coumaryl alcohol (19) (VASSÃO, et al., *Org Biomol. Chem.,* 4:2733-2744, 2006). Three potential mechanisms for the conversion of 19 into 32 included either reduction of the monolignol side-chain (i.e., saturation) followed by dehydration (FIG. 4A), methylation of the phenolic moiety preceding further side-chain modification (FIG. 4C), and/or activation of the terminal (C-9) oxygenated functionality prior to side-chain double bond reduction (FIG. 4B). Pathways A and C (FIG. 4) were eliminated since no experimental evidence in support of either route was obtained.

Interestingly, however, a double-bond reductase was discovered and characterized, which utilized p-coumaryl aldehyde (14) as the preferred substrate to afford the corresponding side-chain reduced aldehyde (45, FIG. 4) (Kasahara, et al., U.S. Pat. No. 6,703,229. Filed Mar. 27, 2001. Issued Mar. 9, 2004; Kasahara, et al., *Phytochemistry,* 2006, 67, 1765-1780; Youn, et al., *J. Biol. Chem.,* 281:40076-40088, 2006). This alkenal reductase activity was the first to be reported in the phenylpropanoid pathway, with the corresponding enzymes isolated from *A. thaliana* (AtDBR) and *Pinus taeda* (PtPPDBR) also being homologous to a terpenoid double bond reductase (pulegone reductase, PulR) from *Mentha piperita* and mammalian alkenal reductases as well. AtDBR and PtPPDBR catalyze the NADPH-dependent reduction of p-coumaryl (14) and coniferyl (16) aldehydes to the corresponding dihydroaldehydes, and AtDBR has also been shown to catalyze the reduction of 4-hydroxynonenal (4-HNE), a pro-apoptotic lipid peroxidation product, to 4-hydroxynonanal (Kasahara, et al., *Phytochemistry,* 2006, 67, 1765-1780; Youn, et al., *J. Biol. Chem.,* 281:40076-40088, 2006). Based on substrate versatility studies and a X-ray crystal structure for AtDBR, a concerted mechanism involving an enol intermediate was proposed for these zinc-independent alkenal reductases (Youn, et al., *J. Biol. Chem.,* 281:40076-40088, 2006). While the corresponding dihydroalcohol product (46) is a well known plant defense metabolite, it was not, however, converted in basil into either chavicol (31) and/or p-anol (37) ((VASSÃO, et al., *Org. Biomol. Chem.,* 4:2733-2744, 2006)). Accordingly, it was not considered as being involved in allyl/propenyl phenol biosynthesis.

Rather, according to aspects of the present invention, a quite novel metabolic process converting monolignols (such as p-coumaryl (19) and coniferyl (21) alcohols) into allyl/propenyl phenols (chavicol (31) and eugenol (33), respectively) was discovered (FIG. 5), with two enzymes being implicated in their formation in planta. The first step is activation of the monolignol side-chain alcohol by conjugation to an activated acid (acyl-CoA), resulting in formation of a monolignol ester. This modification results, in energetic terms, in formation of a more facile leaving group (carboxylate ester), which is more readily displaced by an incoming reducing hydride, e.g., in the form of NAD(P)H. Indeed, such coniferyl alcohol acyl transferases have been recently characterized in basil (*O. basilicum*) (Harrison & Gang, *The* 19*th Rocky Mountain Regional Meeting,* 2006) and *petunia* (*Petunia hybrida*) (Dexter, et al., *Plant J.,* 49:265-275, 2007), utilizing acetyl-CoA and coniferyl alcohol (21) to afford coniferyl acetate (49), and according to present aspects, it is reasonable to expect that substrate-versatile acyltransferases will be able to utilize different monolignols and acyl/aroyl-CoA cofactors to generate different esters. One such ester, p-coumaryl coumarate (50), had been previously shown to serve as substrate for enzyme preparations from *Asparagus officinalis* (Suzuki et al., *J. Chem. Soc., Chem. Commun.,* 1088-1089, 2002) and *Cryptomeria japonica* (Suzuki et al., *J. Chem. Soc., Chem. Commun.,* 2838-2839, 2004), generating the nor-lignans (Z)- and (E)-hinokiresinol (52/53), respectively. Although the proteins responsible for the latter conversions remain to be fully characterized and/or described, potential mechanisms whereby the departing carboxylate (as $CO_2$) facilitates formation of the final C8-C7' bond, without any additional cofactors, can be envisaged (FIG. 6A). It is also possible to propose potential mechanisms where p-coumaryl coumarate (50) (or other p-coumaryl alcohol esters, e.g., p-coumaryl acetate (48)) generates, through the addition of an incoming hydride, chavicol (31) and/or its regioisomer p-anol (37) (FIG. 6B).

Figure 6B:
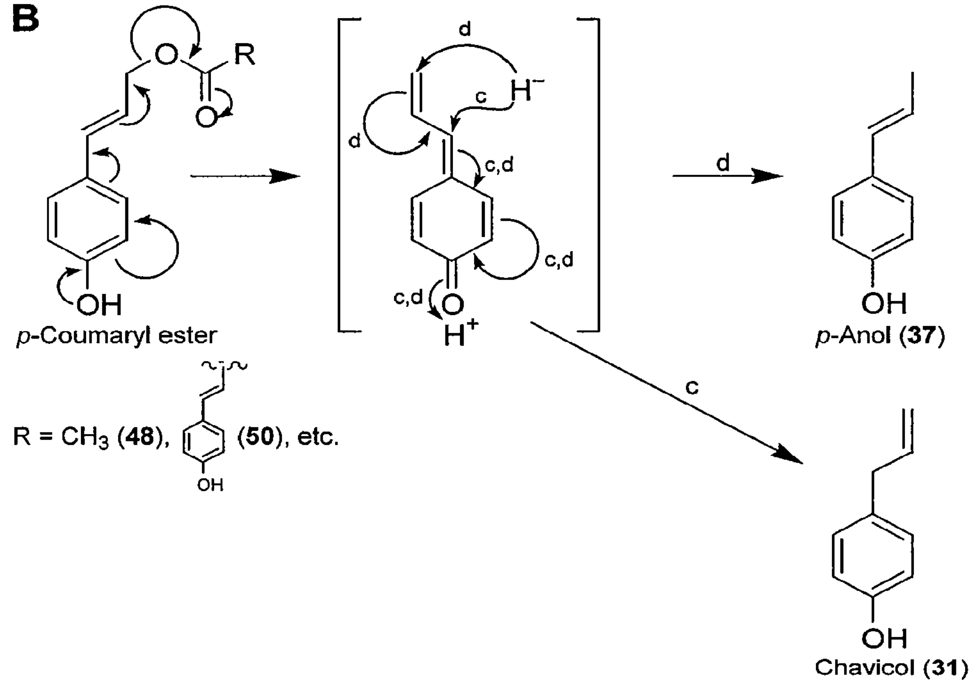

Indeed, according to aspects of the present invention, the second step in monolignol reduction was shown to be the action of regiospecific reductases that transfer a hydride from NADH or NADPH into either the C-7 or C-9 of the corresponding monolignol ester (or a quinone methide derivative thereof), thus forming either an allyl or propenyl phenol, respectively (FIGS. 5, 6B). These regiospecific reductases (e.g. chavicol and eugenol synthase, CS/ES, and isoeugenol synthase, IES) have been studied to a larger extent than the monolignol-specific acyltransferases. Computational analyses of CS/ES isolated from basil and IES from *petunia* indicate greatest homology (~40-45% identity) (Koeduka, et al., *Proc. Natl. Acad. Sci., USA,* 103:10128-10133, 2006) to members of the PIP family of reductases we have either discovered and/or extensively characterized (pinoresinol-lariciresinol, isoflavone, and phenylcoumaran benzylic ether reductases) (Fujita et al., *J. Biol. Chem.,* 274:618-627, 1999; Dinkova-Kostova et al, *J. Biol. Chem.,* 271:29473-29482, 1996; Gang et al., *J. Biol. Chem.,* 274:7516-7527, 1999), and for which crystal structures have been determined (Min, et al., *J. Biol. Chem.,* 278:50714-50723, 2003).

According to particular aspects of the present invention, six such PLR/CS/ES homologues from *L. tridentata* (LtPLRh1 (LtCES1), LtPLRh2 (LtCES2), Lt_PLR13 (LtCES3), LtCES4, LtCES5 and LtCES6) were isolated based on sequence homology, and characterized (FIG. 7) (nucleic acid SEQ ID NOS:1, 3, 5, 19, 19 and 21 and protein SEQ ID NOS:2, 4 and 6, 18, 20 and 22, respectively).

Figures 8A, 8B:
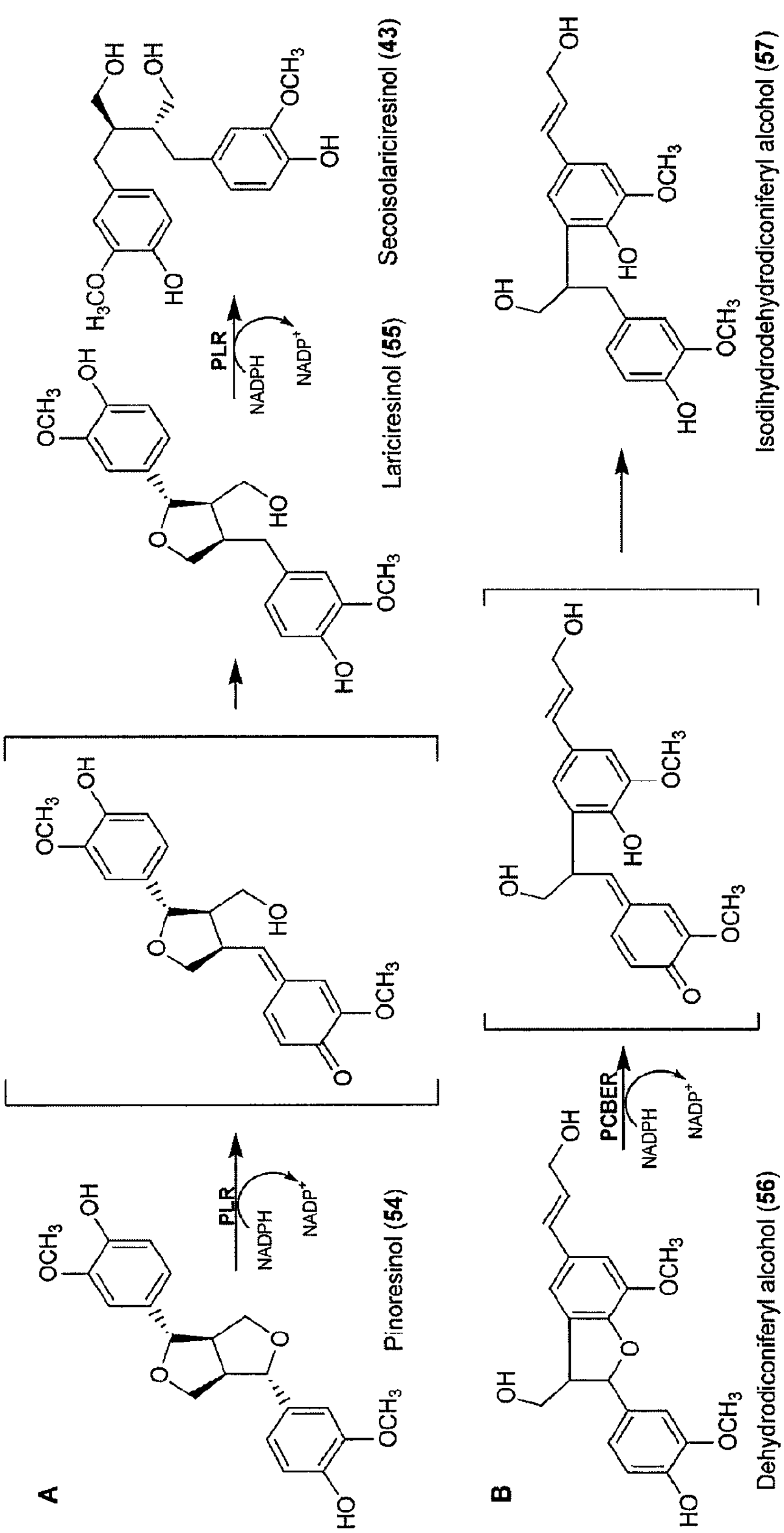
FIGS. 8A and B show, according to exemplary aspects of the present invention, reactions catalyzed by A. PLR and B. PCBER, and shows that the biochemical mechanisms of PLR, PCBER and CS/ES share common properties, including (a) a presumed necessity for a free phenolic functionality in the substrate, indicative of a common quinone methide intermediate.
Figure 9:
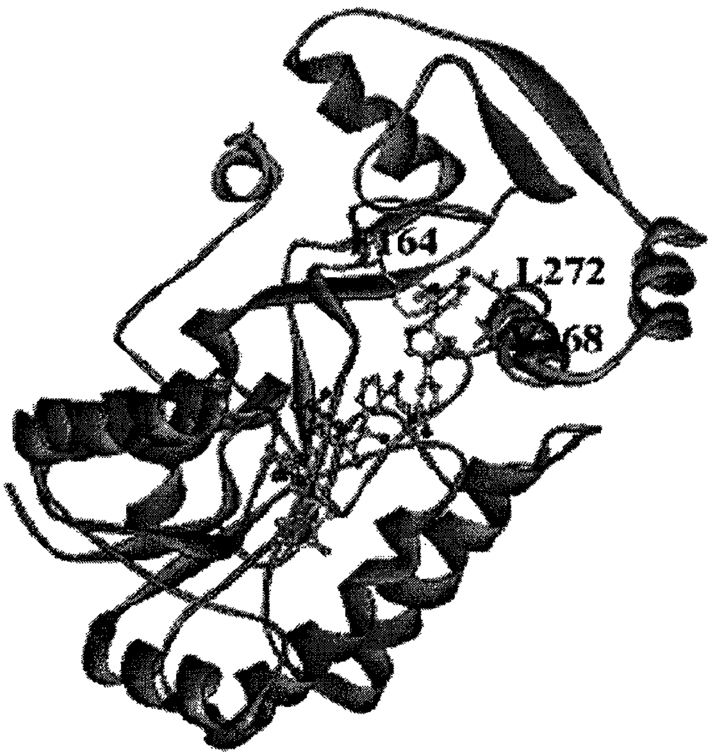
FIG. 9 shows a schematic representation of the crystal structure of TpPLR1 from *T. Plicata* with NADPH and (−)-pinoresinol (54) (Reprinted from Min, et al., *J. Biol. Chem.*, 278:50714-50723, 2003).
Figure 10:
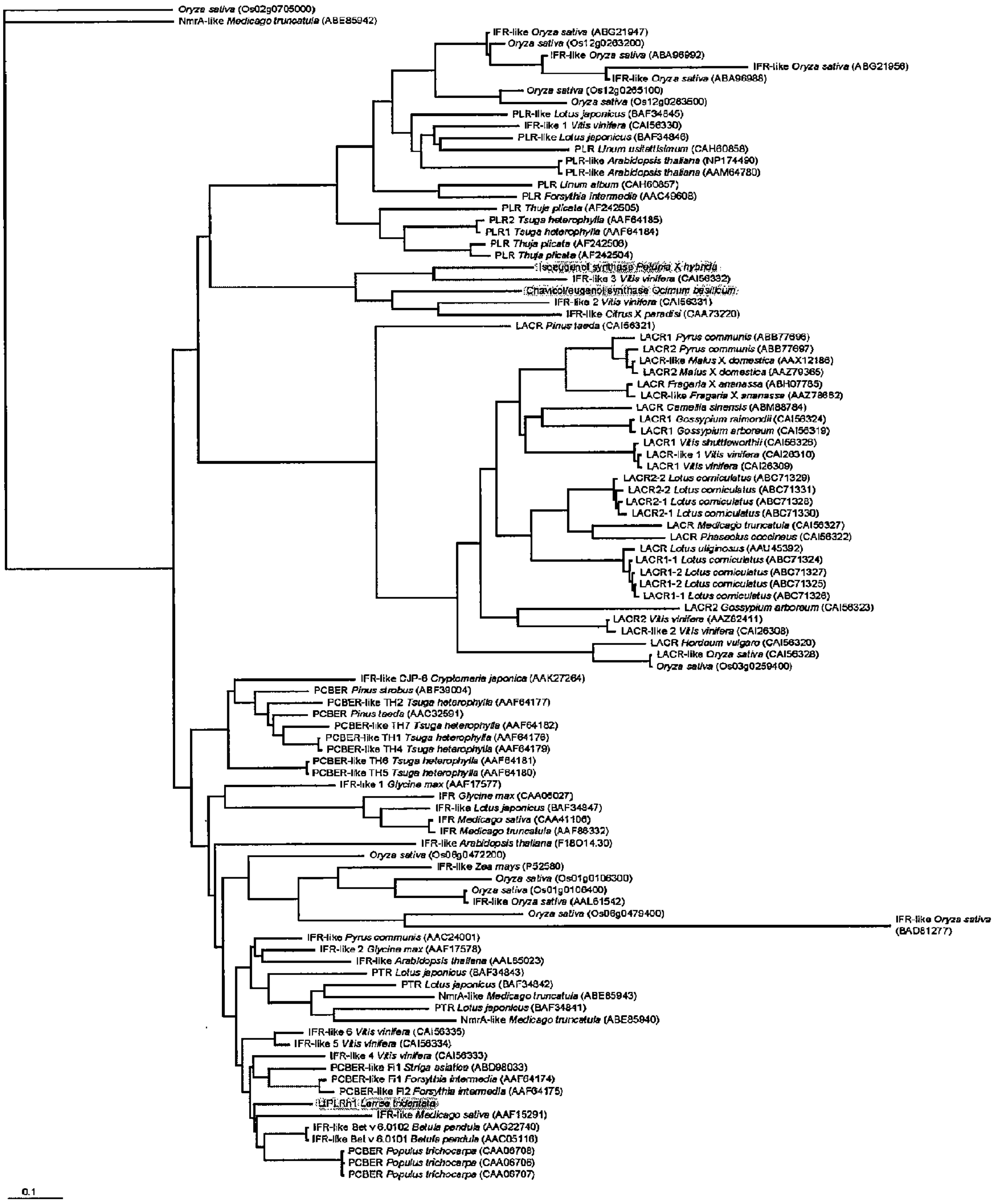
FIG. 10 shows, according to exemplary aspects of the present invention, a phylogenetic analysis of several PIP-reductase homologues from different plant species, with relevant homologues-in basil (ObEGS1), *petunia* (PhIGS1) and creosote bush (LtPLRh1; as referred to herein as LtCES1) highlighted. IFR—isoflavone reductase; LACR—leucoanthocyanidin reductase; NmrA—nitrogen metabolite repression regulator; PCBER—phenylcoumaran benzylic ether reductase; PLR—pinoresinol lariciresinol reductase; PTR—pterocarpan reductase. Sequences were obtained from the NCBI database and filtered for <0.75 sequence difference, ClustalW-aligned and subjected to neighbor-joining phylogenetic analysis using PHYLIP.

While PLR's are involved in formation of other medicinally important plant metabolites (e.g. podophyllotoxin (42) and secoisolariciresinol (43)) and various plant defense compounds (e.g. plicatic acid (30) in western red cedar heartwood), the biochemical mechanisms of PLR, PCBER and CS/ES share common properties, including (a) a presumed necessity for a free phenolic functionality in the substrate, indicative of a common quinone methide intermediate (FIGS. 5 and 8), and (b) a highly conserved Lys residue (K138 in PLR from *Thuja plicata*, K133 in its homologue in *L. tridentata*, K132 in CS/ES from basil) required for catalysis. FIG. 9 depicts the X-ray crystal structure of one member of this class of reductases, PLR from *T. plicata* (Min, et al., *J. Biol. Chem.,* 278:50714-50723, 2003). Based on the proposed catalytic mechanisms of CS/ES and PLR, applicants appreciated that a high level of similarity would be observed between these proteins. All of the PIP reductases, as well as CS/ES, utilize NAD(P)H as the source of a hydride which is regiospecifically (or stereospecifically) added to a carbon originated from a phenylpropanoid side-chain (i.e., either a monolignol derivative or dimer). In fact, a brief phylogenetic analysis indicates that these homologues cluster together with PLR (e.g., from *T. plicata*), PCBER (e.g., from *P. taeda*), IFR (e.g., from *Medicago*) and leucoanthocyanidin reductases (LACR, e.g. from *Vitis vinifera*) (with the *L. tridentata* homologue clustering closer to more distant PCBER and IFR homologues) (FIG. 10).

The biochemical characteristics of these enzymes have been studied, with basil CS/ES and *petunia* IES reported to have substrate affinities ($K_m$, coniferyl acetate (49)] of 1.6-5.1 mM and $V_{max}$ of 7-20 pkat $\mu g^{-1}$ protein. These are indicative of relatively low substrate affinity, although not far from the range of other enzymes involved in volatile oil biosynthesis. Additionally, the corresponding PLR homologue in the creosote bush (*L. tridentata*) catalyzes similar conversions, but interestingly with even higher catalytic efficacy ($K_m$ values of a few hundred μM and $V_{max}$ values of a few hundred pkat $\mu g^{-1}$ protein for coniferyl acetate (49), p-coumaryl acetate (48) and p-coumaryl coumarate (50), see Table 1). According to additional aspects, with respect to the properties of other PIP reductases regarding their abilities to form allyl and propenyl phenols, it is reasonable to expect substrate versatility in PLR's acting on monolignol esters).

TABLE 1

Kinetic, parameters of LtPLRh1 (LtCES1) from *L. tridentata* for different monolignol ester substrates (48-50) (VASSAO, et al., Manuscript in press)), and chavicol/eugenol synthase from basil and isoeugenol synthase from petunia for coniferyl acetate (49) (Koeduka, et al.,, Proc. Natl. Acad. Sci., USA, 103: 10128-10133, 2006).

| | $K_m$ (μM) | $V_{max}$ (pkat $\mu g^{-1}$ prot.) | $k_{cat}$ ($s^{-1}$) | $k_{cat}/K_m$ ($M^{-1} s^{-1}$) |
|---|---|---|---|---|
| LtPLRh1 (LtCES1) | | | | |
| p-Coumaryl acetate (48) | 350 | 200 | 6.80 | 19,500 |
| Coniferyl acetate (49) | 290 | 190 | 6.46 | 22,000 |
| p-Coumaryl coumarate (50) | 210 | 75 | 2.55 | 12,000 |
| ObEGS1 | 5,100 | 20 | 0.7 | 136 |
| PhIGS1 | 1,600 | 7 | 0.3 | 160 |

According to particular aspects, the long-standing question regarding the biochemical formation of these widely used compounds, allyl and propenyl phenols, has now been elucidated and shown to utilize the same pathway precursors as lignin biosynthesis. Proteins (and their corresponding genes) involved in this process have been isolated and characterized, thus providing a novel approach alter and re-engineer the lignification program of woody plants, as well as enabling the production of these compounds in more commonly cultivated plants.

Exemplary uses for Allyl/Propenyl Phenols:

In particular aspects, the biotechnological approaches utilizing the enzymatic machinery described above are applied to produce allyl and propenyl phenols, diverting (to a predetermined extent) some of the carbon flow, for example, from lignin towards these metabolites, while maintaining the resulting plants' capacities to grow and function within acceptable boundaries. The resulting cellulosic biomass thus becomes more amenable to pulp/paper manufacture and/or biofuel production due to the lower lignin contents. Alternatively, oilseed metabolism is manipulated to produce these allyl/propenyl phenol substances in larger amounts. In additional aspects, upon processing and purification, these compounds are used as biofuels, biofuel precursors, flavors/fragrances and/or intermediate chemicals (e.g., as monomers for synthetic polymers, etc.).

In additional aspects, the ability to routinely biotechnologically modify plants and/or cell cultures to produce allyl/propenyl phenols, such as chavicol (31) and eugenol (33), provides the opportunity to consider much larger markets for these products, i.e., in addition to expanding the flavor/fragrance/antiseptic/biocidal markets that currently exist. For instance, in terms of the flavor/fragrance market, the natural vanillin market can potentially be expanded. Driven by consumer preferences towards truly "natural" food products, food additives, and pharmaceuticals, several biocatalytic processes for production of plant-derived metabolites using microbes and plant cell cultures have been developed and patented in recent years (Krings, et al., *Appl. Microbiol. Biotechnol.,* 1998, 49, 1-8; Longo, et al, *Food Technol. Biotechnol.,* 2006, 44, 335-353; Priefert, et al., *Appl. Microbiol. Biotechnol.,* 2001, 56, 296-314; Rabenhorst, et al., U.S. Pat. No. 5,017,388, May 21, 1991, 1991, pp. 3; Schrader et al., *Biotechnol. Lett.,* 2004, 26, 463-472; Shimoni, et al., *J. Biotechnol.,* 2000, 78, 1-9; Yoshimoto, et al., Japan Patent number JP02200192, 1990; and Berger, et al., Genetic engineering. Part III: Food Flavors, in: Encyclopedia of Food Science and Technology, vol. 2 (Y. H. Hui, ed.), Wiley-Interscience, New York. 1991, pp. 1313-1320; all incorporated by reference herein). This enthusiasm has been fueled by the promise to generate transgenic cultures with increased efficacy for production of target metabolites. This approach also a offers economic advantages over conventional chemical syntheses, including better stereospecificity in product formation and lower amounts of waste products being generated upon processing. In particular, production of flavors via biotechnological processes offers an additional economic advantage since, unlike their chemically prepared counterparts, the resulting products can be marketed as "natural" under current U.S. and E.U. legislation. In this regard, successful microbial production of vanillin from various precursors, such as eugenol (33) and isoeugenol (39), has been reported recently, being achieved at relatively high substrate concentrations, e.g. transformation of isoeugenol (20 g/L) using a strain of Serratia marcescens led to vanillin accumulation (3.8 g/L). An enzymatic process for conversion of isoeugenol (39) into vanillin using a ligno stilbene-α,β-dioxygenase from a *Pseudomonas paucimobilis* strain has also been patented. Thus, the technologies are now in hand to permit formation of natural vanillin through established microbial and genetic manipulations in either plants and/or plant/bacterial cell cultures.

According to additional aspects, much larger anticipated potential markets for the allyl/propenyl phenols include the industrial polymers and biofuel/biodiesel. Regarding polymer applications, the expected worldwide production of polystyrenes alone was ~25 million metric tons in 2006, representing sales of 31 billion dollars. Allyl/propenyl phenols can be converted into functionalized polystyrene derivatives, and an increased supply creates the potential for their massive usage as intermediate (monomer) chemicals in industrial polymers. Currently existing applications include eugenol (33)-based polymers, which are widely used in dentistry in zinc oxide impression pastes applied as surgical dressings and temporary cements, as well as specialty modifying (i.e. coating) agents in analytical electrodes.

The functionalized β-methylstyrenes anethole (38) and isoeugenol (39) can be converted into polymers of several thousand Da. However, the potential of such conversions has only been studied to a limited extent relative to their vinyl analogues (i.e. styrene and derivatives thereof), in part due to limited supply/availability, and because propenylbenzenes do not apparently undergo as efficient free radical polymerization reactions as styrenes—even though their electronic configuration is such that a radical intermediate can also be stabilized by the aromatic ring. The most efficient polymerization initiators described thus far for propenylbenzene derivatives are Lewis acids, particularly $AlCl_3$, $SnCl_4$ and $BF_3$.

In general, the steric factors on the monomers define, to a large extent, both polymerization rates and molecular weights of the resulting polymers, with anethole, for example, being more reactive than isoeugenol. Polymerization reactions can proceed through a conventional 1,2-chain formation, similar to styrene, with the propagating species being a Lewis acid-induced carbocation that is added to the double bond of another monomer. This results in a polymer backbone composed of the carbons 7 and 8 of the original monomers. The molecular weights of the resulting polymers are higher at lower temperatures and, in the case of anethole when polymerized by $SnCl_4$, can vary from a few thousand up to about 75,000 Da depending on both temperature and dilution levels. For isoeugenol, the phenolic oxygen moiety also participates in the polymerization reactions, thereby increasing the structural complexity of the resulting polymer(s) so formed (FIG. 11A). Additionally, allylphenols such as methylchavicol (32) and eugenol (33) can form mixed polymers, resulting from the partial rearrangement of the side-chain double bond upon carbocation formation prior to attachment to the polymer chain (FIG. 11*b*).

In further aspects, in terms of uses to provide biofuels, it is noteworthy that ~100 billion gallons of gasoline fuel were consumed in the USA in 2005. In addition, the annual consumption of diesel fuel in 2000, including highway diesel, farms, electric power, railroad, fuel oil (residential, commercial and heating) and kerosene, totaled approximately 57.1 billion gallons.

In yet further aspects, if one considers the annual pulp and paper production in the USA (ca 120 million metric tons/year, 1997 figures), some part of the production of lignins/heartwood lignans and other phenylpropanoid derivatives in commercially important woody plant species is diverted away from their natural biosynthetic pathways, i.e. to afford allyl/propenyl phenols, etc. In principle, the lignin/lignan substances currently produced annually as by-products of pulp/paper industries (more than 50 million tons) could instead be converted to ca 15 billion gallons allyl/propenyl phenols per annum, if fully converted. Nevertheless, any reduction in carbon flow to lignin, or reductions/changes in heartwood-forming constituents, could represent a significant increase in biofuel production.

In additional aspects, allyl and propenyl phenols have relatively high heats of combustion at room temperature, with values generally being about 70% (per weight) of medium chain hydrocarbons such as octane and decane. That is, these allyl/propenyl phenols can generate more energy (per weight) than ethanol. In terms of other relevant properties, using two examples only for illustrative purposes, chavicol (31) has boiling/flash points of 238/102° C. at normal atmospheric pressure and density ~1.01 g/$cm^3$, whereas eugenol (33) values are ~253/112° C. and 1.07 g/$cm^3$ (at 20° C.). Such values are within the ranges needed for biodiesel/biofuel considerations. Their reported freezing points are, however, generally between −10° C. and room temperature, which would reduce their potential as liquid biofuels if used exclusively as such in pure liquid form. This limitation might be circumvented, however, by either blending them into other fuels, similar to the coconut oils added as biofuels to diesel in the Philippines, or through their chemical derivatization to generate materials of lower freezing point prior to biofuel use (e.g., hydrogenation, which may also help reduce pollutant emission upon combustion). Catalytic hydrogenation of side-chain double bonds of allyl/propenylbenzenes is readily achieved at atmospheric pressures, whereas reduction of the aromatic ring typically requires higher temperatures and pressures using traditional metal catalysts (e.g., supported Pd or Raney Ni). Reduced allyl/propenyl phenols have already been generated by such catalytic hydrogenation reactions, e.g. 2-methoxy-4-propyl-cyclohexanol (58, FIG. 12) was obtained in near-quantitative amounts from eugenol (33) (Maillerer, E., U.S. Pat. No. 4,904,465, 1990). Newer catalytic systems, however, have the exciting potential to dramatically improve the reduction conditions, e.g. as recently reported for the quantitative hydrogenation of several benzene analogues, at room temperature and atmospheric hydrogen pressure, using ruthenium-containing methylated cyclodextrin catalysts (Nowicki, et al., *J. Chem. Soc., Chem Commun,* 2006, 296-298). Therefore, according to additional aspects, the presently disclosed biotechnology applications provide important new sources of biofuels/bioenergy.

In summary, the prior art biotechnological lignin-reduction endeavors thus far reported have, in general, resulted in plants apparently unsuitable for large scale cultivation resulting from compromised vasculature, and perhaps higher susceptibility to pathogen attacks as well. Similarly, lignin represents a challenge in the processing of plant biomass (e.g., corn, switchgrass or miscanthus) for biofuel/bioethanol generation using current fermentation techniques. Therefore, applicants have herein provided some solutions through the application of a newly elucidated metabolic process sharing the same lignin biochemical precursors, i.e. the biosynthesis of liquid allyl and propenyl phenols. The pertinent enzymes, genes and specific biochemical precursors in this process have been isolated and described, thus lending themselves to exploitation through bioengineering.

Biologically Active Variants

Variants of the novel disclosed PLR/CS/ES homologue polypeptides have substantial utility in various aspects of the present invention. Variants can be naturally or non-naturally occurring. Naturally occurring variants are found in plants or other life forms and comprise amino acid sequences which are significantly or substantially identical to the amino acid sequences shown herein, and include natural sequence polymorphisms. Species homologs of the protein can be obtained using subgenomic polynucleotides of the invention, as described below, to make suitable probes or primers for screening cDNA expression libraries from other plant species for example, identifying cDNAs which encode homologs of the protein, and expressing the cDNAs as is known in the art.

Non-naturally occurring variants which retain substantially the same biological activities as naturally occurring protein variants, including the PLR/CS/ES homologue activities disclosed herein and the modulation of carbon metabolism, are also included here. Preferably, naturally or non-naturally occurring variants have amino acid sequences (or corresponding nucleic acid sequences) which are at least 45%, 55%, 65%, 75% 85%, 90%, 95%, 97%, 98%, or 99% identical to the amino acid sequence shown herein. More preferably, the molecules are at least 98% or 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.,* 243: 3552-59 (1969) and adopted at 37 C.F.R. §§ 1.821-1.822, abbreviations for amino acid residues are shown in Table 7:

TABLE 7

| Table of Correspondence | | |
|---|---|---|
| SYMBOL | | |
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Praline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Guidance in determining which amino acid residues can be substituted, inserted, or deleted without abolishing biological or immunological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

Such substitutions may be made in accordance with those set forth in TABLE 8 as follows:

TABLE 8

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with other known conservative (or non-conservative) substitutions.

Variants of the PLR/CS/ES homologue polypeptide disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

A subset of mutants, called muteins, is a group of polypeptides in which neutral amino acids, such as serines, are substituted for cysteine residues which do not participate in disulfide bonds. These mutants may be stable over a broader temperature range than native proteins (Mark et al., U.S. Pat. No. 4,959,314).

Preferably, amino acid changes in the PLR/CS/ES homologue polypeptide variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting secreted protein or polypeptide variant. Properties and functions of PLR/CS/ES homologue polypeptide protein or polypeptide variants are of the same type as a protein comprising the amino acid sequence encoded by the nucleotide sequences shown herein, although the properties and functions of variants can differ in degree.

PLR/CS/ES homologue polypeptide variants include glycosylated forms, aggregative conjugates with other molecules, and covalent conjugates with unrelated chemical moieties (e.g., pegylated molecules). PLR/CS/ES homologue polypeptide variants also include allelic variants (e.g., polymorphisms), species variants, and muteins. Truncations or deletions of regions which do not preclude functional activity of the proteins are also variants. Covalent variants can be prepared by linking functionalities to groups which are found in the amino acid chain or at the N- or C-terminal residue, as is known in the art.

It will be recognized in the art that some amino acid sequence of the PLR/CS/ES homologue polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. Thus, the PLR/CS/ES homologue polypeptides of the present invention may include one or more amino acid substitutions, deletions or additions, either from natural mutations or human manipulation.

Of particular interest are substitutions of charged amino acids with another charged amino acid and with neutral or negatively charged amino acids. The latter result in proteins with reduced positive charge to improve the characteristics of the disclosed protein. The prevention of aggregation is highly desirable. Aggregation of proteins not only results in a loss of activity but can also be problematic when preparing pharmaceutical formulations, because they can be immunogenic (Pinckard et al., *Clin. Exp. Immunol.* 2:331-340, 1967; Robbins et al., *Diabetes* 36:838-845, 1987; Cleland et al., *Crit. Rev. Therapeutic Drug Carrier Systems* 10:307-377, 1993).

Amino acids in the PLR/CS/ES homologue polypeptides of the present invention that are essential for function can be identified by methods known in the art, such as site-directed mutagenesis or alanine-scanning mutagenesis (Cunningham and Wells, *Science* 244:1081-1085, 1989). The latter procedure introduces single alanine mutations at every residue in the molecule. The resulting mutant molecules are then tested for biological activity such as the catalytic activities described herein. Sites that are critical for ligand-receptor binding can also be determined by structural analysis such as crystallization, nuclear magnetic resonance or photoaffinity labeling (Smith et al., *J. Mol. Biol.* 224:899-904, 1992 and de Vos et al. *Science* 255:306-312, 1992).

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given PLR/CS/ES homologue polypeptide will not be more than about 50, 40, 30, 25, 20, 15, 10, 5, 3, 2, or 1.

In addition, pegylation of PLR/CS/ES homologue polypeptides and/or muteins is expected to provide such improved properties as increased half-life, solubility, and protease resistance. Pegylation is well known in the art.

Fusion Proteins

Fusion proteins comprising proteins or polypeptide fragments of PLR/CS/ES homologue polypeptides can also be constructed. Fusion proteins are useful for generating antibodies against amino acid sequences and for use in various targeting and assay systems. For example, fusion proteins can be used to identify proteins which interact with a PLR/CS/ES homologue polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can utilize the amino acid sequences disclosed herein (e.g., contiguous amino acid residues corresponding to different reading frames of the PLR/CS/ES homologue coding sequences; frame-shift protein variants, etc) or can be prepared from biologically active variants thereof. The first protein segment can include a full-length PLR/CS/ES homologue polypeptide.

Other first protein segments can consist of amino acid sequence selected from the group consisting of SEQ ID NOS: 2, 4, 6, 18, 20 and 22, and fragments of of SEQ ID NOS:2, 4, 6, 18, 20 and 22 of about 5, about 10, about 20, about 30, about 50 or more contiguous residues in length.

The second protein segment can be a full-length protein or a polypeptide fragment. The second protein can be homologous or heterologous. Heterologous proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions.

These fusions can be made, for example, by a frame-shift process, or alternatively by covalently linking two protein segments or by standard procedures in the art of molecular biology. Recombinant DNA methods can be used to prepare fusion proteins, for example, by making a DNA construct which comprises a coding region for the PLR/CS/ES homologue protein sequence in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wisc.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Screening and Expression:

One skilled in the art will readily recognize that antibody preparations, nucleic acid probes (DNA and RNA) and the like may be prepared and used to screen and recover "homologous" or "related" PLR/CS/ES homologue nucleic acids and proteins from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful for gene isolation. For detection, the antibody is labeled using radioactivity or any one of a variety of second antibody/enzyme conjugate systems that are commercially available, and well-known in the art.

Homologous sequences are found when there is an identity of sequence and may be determined upon comparison of sequence information, nucleic acid or amino acid, or through hybridization reactions between a known PLR/CS/ES homologue and a candidate source. Conservative changes (see in more detail below), such as Glu/Asp, Val/Ile, Ser/Thr, Arg/Lys and Gln/Asn may also be considered in determining sequence homology.

Typically, a lengthy nucleic acid sequence may show as little as 50-60%, 60%-70%, 70% to 80% sequence identity, and more preferably at least about 70% or about 80% sequence identity, between the target sequence and the given plant PLR/CS/ES homologue of interest excluding any deletions which may be present, and still be considered related. Amino acid sequences are considered homologous by as little as 25% sequence identity between the two complete mature proteins (see generally, Doolittle, R. F., Of URFS and ORFS (University Science Books, California, 1987).

To obtain additional PLR/CS/ES homologues, a genomic or other appropriate library prepared from the candidate plant source of interest is probed with conserved sequences from one or more PLR/CS/ES homologue to identify homologously related sequences. Positive clones are then analyzed by restriction enzyme digestion and/or sequencing. When a genomic library is used, one or more sequences may be identified providing both the coding region, as well as the transcriptional regulatory elements of the gene from such plant source. Probes can also be considerably shorter than the entire sequence. Oligonucleotides (see below in more detail) may be used, for example, but should be at least about 10, preferably at least about 15, at least about 18, at least about 19, at least about 20, at least about 25, at least about 50, or at least about 100, and preferably at least about 19 or about 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. When longer nucleic acid fragments are employed (>100 bp) as probes, especially when using complete or large cDNA sequences, moderately high stringencies (for example using 50% formamide at 37° C. with minimal washing) can still be used for screening to obtain signal from the target sample with 20-50% deviation, i.e., homologous sequences.

Not only can PLR/CS/ES homologue sequences such as shown herein be used to identify homologous additional PLR/CS/ES homologue sequences, but the resulting sequences obtained therefrom may also provide a further method to obtain additional PLR/CS/ES homologues from other plant sources. In particular, PCR may be a useful technique to obtain related additional plant PLR/CS/ES homologues from sequence data provided herein. One skilled in the art will be able to design oligonucleotide probes based upon sequence comparisons or regions of typically highly conserved sequence.

Once the nucleic acid sequence is obtained, the transcription, or transcription and translation (expression), of the additional PLR/CS/ES homologue(s) in a host cell is desired, to produce a ready source of the enzyme and/or modify the carbon composition found therein. Other useful applications may be found when the host cell is a plant host cell, in vitro and in vivo. Additionally, as disclosed herein, yeast may be used. For example, by increasing the amount of one or more PLR/CS/ES homologue enzymes available to the plant biosynthetic complex, moulation of carbon flow as described herein may be acheived. In a like manner, for some applications, by decreasing the amount of particular enzymes (e.g., desaturase enzymes and/or fatty acyl elongases) available to the plant, in conjunction with an increase of the amount of one or more PLR/CS/ES homologue enzymes available, a substantial moulation of carbon flow may be acheived.

The nucleic acid sequences which encode plant PLR/CS/ES homologue enzymes may be used in various constructs, for example, as probes to obtain further sequences. Alternatively, these sequences may be used in conjunction with appropriate regulatory sequences to increase levels of the respective PLR/CS/ES homologue enzymes of interest in a host cell for recovery or study of the enzyme in vitro or in vivo or to decrease levels or activities of other enzymes of interest for some applications when the host cell is a plant entity, including plant cells, plant parts (including but not limited to seeds, cuttings or tissues) and plants.

A nucleic acid sequence encoding a novel plant PLR/CS/ES homologue enzyme disclosed herein may include genomic, cDNA or mRNA sequence. “Encoding” means that the sequence corresponds to a particular amino acid sequence either in a sense or anti-sense orientation. By “extrachromosomal” is meant that the sequence is outside of the plant genome of which it is naturally associated. “Recombinant” means that the sequence contains a genetically engineered modification through manipulation via mutagenesis, restriction enzymes, and the like. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the “mature” sequence. The use of a precursor plant PLR/CS/ES homologue DNA sequence is preferred in plant cell expression cassettes. Other transit peptide sequences, such as a transit peptide of seed ACP, may be employed to translocate the plant PLR/CS/ES homologue enzymes of this invention to various organelles of interest. Likewise, once a given plant PLR/CS/ES homologue transit peptide is obtained, it may be used to translocate sequences other than its native coding region.

The complete genomic sequence of the plant PLR/CS/ES homologue enzymes may be obtained by the screening of a genomic library with a probe, such as a cDNA probe, and isolating those sequences which, for example, regulate expression in plant tissue. In this manner, the transcription and translation initiation regions, introns, and/or transcript termination regions of the plant PLR/CS/ES homologue enzymes may be obtained for use in a variety of DNA constructs, with or without the PLR/CS/ES homologue enzymes structural gene. Thus, nucleic acid sequences corresponding to the plant PLR/CS/ES homologue enzymes of this invention may also provide signal sequences useful to direct transport to a cellular organelle (e.g., into a plastid), 5' upstream non-coding regulatory regions (promoters) having useful tissue and timing profiles, 3' downstream non-coding regulatory region useful as transcriptional and translational regulatory regions and may lend insight into other features of the gene.

Once the desired plant PLR!CS/ES homologue nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding an inventive plant PLR/CS/ES homologue may be combined with other non-native, or "heterologous", sequences in a variety of ways. By "heterologous" sequences is meant any sequence which is not naturally found joined to the plant PLR/CS/ES homologue, including, for example, combinations of nucleic acid sequences from the same plant which are not naturally found joined together.

The DNA sequence encoding an inventive plant PLR/CS/ES homologues may be employed in conjunction with all or part of the gene sequences normally associated with the PLR/CS/ES homologue(s). In its component parts, for example, a DNA PLR/CS/ES homologue encoding sequence is combined in a DNA construct having, in the 5' to 3' direction of transcription, a transcription initiation control region capable of promoting transcription and translation in a host cell, the DNA sequence encoding one or more plant PLR/CS/ES homologues, and a transcription and translation termination region.

Potential host cells include both prokaryotic and eukaryotic cells (e.g., plant cells, yeast, etc.). A host cell may be unicellular or found in a multicellular differentiated or undifferentiated organism depending upon the intended use. Inventive cells may be distinguished by having a plant PLR/CS/ES homologue foreign to the wild-type cell present therein, for example, by having a recombinant nucleic acid construct encoding a plant PLR/CS/ES homologue therein.

Depending upon the host, the regulatory regions may vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae,* including genes such as beta-galactosidase, T7 polymerase, tryptophan E and the like.

Generally, the constructs will involve regulatory regions functional in plants, plant tissues (e.g., seed tissue) or other organisms (e.g., yeast) which provide for modified production of plant PLR/CS/ES homologues, and possibly, modification of the carbon composition and/or accumulation (level). The open reading frame, coding for the plant PLR/CS/ES homologue or functional fragments thereof will be joined at its 5' end to a transcription initiation regulatory region such as, for example, the wild-type sequence naturally found 5' upstream to the respective PLR/CS/ES homologue structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, ACP promoters and the like. The transcription/translation initiation regions corresponding to such structural genes are found immediately 5' upstream to the respective start codons. In embodiments wherein the expression of one or more of the PLR/CS/ES homologue proteins is desired in a plant host, the use of all or part of the complete plant PLR/CS/ES homologue/gene is desired; namely all or part of the 5' upstream non-coding regions (promoter) together with the structural gene sequence and 3' downstream non-coding regions may be employed. Alternatively, if a different promoter is desired, such as a promoter native to the plant host of interest or a modified promoter, i.e., having transcription initiation regions derived from one gene source and translation initiation regions derived from a different gene source, including the sequences encoding the PLR/CS/ES homologue of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for carbon pathway modifications and/or accumulation in order to minimize any disruptive or adverse effects of the gene product.

Regulatory transcript termination regions may be provided in DNA constructs of this invention as well. Transcript termination regions may be provided by the DNA sequence encoding the plant PLR/CS/ES homologue or a convenient transcription termination region derived from a different gene source, for example, the transcript termination region which is naturally associated with the transcript initiation region. In particular embodiments (e.g., where the transcript termination region is from a different gene source), it will contain at least about 0.5 kb, preferably about 1-3 kb of sequence 3' to the structural gene from which the termination region is derived.

Plant expression or transcription constructs having a plant PLR/CS/ES homologue as the DNA sequence of interest for increased or decreased expression thereof may be employed with a wide variety of plant life, particularly, plant life involved in the production of, for example, oils for edible and industrial uses. Particular embodiments comprise temperate oilseed crops. Plants of interest include, but are not limited to, rapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledon and monocotyledon species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to *Agrobacterium* infection may be successfully transformed via tripartite or binary vector methods of *Agrobacterium*-mediated transformation. Additionally, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species, the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. Included with the expression construct and the T-DNA will be one or more markers, which allow for selection of transformed *Agrobacterium* and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

Once a transgenic plant is obtained which is capable of producing seed having a modified carbon pathway and/or carbon product composition and/or accumulation level, traditional plant breeding techniques, including methods of mutagensis, may be employed to further manipulate the carbon composition. Alternatively, additional carbon pathway modifying DNA sequences may be introduced via genetic engineering to further manipulate the carbon composition. It is noted that the method of transformation is not critical to this invention. However, the use of genetic engineering plant transformation methods (e.g., to insert a single desired DNA sequence) is critical. Heretofore, the ability to modify the carbon composition of plant oils was limited to the introduction of traits that could be sexually transferred during plant crosses or viable traits generated through mutagensis. Through the use of genetic engineering techniques which permit the introduction of inter-species genetic information and the means to regulate the tissue-specific expression of endogenous genes, a new method is available for the production of, for example plant oils, or modified carbon pathways as described herein, or carbon compositions and/or accumulations using the inventive PLR/CS/ES homologue nucleic acids and proteins. In addition, there is the potential for the development of novel plant oils and products upon application of the tools described herein.

One may choose to provide for the transcription or transcription and translation of one or more other sequences of interest in concert with the expression of a plant PLR/CS/ES homologue in a plant host cell. In particular, the reduced expression of one or more plant enzymes, in combination with expression of a plant PLR/CS/ES homologue may be preferred in some applications.

For providing a plant transformed for the combined effect of more than one nucleic acid sequence of interest, typically, but not necessarily a separate nucleic acid construct will be provided for each. The constructs, as described above, contain transcriptional or transcriptional or transcriptional and translational regulatory control regions. One skilled in the art will be able to determine regulatory sequences to provide for a desired timing and tissue specificity appropriate to the final product in accord with the above principles (e.g., respective expression or anti-sense constructs). When two or more constructs are to be employed, it may be desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

An inventive plant PLR/CS/ES homologue includes any sequence of amino acids, such as a protein, polypeptide, or peptide fragment, obtainable from a plant source which is capable of catalyzing the respective biological activity in a plant host cell, i.e., in vivo, or in a plant cell-like environment, i.e., in vitro. “A plant cell-like environment” means that any necessary conditions are available in an environment (i.e., such factors as temperatures, pH, lack of inhibiting substances) which will permit the enzyme to function.

By decreasing the amount of one or more enzymes, modulation of carbon allocation may be provided. Using antisense, transwitch, ribozyme or some other expression reducing technology (e.g., mutants), a decrease in the amount of one or more PLR/CS/ES homologues available to the plant cell is produced.

By manipulation of various aspects of the DNA constructs (e.g., choice of promoters, number of copies, etc.) and traditional breeding methods, one skilled in the art may achieve even greater modulation of cabon pathways and product accumulation in plant species.

Exemplary Nucleic Acid Sequences:

In addition to the inventive coding sequences of PLR/CS/ES homologue nucleic acid sequences disclosed herein (e.g., SEQ ID NOS:1, 3, 5, 17, 19 and 21 and related genomic and RNA sequence), examples of oligonucleotides of length X (in nucleotides), as indicated by polynucleotide positions with reference to, e.g., SEQ ID NOS: 1, 3, 5, 17, 19 and 21 include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions:

n to (n+(X−1));

where n=1, 2, 3, . . . (Y−(X−1));

where Y equals the length (nucleotides or base pairs) of, for example, SEQ ID NO:1 (927); (LtPLRh1 (LtCES1) orf)

where X equals the common length (in nucleotides) of each oligonucleotide in the set (e.g., X=20 for a set of consecutively overlapping 20-mers); and where the number (Z) of consecutively overlapping oligomers of length X for a given SEQ ID NO of length Y is equal to Y−(X−1). For example Z=927−19=908 of either sense or antisense sets of SEQ ID NO:1, where X=20.

Examples of inventive 20-mer oligonucleotides include the following set of 908 oligomers (and the antisense set complementary thereto), indicated by polynucleotide positions with reference to SEQ ID NO:1:

1-20, 2-21, 3-22, 4-23, 5-24 . . . and 908-927.

Likewise, examples of inventive 25-mer oligonucleotides include the following set of 903 oligomers (and the antisense set complementary thereto), indicated by polynucleotide positions with reference to SEQ ID NO:1:

1-25, 2-26, 3-27, 4-28, 5-29 . . . and 903-927.

The present invention encompasses, for each of SEQ ID NOS:1, 3 and 5, etc. (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to modulate expression (e.g., siRNA and antisense), and to ascertain genetic and epigenetic parameters of the genomic sequence corresponding to SEQ ID NOS:1, 3, 5, 17, 19 and 21. Preferred sets of such oligonucleotides or modified oligonucleotides of length X are those consecutively overlapping sets of oligomers corresponding to SEQ ID NOS:1, 3, 5, 17, 19 and 21 (and to the complements thereof).

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., *BioTechniques* 6:958-976, 1988) or intercalating agents (Zon, *Pharm. Res.* 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage.

Oligonucleotides having modified backbones include those retaining a phosphorus atom in the backbone, and those that do not have a phosphorus atom in the backbone.

Preferred modified oligonucleotide backbones include phosphorothioates or phosphorodithioate, chiral phosphorothioates, phosphotriesters and alkyl phosphotriesters, aminoalkylphosphotriesters, methyl and other alkyl phosphonates including methylphosphonates, 3'-alkylene phosphonates and chiral phosphonates, phosphinates, phosphoroamidates or phosphordiamidates, including 3'-amino phosphoroamidate and aminoalkylphosphoroamidates, and phosphorodiamidate morpholino oligomers (PMOs), thiophosphoroamidates, phosphoramidothioates, thioalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

The antisense oligonucleotide may also comprise at least one modified sugar moiety selected from the group including, but not limited to arabinose, 2-fluoroarabinose, xylulose, hexose and 2'-O-methyl sugar moieties.

The antisense oligonucleotide may comprise at least one modified base moiety which is selected from the group including, but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine (see also U.S. Pat. No. 5,958,773 and patents disclosed therein).

In addition to antisense oligos, representative siRNA sequence regions are disclosed herein; namely, in view of the above algorithm in combination with the teachings on sequences, design (e.g., length, structure, composition, etc), preparation and use thereof, provided herein below under "siRNA." Methods of preparing and using siRNA are generally disclosed in U.S. Pat. No. 6,506,559, incorporated herein by reference (see also reviews by Milhavet et al., *Pharmacological Reviews* 55:629-648, 2003; and Gitlin et al., *J. Virol.* 77:7159-7165, 2003; incorporated herein by reference).

The siRNA may comprise one or more strands of polymerized ribonucleotide, and may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition.

The present invention will now be illustrated by reference to the following examples which set forth particularly advantageous embodiments. However, it should be noted that these embodiments are illustrative and are not to be construed as restricting the claimed invention in any way.

EXAMPLE 1

(Novel Chavicol/Eugenol Synthases were Isolated from *Larrea tridentata*)

Example summary. The creosote bush (*Larrea tridentata*) accumulates a complex mixture of 8-8' regiospecifically linked lignans, of which the potent antioxidant nordihydroguaiaretic acid (NDGA, 40) is the most abundant. Its tetra-O-methyl derivative (M4N, 41) is showing considerable promise in the treatment of the refractory (hard-to-treat) cancers of the head and neck. NDGA (40) and related 9,9'-deoxygenated lignans are thought to be formed by dimerization of allyl/propenyl phenols, phenylpropanoid compounds that lack C-9 oxygenation, thus differentiating them from the more common monolignol-derived lignans. In applicants' ongoing studies dedicated towards elucidating the biochemical pathway to NDGA (40) and its congeners, six pinoresinol-lariciresinol reductase homologues ("PLRh") (SEQ ID NOS: 2, 4, 6, 18, 20 and 22) were isolated from *L. tridentata*, with protein obtained in recombinant form. According to aspects of the present invention all six of these enzymes catalyze the conversion of p-coumaryl (48, 50) and coniferyl (49) alcohol esters into the corresponding allylphenols, chavicol (31) and eugenol (33). Of these six PLRh_Lt proteins, one of these homologues (PLRh_Lt1) (SEQ ID NO:2) was analyzed in greatest detail, and this protein efficiently catalyzes the conversion of p-coumaryl (48, 50) and coniferyl (49) alcohol esters into the corresponding allylphenols, chavicol (31) and eugenol (33), and neither of their propenylphenol regioisomers, p-anol (37) and isoeugenol (39), are formed during this enzyme reaction.

Example overview/rationale. The creosote bush (*Larrea tridentata*), or "chaparral", is a predominant component of shrub vegetation in southern North American deserts, having been traditionally used by Native American populations for various medicinal purposes (1) Other *Larrea* species (*L. ameghinoi, L. cuneifolia, L. divaricata, L. nitida*) are found in desert areas of South America, from where the creosote bush is thought to have geographically originated (2). The species is a rich source of specialized metabolites, including phenolics, terpenoids, saponins and odorous vinyl ketones (3). The regiospecifically 8-8' linked lignan nordihydroguaiaretic acid (NDGA, 40, FIG. 3) is a prevalent and biologically active compound present in leaves, flowers and young stems of *L. tridentata* (and other *Larrea* species) (e.g. NDGA (40) is a strong antioxidant and also a phytotoxic allelochemical). Reported levels of NDGA (40) in creosote bush leaves vary between 3-15% of dry weight (4), and synthetic methods now allow for its versatile production, as well as analogs thereof (5). Notably, NDGA (40) differs from most other natural lignans by lacking an oxygenated functionality at carbons 9 and 9'.

NDGA (40) is abundantly present in aqueous and alcoholic extracts, teas, and, more recently, capsules prepared from the creosote bush. These are traditionally used to treat, most commonly, diseases of renal and gynaecological origins (for an excellent comprehensive review, see (1)). NDGA (40) is a strong antioxidant (6) that has been shown to be an inhibitor of lipoxygenases (7, 8), and can inhibit tumor necrosis factor-α (TNF)-induced apoptosis (9), as well as the growth of several cancer cell lines (10). The semi-synthetic derivative tetra-O-methyl NDGA (M4N, 41, FIG. 3) has antiviral (11)/anti-HIV (12) activities, and can suppress growth of human xenograft tumors (13); it is also proceeding through NIH trials as a treatment for the particularly hard-to-treat cancers of head and neck.

Figure 13:
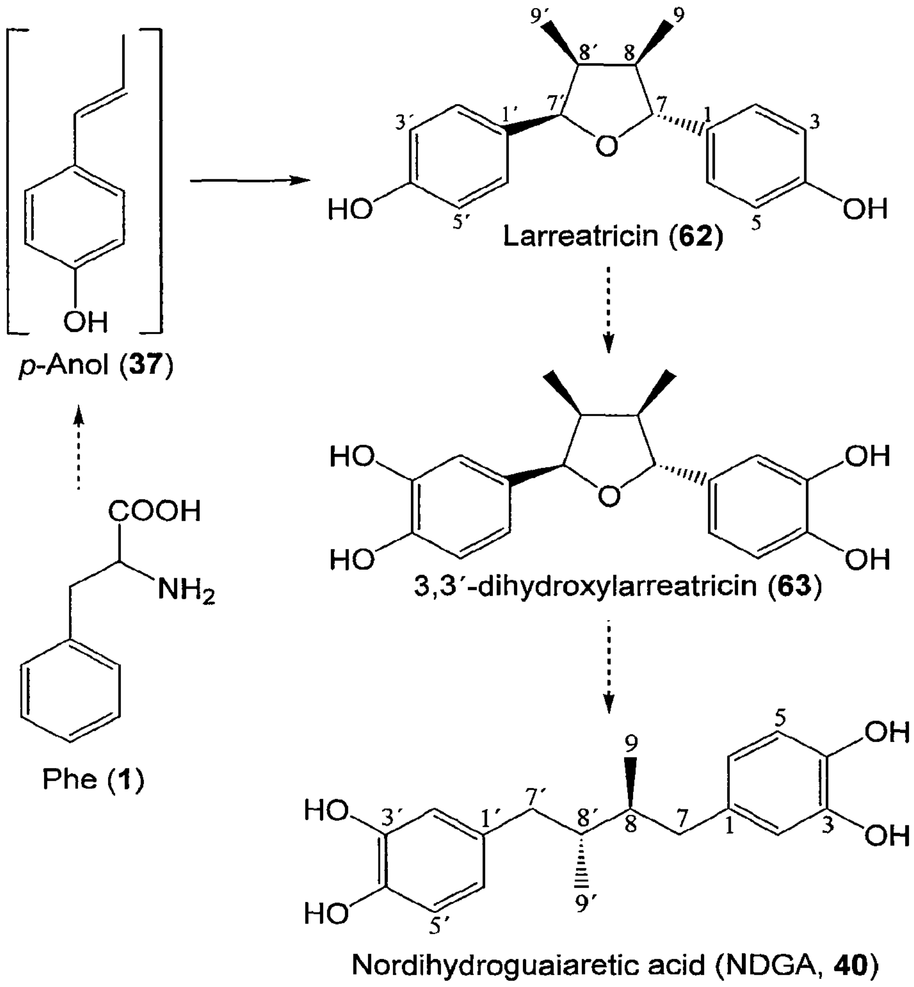
FIG. 13 shows a previously proposed biosynthetic pathway leading to formation of NDGA (40) in *Larrea tridentata*, simplified from Cho et al. Proc. Natl. Acad. Sci., USA 100: 10641-10646. Sequences of proposed reactions are indicated by dotted arrows, and the putative precursor p-anol (37) is indicated by brackets.

Despite the growing potential of clinical uses for NDGA (40) and derivatives thereof, its biosynthetic pathway in planta remains unknown, e.g. the actual phenylpropanoid substrate undergoing dimerization has not been determined. Based on phytochemical studies, a provisional pathway has been proposed (14) and is depicted in FIG. 13, starting from the amino acid Phe (1) as the departure point from primary metabolism to generate, through the phenylpropanoid metabolic pathway, an allylphenol such as p-anol (37). The latter could then serve as the (putatively) protein-controlled radical-radical coupling substrate to afford the 9,9'-deoxygenated furanolignan larreatricin (62). Larreatricin (62) could then be envisaged to undergo sequential hydroxylation, with its furano-ring then reduced to afford NDGA (40). In this regard, an enantiospecific larreatricin 3'-hydroxylase from *L. tridentata* was isolated and characterized (14), but whose role (as well as the role of larreatricin (62) itself) in the NDGA (40) biosynthetic pathway remains to be further investigated. In this proposed pathway, deoxygenation of the terminal (9 and 9') carbons of NDGA (40) would be achieved prior to coupling (i.e. with an allyl/propenyl phenol such as p-anol (37) serving as substrate). The allyl/propenyl phenol substrate, upon dimerization, could afford the 8-8' linked, 9,9'-deoxygenated lignans, thus differing from most other lignans which appear to be hydroxycinnamyl alcohol (monolignol)-derived. On the other hand, utilization of monolignols as substrates for coupling with subsequent deoxygenation could not be ruled out, as experimental evidence for either pathway was insufficient.

Several other 9,9'-deoxygenated lignans (FIG. 14) are also of growing medicinal interest due to their potential biological activities, again emphasizing the need to fully establish their biosynthetic pathways in planta. These include: the cancer cell pro-apoptotic licarin A (64) from *Machilus thunbergii* (15) and *Aristolochia pubescens* (16) the anti-Chagasic (17) (−)-grandisin (65) from *Litsea grandis* (18) and *Piper solmsianum* (19), as well as the antioxidant gomisin A (66) from *Schizandra chinensis*, a plant used in traditional Chinese medicine to protect the liver (20, 21). In a manner analogous to NDGA (40), all of these 9,9'-deoxygenated lignans can be envisaged to be biosynthesized from allyl/propenyl phenol monomers bearing different ring substitution patterns; these would undergo regio- and/or enantio-specific dimerization to afford the lignan carbon skeleta, with further peripheral ring modifications (e.g. hydroxylation, O-methylation, or methylenedioxy-bridge formation).

Allyl/propenyl phenols have also attracted much interest, as monomers, due to their flavor/fragrance properties (22), as well as their potential uses as antimicrobials. Eugenol (33), the most abundant natural allylphenol, is present in several commercially important spices, e.g. cloves and cinnamon. Eugenol (33) has antimicrobial activity against many pathogenic bacteria, fungi and nematodes ((23) and references therein), while being classified as GRAS (Generally Recognized As Safe) by the U.S. Food and Drug Administration for its use as a flavoring agent. Anethole (38) is a major component of anise oil and is used as a flavoring/perfume agent, whereas the regioisomer methylchavicol (32) is present in the essential oil of several herbs like tarragon, and has acaricidal properties (24).

The biosynthetic pathway leading to these monomeric C-9 deoxygenated phenylpropanoids was recently elucidated in basil (*Ocimum basilicum*) and *petunia* (*Petunia hybrida*). It was established that hydroxycinnamyl alcohol esters could serve as substrates for regiospecific NADPH-dependent reductases that catalyze their conversion into allyl/propenyl phenols; i.e. p-coumaryl acetate (48) and p-coumaryl coumarate (50) can be transformed into chavicol (31) and/or p-anol (37), while coniferyl acetate (48) can be converted into eugenol (33) and/or isoeugenol (39) (FIG. 15A) (25, 26). These NAD(P)H-dependent reductases bear highest amino acid homology (TABLES 1a, 1b) to members of the PIP family of enzymes that we have previously extensively characterized, namely pinoresinol-lariciresinol, isoflavone, and phenylcoumaran benzylic ether reductases (27-310.)

Materials and Methods:

Materials. All solvents used, either HPLC or reagent grade, were purchased from Mallinckrodt Baker (Phillipsburg, N.J.). All other chemicals were purchased from Sigma-Aldrich (St. Louis, Mo.). Creosote bush (*Larrea tridentata*) plants were grown from seed (Plants of the Southwest, Santa Fe, N.M.) and maintained in Washington State University greenhouse facilities until required, as in (14).

Instrumentation. $^{1}H$ and $^{13}C$ NMR spectra were acquired on a Varian Mercury 300 spectrometer. Electrostatic ionization mass spectrometry (EIMS) was carried out on an Integrity LC/MS System (Waters, Milford, Mass.) using He as carrier gas and ion source temperature of 205° C. Reversed-phase HPLC analyses employed a Waters Alliance 2690 HPLC system equipped with UV-Vis diode-array detection set at 280 nm, under flow rate of 1 ml $min^{-1}$, linear gradient solvent system A:B ($CH_3CN$-3% HOAc in $H_2O$), 10 to 70% A in 40 min, 100% A from 41 to 43 min, then to 10% A at 44 min, 60 min total run time. Separations used a Symmetry Shield $RP_{18}$ column (Waters; 150×3.9 mm inner diameter, 5 μm particle size).

Chemical syntheses. Chavicol (31), p-coumaryl acetate (48) and p-coumaryl coumarate (50) were prepared as described in (25). Coniferyl acetate (49): Coniferyl alcohol (21, 90 mg, 0.5 mmol) was dissolved in pyridine (1 ml) containing a catalytic amount of DMAP (~1 mg), and $Ac_2O$ (1 ml) was added, with the whole left unstirred for 4 h. Next, EtOAc (60 ml) was added and the whole was washed with cold 1% aqueous HCl (3×30 ml), satd $NH_4Cl$ (5×30 ml), brine (2×30 ml), dried over $Na_2SO_4$ and concentrated in vacuo. The resulting oil was dissolved in pyrrolidine (1 ml) and kept unstirred for 15 min, after which EtOAc (50 ml) was added, with the whole washed with cold 3% aqueous HCl (2×25 ml), satd $NH_4Cl$ (6×25 ml), brine (2×25 ml), dried over $Na_2SO_4$ and concentrated in vacuo. The resulting material was purified by silica gel column chromatography using silica gel pre-treated with EtOH-HOAc (99:1), then reequilibrated in $CHCl_3$ and eluted with $CHCl_3$-EtOAc (3:1) to afford coniferyl acetate (49, 61.8 mg, 0.28 mmol, 56% overall yield), with spectroscopic data in agreement with (26).

Isolation of LtPLRh1 (LtCES1, PLRh_Lt1), LtPLRh2 (LtCES2, PLRh_Lt2), Lt_PLR13 (LtCES3), LtCES4, LtCES5 and LtCES6. A cDNA library was constructed from *L. tridentata* leaf tissue and plated for primary screening. Plates were blotted onto Magna Nylon membranes circles (Micron Separation Inc.), which were then allowed to air dry. The membranes were placed between two layers of Whatman 3MM Chr paper, and cDNA library phage DNA was fixed to the membranes with denaturing in one step by 3 min autoclaving at 100° C. with fast exhaust. The membranes were next washed for 60 min, with gentle shaking at 45° C., with 6× standard saline citrate (SSC) and 0.1% SDS, then prehybridized for 5 h with gentle shaking at 58° C. in preheated 6×SSC, 0.5% SDS, and 5× Denhardt's reagent (prehybridization solution, 200 ml). The $^{32}P$-labeled probe (Fi_PlrII) was denatured (100° C., 10 min), quickly cooled on ice (15 min), and added to fresh preheated hybridization solution (120 ml at 47° C.). The prehybridized membranes were next added to the dish, which was covered with plastic -wrap, and hybridization was performed for 31 h at 47° C. with gentle shaking. The membranes were then washed in 4×SSC and 0.5% SDS (250 ml) for 10 min at RT, transferred to preheated 2×SSC and 0.5% SDS (250 ml), and incubated at 47° C. for 15 min with gentle shaking. After removal from the dish and wrapping in plastic wrap to prevent drying, the membranes were finally exposed to Kodak X-OMAT AR film for 46 h at −80° C. between intensifying screens. Fifteen positive plaques were purified through another round of screening under the same conditions as above. Nine purified cDNA clones were rescued from the phage following Stratagene's in vivo excision protocol. The cDNAs rescued in pBluescript SK(−) were sequenced using T3 and T7 primers, and particular cDNA clones showed high homology (e.g., some with >60% identity) to known PLR-reductases (TABLE 1C), thus being named LtPLRh1 (LtCES1, PLRh_Lt1), LtPLRh2 (LtCES2, PLRh_Lt2), and Lt_PLR13 (LtCES3). The genes (e.g., LtPLRh1 (LtCES1)) were amplified with a sticky BamH I 5'-terminal end and a sticky EcoR I 3'-terminal end. After ligation to the BamH I and EcoR I pre-digested pGEX-4T-1 plasmid vector, the respective expression construct (e.g., LtPLRh1/pGEX-4T-1) was transformed into TOP10 cells for sequence verification.

The three clones LtCES4, LtCES5 and LtCES6 were isolated using degenerate primers designed from regions of homology between LtCES1 and LtCES2. They are about 88% similar and 75% identical to LtCES1 at the protein seqeunce level (See Tables 1D, E and F).

Figure 16:
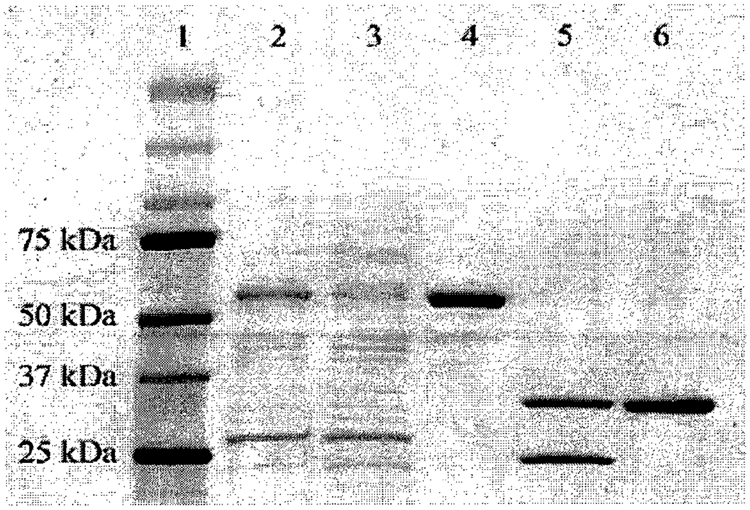
FIG. 16 shows purification of LtPLRh1 (LtCES1) from a heterologous *E. coli* bacterial system. Lane 1 shows molecular weight markers, lane 2 shows the crude enzyme extract, lanes 3 and 4 show the GST-affinity purification flow-through and fusion protein eluate, respectively, lane 5 shows the resulting mixture after thrombin incubation, and lane 6 shows the final LtPLRh1 (LtCES1) (34 kDa) purified to apparent homogeneity.

Protein Purification. For LtPLRh1 (LtCES1) expression, for example, purified plasmid DNA, LtPLRh1 (LtCES1)/pGEX-4T-1, was transformed into BL21-CodonPlus® (DE3)-RIL *E. coli* cells according to Stratagene's instructions. Transformed cells (250 ml cultures) were grown in Fernbach flasks at 37° C. with shaking (230 rpm) to $OD_{600}$~0.8-1.0 in LB medium supplemented with 100 μg/ml carbenicillin. Cell suspensions were cooled down on ice with gentle agitation for 20 min and induced with IPTG to a final concentration of 0.5 mM. After 24 h incubation at 20° C. (230 rpm), cells were pelleted by centrifugation (3500×g, 25 min, 4° C.) and stored at −80° C. for at least 2 h to facilitate cell lysis. Pellets were thawed at 37° C. for 5 min and resuspended in 25 ml of BugBuster® Protein Extraction Reagent (Novagen) containing 25 μl Benzonase® nuclease (25 units/μl) and 2 μl rLysozyme™ solution (30 kilounits/μl). After incubation at room temperature for 5 min with gentle shaking, the cell suspension was left on ice for 30 min and subsequently centrifuged (16,000×g, 25 min, at 4° C.) to remove cell debris. After filtration (0.45 μm), the supernatant (25 ml)

was incubated for 15 min at room temperature with Glutathione Sepharose 4B resin (1 ml bed volume, GE Healthcare) pre-equilibrated with 20 ml 1× PBS buffer (140 mM NaCl, 2.7 mM KCl, 10.1 mM $Na_2HPO_4$, 1.8 mM $KH_2PO_4$, pH adjusted to 7.3), with the whole transferred to a Poly-Prep® Column (Bio-Rad), which was then washed with 50 ml of ice-cold 1× PBS buffer. The bound material was eluted with 10 mM glutathione in 50 mM Tris-HCl, pH 8.0. Fractions containing the GST-fusion protein (identified by SDS-PAGE analysis) were combined, and thrombin protease was added (10 cleavage units per mg of fusion protein) with incubation at RT for 12 h. Once digestion was complete, glutathione was removed by extensive dialysis (1000 volumes) against 1× PBS buffer, followed by removal of GST-tag on Glutathione Sepharose 4B. The LtPLRh1 (LtCES1), purified to apparent homogeneity, was eluted in the flow-through volume of the column (FIG. 16).

Site-directed mutagenesis generation of LtPLRh1 (LtCES1) _K133A. Originally, the LtPLRh1 (LtCES1)/pGEX-4T-1 constructed plasmid DNA was maintained in *E. coli* TOP 10 cells ($dam^+/dcm^+$ strain). Using plasmid DNA isolated from the *E. coli* strain as a template, site-directed mutagenesis of LtPLRh1 (LtCES1) was carried out using a QuickChange® XL Site-Directed Mutagenesis Kit (Stratagene) with the primers 5'-CTACATTTGAAATGGCGGCTCAACTCCGCAG-3' (SEQ ID NO:13) and 5'-CTGCGGAGTTGAGCCGCCATTTCAAATGTAG-3' (SEQ ID NO:14) for K133A single point mutation. The PCR reaction was performed following the manufacturer's instructions, with 7-min extension cycles at 68° C. In order to remove the parental DNA template, PCR products were subjected to Dpn I restriction enzyme digestion reaction and then directly transformed into *E. coli* TOP10 cells. After selection on LB medium supplemented with 100 μg/ml carbenicillin, positive transformants were subjected to DNA sequencing with pGEX vector specific primers (sense: 5'-GGGCTGGCAAGCCACGTTTGGTG-3' (SEQ ID NO:15); antisense: 5'-CCGGGAGCTGCATGTGTCAGAGG-3' (SEQ ID NO:16)). After sequence confirmation, the LtPLRh1 (LtCES1)/pGEX-4T-1 vector construct containing the K133A point mutation was used for transformation of BL21-CodonPlus® (DE3)-RIL *E. coli* cells (Stratagene), with the positive clone designated as the LtPLRh1_K133A mutant. The LtPLRh1_K133A mutant protein was heterologously expressed, purified and assayed following the procedure described above for the wild type LtPLRh1 (LtCES1) protein.

Enzymatic assays. All assays were performed at 30° C. in 250 μl of the corresponding buffered solutions (at 100 mM buffer concentration) containing 0.5 μg LtPL LtPLRh1 (LtCES1) Rh1 and 1.0 mM NADPH, and were terminated by addition of 25 μl glacial acetic acid and freezing. Chavicol/eugenol synthase activity assays were individually performed in Bis-Tris propane buffer (pH 7.55) containing 0.4 mM p-coumaryl coumarate (50), p-coumaryl acetate (48) or coniferyl acetate (49). Assays were carried out for 1 to 120 min; controls included both boiled enzyme extracts and omission of substrates.

pH optima: Assays were carried out for 30 min at each pH (MES at pH 5.35, 5.73, 5.97, 6.39 and 6.83, Bis-Tris propane at pH 6.5, 7.0, 7.55, 8.03, 8.53, 9.0 and 9.59, AMPD at pH 8.37, 9.02, 9.49, 9.82, 10.16, 10.38), and contained 1.0 mM p-coumaryl coumarate (50), coniferyl acetate (49), or 0.5 mM p-coumaryl acetate (48).

Kinetic parameters ($K_m$ and $V_{max}$): Three sets of triplicate assays were carried out for 5 min in Bis-Tris propane buffer at pH 7.55, and contained different concentrations of p-coumaryl acetate (48), p-coumaryl coumarate (50) or coniferyl acetate (49) (3.2 μM-1 mM).

Inhibition studies: Assays were carried out in duplicate for 5 min in Bis-Tris propane buffer at pH 7.55, and contained 0.2 mM p-coumaryl acetate (48) or coniferyl acetate (49), and different concentrations of p-coumaryl alcohol (19), coniferyl alcohol (21), p-coumaric acid (4), chavicol (31) or eugenol (33) (0-0.5 mM).

Results and Discussion:

This Example 1 discloses the the isolation and characterization of six *L. tridentata* PIP reductase homologues (LtPLRh1 (LtCES1, PLRh_Lt1), LtPLRh2 (LtCES2, PLRh_Lt2), Lt_PLR13 (LtCES3), LtCES4, LtCES5 and LtCES6) (SEQ ID NOS:2, 4 6, 18, 20 and 22. respectively) that catalyze the C-7 reduction of p-coumaryl and coniferyl alcohol esters (48-50) (TABLES 1A, 1B and 1C) (FIG. 7), in the presence of NADPH or NADH, to form chavicol (31) and eugenol (33), respectively. In particular the *L. tridentata* PIP reductase homologue (LtPLRh1 (LtCES1)) has been characterized in most detail, and efficiently catalyzes the C-7 reduction of p-coumaryl and coniferyl alcohol esters, in the presence of NADPH or NADH, to form chavicol and eugenol, respectively. Based on previously reported kinetic parameters for the recently characterized homologues in basil and *petunia* (26), this enzyme appears to be over 100-fold more efficient for eugenol (33) formation. (LtCES1) also reduces p-coumaryl alcohol esters (48/50) to afford chavicol (31) with comparable substrate affinity and efficiency. Amino acid homologies between LtPLRh1 (LtCES1, PLRh_Lt1) and its basil/*petunia* homologues are relatively low within the PIP enzyme family, with the two latter enzymes being closer homologues of bona fide PLRs from other organisms than LtPLRh1 (LtCES1).

TABLE 1A

Alignment of amino acid sequences of LtPLRh1 (SEQ ID NO:2), LtPLRh2 (SEQ ID NO:4) and Lt__PLR13 (SEQ ID NO:6) to homologues FiPLR1, ObEGS1 and PhIGS1. The putative NADPH-binding domain is indicated by a box, and a conserved Lys residue targeted for site-directed mutagenesis ($K^{133}$ in LtPLRh1 and 2) is indicated by arrows.

| | | |
|---|---|---|
| PLRh_Lt1 | 1 | ---MAQKSKILIIGGTGYIGKFVVEASAKAGRPTFALVRESTV-SDPVKGKLIANFKNLG |
| PLRh_Lt2 | 1 | ---MAQKSKILIIGGTGYIGKSIVEASAKAGHPTFALVRESTV-FHHVKGKLVKNFKDLG |
| Lt_PLR13 | 1 | ----MCKSKVLIVGGTGYLGRRLVKASLALGHETYVLHRAEIG-VDIEKVQMLLSFKEQG |
| PLR_Fi1 | 1 | ----MGKSKVLIIGGTGYLGRRLVKASLAQGHETYILHRPEIG-VDIDKVEMLISFKMQG |
| ObEGS1 | 1 | MEENGMKSKILIFGGTGYIGNHMVKGSLKLGHPTYVFTRPN-----SSKTTLLDEFQSLG |
| PhIGS1 | 1 | --MTTGKGKILILGATGYLGKYMVKASISLGHPTYAYVMPLKKNSDDSKLQLLKEFESLG |

TABLE 1A-continued

Alignment of amino acid sequences of LtPLRh1 (SEQ ID NO:2), LtPLRh2 (SEQ ID NO:4) and Lt_PLR13 (SEQ ID NO:6) to homologues FiPLR1, ObEGS1 and PhIGS1. The putative NADPH-binding domain is indicated by a box, and a conserved Lys residue targeted for site-directed mutagenesis ($K^{133}$ in LtPLRh1 and 2) is indicated by arrows.

```
PLRh_Lt1    57 VNILHGDLNDHESLVKAIKKVDVVISTVG-----NFQIADQVKIIAAIKAAGNVKRFFPS
PLRh_Lt2    57 VNLVHGDINDHDSLLKAIKQVDVVFSTLG-----HHHIGEQHKVIAAIKEAGNVKRYFPS
Lt_PLR13    56 ATLVPGSFADHQSLVNAVKLVDVVICAISGVHIRSHHILLQLKLVDAIKEAGNVKRFLPS
PLR_Fi1     56 AHLVSGSFKDFNSLVEAVKLVDVVISAISGVHIRSHQILLQLKLVEAIKEAGNVKRFLPS
ObEGS1      56 AIIVKGELDEHEKLVELMKKVDVVISALAFP-----QILDQFKILEAIKVAGNIKRFLPS
PhIGS1      59 VTIFYGELSEHDKLVAVFKEVDIVISTLAVP-----QYLEQLKVIEAIKEAGNIKRFVPS

                                           ↓
PLRh_Lt1   112 EFGNDVDRTH--AVEPAKSTFEMKAQLRRTIEAEGIPYTYVSSNFFAGYFLPVLGQVGVT
PLRh_Lt2   112 EFGNDVDRSH--AVDPVKSAYRTKAQIRRAIEAEGIPHTYVSCNFFAGYFLPTLVQLEVT
Lt_PLR13   116 EFGTDPARMEN-AMEPGRVTFDDKMVVRKAIQDAGIPYTYVSANCFAGYFLGGLCQPGSI
PLR_Fi1    116 EFGMDPAKFMDTAMEPGKVTLDEKMVVRKAIEKAGIPFTYVSANCFAGYFLGGLCQFGKI
ObEGS1     111 DFGVEEDRIN--ALPPFEALIERKRMIRRAIEEANIPYTYVSANCFASYFINYLLRP---
PhIGS1     114 EFGNEVDRVR--ALPRFQAVLDNKKKIRRATEAAGIPFTFVSANSLTAYFVDYLLHP---
                                           ↑

PLRh_Lt1   170 APPRDKVTILGDGNQKAVFNKKDDIGTYTIRAADDPRTLNKILYIRPPRNTYSMNELVAL
PLRh_Lt2   170 APPRDKVTILGDGNKKAIFNKEDDIATYAIRAVDDPRTLNKISVIRTPKNTYTMNELVAL
Lt_PLR13   175 IPSTEFVLLLGDGTKKAIYVDEHDIAMYTIKAIDDPRTLNKTVYIRPPVNILSQLEVVKI
PLR_Fi1    176 LPSRDFVIIHGDGNKKAIYNNEDDIATYAIKTINDPRTLNKTIYIS PKNILSQREVVQT
ObEGS1     166 YDPKDEITVYGTGEAKFAMNYEQDIGLYTIKVATDPRALNRVVIYRPSTNIITQLELISR
PhIGS1     169 RQKSEQVTIYGSGDAKAVLNYKEDVAAYTIKAADDPRAANRVLIIKPPKNIVSQLDLVSS

PLRh_Lt1   230 WEKKIGKTLEKTYVPEEQLLKNIQEAEIPWNVVLAINHSVFVKGDHTNFAIKPSFGVEAS
PLRh_Lt2   230 WEKKIGKSLEKIYVPEDQILKNIQESPFSTQVMLSINHSVFVKGDQTNFDIDPSFGVEAT
Lt_PLR13   235 WEKLIGKELQKTSISKEDFLESMKGQNYAEQVGLTHYYHVCYEGCLANFEIGEEG-VEAT
PLR_Fi1    236 WEKLIGKELQKITLSKEDFLASVKELEYAQQVGLSHYHDVNYQGCLTSFEIGDE--EEAS
ObEGS1     226 WEKKIGKKFKKIHVPEEEIVALTKELPEPENIPIAILHCLFIDGATMSYDFKEN-DVEAS
PhIGS1     229 WEKTTGSTLKMTHISEQEIIKLSESINFPENIHASILHNIFIAGAQLSFELTQDHDLEAS

PLRh_Lt1   290 ELYPDVKYTTVEEYLSQFV----------------
PLRh_Lt2   290 ELYPDVNYTTVEEYLDQFV----------------
Lt_PLR13   294 QLYPEIKYVTVEQYMKRYL----------------
PLR_Fi1    294 KLYPEVKYTSVEEYLKRYV----------------
ObEGS1     285 TLYPELKFTTIDELLDIFVHDPPPPASAAF-----
PhIGS1     289 ELYPNYNYTSVDEYLKICLVNPPKPKLATYAQPST
```

TABLE 1B

Percentages of amino acid similarity and identity among LtPLRh1 (LtCES1), LtPLRh2 (LtCES2),, Lt_PLR13 (LtCES3),, FiPLR1, ObEGS1 and PhIGS1.

| | Identity | | | | |
|---|---|---|---|---|---|
| Simirarity | PLRh_Lt2 | Lt_PLR13 | PLR_Fi1 | ObEGS1 | PhIGS1 |
| PLRh_Lt1 | 88.0 | 64.1 | 65.1 | 63.7 | 62.2 |
| | 78.2 | 46.8 | 48.9 | 44.4 | 42.0 |
| PLRh_Lt2 | | 63.8 | 64.7 | 61.5 | 59.8 |
| | | 45.5 | 48.9 | 41.0 | 40.8 |
| Lt_PLR13 | | | 86.5 | 59.6 | 59.4 |
| | | | 74.4 | 38.8 | 38.0 |
| PLR_Fi1 | | | | 61.1 | 58.5 |
| | | | | 39.9 | 38.4 |
| ObEGS1 | | | | | 70.0 |
| | | | | | 50.5 |

TABLE 1C

Percentages of nuclei acid (cDNA) similarity and identity among LtPLRh1 (LtCES1),, LtPLRh2 (LtCES2),, Lt__PLR13 (LtCES3), FiPLR1, ObEGS1 and PhIGS1.

| | Identity | | | | |
|---|---|---|---|---|---|
| Simirarity | PLRh__Lt2 | Lt__PLR13 | PLR__Fi1 | ObEGS1 | PhIGS1 |
| PLRh__Lt1 | 81.2 | 59.0 | 60.1 | 56.4 | 55.6 |
| (LtCES1) | 81.2 | 58.3 | 58.8 | 54.9 | 54.5 |
| PLRh__Lt2 | | 58.4 | 58.6 | 55.0 | 55.5 |
| (LtCES2) | | 57.6 | 57.2 | 53.4 | 54.6 |
| Lt__PLR13 | | | 73.6 | 58.0 | 54.9 |
| (LtCES3) | | | 73.4 | 54.7 | 53.1 |
| PLR__Fi1 | | | | 56.2 | 56.1 |
| | | | | 53.2 | 53.5 |
| ObEGS1 | | | | | 61.9 |
| | | | | | 61.3 |

TABLE 1D

Comparison of exemplary LtCES (LtCES1, LtCES2, LtCES4, LtCES5 and LtCES6) Peptides (SEQ ID NOS:2, 4, 18, 20 and 22, respectively).

```
LtCES1     1 MAQKSKILIIGGTGYIGKFVVEASAKAGRPTFALVRESTVSDPVKGKLIANFKNLGVNIL
LtCES2     1 MAQKSKILIIGGTGYIGKSIVEASAKAGHPTFALVRESTVPHHVKGKLVKNFKDLGVNLV
LtCES4     1 MAQKEKILIIGGTGYIGKSIVEASAKAGHPTFALVRESTVPHHVKGKLVKNFKDLGVNLV
LtCES5     1 MAQKSKILIIGGTGYIGKSIVEASAKAGHPTFALVRESTVPHHVKGKLVKNFKDLGVNLV
LtCES6     1 MAQKSKILIIGGTGYIGKSIVEASAKAGHPTFALVRESTVPHHVKGKLVKNFKDLGVNLV

LtCES1    61 HGDLNDHESLVKAIKKVDVVISTVGNFQIADQVKIIAAIKAAGNVKRFFPSEFGNDVDRT
LtCES2    61 HGDINDHDSLLKAIKQVDVVFSTLGHHHIGDQHKVIAAIKEAGNVKRYFPSEFGNDVDRS
LtCES4    61 HGDIMDHESLLKAIKQVDVVFSTLGHHHIGDQHKVIAAIKEAGNVKRYFPSEFGNDVDRS
LtCES5    61 HGDINDHESLLKAIKQVDVVFATLGHHHIGDQHKVIAAIKEAGNVKRYFPSEFGNDVDRA
LtCES6    61 HGDINDHESLLKAIKQVDVVFSTLGHHHIGDQHKVIAAIKEAGNVKRYFPSEFGNDVDRS

LtCES1   121 HAVFPAKSTFEMKAQLRRTIEAEGIPYTYVSSNFFAGYFLPVLGQVGVTAPPRDKVTILG
LtCES2   121 HAVDPVKSAYRTKAQIRRAIEAEGIPHTYVSCNFFAGYFLPTLVQLEVTAPPRDKVTILG
LtCES4   121 HAVDPVKSAYRTKAQIRRAIEAEGIPHTYVSCNFFAGYFLPTLVQLEVTAPPRDKVTILG
LtCES5   121 HAVDPVKSAYRTKAQIRRAIEAEGIPHTYVSCNFFAGYFLPTLVQLEVTAPPRDKVTILG
LtCES6   121 HAVDPVKSAYRMKAQIRRAIEAEGIPHTYVSCNFFAGYFLPTLVQLEVTAPPRDKVTILG

LtCES1   181 DGNQKAVFNKEDDIGTYTIRAADDPRTLNKILYIRPPRNTYSMNELVALWEKKIGKTLEK
LtCES2   181 DGNKKAIFNKKDDIATYAIRAVDDPRTLNKISYIRTPKNTYTMNELVALWEKKIGKSLEK
LtCES4   181 DGNKKAIFNKEDDIATYAIRAVDDPRTLNKILYIRTPKNTYTMNELVALWEKKIGKSLEK
LtCES5   181 DGNKKAIFNKEDDIATYAIRAVDDPRTLNKILYIRTPKNTYTMNELVALWEKKIGKSLEK
LtCES6   181 DGNKKAIFNKKDDIATYAIRAVDDPRTLNKILYIRTPKNTYTMNELVALWEKKIGKSLEK

LtCES1   241 TYVPEEQLLKNIQEAEIPWNVVLAINHSVFVKGDHTNFAIKPSFGVEASELYPDVKYTTV
LtCES2   241 IYVPEDQILKNIQESPESTQVMLSINHSVFVKGDQTNFDIDPSFGVEATELYPDVNYTTV
LtCES4   241 IYVPEDQILKNIQESPFSTQVMLSINHSVFVKGDQTNFDIDLSFGVEATELYPDVNYTTV
LtCES5   241 IYVPEDQILKNIQESPFSTQVMLSINHSVFVKGDQTNFDIDPSFGVEATELYPDVNYTTV
LtCES6   241 IYAPEDQILKNIQESPESTQVMLSINHSVFVKGDQTNFDIDLSFGVEATELYPDVNYTTV

LtCES1   301 EEYLSQFV
LtCES2   301 EEYLDQFV
LtCES4   301 EEYLDQFV
LtCES5   301 EEYLDQFV
LtCES6   301 EEYLDQFV
```

TABLE 1E

Similarity and Identity based on Peptide Sequence (%)

| | LtCES2 | LtCES4 | LtCES5 | LtCES6 |
|---|---|---|---|---|
| LtCES1 | 88.0 | 88.3 | 88.0 | 88.0 |
| | 78.2 | 78.9 | 78.6 | 78.6 |
| LtCES2 | | 99.7 | 99.4 | 98.7 |
| | | 99.4 | 99.0 | 98.4 |
| LtCES4 | | | 99.7 | 99.0 |
| | | | 99.7 | 99.0 |
| LtCES5 | | | | 99.4 |
| | | | | 99.4 |

TABLE 1F

Similarity and Identity based on cDNA Sequence (%)

| | LtCES2 | LtCES4 | LtCES5 | LtCES6 |
|---|---|---|---|---|
| LtCES1 | 81.2 | 81.3 | 81.2 | 81.4 |
| | 81.2 | 81.3 | 81.2 | 81.4 |
| LtCES2 | | 99.6 | 99.4 | 99.4 |
| | | 99.6 | 99.4 | 99.4 |
| LtCES4 | | | 99.4 | 99.4 |
| | | | 99.4 | 99.4 |
| LtCES5 | | | | 99.6 |
| | | | | 99.6 |

In initial studies of lignan biosynthesis in *Larrea tridentata*, two homologues (>60% identity) of a *Forsythia inter-*

*media* pinoresinol-lariciresinol reductase (FiPLR1) were isolated from a creosote bush cDNA library using a PLR probe (Fi_PlrII). These were provisionally annotated as LtPLRh1 (LtCES1) and 2, respectively. LtPLRh1 was successfully expressed, in soluble form, in an *E. coli* heterologous system as a 60 kDa GST fusion protein which, after purification by affinity to a Glutathione Sepharose 4B resin, had the 26 kDa *Schistosoma japonicum* GST protein cleaved by incubation with thrombin protease. Further purification to apparent homogeneity using Glutathione Sepharose 4B resin afforded the “native” 34 kDa LtPLRh1 in the flow-through eluent (FIG. 16). LtPLRh2 has >80% identity to LtPLRh1.

LtPLRh1 (PLRh_Lt1), LtPLRh2 (PLRh_Lt2), and Lt_PLR13 are homologues of members of the “PIP” family of aromatic reductases (pinoresinol-lariciresinol, isoflavone and phenylcoumaran benzylic ether reductases (TABLE 1A) that Applicants have extensively characterized (27-32). A fourth class of these proteins is able to catalyze the formation of eugenol (33) and isoeugenol (39) from coniferyl acetate (49) (i.e. the recently described ObEGS1 and PhIGS1 from basil and *petunia* (26), respectively), whereas another study indicated that basil cell-free extracts were able to additionally convert p-coumaryl alcohol esters (48/50) into chavicol (31) (25). Thus, all of these enzymes catalyze the NADPH-dependent reductions of the phenylpropanoid-derived moieties of various phenylpropanoids in either a regio- or enantiospecific manner (FIG. 15A-D)). Of these, the creosote bush homologues LtPLRh1 and 2 are 88% similar and 78% identical to each other, as well as being 64% similar and 49% identical to the bonafide PLR from *F. intermedia*. On the other hand, they only have about 60% similarity/40% identity to the enzymes found in *petunia* and basil. The latter two are, in turn, 56-58% homologous/38-40% identical to FiPLR (TABLE 1B). A brief phylogenetic study of several proteins bearing homology to LtPLRh1 indicates closest homology to several PLR (e.g. from *Thuja plicata*), PCBER (e.g. from *Pinus taeda*), IFR (e.g. from *Medicago*) and leucoanthocyanidin reductases (e.g. from *Vitis vinifera*), with ObEGS1 and PhIGS1 clustering closer to bona fide PLRs than LtPLRh1, which clusters closer to more distant PLR/PCBER homologues (FIG. 10).

Several members of the PIP enzyme family have been previously characterized, with three-dimensional structures determined by X-ray crystallography and some of the catalytically relevant residues assigned (31). The phosphate-binding sequence of the well-known dinucleotide-binding site (Rossmann fold) could be readily assigned to GxxGxxG in the N-terminal 11-17 amino acids of LtPLRh1 and 2, these being homologous to residues 10-16 in FiPLR1, 14-20 in EGS1 and 12-18 in IGS1, respectively (TABLE 1A). In addition, $Tyr^{15}$ and $Ile^{16}$ (Leu in FiPLR1 and PhIGS1), which were proposed in (31) to interact with the pyrophosphate group of NADPH, are present in LtPLRh1, as are $Ser^{41}$ and $Arg^{137}$ which were proposed to bind to the O-3' of adenosine and O-3' of the ribose, respectively. Three other conserved residues further implicated in NADPH binding are also present in LtPLRh1; $Lys^{45}$ involved in the formation of a salt bridge to the 2'-phosphate of NADPH, as well as $Arg^{36}$ and $Phe^{155}$, which are thought to stack against the nicotinamide moiety of the cofactor. More importantly, a Lys residue that is conserved among all PIP reductases, and which is thought to be involved in catalysis as a general base, is also present in LtPLRh1 ($K^{133}$ in LtPLRh1 and 2, $K^{132}$ in ObEGS1, $K^{135}$ in PhIGS1, and $K^{138}$ and $K^{139}$ in PLR from *T. plicata* and *F. intermedia*, respectively).

The biochemical function of LtPLRh1 was initially elusive, as in vitro studies showed at best marginal activity towards pinoresinol (54), larreatricin (62), nectandrin B (72), licarin A (64), dehydrodiconiferyl alcohol (56), and the commercially available isoflavones genistein (73) and biochanin A (74). Thus, LtPLRh1 did not function as an efficient PLR, PCBER or IFR with the substrates tested.

Recently, p-coumaryl and coniferyl alcohol esters (e.g. 48-50) were shown to be substrates for the crucial C9 deoxygenation leading to the corresponding allyl/propenyl phenols (25, 26) by the aforementioned PIP-homologues ObEGS1 and PhIGS1 (26), i.e. to afford chavicol (31), eugenol (33) and/or isoeugenol (39), respectively. Allyl/propenyl phenols have been proposed to serve as substrates for oxidative coupling reactions that lead to 9,9'-deoxygenated lignans such as, in the creosote bush, larreatricin (62) and NDGA (40) (14), i.e. deoxygenation of the terminal carbons of these lignans was achieved at a monomeric stage, prior to coupling. Thus, Applicants determined whether LtPLRh1 showed similar catalytic properties, even though it has relatively low homology (within the PIP reductases) to either ObEGS1 or PhIGS1.

The potential substrates, p-coumaryl acetate (48), p-coumaryl coumarate (50) and coniferyl acetate (49) were synthesized from commercial precursors by routes previously used in our laboratory, as were the chavicol (31) and p-anol (37) used as chromatographic/spectroscopic standards (25, 33). Eugenol (33) and isoeugenol (39), the putative products derived from coniferyl alcohol esters, were both commercially available.

Upon incubation of these potential substrates in the presence of NADPH (or NADH) as a hydride donor, LtPLRh1 was able to efficiently convert each substrate into the corresponding allylphenols, chavicol (31) and eugenol (33) (FIG. 15A). LtPLRh1 has a pH optimum of ~7.5, with apparent kinetic parameters for substrates 48-50 summarized in TABLE 2. The observed reduction of p-coumaryl (48/50) and coniferyl (49) alcohol esters to afford a deoxygenated side-chain is therefore analogous to the one recently described in basil (25, 26), which accumulates allylphenols in its essential oils, thus indicating a common pathway for their production in planta.

TABLE 2

LtPLRh1 apparent kinetic parameters measured towards p-coumaryl coumarate (50), p-coumaryl acetate (48) and coniferyl acetate (49).

| | Substrate | $K_m$ (μM) | $V_{max}$ (pkat/μg) | $k_{cat}$ ($s^{-1}$) | $k_{cat}/K_m$ ($M^{-1}$ $s^{-1}$) |
|---|---|---|---|---|---|
| LtPLRh1 | p-coumaryl coumarate (50) | 210 | 75 | 2.55 | 12,000 |
| | p-coumaryl acetate (48) | 350 | 200 | 6.80 | 19,500 |
| | coniferyl acetate (49) | 290 | 190 | 6.46 | 22,000 |
| ObEGS1 | coniferyl acetate (49) | 5,100 | 20 | 0.7 | 160 |
| PhIGS1 | coniferyl acetate (49) | 1,600 | 7 | 0.3 | 136 |

Values for ObEGS1 and PhIGS1 are as reported in (26) for coniferyl acetate (49).

As with other PIP reductases (34), Applicants were able to observe some substrate versatility with LtPLRh1 regarding the phenolic substitution patterns, as well as the carboxylic leaving group and the enzymatic cofactor. In this aspect, LtPLRh1 differs from the reductases reported in basil and *petunia*, which apparently can only utilize NADPH and coniferyl acetate (49) to form eugenol (33) and isoeugenol (39), respectively (26). This observed substrate versatility is, though, in agreement with results obtained with a Thai basil enzymatic preparation (25), where both p-coumaryl acetate (48) and coumarate (50) served as substrates with NADPH and NADH both serving as cofactors. Additionally, recombinant LtPLRh1 apparently reduces coniferyl acetate (49) >100-fold more efficiently than its reported homologues in basil and *petunia*, with comparable efficacies for p-coumaryl alcohol esters (48/50) (TABLE 2).

Applicants were unable to observe traditional Michaelis-Menten kinetic behavior with LtPLRh1, with substrate concentrations above those at activity maxima (~0.2-0.4 mM) leading, in our assay system, to diminished LtPLRh1 activity (i.e. substrate inhibition). This kinetic behavior had been observed previously with PLR (34), and LtPLRh1 inhibition seems to be caused by presence of substrate, and not enzymatic products (chavicol (31) or eugenol (33)), or hydrolysis side-products (p-coumaryl alcohol (19), coniferyl alcohol (21) or p-coumaric acid (4)); thus the kinetic parameters reported herein are apparent values. As previously described in (25), the monolignol esters (48-50) used as substrates are unstable in aqueous solutions, with hydrolysis side-reaction products (i.e. p-coumaryl and coniferyl alcohols (19/21), as well as p-coumaric acid (4) in assays including p-coumaryl coumarate (50)) being observed in all assays and negative controls.

Next, it was instructive to investigate the effects of site-directed mutagenesis of LtPLRh1_$K^{133}$, which, as described above, is considered to be involved in general acid/base catalysis. A point mutation of this charged residue to the catalytically inert amino acid alanine (K133A) resulted in abolishment of enzymatic activity. This loss of catalytic efficiency thus again apparently confirms the role of $K^{133}$ in catalysis, possibly as a general base as proposed before with other PIP enzymes, i.e. PLR_Tp1 from *T. plicata* (31), where $K^{138}$ is in proximity to the phenolic substrate, and its Ala substitution leads to enzyme deactivation.

The slightly basic pH optimum for LtPLRh1, along with the inefficiency of Ala133 as a general base that could abstract the substrate phenolic proton, both support the formation of a quinone methide intermediate in the catalytic mechanism (FIG. 15A-C), though this remains to be further examined. Quinone methide intermediates have been implicated in the catalytic mechanism of other PIP reductases, e.g. in [35] and, more recently, in studies of substrate versatility of PLR_Tp1 from *T. plicata*, which uses several p-hydroxylated phenylpropanoid substrates (i.e. pinoresinol (54), medioresinol (69), syringaresinol (70), FIG. 3B, D) but fails to reduce substrates with no free phenolic groups (i.e. sesamin (71), FIG. 15D) (34).

In our previously proposed biosynthetic pathway for NDGA generation (FIG. 13, (14)), the phenylpropanoid pathway, followed by side-chain deoxygenation, affords p-anol (37) as a substrate for protein-controlled radical-radical dimerization to form the 8,8'-coupled lignan, larreatricin (62), which is further modified to form NDGA (40). Here, LtPLRh1 forms chavicol (31), whose side-chain terminal double bond precludes a similar 8,8' radical coupling reaction. The pertinence of these findings to lignan biosynthesis is presently under investigation, in order to elucidate the specific steps leading to the formation of NDGA (40).

Therefor, this Example 1 describes regiospecific NAD(P)H-dependent reductase from *Larrea tridentata*, LtPLRh1, that catalyzes the reduction of p-coumaryl (48, 50) and coniferyl (49) alcohol esters to afford the corresponding allylphenols, chavicol (31) and eugenol (33). The enzyme is homologous to members of the PIP family of reductases, all of which catalyze the reduction of phenylpropanoid-derived side-chains. Site-directed mutagenesis of a catalytically active Lys residue conserved among other PIP homologues has rendered the enzyme ineffective. The LtPLRh1 kinetic parameters measured indicate an enzyme with comparable efficacy relative to other PIP reductases acting on their respective substrates, but >100-fold higher activity than the enzymes reported in basil and *petunia*. The significance of these results, as well as an understanding of the substrate versatilities and the actual biological roles of these enzymes, along with their evolutionary relationships, are currently the target of our investigations.

References Relating to Example 1

[1] S. Arteaga, A. Andrade-Cetto, R. Cárdenas, J. Ethnopharmacol. 98 (2005) 231-239.

[2] V. V. Lia, V. A. Confalonieri, C. I. Comas, J. H. Hunziker, Mol. Phylogenet. Evol. 21 (2001) 309-320.

[3] T. J. Mabry, D. R. DiFeo Jr., M. Sakakibara, C. F. Bohnstedt Jr., D. Seigler, in: T. J. Mabry, J. H. Hunziker, and D. R. DiFeo Jr., (Eds.), Creosote Bush. Biology and Chemistry of *Larrea* in New World Deserts, Dowden, Hutchinson & Ross, Inc., Pennsylvania, 1977, pp. 115-134.

[4] P. W. Hyder, E. L. Fredrickson, R. E. Estell, M. Tellez, R. P. Gibbens, Biochem. Syst. Ecol. 30 (2002) 905-912.

[5] M. H. Gezginci, B. N. Timmermann, Tetrahedron Lett. 42 (2001) 6083-6085.

[6] H. Abou-Gazar, E. Bedir, S. Takamatsu, D. Ferreira, I. A. Khan, Phytochemistry 65 (2004) 2499-2505.

[7] H. Ye, H.-R. Bi, C.-L. Lü, X.-B. Tang, D.-L. Zhu, Acta Phys. Sinica 57 (2005) 612-618.

[8] P. Campello-Costa, A. M. Fosse-Júnior, P. Oliveira-Silva, C. A. Serfaty, Neuroscience 139 (2006) 979-989.

[9] C. A. Culver, S. M. Michalowski, R. C. Maia, S. M. Laster, Life Sci. 77 (2005) 2457-2470.

[10] J. D. Lambert, S. Sang, A. Dougherty, C. G. Caldwell, R. O. Meyers, R. T. Dorr, B. N. Timmermann, Phytochemistry 66 (2005) 811-815.

[11] J. Craigo, M. Callahan, R. C. C. Huang, A. L. DeLucia, Antiviral Res. 47 (2000) 19-28.

[12] J. R. Hwu, W. N. Tseng, J. Gnabre, P. Giza, R. C. C. Huang, J. Med. Chem. 41 (1998) 2994-3000.

[13] R. Park, C.-C. Chang, Y.-C. Liang, Y. Chung, R. A. Henry, E. Lin, D. E. Mold, R. C. C. Huang, Clin. Cancer Res. 11 (2005) 4601-4609.

[14] M.-H. Cho, S. G. A. Moinuddin, G. L. Helms, S. Hishiyama, D. Eichinger, L. B. Davin, N. G. Lewis, Proc. Natl. Acad. Sci. USA 100 (2003) 10641-10646.

[15] B.-Y. Park, B.-S. Min, O.-K. Kwon, S.-R. Oh, K.-S. Ahn, T.-J. Kim, D.-Y. Kim, K. Bae, H.-K. Lee, Biol. Pharm. Bull. 27 (2004) 1305-1307.

[16] I. R. Nascimento, L. M. X. Lopes, Phytochemistry 52 (1999) 345-350.

[17] N. P. Lopes, P. Chicaro, M. J. Kato, S. Albuquerque, M. Yoshida, Planta Med. 64 (1998) 667-669.

[18] D. Holloway, F. Scheinmann, Phytochemistry 13 (1974)1233-1236.

[19] R. C. C. Martins, L. R. Latorre, P. Sartorelli, M. J. Kato, Phytochemistry 55 (2000) 843-846.

[20] M. Nomura, M. Nakachiyama, T. Hida, Y. Ohtaki, K. Sudo, T. Aizawa, M. Aburada, K.-I. Miyamoto, Cancer Lett. 76 (1994) 11-18.

[21] L. Opletal, H. Sovová, M. Bártlová, J. Chromatogr. B 812 (2004) 357-371.

[22] R. Croteau, T. M. Kutchan, N. G. Lewis, in: B. Buchanan, W. Gruissem, and R. Jones, (Eds.), Biochemistry & Molecular Biology of Plants, chapter 24, American Society of Plant Physiologists, 2000, pp. 1250-1318.

[23] D. R. Gang, J. Wang, N. Dudareva, K. H. Nam, J. E. Simon, E. Lewinsohn, E. Pichersky, Plant Physiol. 125 (2001) 539-555.

[24] H.-S. Lee, J. Food Prot. 68 (2005) 1208-1210.

[25] D. G. Vassão, D. R. Gang, T. Koeduka, B. Jackson, E. Pichersky, L. B. Davin, N. G. Lewis, Org. Biomol. Chem. 4 (2006) 2733-2744.

[26] T. Koeduka, E. Fridman, D. R. Gang, D. G. Vassão, B. L. Jackson, C. M. Kish, I. Orlova, S. M. Spassova, N. G. Lewis, J. P. Noel, T. J. Baiga, N. Dudareva, E. Pichersky, Proc. Natl. Acad. Sci. USA 103 (2006) 10128-10133.

[27] A. Chu, A. Dinkova, L. B. Davin, D. L. Bedgar, N. G. Lewis, J. Biol. Chem. 268 (1993) 27026-27033.

[28] A. T. Dinkova-Kostova, D. R. Gang, L. B. Davin, D. L. Bedgar, A. Chu, N. G. Lewis, J. Biol. Chem. 271 (1996) 29473-29482.

[29] M. Fujita, D. R. Gang, L. B. Davin, N. G. Lewis, J. Biol. Chem. 274 (1999) 618-627.

[30] D. R. Gang, H. Kasahara, Z.-Q. Xia, K. Vander Mijnsbrugge, G. Bauw, W. Boerjan, M. Van Montagu, L. B. Davin, N. G. Lewis, J. Biol. Chem. 274 (1999) 7516-7527.

[31] T. Min, H. Kasahara, D. L. Bedgar, B. Youn, P. K. Lawrence, D. R. Gang, S. C. Halls, H. Park, J. L. Hilsenbeck, L. B. Davin, N. G. Lewis, C. Kang, J. Biol. Chem. 278 (2003) 50714-50723.

[32] D. R. Gang, A. T. Dinkova-Kostova, L. B. Davin, N. G. Lewis, in: P. A. Hedin, R. M. Hollingworth, E. P. Masler, J. Miyamoto, and D. G. Thompson, (Eds.), Phytochemicals for Pest Control, ACS Symp. Series, vol. 658, Washington, D.C., 1997, pp. 58-89.

[33] S.-J. Kim, M.-R. Kim, D. L. Bedgar, S. G. A. Moinuddin, C. L. Cardenas, L. B. Davin, C. Kang, N. G. Lewis, Proc. Natl. Acad. Sci. USA 101 (2004) 1455-1460.

[34] K.-W. Kim, S. G. A. Moinuddin, L. B. Davin, C. Kang, N. G. Lewis, manuscript in preparation.

[35] T. Katayama, L. B. Davin, A. Chu, N. G. Lewis, Phytochemistry 33 (1993) 581-591.

[36] J. Felsenstein, PHYLIP (Phylogeny Inference Package) version 3.5c, distributed by the author (1993).

EXAMPLE 2

Reaction Tissue Formation in Alfalfa, *Medicago sativa* L. (Fabaceae), Wild Type and p-Coumarate-3-Hydroxylase Down-Regulated Lines and their Stem Tensile Modulus Properties Example summary. The discovery of reaction tissue in the forage crop alfalfa (*Medicago sativa* L.) is described, which to applicants knowledge, has not hitherto been established as occurring in herbaceous perennials. It was first observed during an investigation of a transgenic alfalfa line reduced in overall lignin content, but was also formed in the wild type line as well. The transgenic alfalfa line, obtained through standard down-regulation of the gene encoding p-coumarate-3-hydroxylase (pC3H), was reduced in lignin content by circa 64%, as expected from our previous metabolic flux analyses (Anterola et al., 2002). Comparison of the pC3H down-regulated (pC3H-I) and WT lines established several differences, however, when employing microscopy analyses and biomechanical testing of various (internodal) alfalfa branch sections. Relative to WT, the pC3H-I line: (a) apparently more rapidly formed reaction tissue containing gelatinous fibers with adjacent thick-walled fibers (presumed to be 'intermediate' tissue) during development and in greater amount; (b) had an increased volume of xylem tissue, and (c) had comparable tensile dynamic modulus properties. These findings thus establish the (limited) ability of this perennial angiosperm to form (inducible) reaction tissue, in a manner somewhat analogous to that of woody arborescent angiosperms. Finally, with the recent rapidly growing interest in lignocellulosic materials for biofuels (e.g. bioethanol), the potential of effectuating reductions in lignin amounts in (woody) angiosperms with increased formation of reaction (tension wood) tissue is discussed. This is because the latter tissues are often viewed as a deleterious trait for many agronomic/forestry applications, e.g. due to the difficulties experienced in their subsequent processing for many industrial/commercial applications.

Example overview. Lignins, nature's second most abundant vascular plant biopolymer, next to cellulose, has essential roles in both structural support and in providing conduits for water and nutrient transport; they also provide a physical barrier to opportunistic pathogens/herbivores (Lewis et al., 1999). Recently, biotechnological reduction of lignin amounts in transgenic lines of economically important plant species has been a research emphasis in several laboratories, with various potential benefits being anticipated (Anterola and Lewis, 2002). These include, for example, decreased lignin by-product waste generation during pulp/paper production, improved animal feed digestibility, as well as better lignocellulosic feedstocks for biofuel/bioethanol production. In most cases, however, reductions in lignin content are accompanied by (presumably unintended) pleiotropic consequences, i.e. such as stunted growth of the resulting phenotypes (Patten et al., 2005; Laskar et al., 2006), and/or in weakened vasculature/weakened stem strengths (see Anterola and Lewis, 2002 for examples). Such effects serve to remind that the general understanding of the physiology and metabolism of plants—particularly, as regards formation of various lignified and unlignified cell wall types—is still severely lacking (for example, see Davin and Lewis, 2005).

One of the species of current agronomic interest is alfalfa (*Medicago sativa* L.), a major forage crop of high nutritional feed value with an important role in soil nitrogen recycling. In this study, therefore, we examined the effects of modulation of p-coumarate-3-hydroxylase (pC3H) gene expression in this species, in terms of not only lignin deposition but also the effects on overall stem vasculature properties and architecture. This enzymatic step was discovered by Heller and Kühnl (1985) using parsley (*Petroselinum crispum*) cell suspension cultures, with p-coumaryl shikimate being its substrate and not p-coumaric acid (FIGS. 17A, B). The encoding gene in *Arabidopsis thaliana* was later described by Schoch et al. (2001).

In this Example, applicants disclose that formation of reaction (tension) tissue occurs in wild type (WT) alfalfa (designated WT C-1) and whose amounts have also apparently increased in the pC3H down-regulated line (e.g. pC3H-I), as did the overall xylem volume. Yet, in spite of the greatly reduced lignin content (~64%), there were apparently no significant differences between both lines in terms of material strength properties (i.e. as shown by tensile dynamic modulus testing) of young developing alfalfa branches. It is thus proposed that formation of reaction tissue may be increased in alfalfa and other angiosperms when the overall vasculature is weakened through reducing lignin content(s). This can then serve as a compensatory mechanism in order to attempt to maintain needed biophysical/biomechanical properties of the overall vasculature, which would otherwise be weakened.

Materials and Methods:

Plant tissue. Transgenic alfalfa lines were generated by Reddy et al. (2005), with samples of all alfalfa (*Medicago sativa* L.) lines, WT (control, WT C-1) and pC3H down-regulated transgenic lines maintained and vegetatively-propagated in Washington State University greenhouses. Growing conditions included a light intensity of ~150 mmol $m^{-2}$ $s^{-1}$ with a 15 h light/9 h dark cycle at 21 and 16° C., respectively, and a humidity range of 20 to 35%. Young (~4 years of age) black cottonwood trees (*Populus balsamifera* ssp. *trichocarpa* (Torr. et A. Gray) Brayshaw) were grown outdoors on the Washington State University campus with branches of ~1 cm in diameter collected for microscopy analyses.

Lignin analyses. Acetyl bromide and thioacidolysis analyses were carried out as described in Patten et al. (2005) using 3 or more (vegetatively-propagated) plants per line.

Dynamic mechanical analyses (modulus of elasticity). For each WT C-1 and pC3H-I alfalfa line, following 3 weeks of growth after cut-back, 3 branches were collected, each from individual plants. Internodes 2, 5 and 8 (numbered starting from the apical end of the branch) were individually sampled at ~25 mm in length. Specimens of internode segments were tested in the tension mode using a TRITEC 2000 Dynamic Mechanical Analyzer (Triton Technology Ltd., Nottinghamshire, UK). The specimen free length was 10 mm and the diameter ranged from 1 to 1.7 mm. The test consisted of a dynamic strain sweep in the linear viscoelastic range from 0.003% to 0.03% performed at a frequency of 0.5 Hz and at a constant temperature of 30±1° C. To evaluate significant differences in dynamic moduli, the storage (E') and loss (E") modulus of each sample was recorded at a 0.02% strain level and the data compared with a paired t-test.

Growth measurements. Alfalfa WT C-1 and pC3H-I lines were used for statistical analyses, where each line had 2 plants with 8 weeks of growth after cut-back. All plants within each alfalfa line were vegetatively-derived from self-stock. Branches (not individual plants) were chosen as the experimental unit because they represent the greatest variability within these lines as well as comprising the key component of aerial growth in alfalfa in general. Thus sampling was made collectively from plants within a given line with a total of ten crown bud-derived branches (N=10) sampled from each of the WT C-1 and pC3H-I lines. Since alfalfa branch growth is rapid and pC3H-I lags in flower development by at least 5 weeks relative to WT C-1 (see also Reddy et al., 2005), branches at an equivalent maturity (8 weeks) were selected based on the presence of flower buds/flowers, so as to avoid young or axillary branches less than 8 weeks of age. The number of internodes (stem regions between leaves) and the lengths of each internode were next recorded with hand-cut sections being immediately harvested. Total stem lengths, individual internode lengths, and numbers of internodes were recorded with means and standard errors (SE) calculated and analyzed by t-test ($\alpha$=0.05) using Microsoft Excel® software.

Lignin histochemistry. For lignin visualization (FIG. 18), sections were hand-cut from internodes 2, 3, and 8 of 3-week old branches of both WT C-1 and pC3H-I lines. Wiesner reagent (phloroglucinol-HCl) was employed to detect lignin (in general), whereas the Mäule reagent was used to localize S lignin (Patten et al., 2005).

Gelatinous fiber histochemistry. For gelatinous fiber (gf) visualization, zinc chloro-iodide (Herzberg reagent) (Scurfield, 1972; Grzeskowiak et al., 1996) was employed. For imaging at lower magnifications, fresh hand-cut sections from internode (IN) 2 to the most basal internode, (plants 8 weeks of age), were imaged within 20 minutes of reagent application. Gelatinous layers within fibers were identified by a red-purple coloration, in contrast to the orange-brown coloration of surrounding (and presumably lignified) fiber cell walls (after Scurfield, 1972).

Additionally, zinc chloro-iodide was used as part of a comparative study i.e. with a single mature internode (IN20) from both lines, as well as from a branch of black cottonwood. Safranin O and astra blue staining (Srebotnik and Messner, 1994; Vazquez-Cooz and Meyer, 2002) were also utilized, to confirm further the zinc chloro-iodide visualization results, as well as phloroglucinol-HCl to correlate with lignification (described above). The comparative study employed serial cryosections (~10 microns in thickness) obtained from fresh frozen tissues cut on a Reichert-Jung Cryocut 1800 cryomicrotome (Leica Microsystems, Deerfield, Ill., USA). Light micrographs were recorded using an Olympus BH-2 light microscope equipped with a ProgRes C12plus digital camera (JENOPTIK, Jena, Germany).

Gelatinous fiber occurrence and distribution. Hand-cut internodal (IN) sections (475 sections) were prepared from IN2 to the most basal internode of each branch (N=10), for each alfalfa line (as for growth measurements). These were then scored for the presence of gelatinous fibers (gf) and non-gelatinous thick-walled fibers (tf), respectively, in primary and secondary reaction tissues using zinc chloro-iodide for visualization (Scurfield, 1972) (see histochemistry section). The sections (>1000) were imaged in detail at several magnifications using light microscopy as described above. Following scoring for the presence of xylary gf or tf cells, the respective means were statistically analyzed by Students t-testing. Images of sections from IN5 (i.e. earliest internode found to have gf cells in either line) to the most basal internode of each branch (10 branches per line) were individually measured for total xylem and total gf cell areas using ImageJ software (Rasband, 1997), with respective values also compared statistically by Students t-testing. The extent of tf cell formation was not examined because it was not possible to resolve tf from normal fiber cells at the low magnification required to accurately measure area; zinc chloro-iodide (and safranin O/astra blue) staining do not differentiate between tf and normal fiber cells.

Cell wall ultrastructure. Identification of reaction vs. normal cell types was further confirmed using transmission electron microscopy (TEM). Samples were harvested from a mature internode (IN20) from both WT C-1 and pC3H-I lines, as well as from branch tissue of black cottonwood as a control. Tissues (≤5 $mm^2$) were fixed in 2% paraformaldehyde and 1.25% glutaraldehyde in 50 mm Pipes buffer (pH 7.2) overnight at 4° C. Samples were dehydrated using a standard ethanol series, gradually infiltrated with L.R. White resin (London Resin Co., Reading, UK) and heat cured. Thin sections were obtained using a diamond knife mounted to a Reichert Ultracut R ultramicrotome (Reichert-Jung GmbH, Heidelberg, Germany) with sections then mounted on formvar-coated 200-mesh nickel grids. Sections were stained with a 3:1 dilution of 4% (w/v) uranyl acetate and 1% (w/v) $KMnO_4$, with samples observed at 100 kV using a JEOL JEM-1200 EX transmission electron microscope (JEOL, Tokyo, Japan).

Results:

Measurement of branch growth/internode elongation. Branches (N=10) were measured following 8 weeks of growth after cut-back. No significant difference was found ($p>0.05$) between the total stem lengths and total numbers of internodes for the two alfalfa lines (TABLE 3 and total internode (IN) numbers higher in pC3H-I than in WT C-1. In turn, the mean internode length for pC3H-I was significantly shorter ($p<0.05$), i.e. 3.17±0.15 cm vs. that of WT C-1 (3.76±0.14 cm). To examine this further, the single longest internode in each stem (as a "standard" for growth potential) was selected and both lines were again compared; the pC3H-I line had a significantly shorter "longest" internode (7.03±0.35 cm) than WT C-1 (8.05±0.36 cm) ($p<0.05$) (Table 3).

TABLE 3

Comparison of gross phenotypic differences between alfalfa WT C-1 and down-regulated pC3H-I lines.

| Parameter | C-1 Mean ± SE | pC3H-I Mean ± SE | P value (*p ≤ 0.05) |
|---|---|---|---|
| Branch length (cm) | 85.95 ± 1.34 | 77.88 ± 1.31 | 0.159 |
| IN (internode) number per branch | 22.9 ± 0.60 | 24.6 ± 0.69 | 0.188 |
| Average IN length per branch (cm) | 3.76 ± 0.14 | 3.17 ± 0.15 | 0.005* |
| Single longest IN per branch (cm) | 8.05 ± 0.36 | 7.03 ± 0.35 | 0.042* |

Notes:
N = 10 branches for both lines;
IN, internode;
P, probability;
SE, standard error;
asterisks denote probability ≤0.05.

Lignin deposition patterns. Plants aged 3 weeks following cut-back were sampled from both lines, with samples representing 3 stages of growth: early primary xylem development with no interfascicular fiber development (IN2), development of primary interfascicular fibers (IN3), and secondary growth (IN8), respectively. Chemical analyses (TABLE 4) included both estimations of acetyl bromide (AcBr) lignin contents and monomeric (H, G, S) compositions, as determined by thioacidolysis degradation (described in Patten et al., 2005). Histochemical analyses employed hand-cut sections treated with either Wiesner or Mäule reagent in order to localize patterns of presumed lignin deposition (Patten et al., 2005). Historically, the Wiesner reagent (phloroglucinol-HCl) is employed as a general stain (pink to red coloration) to detect p-hydroxycinnamyl aldehyde end-groups in macromolecular lignin of plant tissues. Although frequently referenced as coniferyl aldehyde specific (e.g. by Sarkanen and Ludwig, 1971), the reagent reacts with all three p-hydroxycinnamyl aldehydes (Pomar et al., 2002; Jourdes et al., 2007a). By contrast, the Mäule reagent is considered specific, and is employed to differentiate between (apparent) S moieties from the H and G components (red vs. brown coloration, respectively) (Iiyama and Pant, 1988; Nakano and Meshitsuka, 1992; Patten et al., 2005). Since both reagents give only temporary visualization of color, images were recorded within 20 minutes of reagent application.

TABLE 4

Estimated lignin contents and monomeric compositions for alfalfa WT C-1 and pC3H-I lines.

| | | AcBr Lignin* (% CWR) | Lignin-derived monomers released through thioacidolysis (μmoles/g CWR) H | G | S | H + G + S | H:G:S ratio |
|---|---|---|---|---|---|---|---|
| C-1 | IN 2 | 8.7 ± 0.4 | 4.4 ± 0.5 | 47.0 ± 2.3 | 9.8 ± 0.4 | 61.2 ± 3.1 | 10:107:22 |
| | IN 3 | 17.1 ± 0.1 | 12.3 ± 2.1 | 135.4 ± 5.1 | 51.8 ± 1.6 | 199.5 ± 6.2 | 10:110:42 |
| | IN 8 | 26.1 ± 0.7 | 11.1 ± 1.1 | 254.4 ± 6.3 | 115.3 ± 3.1 | 380.8 ± 8.2 | 10:229:104 |
| pC3H-I | IN 2 | 5.5 ± 0.2 | 6.2 ± 0.5 | 3.7 ± 0.5 | 0.3 ± 0.1 | 10.2 ± 1.1 | 10:6:0.5 |
| | IN 3 | 7.1 ± 0.1 | 14.6 ± 2.1 | 6.3 ± 1.4 | 1.7 ± 0.2 | 22.6 ± 3.1 | 10:4.3:1.2 |
| | IN 8 | 9.4 ± 0.1 | 31.9 ± 2.1 | 11.0 ± 1.0 | 5.6 ± 0.5 | 48.5 ± 3.6 | 10:3.5:1.8 |

Notes:
*AcBr lignin = estimated acetyl bromide solubilized lignin content; thioacidolysis: estimation of monomeric compositions and releasable amounts in lignins; IN = internode number (from branch apex); CWR = cell wall residue.

Figures 18A, 18B, 18C, 18D, 18E, 18F, 18G, 18H, 18I, 18J, 18K, 18L:
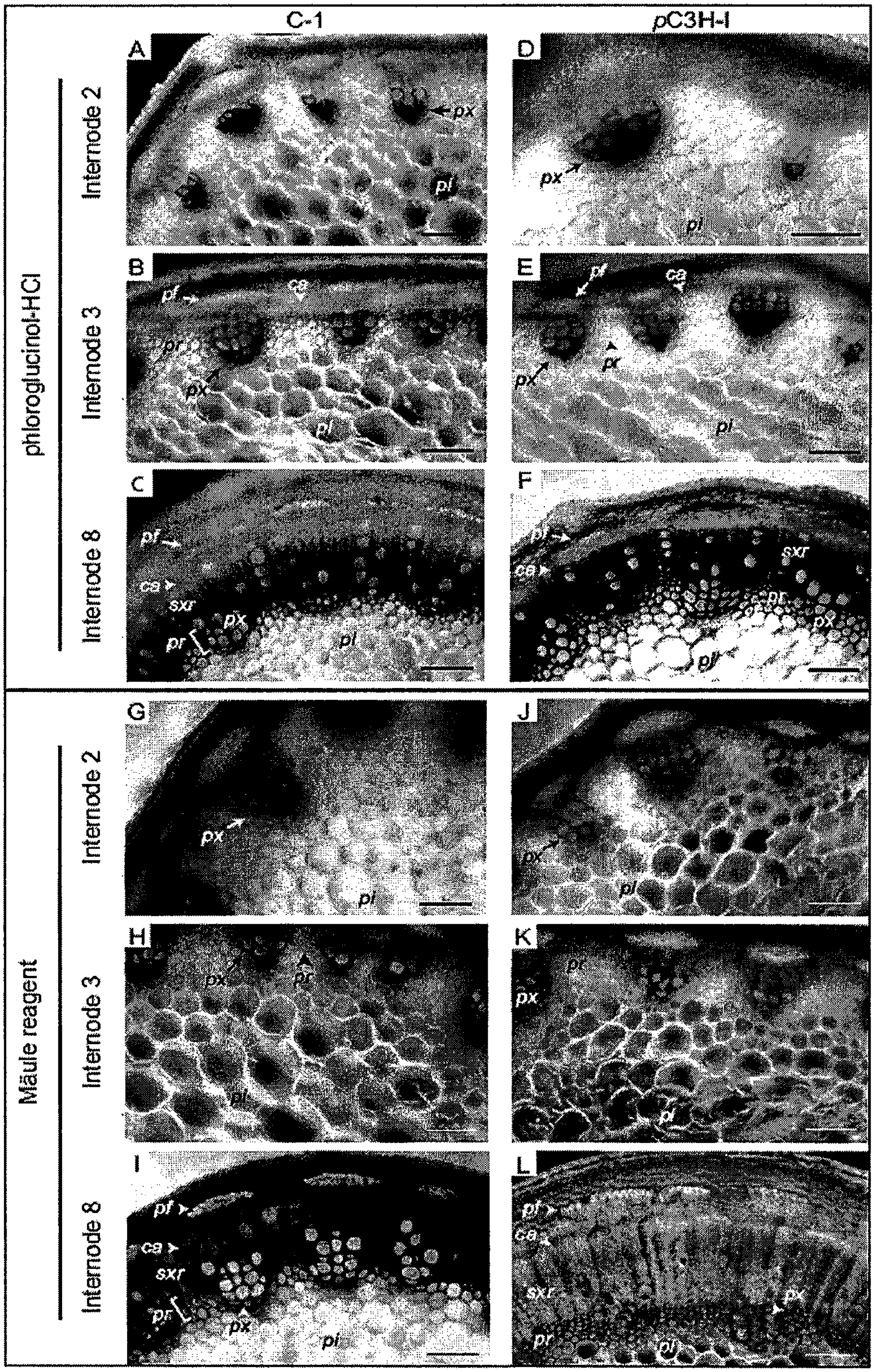
FIGS. 18A-L show, according to exemplary aspects of the present invention, Histochemical staining for lignin in internodes (IN) 2, 3, and 8 of WT C-1 (Control) and pC3H-I alfalfa lines. Phloroglucinol-HCl staining (pink to red coloration) demonstrates very similar patterns of lignification between WT C-1 (A-C) and pC3H-I (D-F), beginning with the primary xylem (px) in IN2 (A, D), then proceeding into the developing primary ray (pr) of IN3 (B, E), and extending throughout the maturing secondary xylem region (sxr) of IN8 (C, F). Phloroglucinol-HCl does not distinguish between H-, G-, or S-type lignins and is a qualitative test. The Mäule reagent (G-L) reacts to S-type lignin as red coloration and to H- and G-type lignins by a golden brown coloration; it is also a qualitative test. S lignin is specific to fiber cells, detectable first in pr of both lines (H, K), and extending throughout the sxr in IN8 only in WT C-1 (I). Very little S-type lignin is detected in the sxr of pC3H-I (L). Scales=150 μm (A-C, E-L); 100 μm (D). Samples were imaged using differential contrast light microscopy. Abbreviations: ca, cambium; pi, pith; pf, phloem fibers; pr, primary ray; px, primary xylem; sxr, secondary xylem region.

WT alfalfa lignin analyses. Histochemical analyses indicated that the earliest phase of lignification (IN2) occurred in the primary xylem (px) of the WT C-1 line. It is apparently limited to either H- and/or H/G-lignin deposition, as suggested by Wiesner (pink-red coloration; FIG. 18A) and Mäule (golden-brown coloration; FIG. 18G) reagents, respectively. This is supported by the lignin chemical analyses, which gave an overall estimated content of ~8.7% lignin, largely of G character, with smaller amounts of H and S moieties (H:G:S ratio of 10:107:22, TABLE 4. Slightly later in development of the WT C-1 vascular tissue (IN3), the cambium (ca) has formed a contiguous circumferential band of cells (FIG. 19B), and lignification has apparently extended throughout the pr (i.e. primary medullary or interfascicular ray tissue), and is initiated in the phloem fibers (pf, phloroglucinol-HCl, red coloration, FIG. 18B). This phase of lignification now also apparently involves some detectable S lignin deposition, in at least the pr (Mäule reagent, light to dark red coloration, FIG. 18H). Again, this is supported by the chemical analyses, which indicated the overall lignin content had essentially doubled (to ~17%), with the S content increased about 5 fold overall and with an H:G:S ratio of 10:110:42.

With further development (IN8), the WT C-1 line extends its lignification throughout the pr, sxr, and pf cells, as well as being very faintly stained in the pith, pi (phloroglucinol-HCl, red coloration, FIG. 18C). Using differential Mäule staining, the xylem cells of both the pr and the sxr appeared to contain H and/or H/G moieties (brown coloration), while fiber cells of pr, sxr and pf apparently also had S-containing lignins (dark red coloration) (FIG. 18I). This interpretation was supported further by chemical analyses, with overall lignin amounts (~26.1%) now being close to those of maturation levels, and where the H:G:S ratio 10:229:104 was mainly indicative of differential increases in G and S deposition (TABLE 4).

pC3H-I alfalfa lignin analyses. Lignification of px in IN2 of pC3H-I was again mainly of H- or H-/G-type character, as visualized by use of phloroglucinol-HCl (pink-red coloration, FIG. 14D), but not of S- since the Mäule reaction staining gave a brown (rather than red) coloration (FIG. 14J). This interpretation was also supported by chemical analyses, which indicated a slightly lower AcBr lignin content of ~5.5% (vs. ~8.7% in WT C-1) (Table 2). Moreover, the presumably H-lignin derived releasable monomeric moieties were only slightly increased relative to WT C-1, whereas the G/S amounts had decreased by at least an order of magnitude (H:G:S ratio of 10:6:0.5). Taken together, these observations appear thus to be in harmony with the initial phase of H-lignin deposition being generally unaffected by pC3H down-regulation as anticipated (Anterola and Lewis, 2002). Deposition of S-lignin within the pr of IN3 occurs as in WT C-1 (Mäule reagent, light red coloration, FIGS. 14K and H, respectively) and corresponds well to the chemical analyses with lignin contents having increased slightly (~7.1%) with an H:G:S ratio now of 10:4.3:1.2 (TABLE 4).

At IN8, and like WT C-1 (FIG. 18C), the transgenic line (FIG. 18F) displayed an apparently uniform deposition of H- and/or H/G-lignins in the pr, sxr and pf, as well as a faint staining again in the pi as indicated by positive Wiesner reagent staining. However, the Mäule reagent only gave intense S-lignin staining in the pr cell walls, as evidenced by the distinctive red band adjacent to the pi (FIG. 18L), which had been initiated previously (FIG. 18K). By comparison, a lighter and more uneven coloration of the sxr occurred, this being interpreted as indicative of a very limited S lignin deposition. The pi also appeared to have a similar pattern of faint staining relative to that of WT C-1. Chemical analyses, in turn, indicated that the lignin contents were now ~9.4%, thereby reflecting a very large decrease in overall lignin amount when compared to WT C-1 levels (~26. 1%) (TABLE 4). Likewise, thioacidolysis analyses again established that while the H-monomeric component dominated, there were, however, small increases in both G and S contents as well (H:G:S ratio of 10:3.5:1.8). These data, when taken together, demonstrate that pC3H-I is, nevertheless, forming small amounts of a primarily H-type lignin during growth/development.

Estimation of alfalfa branch tensile dynamic moduli. The tensile dynamic moduli, storage and loss moduli, were determined for both lines. The storage and loss moduli represent the elastic and viscous components of the material properties, respectively, and as such provide a measure of viscoelastic behavior. Branch internodes were harvested at 3 weeks (post cut-back), with these representing: early primary xylem development (with little to no fiber development), IN2; where internode elongation is thought to end and secondary growth begins, IN5 (Vallet et al., 1998); and where there is a large volume of lignified secondary xylem growth, IN8.

Figure 19:
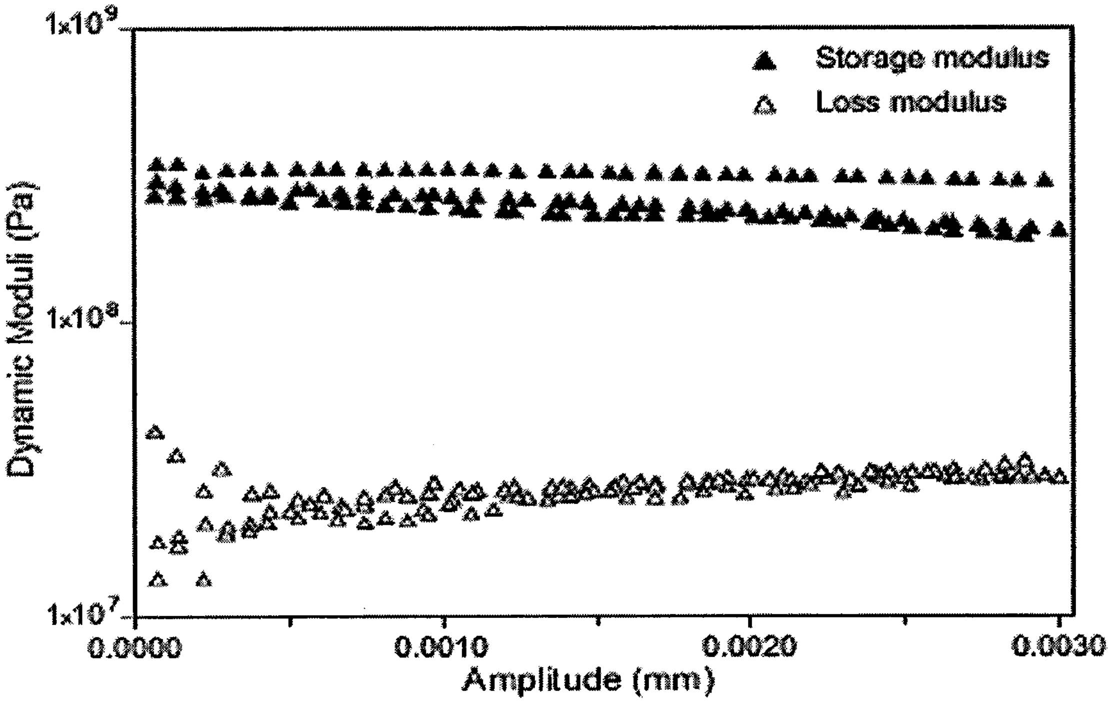
FIG. 19 shows, according to exemplary aspects of the present invention, an example of Dynamic Mechanical Analyses (DMA) strain scans using internode section 8 of pC3H-I. Data show 3 replicate specimens from the pC3H-I line, internode 8, tested in tension at 0.5 Hz, 30° C.
Figure 20:
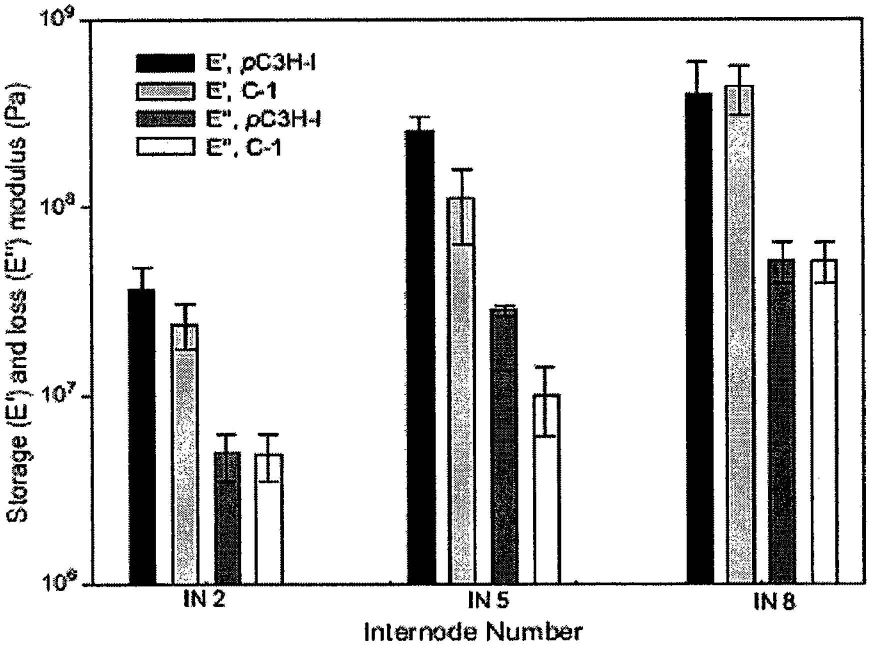
FIG. 20 shows, according to exemplary aspects of the present invention, mean dynamic moduli for internodes 2, 5 and 8 from WT C-1 and transgenic pC3H-I stems. Data are obtained from measurements in tension at 0.5 Hz, 30° C. and 0.02% dynamic strain level, respectively.

Dynamic moduli determinations were thus made in triplicate for each internode of both lines and with reasonably good reproducibility (see FIG. 19 for example using p-C3H-I). That is, there was a marked increase observed in storage (E') and loss (E") moduli with internode development/maturation for both lines, indicative of enhanced material properties (FIG. 20). Upon Students t-test comparison of data collected (p values=0.267, 0.116, and 0.810 for internodes 2, 5 and 8, respectively), however, no significant difference in the storage modulus (E') was detected between lines WT C-1 and pC3H-I. Similarly, no significant difference in the loss modulus (E") was detected between both lines (p values=0.979 and 0.225 for internodes 2 and 8, respectively) except for internode 5 (p value=0.006) (FIG. 20). Apparently, at internode 5, the pC3H-I branch material has a higher loss modulus than that of WT C-1, but whether this particular difference is an artifact resulting from the small number of replicates or is a significant difference was not investigated further. In any case, the overall data suggested that despite a range in lignin reduction (i.e. ~37% to 64% in IN2 and IN8, respectively, relative to WT C-1 levels), the pC3H-I line was capable of maintaining comparable storage and loss tensile modulus properties to that of WT values. As described below, an explanation for these observations was then needed to be identified/rationalized.

Reaction tissue histochemistry. Zinc chloro-iodide is one of several reagents used to detect reaction tissue (Scurfield, 1972) and was employed as the primary histochemical stain in this study. This dye can yield variable results because it does not react directly with cell wall bound molecules (such as aldehydes in the manner of phloroglucinol-HCL or the Mäule reagent), but instead intercalates into the cell wall, which can vary in structure and therefore differentially exclude the dye (Grzeskowiak et al., 1996). This is especially true of transitional cells, which may have variable numbers of secondary cell walls and which were also previously observed to have quite variable histochemical properties when stained with zinc chloro-iodide (Scurfield, 1972; Grzeskowiak et al., 1996). As such, Scurfield (1972) generally described the G-layer of *Eucalyptus* ssp. as having a 'purple-red' coloration (with surrounding walls colored yellow) while the general coloration of transitional cells appeared 'yellowish-red', albeit with variability in coloration corresponding to variable cell structure. Grzeskowiak et al. (1996) also observed a red-purple coloration in the G-layers of *Populus* with the normal cells being yellow. Applicants followed these observations for our interpretation of staining alfalfa reaction tissues.

Figures 21A, 21B, 21C, 21D, 21E, 21F, 21G, 21H:
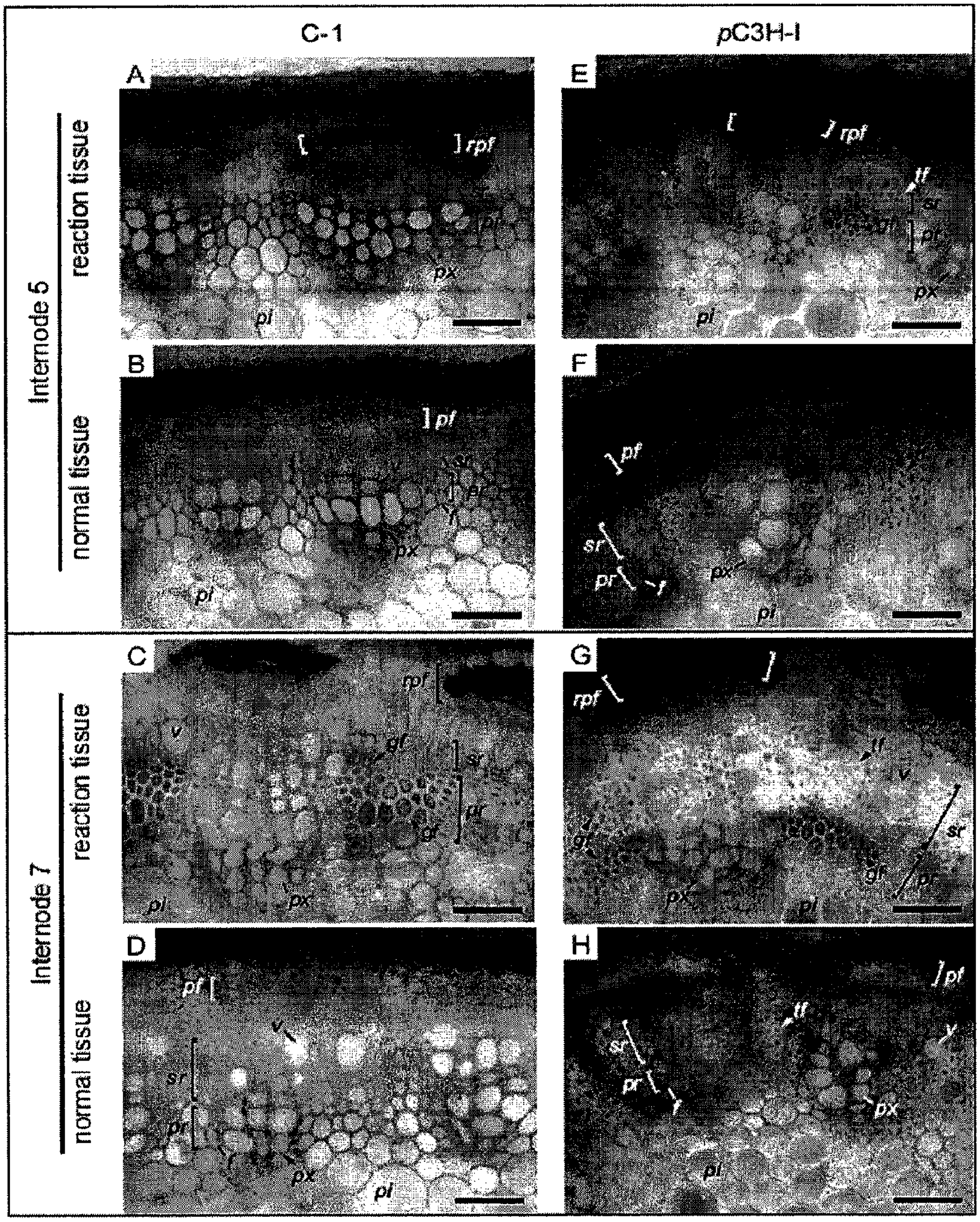
FIGS. 21A-H show, according to exemplary aspects of the present invention, Development of gelatinous fibers (gf) and reaction phloem fibers (rpf) using zinc chloro-iodide histochemistry. There are no apparent gf cells in internode (IN) 5 of WT C-1 in either reaction (A) or normal (B) tissues and so tissue type was defined by thickened and darkly stained reaction phloem fibers (rpf) in A relative to pf in normal tissue (B). Early gf of primary (pr) and secondary ray (sr) tissues, as well as adjacent yellow-colored thick-walled fibers (tf) of sr tissue appear at IN5 in the pC3H-I line (E). Additionally, normal tissue of IN5 has abundant tf cells in the sr region (F). By IN7, gf appear in WT C-1 in both the pr and sr regions of reaction tissue (C), but are not evident in the normal WT C-1 tissue (D). By IN7, pC3H-I forms gf not only in the pr and sr of reaction tissue, but also tf in the sr. Moreover, this sr may be transitional tissue given the presence of both tf cells and differentially colored gf cells. Normal tissue of pC3H-I forms tf cells as well (H), but not in WT C-1 at this stage of growth (C, D). Images were taken using differential interference contrast light microscopy. Scales=75 μm. Abbreviations: f, fibers of normal primary tissues; gf, gelatinous fibers; pf; phloem fibers of normal tissue; pi, pith; pr, primary ray tissue; px, primary xylem; rpf, reaction phloem fibers; sr, secondary ray tissue; tf, thick-walled fibers; v, vessel.
Figures 22A, 22R:
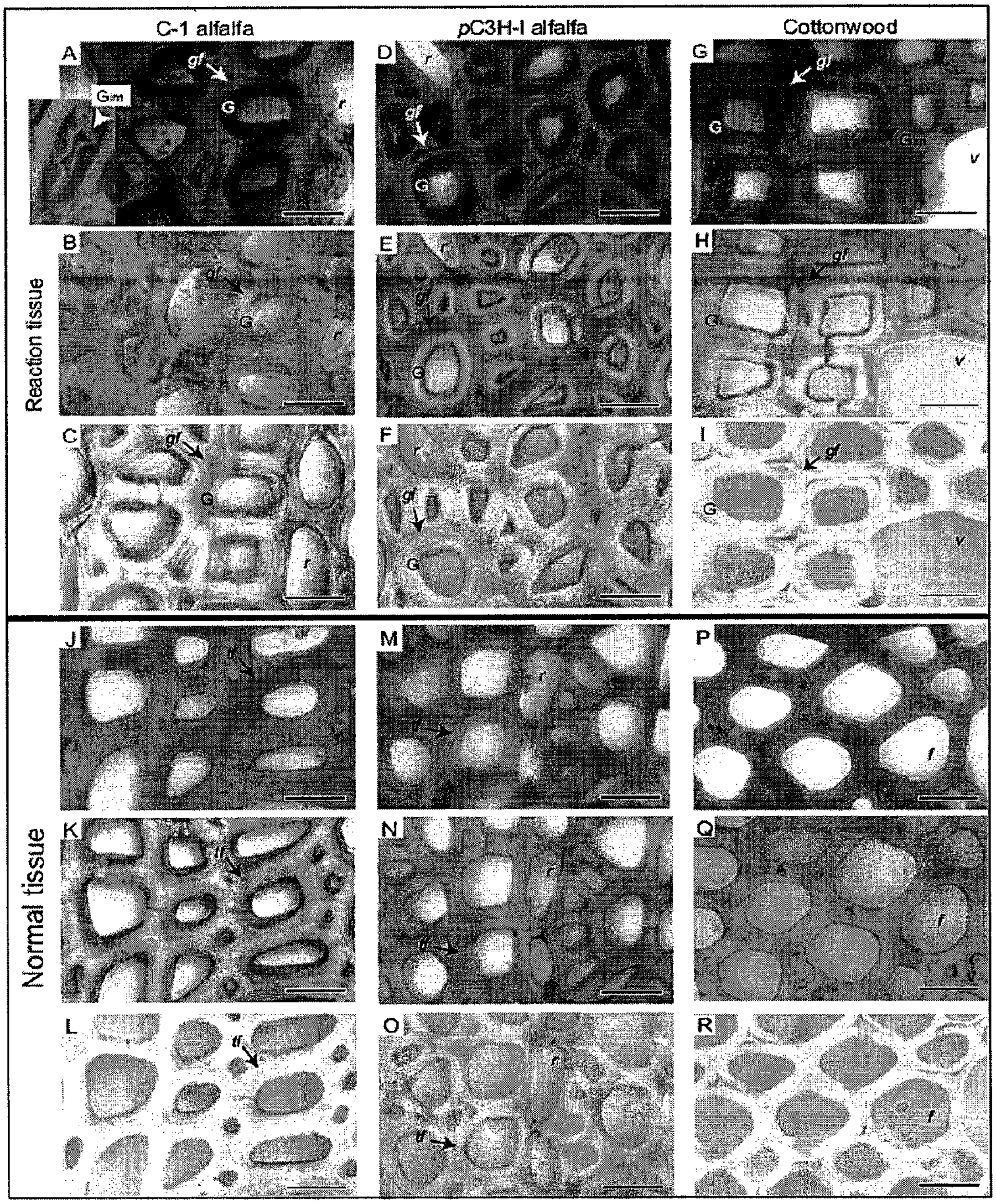
FIGS. 22A-R show, according to exemplary aspects of the present invention, Comparative histochemistry of reaction and normal tissues in alfalfa with black cottonwood for a positive control. Zinc chloro-iodide was used to detect gelatinous layers (G-layer) as a dark red-brown layer closest to the lumen of gelatinous fiber (gf) cells in WT C-1 (A) and pC3H-I (D) alfalfa lines, as well as black cottonwood (G). The surrounding cell wall layers stained orange to yellow with this reagent. An apparent inner layer ($G_{im}$) appeared orange within the G-layer of a few cells, e.g. in WT C-1 alfalfa (A) and black cottonwood (G). Double staining with safranin O/astra blue was used to confirm the presence of the G layer by a blue coloration relative to the surrounding cell wall layers (a pink to red coloration) (B, E, H). Upon staining with phloroglucinol-HCL, little to no lignin was detected in the G-layers; pink coloration suggested lignin in the adjoining cell wall layers (C, F, I). Thick walled fibers (tf), occurring in alfalfa normal tissue (and transitional tissues, data not shown), were tested with the same three reagents (J-O) and found to stain very closely to normal fibers (f) of cottonwood (P-R) with no indication of G-layers. Scales=10 μm. Abbreviations: f, normal fiber; G, G-layer; Gim, G-layer with inner membrane; gf, gelatinous fiber; tf; thick-walled fiber; r, ray cell; v, vessel.

Using hand-cut internodal sections made from ten branches of both lines, three interesting observations were made following zinc chloro-iodide staining (FIGS. 21 and 22). First, many of the sections examined stained positively for gelatinous fiber (gf) presence as noted in FIGS. 21C, E and G (for IN5 and 7), with this being even more pronounced in older internodes (e.g. IN20; FIG. 22A, D). Secondly, the branch tissues could be visually separated into xylary tissues having either red-purple stained gf or tissues which stained yellow to orange and lacked gf cells (normal/transitional tissues). Thirdly, both plant lines formed thick-walled fibers (tf), which were physically similar to gf cells, but stained entirely orange to yellow and were restricted to secondary growth (see FIGS. 21E-H and 6J, M).

Primary and secondary reaction tissues. Using the zinc chloro-iodide reagent, the presence or absence of xylary gf cells could be resolved by internode and by tissue type (primary vs. secondary), with the respective calculated means and standard errors compared by Students t-test. As the reaction response has been reported to occur earlier in phloem than in xylem (Scurfield and Wardrop, 1962), the detection of presumed reaction phloem fibers (rpf) cells (Scurfield and Wardrop, 1962; Wardrop, 1964; Côté et al., 1969) allowed for facile identification of reaction tissue in even the youngest internodes lacking gf cells (for example, IN5 in WT C-1, FIGS. 21A vs. B, for rpf vs. normal pf, respectively). Additionally, xylem region gf cells were found to occur significantly ($p<0.05$) earlier in the primary tissue of the pC3H-I line relative to WT C-1, i.e. the reaction tissue had developed by IN5 (mean: 4.70±0.47) in the primary ray tissue of pC3H-I, whereas it occurred later at IN7 (6.70±0.62) in WT C-1 (for examples, see FIGS. 21E vs. 21C, respectively). Results for the secondary reaction tissue were also statistically significant ($p<0.05$), with gf cells appearing by IN5 (5.5±0.40) in pC3H-I and by IN7 (7.5±0.65) in WT C-1.

Primary and secondary transitional and normal tissues. Fiber cells (f) of the normal primary tissues of both lines appeared yellow to orange and lacked any detectable G-layers 'proper' (i.e. red/purple in color; FIGS. 21B, D, F, and H). It should be noted that while gf cells were absent, the primary ray tissue in the early internodes (i.e. IN3-5) of both lines still stained a uniform red to orange (for example, see pr of IN5 WT C-1, FIGS. 21A, B). This primary ray coloration is likely due to the low lignin contents of the early internodes and was scored as a negative, unless obvious gf cells were present.

Presumed transitional tissues frequently occurred in which gf cells had a typical dark inner layer, and light yellow outer layers (gf in sr, FIG. 21G). Transitional tissues are known to be highly variable (Scurfield and Wardrop, 1963) and may include tf cells as well.

Moreover, thick-walled fibers (tf) were considered here to comprise transitional tissues in alfalfa, due to their swollen inner walls (similar to gf cells), but stained orange to yellow (as in normal tissues). Additionally, formation of tf cells occurs first in close proximity to gf cells 'proper' and then extends further around the stem with internode maturity. Interestingly, scoring of tf cells showed the greatest differential ($p<0.05$) between the lines, with tf cells appearing by IN5 ($5.90\pm0.35$) in the pC3H-I line (for example, FIG. 21E) and later at IN12 ($12.50\pm1.81$) for WT C-1 (data not shown).

Comparisons of reaction versus lignin histochemistry. Serial sections were obtained from mature reaction and normal tissues (IN20) of both alfalfa lines and from reaction and normal branch tissue of black cottonwood (*Populus balsamifera* ssp. *trichocarpa*). The latter was used as a positive control, since cottonwoods are well known to form gf cells (Kaeiser and Boyce, 1965; Côté et al., 1969; Isebrands and Bensend, 1972).

G-layer. Upon staining with zinc chloro-iodide, the G-layers within gf cells in cottonwood were readily observed as red-brown in color amid a background of orange cell walls (FIG. 18G), as well as in IN20 of the WT C-1 (FIG. 22A) and pC3H-I (FIG. 22D) lines. These results were further confirmed by the use of safranin O and astra blue staining. Using this approach, the G-layers appeared blue against a pink-red background in all samples examined (FIGS. 22B, E, H). Lignin was next localized in the serial sections by use of phloroglucinol-HCl as before to compare with the above observations, and was detected as a pale pink color since thin (10 μm) serial sections were used. In all samples, and as expected, there was little to no pink coloration in the G-layer, indicating little to no lignin being present (FIGS. 22C, F, I). By contrast, the surrounding cell walls appeared faint pink in color, indicative of the presence of lignified elements.

Transitional and normal tissues. Interestingly, a few gf cells observed in cottonwood (FIG. 18G) and the WT C-1 line (inset, FIG. 22A) displayed a thin orange coloration internal to the G-layer, almost like an inner membrane ($G_{im}$). Similar cells ($G_{im}$) were also observed in older internodes (>IN20) in sections from the pC3H-I line (data not shown) and are believed to represent part of the transitional tissue.

On the other hand, thick-walled fibers (tf) in the case of both alfalfa lines appear to have histochemistry closer to normal cells than to the $G_{im}$. These were therefore compared in serial section to normal fibers (f) of cottonwood. In the alfalfa tf and the cottonwood f; G-layers (of reaction wood 'proper') were considered to be absent as evidenced by the lack of a red to purple-brown coloration using zinc chloro-iodide staining (FIGS. 22J, M, P), or characteristic blue cell wall layers by safranin O and astra blue double staining (FIGS. 22K, N, Q). There was, however, a small amount of blue coloration around the lumens of the tf in the pC3H-I line (FIG. 22N), which provisionally may reflect either decreased lignification or a minor artifact of double staining. In any case, there were no G-layers (as in reaction wood 'proper') observable in the tf of this line or in the other samples. Finally, phloroglucinol-HCl histochemistry was found to be similar among all plant samples with tf, wherein pink coloration, indicative of lignification, was present throughout the cell walls (FIGS. 22L, O, R).

Quantification of xylem and xylem reaction tissue areas. Images (of the sections above) were digitally measured using ImageJ software as described in the Materials and Methods. Images of internodes 2 to 4 were excluded since they generally lack gf cells. It was calculated that the pC3H-I line formed significantly ($p<0.05$) larger amounts of both reaction ($0.436\pm0.07$ $mm^2$ vs. $0.275\pm0.05$ $mm^2$) and total xylem tissue ($1.95\pm0.18$ $mm^2$ vs. $1.43\pm0.15$ $mm^2$) than WT C-1 (TABLE 5).

TABLE 5

Comparison of average total areas for xylem region and for xylem reaction tissues (with gelatinous fibers, gf) between alfalfa WT C-1 and pC3H-I lines. Samples were collected from internodes 5 (i.e. 1st reported occurrence of gf) to the basal most internode for 10 branches from each line.

| Parameter | C-1 Mean ± SE | pC3H-I Mean ± SE | P value (*p ≤ 0.05) |
|---|---|---|---|
| Average xylem area per branch ($mm^2$) | 1.43 ± 0.15 | 1.95 ± 0.18 | 0.020* |
| Average xylem reaction area per branch ($mm^2$) | 0.275 ± 0.05 | 0.436 ± 0.07 | 0.034* |

Notes:
N = 10 branches for both lines;
P, probability;
SE, standard error; asterisks denote probability ≤0.05;
thick-walled fiber cell regions were not measured due to staining characteristics being indistinguishable from normal fiber cell regions at low magnification.

Cell wall ultrastructure. Samples were collected as for the comparative histochemical analyses using both alfalfa and black cottonwood, but processed for TEM analyses. Three cell types: gelatinous fibers (gf), normal fibers (f), and vessels (v) were compared to each other and among plant lines (FIG. 23).

Figures 23A, 23B, 23C, 23D, 23E, 23F, 23G, 23H:
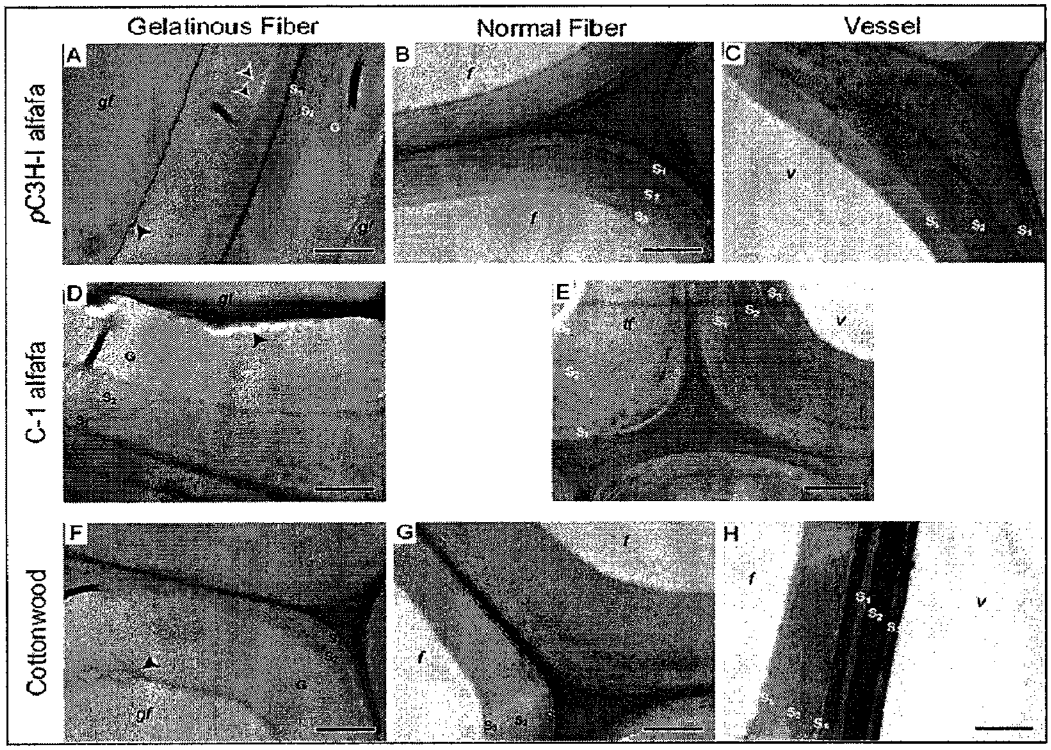
FIGS. 23A-H shows, according to exemplary aspects of the present invention, transmission electron micrographs of the reaction tissues of alfalfa pC3H-I (A,B,C) and WT C-1 (D,E), as well as the control reaction wood species: black cottonwood (F,G,H). The gelatinous fibers (gf) are characterized by a gelatinous layer (G-layer), a reduced middle secondary wall ($S_2$) (as compared to normal fibers) and the absence of a third (inner) secondary wall in all three plant types (A, D, F). The G-layers show lighter staining relative to the lignified $S_2$, a characteristic uneven inner lamellae (arrowheads, A, D, F) and a slight pulling away from the $S_2$ (double arrowheads, A). Normal wood fibers (f) lack the G-layer and show all three secondary cell wall types ($S_1$, $S_2$, $S_3$) (B, E, G) in all three plant samples. Vessel (v) cell wall structure is also very similar between the three plant samples (C, E, H). Scales=1 μm. Abbreviations: f, fiber; gf, gelatinous fiber; tf, thick-walled fiber; $S_x$, secondary subwall layer; v, vessel.

Gelatinous fibers. The data so obtained with these sections correlated very well with previous reports on ultrastructure of gf cells. For cottonwood gf cells, it was readily possible to observe relatively thin $S_1$ and $S_2$ secondary layers, along with the characteristic thick G-layer (FIG. 23F). Likewise, gf cells in both the WT C-1 (FIG. 23D) and pC3H-I (FIG. 23A) lines were constructed of the same number and type of cell wall layers ($S_1$, $S_2$, and G) with the G-layer appearing thickest as noted above for cottonwood. Moreover, the characteristically uneven inner 'warty' layer (after Isebrands and Bensend, 1972) was also clearly visible in each line/species examined (black arrowheads, FIGS. 23A, D, F).

It should be noted, however, that the thickness of the G-layer was variable even among adjacent fiber cells within each plant line and species examined (data not shown), in agreement with previous reports of such variability (Côté et al., 1969; Isebrands and Bensend, 1972). Furthermore, all three samples displayed the characteristic (preparation) artifacts of G-layers, involving a slight detachment from the $S_2$ subwall layer (double arrowheads, FIG. 23A) and tissue folding upon interaction with grid coating (seen as a black line in the G-layer, FIGS. 23A, D, F); such artifacts related to G-layer analysis have been reported on numerous occasions (Côté et al., 1969; Clair et al., 2005).

'Normal' fibers. By contrast, the normal tissue fibers (f) of all plant lines/species examined had the expected 3 secondary subwall layers, ($S_1$, $S_2$, and $S_3$); (FIGS. 23B, G), which were also of variable thickness. A thick-walled fiber (to cell is also clearly visible in the WT C-1 (FIG. 23E).

Vessels. Finally, vessel elements were imaged from the same sections/grids to confirm that secondary tissue was examined and to compare with fiber cells for cell wall structure. The vessels (v) in all lines/species displayed the expected secondary cell wall architecture, including 3 lignified subwall layers, $S_1$, $S_2$, $S_3$ (v, FIG. 23C, E, H). Additionally, the vessels stained more intensely than the fiber cell walls, especially in $S_2$, presumably due to differential lignin content/compositions of these cell wall types (for example, see FIG. 23H).

Other general characteristics of reaction tissue in alfalfa. Besides the gf 'proper' (which may or may not be present in some species), other characteristics of reaction wood were considered.

Spiral patterning of reaction tissue. It was noted that older branch internodes (e.g. >IN12) of both alfalfa lines also contained reaction tissue that occurred in spiral/banded patterns (data not shown). These patterns extended to being nearly circumferential in the woody crown tissue of both lines. Such patterns are likely related to the rapid growth and the subsequent tensile stress gradient thus generated around the stems in both lines during growth and development, with more stresses experienced/perceived by the pC3H down-regulated line due to its reduced lignin content. Spiral reaction wood patterns have also been observed for saplings and rapidly growing trees (reviewed in Barnett and Jeronimidis, 2003).

Variable eccentric growth. Since eccentric growth (i.e. larger radius) is frequently found on the upper side (tension wood) of branches of tree species (Wardrop, 1964), it was instructive to ascertain if similar histology occurred in alfalfa branches. Interestingly, while some branch samples displayed a larger radius where gf cells occurred, others either lacked eccentric growth (but had reaction tissue) or had elongated eccentric growth that only somewhat correlated to spiral patterned reaction tissue (data not shown). Given the variability noted, however, with the data obtained, eccentric growth was considered to be an unreliable character of reaction tissue in alfalfa. This is consistent with previous observations that herbaceous species do not usually form eccentric growth in relation to reaction tissue (Wardrop, 1964).

Example Discussion:

pC3H is involved in regulation of carbon flux into the G and S segments during macromolecular lignin assembly (Anterola and Lewis, 2002, Anterola et al., 2002). Reduction of pC3H activity would thus be expected to result in formation of a lignin-reduced phenotype, albeit largely derived from p-hydroxycinnamyl alcohol (H) moieties. This is because it is very well-documented that the H-phase of lignification precedes deposition of both G and S moieties (Fergus and Goring, 1970a, b; Whiting and Goring, 1982; Terashima and Fukushima, 1988; Fukushima and Terashima, 1991). Indeed, as expected, the net effect of down-regulating (or mutating) pC3H in *A. thaliana* results in a depleted lignin phenotype (~64% lignin reduction relative to WT at maturation; Jourdes et al., 2007a) and largely containing H-units. However, this plant line was also severely dwarfed due to unknown 'pleiotropic' effects, and its vascular apparatus was greatly impaired (Jourdes et al., 2007a, see also Franke et al., 2002).

Figure 24:
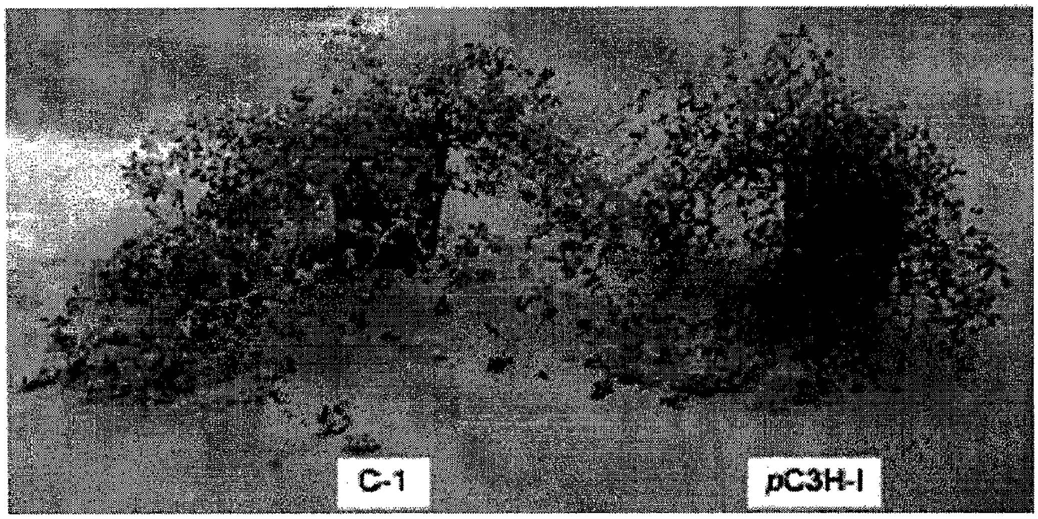
FIG. 24 shows, according to exemplary aspects of the present invention, WT C-1 and pC3H-I alfalfa line phenotypes at 4 weeks of growth following cut-back. WT C-1 has formed numerous flower buds while the pC3H-I line has few to none.

In the case of alfalfa, 11 lines down-regulated in pC3H activity were generated of which line pC3H-I was selected for further study, as it had overall the lowest lignin content (~9.4%) relative to that of WT (WT C-1, 26.1%), i.e. corresponding to a circa 64% reduction in lignin amounts. Moreover, pC3H-I predictably had greatly reduced S/G levels in the lignin formed, such that the lignin was mainly of H-character. It is likely that the effects of this genetic manipulation, which resulted in reduced carbon flux/altered lignin composition/reduced lignin content, are continually perceived and responded to during pC3H-I growth/development, i.e. ultimately resulting in global gene expression changes. That is, lacking an ability to preferentially form vascular tissues with normal lignin content/composition (as for the WT C-1 line), the pC3H-I stem vascular apparatus developmental processes were altered. In fact, relative to WT C-1, the pC3H-I line displayed delayed flowering (by ~5 weeks) (FIG. 24).

Differential patterns of internode elongation. Alfalfa internode length and tissue development is highly variable (Engels and Jung, 1998) and as such 10 branches per line were sampled to allow for statistical comparisons. It was thus found that the average internode length among sampled branches of pC3H-I was shorter than that of WT C-1 (TABLE 3). Since internode elongation is a feature of primary (and not secondary) growth, it follows that pC3H-I begins secondary growth earlier than WT C-I. This may in part account for why pC3H-I forms gf and tf cells earlier than WT C-1 and also forms more xylem tissue and xylem reaction tissues (with gf cells). Interestingly, early cessation of internode elongation is well-documented in numerous angiosperm species in response to mechanical challenges, such as controlled bending, shaking or brushing (Mitchell, 1996: Garner and Björkman, 1997, 1999; Coutand and Moulia, 2000; Coutand et al., 2000). Perhaps this apparent reduction in internodal elongation is also induced by perception of potential weakening of the overall vascular apparatus through the reduction in lignin content.

Differential patterns of lignin deposition. One noteworthy difference in histochemical staining for lignin was found between the alfalfa lines and suggested that reduction of lignin content in pC3H-I was more specific to secondary growth (FIG. 18).

While the reasons for the apparent qualitative histochemical differences in S-lignin deposition between the pr/pf and the sxr region of pC3H-I remain to be established, one possibility is that deposition is differentially regulated between primary and secondary growth in alfalfa. It is well-known that the deposition of specific lignin types is regulated both spatially (i.e. by tissue, cell and cell wall type) and temporally (e.g. in the order: HG in xylem/vessels, HGS in angiosperm fibers). On the other hand, we have not ruled out the possibility that observed differences in patterns of lignin deposition may be due to specific promoter (artifact) effects introduced by use of the heterologous pal2 bean promoter. These observations thus again underscore the complexity of studying lignification proper in planta.

Material properties of alfalfa. In terms of physiological function, reaction (tension) woody tissue formation provides a mechanism to respond to changes in perceived longitudinal stress (see Pilate et al., 2004), i.e. via formation of G-layers (within the gf) which apparently lack lignin (Norberg and Meier, 1966; Côté et al., 1969). These include structural stresses, such as axial displacement (bending) (Wardrop, 1964; Scurfield, 1973; Barnett and Jeronimidis, 2003), internal axial stresses (i.e. rapidly growing upright stems) (Isebrands and Bensend, 1972; Fisher and Stevenson, 1981; Barnett and Jeronimidis, 2003), as well as those introduced by the twining habit of some vines (Meloche and Vaughn, 2006). Given the mechanical support provided by this tissue type, angiosperm reaction tissues are also known to be cellulose-rich/lignin deficient.

Interestingly, numerous genetically modified plant lines, altered in lignin content/composition, have been shown to possess weaker stems and a weaker vascular integrity than the corresponding WT lines (reviewed by Anterola and Lewis, 2002). For instance, a transgenic tobacco line, down-regulated in cinnamyl alcohol dehydrogenase (CAD) activity, had a lower longitudinal tensile modulus than WT (Hepworth and Vincent, 1998). Additionally, a double mutation (knockout) of CAD genes in *A. thaliana* resulted in an extensively depleted lignin phenotype, with a tendency for the stems to become prostrate (Sibout et al., 2005; Jourdes et al., 2007b). The stem sections, however, were also significantly reduced in storage tensile modulus (Jourdes et al., 2007b), in keeping with the observed phenotype.

Thus, the comparable tensile dynamic moduli observed for both WT and the pC3H-I down-regulated line suggests that a compensatory mechanism is in effect to attempt to maintain the needed structural properties. That is, the increased formation of gf and tf cells in the pC3H-I line may in part compensate for the decreased lignin contents, and thus in offsetting decreased structural support/vascular integrity which would otherwise result. However, any correlation such as being proposed herein, will require detailed analyses of various lines containing different amounts of lignin (i.e. intermediary between WT and the pC3H-I line) to establish what correlations with anatomical changes can be made.

Reaction tissue. Woody plants have a mechanism for controlling both branch orientation and restoration of vertical alignment when stems are displaced from the (normal) vertical alignment. In both gymnosperms and angiosperms, this mechanism leads to formation of various tissues, collectively referred to as 'reaction wood', and which are frequently separated from normal wood by so-called 'transitional' wood (with intermediate characteristics). In gymnosperms, reaction tissue is termed compression wood and contains an increased H-lignin content (Timell, 1986; Fukushima and Terashima, 1991). While this has often been considered to result from differences in gravity perception (i.e. via signaling and transduction), this process can be duplicated in microgravity through mechanical bending (Kwon et al., 2001). It is poorly understood though how these (stress) signals are perceived and how the signal cascade is transduced leading to reaction tissue formation.

Woody angiosperms have a quite distinct, but somewhat complementary, mechanism leading to another form of reaction tissue known as tension wood. In general, it is characterized by much lower lignin contents, as well as reduced numbers and diameter of vessel elements present (Wardrop, 1964; Kucera and Philipson, 1977). However, other characteristics of woody angiosperm reaction tissue are highly variable, including whether gelatinous fibers (gf) and/or eccentric growth patterns (due to differing radii between upper and lower sides of the branch) occur (Wardrop, 1964; Kucera and Philipson, 1977) Nevertheless, the gf cell type has frequently been used as a diagnostic character of tension wood and is distinguished by a gelatinous (G-) layer, which has a gel-like appearance under magnification and often replaces one or more subwall layers of the fiber secondary cell wall (Wardrop, 1964; Carlquist, 2001). Furthermore, the higher tensile strength and Young's modulus found in tension wood (relative to normal wood) (Barnett and Jeronimidis, 2003; Clair et al., 2003) is thought to be partly due to the high tensile strength generated by orientation of the cellulose microfibrils within the G-layer (Yamamoto et al., 1993; Prodhan et al., 1995). It should also be noted that at least three 'fiber' cell types (tracheids, fiber-tracheids and libriform fibers) occur in dicotyledons, and which can form G layers under tensile stress (Carlquist, 2001).

Reaction tissue identification and differential formation in alfalfa. Gelatinous fibers 'proper' were found to stain red-purple using zinc chloro-iodide in both alfalfa lines as compared to cottonwood reaction tissue in this study and as described in previous studies of reaction wood in trees (Scurfield, 1972; Grzeskowiak et al. 1996). Applicants confirmed the presence of gf cells in alfalfa in the same way using safranin O/astra blue and then by comparison of cell wall ultrastructure to known gf cells of tree species.

With positive identification of reaction tissue in alfalfa (WT C-1 and the pC3H-I lines), we sought to determine whether reaction tissue formation in the pC3H-I was more extensive than that of WT C-1, possibly allowing pC3H-I to compensate for lost mechanical strength following lignin down-regulation. Results showed that initiation of gf formation in pC3H-I begins on average two internodes earlier than WT C-1 and is possibly related to an apparently earlier cessation of internode elongation (earlier secondary growth) in the pC3H-I. Additionally, the pC3H-I was shown to form more total xylem area and more total reaction xylem area than the WT C-1. These data may help in part explain the phenomenological observation of Reddy et al. (2005) that pC3H down-regulated alfalfa lines appeared to produce higher amounts of cellulose. It is still not clear whether increased reaction tissue formation in pC3H-I is a sole and direct effect of reduced lignin contents or if there are additional effects resulting from genetic manipulation. Future work will address this issue using other transgenic pC3H down-regulated alfalfa lines as indicated above.

Transitional tissue identification and differential formation in alfalfa. Besides gf cells 'proper', small groups of similar cells with an 'inner membrane' ($G_{im}$, FIG. 18) were observed in tissue of both alfalfa lines and cottonwood. Fibers with a similar inner membrane have been previously reported and proposed to be lignified (Scurfield and Wardrop, 1963; Scurfield, 1972; Joseleau et al., 2004; Gierlinger and Schwanninger, 2006). However, Applicants were not able to confirm lignification of this inner layer by phloroglucinol-HCl staining. Furthermore, while it was noted that the occurrence of $G_{im}$ was generally uncommon in both alfalfa lines and the cottonwood sample, the number of $G_{im}$ cells increased as alfalfa tissues became more woody. Such cell types ($G_{im}$) may be related to transitional tissue (i.e. between reaction and normal tissue) (Scurfield and Wardrop, 1963).

Additionally, we observed thick-walled fibers (tf) directly in contact with gf cells 'proper', as well as developing later throughout the areas of stems lacking gf cells 'proper'. The tf cells had a physical appearance similar to the swollen irregularly shaped gf cells, but showing variable staining (orange to yellow by zinc chloro-iodide), perhaps indicating a cell wall chemistry intermediate to that of reaction tissue (predominately red-purple) and normal tissue (yellow). These cells seem to correspond with Scurfield's (1972) reports of transitional tissue staining variably with zinc chloro-iodide. He reasoned that the histochemical variability was probably due to the variable ultrastructure of such transitional fibers, which had variable numbers of secondary cell walls in addition to a G-layer of variable width. Interestingly, preliminary descriptions of xylary tf cells have been reported by Vallet et al. (1996) and Engels and Jung (1998), but without comment on their physiological roles or prevalence. It is very likely that the tf cells comprise transitional tissues, but it is also recognized that the inner cell wall swelling of both gf and tf cells may be exaggerated due to artifact during sample preparation (Côté et al., 1969; Clair et al., 2005).

Interestingly, tf cell formation occurred (on average) seven intemodes later in WT C-1 than in the pC3H-I. Although it was not possible to accurately calculate the area of tf cells (see Materials and Methods), the observation that this cell type occurs so much earlier in pC3H-I indicates that tf cells (transitional tissues) are induced in the pC3H-I at the same time as gf cells. Presumably, WT C-1 possesses enough mechanical strength to support all but the most basal intemodes of the branch without if cell formation in addition to gf cells.

Example Summary:

To Applicants' knowledge, this specification represents the first description of reaction tissue in this species, even though the alfalfa growth habit itself suggests a capacity for its formation, i.e. since woody alfalfa tissue is formed in the basal portion of the plant (the 'crown') in order to survive winter (Undersander et al., 1997), and the developing branches elongate rapidly with variable displacement from a vertical alignment. Reaction tissue has, however, been reported in numerous woody members of the family Fabaceae (to which alfalfa belongs) (Onaka, 1949; Nečesaný, 1955; Wardrop, 1964; Höster and Liese, 1966; Fisher and Stevenson, 1981).

It can thus be provisionally anticipated that in many, if not all, lignin-reduced woody (gymnosperm and angiosperm) plants, the formation of reaction/transitional wood is to be an expected consequence, i.e. whereby the organism utilizes its pre-existing mechanisms normally employed to reinforce branches and/or leaning stems. In possible agreement with this, several transgenic poplar trees, down-regulated for CAD activity (downstream of pC3H), were also suspected to have an apparently altered ability to form G-layers although no data was reported (Pilate et al., 2004). If correct, as predicted herein, this would not be a preferred outcome for many forestry/pulp and paper applications due to the deleterious properties of gelatinous fibers, resulting in poor strength quality due to decreased bonding properties (Dickison, 2000).

Nevertheless, how these biochemical processes, leading to reaction tissue formation, are initiated (including perception of the need for its formation, and activation of the various biochemical pathways involved) are very important questions that remain to be fully delineated. Indeed, obtaining a detailed biochemical understanding of the factors controlling reaction wood formation in rapidly growing species, such as fast growing trees, and how this can be controlled, is of obvious importance to the forestry industry, e.g. in terms of developing approaches to obtain woody tissues of the desired quality for humanity's various needs.

Literature Cited in this Example 2:

Anterola, A. M. and N. G. Lewis. 2002. Trends in lignin modification: a comprehensive analysis of the effects of genetic manipulations/mutations on lignification and vascular integrity. *Phytochemistry* 61: 221-294.

Anterola, A. M., J.-H. Jeon, L. B. Davin, and N. G. Lewis. 2002. Transcriptional control of monolignol biosynthesis in *Pinus taeda:* factors affecting monolignol ratios and carbon allocation in phenylpropanoid metabolism. *The Journal of Biological Chemistry* 277: 18272-18280.

Barnett, J. R., and G. Jeronimidis. 2003. Reaction wood. In J. R. Barnett and G. Jeronimidis [eds.], Wood quality and its biological basis, 118-136. Blackwell Publishing Ltd., Oxford, U.K.

Carlquist, S. 2001. Comparative wood anatomy: Systematic, ecological, and evolutionary aspects of dicotyledon wood. Springer-Verlag, Berlin, Germany.

Clair, B., J. Ruelle, and B. Thibaut. 2003. Relationship between growth stress, mechanical-physical properties and proportion of fibre with gelatinous layer in chestnut (*Castanea sativa* Mill.). *Holzforschung* 57: 189-195.

Clair, B., J. Gril, K. Baba, B. Thibaut, and Sugiyama. 2005. Precautions for the structural analysis of the gelatinous layer in tension wood. *International Association of Wood Anatomists Journal* 26: 189-195.

Côté, W. A., A. C. Day, and T. E. Timell. 1969. A contribution to the ultrastructure of tension wood fibers. *Wood Science and Technology* 3: 257-271.

Coutand, C., and B. Moulia. 2000. Biomechanical study of the effect of a controlled bending on tomato stem elongation: local strain sensing and spatial integration of the signal. *Journal of Experimental Botany* 51: 1825-1842.

Coutand, C., J. L. Julien, B. Moulia, J. C. Mauget, and D. Guitard. 2000. Biomechanical study of the effect of a controlled bending on tomato stem elongation: global mechanical analysis. *Journal of Experimental Botany* 51: 1813-1824.

Davin, L. B. and N. G. Lewis. 2005. Lignin primary structures and dirigent sites. *Current Opinion in Biotechnology* 16: 407-415.

Dickison, W. C. 2000. Integrative Plant Anatomy. Harcourt Academic Press, Burlington, Mass., USA.

Engels, F. M., and H. G. Jung. 1998. Alfalfa stem tissues: Cell-wall development and lignification. *Annals of Botany* 82: 561-568.

Fergus, B. J., and D. A. I. Goring. 1970a. The location of guaiacyl and syringyl lignins in birch xylem tissue. *Holzforschung* 24: 113-117.

Fergus, B. J., and D. A. I. Goring. 1970b. The distribution of lignin in birch wood as determined by ultraviolet microscopy. *Holzforschung* 24: 118-124.

Fisher, J. B., and J. W. Stevenson. 1981. Occurrence of reaction wood in branches of dicotyledons and its role in tree architecture. *Botanical Gazette* 142: 82-95.

Franke, R, M. R. Hemm, J. W. Denault, M. O. Ruegger, J. M. Humphreys, and C. Chapple. 2002. Changes in secondary metabolism and deposition of an unusual lignin in the ref8 mutant of *Arabidopsis. The Plant Journal* 30: 47-59.

Fukushima, K., and N. Terashima. 1991. Heterogeneity in formation of lignin. Part XV. Formation and structure of lignin in compression wood of *Pinus thunbergii* studied by microautoradiography. *Wood Science and Technology* 25: 371-381.

Garner, L. C., and T. Björkman. 1997. Using impedance for mechanical conditioning of tomato transplants to control excessive stem elongation. *HortScience* 32: 227-229.

Garner, L. C., and T. Björkman. 1999. Mechanical conditioning of tomato seedlings improves transplant quality without deleterious effects on field performance. *HortScience* 34: 848-851.

Gierlinger, N., and M. Schwanninger. 2006. Chemical imaging of poplar wood cell walls by confocal raman microscopy. *Plant Physiology* 140: 1246-1254.

Grzeskowiak, V., F. Sassus, and M. Fornier. 1996. Coloration macroscopique, retraits longitudinaux de maturation et de séchage du bois de tension du peuplier (*Populus* x *euramericana* cv 1.214). *Annales des Sciences Forestières* 53: 1083-1097.

Heller, W., and T. Kühnl. 1985. Elicitor induction of a microsomal 5-O-(4 coumaroyl) shikimate 3'-hydroxylase in parsley cell suspension cultures. *Archives of Biochemistry and Biophysics* 241: 453-460.

Hepworth, D. G., and J. F. V. Vincent. 1998. The mechanical properties of xylem tissue from tobacco plants (*Nicotiana tabacum* 'Samsun'). *Annals of Botany* 81: 751-759.

Höster, H.-R., and W. Liese. 1966. Über das vorkommen von reaktionsgewebe in wurzeln und ästen der dikotyledonen. *Holzforschung* 20: 80-90.

Iiyama, K., and R. Pant. 1988. The mechanism of the Mäule colour reaction introduction of methylated syringyl nuclei into softwood lignin. *Wood Science and Technology* 22: 167-175.

Isebrands, J. G., and D. W. Bensend. 1972. Incidence and structure of gelatinous fibers within rapid-growing eastern cottonwood. *Wood and Fiber* 4: 61-71.

Joseleau, J.-P., T. Imai, K. Kuroda, and K. Ruel. 2004. Detection in situ and characterization of lignin in the G-layer of tension wood fibers of *Populus deltoides. Planta* 219: 338-345.

Jourdes, M., A. M. Patten, D. D. Laskar, G. L. Helms, V. R. Franceschi, L. B. Davin, and N. G. Lewis. 2007a. (Manuscript submitted).

Jourdes, M., C. L. Cardenas, D. D. Laskar, S. G. A. Moinuddin, E. E. Brown, M.-P. Laborie, L. B. Davin, and N. G. Lewis. 2007b. Why lignins are not poly-p-hydroxycinnamaldehydes: A comprehensive analysis of structural defects introduced on lignin template polymerization and vascular integrity through cinnamyl alcohol dehydrogenase (CAD) mutations in *Arabidopsis*. Phytochemistry (in press)

Kaeiser, M., and S. G. Boyce. 1965. The relationship of gelatinous fibers to wood structure in eastern cottonwood (*Populus deltoides*). *American Journal of Botany* 52: 711-715.

Kucera, L. J., and W. R. Philipson. 1977. Occurrence of reaction wood in some primitive dicotyledonous species. *New Zealand Journal of Botany* 15: 649-654.

Kwon, M., D. L. Bedgar, W. Piastuch, L. B. Davin, and N. G. Lewis. 2001. Induced compression wood formation in Douglas fir (*Pseudotsuga menziesii*) in microgravity. *Phytochemistry* 57:847-857.

Laskar, D. D., M. Jourdes, A. M. Patten, G. L. Helms, L. B. Davin, and N. G. Lewis. 2006. The *Arabidopsis* cinnamoyl CoA reductase irx4 mutant has a delayed but coherent (normal) program of lignification. *The Plant Journal* 48: 674-686.

Lewis, N. G., L. B. Davin, and S. Sarkanen. 1999. The nature and function of lignins. In Sir D. H. R. Barton, K. Nakanishi, and O. Meth-Cohn [eds.-in-chief] Comprehensive natural products chemistry. vol. 3, 617-745. Carbohydrates and their derivatives including tannins, cellulose and related lignins, Elsevier Science, London, UK.

Meloche, C. G., and K. C. Vaughn. 2006. Gelatinous fibers are critical in coiling of tendrils and twining of vines. Plant Biology 2006: Annual conference of the American Society of Plant Biologists, Boston, Mass., USA, 5-9 Aug. 2006 (Abstract no. 116).

Mitchell, C. A. 1996. Recent advances in plant responses to mechanical stress: theory and application. *HortScience* 31: 31-35.

Nakano, J., and G. Meshitsuka. 1992. The detection of lignin. In S. Y. Lin and C. W. Dence [eds.], Methods in Lignin Chemistry, 23-32. Springer-Verlag, Berlin, Germany.

Nečesaný, V. 1955. Vyskyt reakčního dřeva s hlediska taxonomického. Sborník vysoké školy zěmědelskéé a lesnické fakulty v Brně. Řada C. 3: 131-149.

Norberg, P. H., and H. Meier. 1966. Physical and chemical properties of the gelatinous layer in tension wood fibers of aspen (*Populus tremula* L.). *Holzforschung* 20:174-178.

Onaka, F. 1949. Studies on compression and tension wood. *Wood Research: Bulletin of the Wood Research Institute. Kyoto University.* 1: 1-88.

Patten, A. M., C. L. Cardenas, F. C. Cochrane, D. D. Laskar, D. L. Bedgar, L. B. Davin, and N. G. Lewis. 2005. Reassessment of effects on lignification and vascular development in the irx4 *Arabidopsis mutant. Phytochemistry* 66: 2092-2107.

Pilate, G., B. Chabbet, B. Cathala, A. Yoshinaga, J.-C. Leplé, F. Laurans, C. Lapierre, and K. Ruel. 2004. Lignification and tension wood. *Comptes Rendus Biologies* 327: 889-901.

Pomar, F., F. Merino, and A. R. Barceló. 2002. O-4-Linked coniferyl and sinapyl aldehydes in lignifying cell walls are the main targets of the Wiesner (phloroglucinol-HCl) reaction. *Protoplasma* 220: 17-28.

Prodhan, A. K. M. A., R. Funada, J. Ohtani, H. Abe, and K. Fukazawa. 1995. Orientation of microfibrils and microtubules in developing tension-wood fibres of Japanese ash (*Fraxinus mandshurica* var. *japonica*). *Planta* 196: 577-585.

Rasband, W. S. 1997-2006. ImageJ software: version 1.36b. U.S. National Institutes of Health, Bethesda, Md., USA. Website (rsb.info.nih.gov/ij) [Accessed 13 Mar. 2006].

Reddy, M. S. S., F. Chen, G. Shadle, L. Jackson, H. Aljoe, and R. A. Dixon. 2005. Targeted down-regulation of cytochrome P450 enzymes for forage quality improvement in alfalfa (*Medicago sativa* L.). *Proceedings of the National Academy of Sciences of the United States of America* 102: 16573-16578.

Sarkanen, K. V., and C. H. Ludwig. 1971. Definition and Nomenclature. In K. V. Sarkanen and C. H. Ludwig [eds.], Lignins: Occurrence, formation, structure and reactions, 1-18. John Wiley and Sons, Inc., New York, N.Y., USA.

Schoch, G., S. Goepfert, M. Morant, A. Hehn, D. Meyer, P. Ullmann, and D. Werck-Reichhart. 2001. CYP98A3 from *Arabidopsis thaliana* is a 3'-hydroxylase of phenolic esters, a missing link in the phenylpropanoid pathway. *The Journal of Biological Chemistry* 276: 36566-36574.

Scurfield, G., and A. B. Wardrop. 1962. The nature of reaction wood: VI. The reaction anatomy of seedlings of woody perennials. *Australian Journal of Botany* 10: 93-105.

Scurfield, G., and A. B. Wardrop. 1963. The nature of reaction wood: VII. Lignification in reaction wood. *Australian Journal of Botany* 11: 107-116.

Scurfield, G. 1972. Histochemistry of reaction wood cell walls in two species of *Eucalyptus* and in *Tristania conferta* R. BR. *Australian Journal of Botany* 20: 9-26.

Scurfield, G. 1973. Reaction wood: Its structure and function: Lignification may generate the force active in restoring the trunks of leaning trees to the vertical. *Science* 179: 647-655.

Sibout, R., A. Eudes, G. Mouille, B. Pollet, C. Lapierre, L. Jouanin, and A. Seguin. 2005. Cinnamyl alcohol dehydrogenase-C and -D are the primary genes involved in lignin synthesis in the floral stem of *Arabidopsis. The Plant Cell* 17: 2059-2076.

Srebotnik, E. and K. Messner. 1994. A simple method that uses differential staining and light microscopy to assess the selectivity of wood delignification by white rot fungi. *Applied and Environmental Microbiology* 60:1383-1386.

Terashima, N, and K. Fukushima. 1988. Heterogeneity in formation of lignin—XI: An autoradiographic study of the heterogeneous formation and structure of pine lignin. *Wood Science and Technology* 22: 259-270.

Timmel, T. E. 1986. Compression wood in Gymnosperms. Springer-Verlag, New York, N.Y., USA Undersander, D. P. Vassalotti, and D. Cosgrove. 1997. Alfalfa: germination and growth. Publication A3681. University of Wisconsin Cooperative Extension Publishing, Madison, Wis., USA.

Vallet, C., B. Chabbert, Y. Czaninski, and B. Monties. 1996. Histochemistry of lignin deposition during sclerenchyma differentiation in alfalfa stems. *Annals of Botany* 78: 625-632.

Vallet, C., G. Lemaire, B. Monties, and B. Chabbert. 1998. Cell wall fractionation of alfalfa stem in relation to internode development: biochemistry aspect. *Journal of Agricultural and Food Chemistry* 46: 3458-3467.

Vazquez-Cooz, I. and R. W. Meyer. 2002. A differential staining method to identify lignified and unlignified tissues. *Biotechnic and Histochemistry* 77: 277-282.

Wardrop, A. B. 1964. The Reaction Anatomy of Arborescent Angiosperms. In M. H. Zimmermann [ed.]. The Formation of Wood in Forest Trees, 405-456. Academic Press, New York, N.Y., USA.

Whiting, P., and D. A. I. Goring. 1982. Chemical characterization of tissue fractions from the middle lamella and secondary wall of black spruce tracheids. *Wood Science and Technology* 16: 261-267.

Yamamoto, H., T. Okuyama, and M. Yoshida. 1993. Generation process of growth stresses in cell walls V. Model of tensile stress gradient in gelatinous fibers. *Mokuzai Gakkaishi* 39: 118-125.

EXAMPLE 3

Chavicol/Eugenol for Biofuels/Intermediate Chemicals

Example summary. This Example relates to advances made by applicants and which result in formation of two well-known molecules: chavicol and eugenol. Both substances have historically been used as flavor/fragrant components from Tanzania, Madagascar and Indonesia; however, the biochemical/biotechnological manipulations disclosed herein provide for the diversion of monolignols from lignin/lignan formation in plant species to instead diverting these compounds for use, for example, in biodiesel or polymer production (plastic replacement), i.e., in addition to their current roles in human nutrition and medicine.

Example overview. Recognition of a growing national emergency has resulted from escalating costs of petroleum-derived products worldwide, political instability of petroleum-producing regions throughout the world and an increasing recognition of an ever-dwindling (unsustainable) supply of petroleum products for future generations. Coupled to an ever-increasing human population, and an ever-increasing demand for petroleum products, this has resulted in a growing awareness that humanity needs to urgently identify solutions to circumvent this serious problem in a sustainable, reliable, manner. These issues relate not only to fuels but also to producing sufficient quantities of petroleum-based polymers, such as polyethylenes, polystyrenes and other products; about 12% of all petroleum is used for non-fuel/non-energy purposes.

A major potential sources of renewable energy/biofuels is that from plant biomass, i.e. through fermentation of polymeric carbohydrates to give ethanol. While the capacity of ethanol production in the USA has steadily grown over the last decade, predominantly from partial fermentation of corn stem residues, there are two major scientific hurdles that have not yet been overcome. The first is that of the polymeric lignins, which make up ca. 20-30% of all plant stem biomass, and which are Nature's second most abundant organic materials. Under current fermentation processes, lignins cannot readily be converted into either ethanol and/or other liquid/gaseous fuels. Indeed, there are still no isolated enzymes and/or proteins known to effectively degrade the lignin macromolecules, in contrast to reports in the nineteen-eighties that indicated this problem had been solved. Secondly, the polymeric lignins themselves represent a formidable physical barrier in biomass for efficient carbohydrate fermentation, and thus their presence represents a critical barrier in making these technologies more economical.

There are, therefore, compelling reasons to identify novel ways to more effectively utilize the lignin biopolymers and/or the carbon allocated for the lignin-forming pathway.

Biotechnological manipulations of both lignin contents and compositions in various plant species have been successfully obtained, but not without a price. Generally, the effects of drastically reducing lignin contents in vascular plants results in significant impairment of the vascular apparatus, the integrity of which is required for plants to withstand compressive forces and other environmental challenges (e.g., wind, rain, snow, etc.), as well as for efficiently transporting nutrients and water. Such defects, e.g., collapsed vessels, etc. (for a discussion and examples see Anterola and Lewis[1]) can potentially lead to serious difficulties in growing biotechnologically modified plant lines in the wild due to a compromised vascular apparatus, i.e., as this can lead to premature lodging, (vasculature) collapse of plant stems, during growth/development. Therefore, prefereably, an appropriate balance is maintained between growing vascular plants for commercial purposes, and reducing/modifying lignin content and/or composition. However, while the precise extent to which lignin polymer composition and content can ultimately be modified is yet to be fully appreicated, there are, according to particular aspects of the present invention, alternative ways to produce renewable energy biofuels while striking an adequate balance between lignin content/composition and sufficient structural integrity.

The present inventive methods could be applied, for example, either in oilseed-bearing plants (e.g., canola) or in heartwood-forming tissues of trees (e.g., western red cedar) used for lumber and pulp/paper products. In the latter, heartwood formation is generally accompanied by a massive deposition of non-structural low molecular weight molecules, such as the lignan, plicatic acid (30), which, in western red cedar can be ~20% of the overall dry weight of the stem. These processes (oilseed and heartwood formation/deposition of metabolites), as well as judicial modification of lignin content and composition, thus offer the potential to rationally optimize plant feedstocks for biofuel/bioenergy either directly in specific crops or indirectly as part of wood processing for pulp/paper, specialty chemicals, etc.

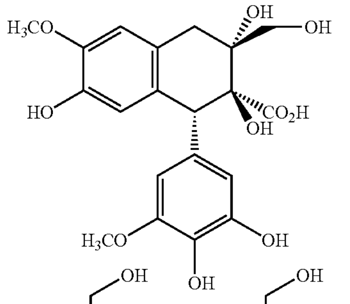

Plicatic acid

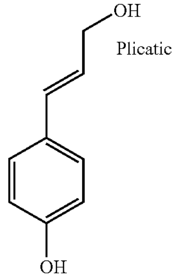

p-Coumaryl alcohol

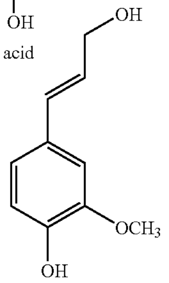

Coniferyl alcohol

-continued

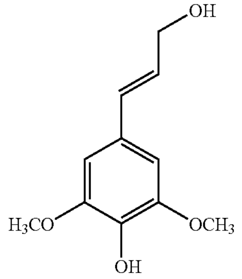

Sinapyl alcohol

As discussed herein, lignins are biopolymeric materials derived from the one-electron oxidation of monolignols, p-coumaryl (19), coniferyl (21) and sinapyl (23) alcohols, whereas the lignans in heartwood tissues are low molecular weight metabolites derived from the same precursors. At ambient temperatures, the precursor monolignols are relatively unstable and reactive solid compounds, whereas the final lignin biopolymers are quite intractable biopolymers and the heartwood lignans are solids that can be extracted by aqueous/organic mixtures. In general, it requires strenuous chemical (pulping) conditions to solubilize the lignin-derived material from (woody) plant cell walls, i.e., via chemical pulping using either strong caustic or strong acid solutions at elevated temperatures and pressures. Lignin removal, however, is essential if effective fermentation of carbohydrate biomass is an objective.

Applicants have previously discovered a class of enzymes that we have depicted as pinoresinol-lariciresinol and phenylcoumaran benzylic ether reductases (PLRs and PCBERs, FIGS. 8A and 8B) (Chu, et al., *J. Biol. Chem.* 268:27026-27033; Dinkova-Kostova, et al., *J. Biol. Chem.* 271:29473-29482; Fujita, et al., *J. Biol. Chem.* 274:618-627; Gang, et al., *J. Biol. Chem.* 274:7516-7527; Min, T., et al., *J. Biol. Chem.* 278:50714-50723); the former convert monolignol-derived dimers (lignans) into valuable medicinal products, such as the cancer-preventative compounds, secoisolariciresinol and matairesinol. They also represent major intermediates to various heartwood-accumulating lignans (i.e., plicatic acid) in trees, such as western red cedar.

Presently, a new but analogous pathway utilizing monolignols has been discovered, which applicants consider has extraordinarily promising potential for either biofuels, intermediate chemicals or as an improved and stable source of the spice (chavicol (31) and eugenol (33)) components. For example, the latter is widely used in medical and dental applications due to its biocidal and analgesic properties. In the pathway to these two allylphenols, the monolignol precursors are first biochemically activated (via ester formation) and then subsequently converted into the highly combustible liquid fuels, the aromatic hydrocarbons, chavicol (31) and eugenol (33) (FIG. 5C). Importantly, the protein involved, chavicol/eugenol synthase (CS/ES), is a homologue of our PLR/PCBER proteins, whose encoding cDNA hybridizes under the same conditions as for PLR. The proteins of interest are thus trivially depicted as bifunctional chavicol/eugenol synthases.

According to particular aspects of the present invention, this discovery provides novel methods for diverting monolignol flow away from lignin biopolymer formation, or from heartwood lignan accumulation/deposition, to that engendering formation of the potential product liquid fuels/intermediate chemicals of interest. In additional aspects, this strategy enhances oilseed production as well, both in relative amounts of bioproduct/biofuels and their calorific value. In further aspects, these products (chavicol (31)/eugenol (33)) would be removed, leaving the remaining (lignin-reduced) biomass able to be more efficiently fermented for ethanol production.

Preferably, two genes encoding respective proteins are used to provide proteins that can: (i) acylate monolignol precursors to afford the corresponding acylated derivatives (e.g., the acylating transferase family from *Taxus brevifolia;* Chau, et al., *Arch Biochem Biophys* 430:237-246, 2004.), and (ii) convert the latter into liquid biofuel/intermediate chemicals (e.g., using the presently disclosed novel CS/ES homologues). Alternatively, the monolignols can be chemically acylated, followed by conversion by CS/ES.

Cultured Cell Aspects:

In particular aspects, chavicol (31)/eugenol (33) (or isomers) thereof are produced in bacterial and plant cell cultures. In certain embodiments, *E. coli* and tobacco (*N. tabacum*) cell cultures are used to convert p-coumaryl (19) and coniferyl (21) alcohols, both lignin and lignan precursors, into the allylphenols, p-chavicol (b) and eugenol (33), or the regioisomers, p-anol (37) and isoeugenol (39). In the case of bacterial cell-cultures, transformed *E. coli* cells harboring the genes encoding the monolignol acyl transferase and the chavicol/eugenol synthases (CS/ES) are used.

Biotransformation of p-coumaryl/coniferyl alcohols in *E. coli* by heterologous expression of acyltransferase from *Taxus* sp and chavicol synthase or eugenol synthase. In particular aspects, the genes encoding these two proteins are cloned into a coexpression vector such as the pET-30 Ek/LIC vector offered by Novagen/EMD (Held, et al., *inNovations* 18, 3-6; Loomis, et al., *inNovations* 15, 2-6; and Novy, R., et al., *inNovations* 15, 2-6), which uses the LIC Duet Adapter method for simultaneous cloning of two open reading frames. This construct is expressed in an *E. coli* host strain compatible for coexpression such as BL21 (DE3). The substrate p-coumaryl (19)/coniferyl (21) alcohol is incubated with the transgenic *E. coli* coexpressing these two proteins and the end products are analyzed. Compounds resulting from monolignol metabolism are preferably analyzed by HPLC. Preferably, an assay is first conducted to determine tolerance levels of *E. coli* towards monolignol acetate concentration. Eugenol (33) substrate conversion to ferulic acid (6) and vanillin has been previously studied successfully in an *E. coli* coexpression system (Overhage, et al., *Appl. Environ. Microbiol.* 69, 6569-6576, 2003). Recombinant *E. coli* cells expressing a combination of plant biosynthetic genes have also been shown to efficiently convert phenylpropionic acids to stilbene compounds (Watts, et al., *BMC Biotechnol.* 6, 22, 2006).

The obtained transformed cell lines are used to determine the optimal conditions (e.g., pH, temperature, light intensity, effects of varying IPGT concentrations, cell culture induction, growth and residence times of cell cultures, cell culture viability, product collection and optimization (e.g., via decanting, concentration on solid matrixes, product stability, etc.) for conversion of p-coumaryl (19)/coniferyl (21) alcohol esters into acccumulated desired allylphenols, such as chavicol (31) and eugenol (33). In particular tobacco cell culture embodiments, the tobacco cells are transformed with both genes, under control of, for example, the 35S CaMV promoter to provide cells to accumulate chavicol (31)/eugenol (33), and/or convert p-coumaryl (19)/coniferyl (21) alcohols into these products, respectively.

Plant Aspects:

In additional aspects, either oilseed (e.g., rapeseed) or heartwood-forming plants are transformed (genetically modified) to produce, in large quantity, chavicol (31) and eugenol (33). In certain embodiments allylphenol/propenylphenol accumulation is engeineered in both tobacco and canola plant lines.

Tobacco transformation. In certain additional spects, these two genes are cotransformed into *Nicotianum tabacum* to provide a modified biosynthetic expression system in planta. In certain embodiments, expression of the heterologous proteins is driven by a tissue specific promoter such as the one associated with CAD activity (Kim, et al., *Proc. Natl. Acad. Sci., USA* 101:1455-1460, 2004). Tobacco plant cells are, for example, transformed using *Agrobacterium* cocultivation using the appropriate methods for either leaf (An, et al., *Plant Physiol.* 81:301-305, 1986) or callus (Mayo, et al., *Nature Protocols* 1:1105-1111, 2006) tissue. Briefly, this protocol involves co-cultivation of leaf pieces with *Agrobacterium* for two days, followed by transfer to shoot induction agar plates containing BA (benzyladenine) or callus induction medium containing NAA (naphthaleneacetic acid) and BA. A more detailed procedure for tobacco leaf transformation is as follows. Cell cultures will be obtained from the transformants following standard procedures.

General procedure used for tobacco plant transformation and regeneration. *Agrobacterium tumefaciens* LBA4404/pC2760 are transformed with DNA plasmid preparations of each of the final constructs. Overnight cultures of these Agrobacteria are then grown in 2 ml YEP medium containing kanamycin (10 μg/ml), glucose (0.4%) and acetosyringone (50 μM). Leaf pieces from 6 week old sterile tobacco plants of the wild type line, growing in MS medium in Magenta boxes, are placed upside down into 4 ml sterile MS medium containing 6-benzylaminopurine (BA, 0.5 μg) and naphthalene acetic acid (NAA, 2 μg/ml) and placed in a dark 28° C. incubator. After 2-3 days, the leaf pieces are washed off with MS medium containing the same BA and NAA concentrations and placed upside down onto 0.6% Phytagar MS plates containing BA (1.0 μg/ml) and NAA (0.1 μg/ml) and kanamycin (50 μg/ml), carbenicillin (100 μg/ml), and cefotaxime (200 μg/ml) and the plates are placed under low light (50 μmol) conditions. It usually takes 4-8 weeks for shoots to become visible. After 4-8 weeks or as soon as shoots start to appear, the shoots are picked and transferred to 0.4% Phytagar MS plates containing only sucrose (15 g/l) and BA (1.0 μg/ml) and NAA (0.1 μg/ml) with kanamycin (50 μg/ml), carbenicillin (100 μg/ml) and cefotaxime (200 μg/ml) and the plates are put into stronger light (150 μmol) for shoot and root stimulation. After about two weeks on this medium, the plantlets are then transferred to MS plates containing only sucrose (15 g/l) plus NAA (0.1 μg/ml) with kanamycin (50 μg/ml), carbenicillin (50 μg/ml), and cefotaxime (200 μg/ml) to encourage root formation. When roots start to appear, the plants are transferred to Magenta squares containing sucrose (15 g/l) plus kanamycin (25 μg/ml), carbenicillin (50 μg/ml), and cefotaxime (200 μg/ml). When a strong root system develops and the plants are growing well, they are transferred to pots containing potting medium. After hardening off for 1-2 weeks, the plants are sent to the greenhouse to grow to maturity.

In certain aspects, a tobacco line is directed towards increasing allylphenol formation in both leaf and stem tissues, with the latter providing validation for heartwood deposition. In additional embodiments, the canola line is directed/engineered to oilseed metabolite accumulation.

In particular tobacco plant aspects, in combination with introducing/overexpressing the chavicol/eugenol synthases and acyltransferases, partial to full down-regulation of lignification is acheived with increasing allyl/propenyl phenol formation. In certain embodiments, the plant lines are transformed, under control of both 35S and native promoters (e.g., using the monolignol pathway promoter for the last step to the monolignols, cinnamyl alcohol dehydrogenase), to provide for (a) allyl/propenyl phenol formation; (b) altered stem properties and (c) ease of fermentation of the remaining material to afford ethanol (relative to wild-type lines).

Canola (*Brassica napus*) transformation: In additional aspects, canola is transformed with the same constructs as described above using *Agrobacterium* cocultivation procedures as outlined by Cardoza et al.(Cardoza & Stewart, In *Trangenic Crops of the World—Essential Protocols*. (Curtis, I. S., ed), pp. 379-387, 2004 Kluwer Academic Publishers; and Cardoza & Stewart, *Plant Cell Rep.* 21:599-604, 2003). Briefly, hypocotyl segment explants are cocultivated with the *Agrobacterium* harboring the binary vector constructs for two days, washed off, then placed onto a preconditioning MS medium containing the auxin hormone analog 2,4-D. After two weeks, these hypocotyls explants are transferred to organogenesis promoting medium containing BAP (6-benzylaminopurine), zeatin and silver nitrate. Two weeks later, the shoots are transferred to a shoot development medium containing BAP and zeatin. The shoots are then transferred to shoot elongation medium containing BAP. Finally, elongated shoots are transferred to rooting medium containing IBA.

In particular canola plant aspects, allylphenol/phenol is targeted to oilseed tissues, to provide production yield(s).

References Cited for this Example 3:

1. Anterola, A. M. and Lewis, N. G. (2002) Trends in lignin modification: A comprehensive analysis of the effects of genetic manipulations/mutations on lignification and vascular integrity. *Phytochemistry* 61, 221-294.

2. Chu, A., Dinkova, A., Davin, L. B., Bedgar, D. L. and Lewis, N. G. (1993) Stereospecificity of (+)-pinoresinol and (+)-lariciresinol reductases from *Forsythia intermedia. J. Biol. Chem.* 268, 27026-27033.

3. Dinkova-Kostova, A. T., Gang, D. R., Davin, L. B., Bedgar, D. L., Chu, A. and Lewis, N. G. (1996) (+)-Pinoresinol/(+)-lariciresinol reductase from *Forsythia intermedia:* protein purification, cDNA cloning, heterologous expression and comparison to isoflavone reductase. *J. Biol. Chem.* 271, 29473-29482.

4. Fujita, M., Gang, D. R., Davin, L. B. and Lewis, N. G. (1999) Recombinant pinoresinol/lariciresinol reductases from western red cedar (*Thuja plicata*) catalyze opposite enantiospecific conversions. *J. Biol. Chem.* 274, 618-627.

5. Gang, D. R., Kasahara, H., Xia, Z.-Q., Vander Mijnsbrugge, K., Bauw, G., Boerjan, W., Van Montagu, M., Davin, L. B. and Lewis, N. G. (1999) Evolution of plant defense mechanisms: relationships of phenylcoumaran benzylic ether reductases to pinoresinol-lariciresinol and isoflavone reductases. *J. Biol. Chem.* 274, 7516-7527.

6. Min, T., Kasahara, H., Bedgar, D. L., Youn, B., Lawrence, P. K., Gang, D. R., Halls, S. C., Park, H., Hilsenbeck, J. L., Davin, L. B., Lewis, N. G. and Kang, C. H. (2003) Crystal structures of pinoresinol-lariciresinol and phenylcoumaran benzylic ether reductases and their relationship to isoflavone reductases. *J. Biol. Chem.* 278, 50714-50723.

7. Koeduka, T., Fridman, E., Gang, D. R., Vassao, D. G., Jackson, B. L., Kish, C. M., Orlova, I., Spassova, S. M., Lewis, N. G., Noel, J. P., Baiga, T. J., Dudareva, N. and Pichersky, E. (2006) From the Cover: Eugenol and isoeugenol, characteristic aromatic constituents of spices, are biosynthesized via reduction of a coniferyl alcohol ester. *Proc. Natl. Acad. Sci. U.S.A.* 103, 10128-10133.

8. Vassao, D. G., Davin, L. B. and Lewis, N. G. (2006) Provisional Patent Application: Protein encoding chavicol/eugenol synthase.

9. Vassao, D. G., Gang, D. R., Koeduka, T., Jackson, B., Pichersky, E., Davin, L. B. and Lewis, N. G. (2006) Chavicol formation in sweet basil (*Ocimum basilicum*): cleavage of an esterified C9 hydroxyl group with NAD(P)H-dependent reduction. *Org. Biomol. Chem.* 4, 2733-2744.

10. Vassão, D. G., Milhollan, J. K., Kim, S.-J., Eichinger, D., Davin, L. B. and Lewis, N. G. (2006) Enzymatic formation of the allylphenols chavicol and eugenol by a regiospecific NAD(P)H-dependent reductase in the creosote bush (*Larrea tridentata*). (Manuscript in preparation).

11. Bauer, K., Garbe, D. and Surburg, H. (2001) Natural raw materials in the flavor and frangrance industry. In *Common Fragrance and Flavor Materials: Preparation and Uses*. (Bauer, K., Garbe, D. and Surburg, H., eds), pp. 167-226, Wiley-VCH 12. Peterson, C. L. Potential Production of Biodiesel. www.uidaho.edu/bioenergy/BiodieselEd/publication/02.pdf 13. Chau, M., Walker, K., Long, R. and Croteau, R. (2004) Regioselectivity of taxoid-O-acetyltransferases: heterologous expression and characterization of a new taxadien-5alpha-ol-O-acetyltransferase. *Arch Biochem Biophys* 430, 237-246.

14. Held, D., Yaeger, K. and Novy, R. New coexpression vectors for expanded compatibilitiesin *E. coli. inNovations* 18, 3-6.

15. Loomis, K., Sternard, B., Rupp, S., Held, D., Yaeger, K., Novy, R. and Wong, S. Coexpression of multiple target proteins in *E. coli. inNovations* 15, 2-6.

16. Novy, R., Yaeger, K., Held, D. and Mierendorf, R. Coexpression of multiple target proteins in *E. coli. inNovations* 15, 2-6.

17. Overhage, J., Steinbuchel, A. and Priefert, H. (2003) Highly efficient biotransformation of eugenol to ferulic acid and further conversion to vanillin in recombinant strains of *Escherichia coli. Appl. Environ. Microbiol.* 69, 6569-6576.

18. Watts, K. T., Lee, P. C. and Schmidt-Dannert, C. (2006) Biosynthesis of plant-specific stilbene polyketides in metabolically engineered *Escherichia coli. BMC Biotechnol.* 6, 22.

19. Kim, S.-J., Kim, M.-R., Bedgar, D. L., Moinuddin, S. G. A., Cardenas, C. L., Davin, L. B., Kang, C.-H. and Lewis, N. G. (2004) Functional reclassification of the putative cinnamyl alcohol dehydrogenase multigene family in *Arabidopsis. Proc. Natl. Acad. Sci., USA* 101, 1455-1460.

20. An, G., Watson, B. D. and Chiang, C. C. (1986) Transformation of tobacco, tomato, potato, and *Arabidopsis thaliana* using a binary Ti vector system. *Plant Physiol.* 81, 301-305.

21. Mayo, K. J., Gonzales, B. J. and Mason, H. S. (2006) Genetic transformation of tobacco NT1 cells with *Agrobacterium tumefasciens*. Nature Protocols 1, 1105-1111.

22. Cardoza, V. and Stewart, C. N. (2004) *Agrobacterium*-mediated transformation of canola. In *Trangenic Crops of the World—Essential Protocols*. (Curtis, I. S., ed), pp. 379-387, Kluwer Academic Publishers 23. Cardoza, V. and Stewart, C. N. (2003) Increased *Agrobacterium*-mediated transformation and rooting efficiencies in canola (*Brassica napus* L.) from hypocotyl segment explants. *Plant Cell Rep.* 21, 599-604.

EXAMPLE 4

Plant Cell Walls are Enfeebled when Attempting to Preserve Native Lignin Configuration with poly-p-hydroxycinnamaldehydes: Evolutionary Implications Example summary. This Example relates to the effects of disruption of lignin macromolecular configuration and stem vascular integrity through CAD mutations. With such mutations, template polymerization was attempted but aborted at an early stage of cell-wall phenolic deposition when p-hydroxycinnamaldehydes were employed as substrates.

More specifically, the lignin deficient double mutant of cinnamyl alcohol dehydrogenase (CAD, cad-4, cad-5 or cad-c, cad-d) in *Arabidopsis thaliana* (Sibout et al., 2005), was comprehensively examined for effects on disruption of native lignin macromolecular configuration; the two genes encode the catalytically most active CAD's for monolignol/lignin formation (Kim et al., 2004). The inflorescence stems of the double mutant presented a prostrate phenotype with dynamic modulus properties greatly reduced relative to that of the wild type (WT) line due to severe reductions in macromolecular lignin content. Interestingly, initially the overall pattern of phenolic deposition in the mutant was apparently very similar to WT, indicative of comparable assembly processes attempting to be duplicated. However, shortly into the stage involving (monomer cleavable) 8-O-4' linkage formation, deposition was aborted. At this final stage, the double mutant had retained a very limited ability to biosynthesize monolignols as evidenced by cleavage and release of ca 4% of the monolignol-derived moieties relative to the lignin of the WT line. In addition, while small amounts of cleavable p-hydroxycinnamaldehyde-derived moieties were released, the overall frequency of (monomer cleavable) 8-O-4' inter-unit linkages closely approximated that of WT for the equivalent level of lignin deposition, in spite of the differences in monomer composition. Additionally, 8-5' linked inter-unit structures were clearly evident, albeit as fully aromatized phenylcoumaran-like substructures.

The data are interpreted as a small amount of p-hydroxycinnamaldehydes being utilized in highly restricted attempts to preserve native lignin configuration, i.e. through very limited monomer degeneracy during template polymerization which would otherwise afford lignins proper in the cell wall from their precursor monolignols. The defects introduced (e.g. in the vascular integrity) provide important insight as to why p-hydroxycinnamaldehydes never evolved as lignin precursors in the 350,000 or so extant vascular plant species. Prior to investigating lignin primary structure proper, it is instructive to initially define the fundamental characteristics of the biopolymer(s) being formed, such as inter-unit frequency and lignin content, in order to design approaches to determine overall sequences of linkages.

Example overview. The compelling question of whether monolignol-derived macromolecular lignin configuration results from either non-random or random coupling is only now being fully addressed, in terms of beginning to design definitive experiments and approaches to distinguish between such possibilities (Davin & Lewis, 2005). Yet this is a matter of profound importance, whether considering lignin's potential for improved utilization of lignocellulosics for the wood, pulp, and paper industries, or as a source of (new) biofuels, biopolymers, or ruminant feedstocks. Moreover, establishing how macromolecular lignin configuration is actually engendered is also of fundamental importance for science itself, particularly being Nature's second most abundant vascular plant substances next to cellulose (Lewis and Yamamoto, 1990, Lewis et al., 1999; Croteau et al., 2000; and Anterola & Lewis, 2002).

Some reports have extended the fifty year old unproven random assembly hypothesis to now include the facile/seamless incorporation of non-lignin (phenolic) moieties into lignin biopolymers should monolignol 19, 21 and 23(FIG. 5) supply be diminished (Ralph et al, 1997, 19998 and 2004a).

Such instances have been proposed to occur when the monolignol pathway steps are either mutated or down-regulated, and have led to repeated suggestions of a compensatory combinatorial biochemistry (random coupling) mechanism being in effect using different non-monolignol precursors (Ralph et al, 2004a). This, in turn, has led to other notions that lignin structure is not particularly important, from either physiological and/or structural perspectives (Ralph et al, 1997), as well as lignins being able to accommodate a remarkable level of plasticity in overall structure.

Recent studies of altering lignin deposition processes (i.e. in terms of overall amounts and/or differing monomeric compositions) have continued without first establishing how lignin assembly/macromolecular configuration proper is actually and definitively biochemically achieved. On the other hand, our emerging knowledge of how lignification occurs (at least in terms of modulating monolignol supply and composition) has been comprehensively critiqued and re-interpreted, in terms of predictability from a non-random assembly perspective (Anterola & Lewis, 2002). Regularity in lignin structure has also been proposed by several investigators (Sarkanen et al., 1984; Garver et al., 1989; Banoub & Delmas, 2003), e.g., based upon physico-chemical analysis of soluble lignin derivatives produced under alkaline kraft pulping conditions. Related studies have reported that, following formation of lignin primary structure, chain replication next occurs via a template polymerization process with incoming monolignols (radicals) being aligned prior to coupling through strong non-covalent bond interactions on the preformed lignin macromolecule(s) (Guan et al., 1997; Sarkanen, 1998; Chen & Sarkanen, 2003).

Yet, in apparent support of the plasticity model for random/combinatorial lignin macromolecular assembly, examples of surrogate monomers reportedly included 2-methoxybenzaldehyde (76), feruloyl tyramine (78), as well as a range of other non-monolignol moieties, such as acetosyringone (77) (FIG. 25) and related phenolics (Ralph et al, 1997; Boudet, 1998). Such moieties were initially reported as being incorporated into lignins at "substantial levels" when plants were mutated/down-regulated in cinnamyl alcohol dehydrogenase (CAD, E.C. 1.1.1.195) and cinnamoyl CoA reductase (CCR, E.C. 1.2.1.44) (Ralph et al, 1998). However, there were no precise levels of quantification reported to gain needed insight into what substantial meant in terms of lignification. From first principles, many of these moieties could not be anticipated to freely participate in a [core] free-radical polymerization process, other than in chain termination reactions for example.

The 2-methoxybenzaldehyde (76) report has since essentially been retracted (Ralph et al, 1998). Moreover, no evidence for feruloyl tyramine (78) serving as either a general biochemical "signature" for CCR downregulation/mutation (Chabannes et al., 2001) and/or as being incorporated into lignin (Ralph et al, 1998; Chabannes et al., 2001) could be independently confirmed in our own studies (of the CCR-irx4 mutant) (Patten et al., 2005; Laskar et al., 2006). Instead, as could perhaps be anticipated, only a delayed but coherent deposition pattern of lignification occurred due to the depletion in monolignol supply rate and/or presumed attenuation of free CoASH levels in the lignifying cells (Laskar et al., 2006). Nor was any compelling evidence obtained for incorporation of other non-monolignol phenolic moieties, e.g. acetosyringone (77) and hydroxycinnamic acids (4-8) into the core macromolecular lignin framework as a result of CCR mutation. Instead, the overall levels of these moieties in CCR-down-regulated tobacco lines apparently only accounted for ~0.04-0.07% of the lignified cell-wall residue (CWR) (Anterola & Lewis, 2002), and would thus be of minor significance at best. Such moieties, however, were not observed in the lignin isolates from the *Arabidopsis* CCR mutant, at least down to the levels of NMR spectroscopic detection employed (Laskar et al., 2006). These data, therefore, place considerable restrictions on the proposed concept of lignin plasticity and seamless combinatorial biochemistry using surrogate monomers.

In this Example, applicants have extended their analyses of the CAD multigene family in *Arabidopsis thaliana*. This particular enzyme catalyzes the NADPH-dependent, substrate versatile, reduction of various p-hydroxycinnamaldehydes (e.g. 14-18, FIG. 25) into the corresponding p-hydroxycinnamyl alcohols 19-23. From applicants' previous studies (Kim et al., 2004), it was demonstrated that two isoforms AtCAD5 and AtCAD4 had the highest CAD activities in vitro (of 17 possible CAD gene members annotated), and that these were thus the most likely dominant contributors to the CAD metabolic network involved in lignification. Moreover, the recent generation of an *Arabidopsis* cad-4 cad-5 (cad-c cad-d) double mutant (Sibout et al., 2005), described herein as a CAD double mutant for simplicity, further supported these conclusions. Indeed, it has provided a convenient means for comprehensively studying the effects of "knocking-out" both genes on the formation of the lignified vascular apparatus present in "bolting" stems. Applicants demonstrates that while small amounts of a poly-p-hydroxycinnamaldehyde polymer were formed (i.e. relative to lignin) in the CAD double mutant, the material strength properties (dynamic moduli) of the stem plant material were predictably greatly diminished (i.e. weaker) relative to wild type (WT). This again underscored the evolutionary significance of having a monolignol-derived lignin structure, in both amounts and monomeric compositions, to achieve "normal" physiological functions in intact plant stems. These observations further demonstrated why plant lignins are not poly-p-hydroxycinnamaldehydes, i.e. from either a chemical structure or a physiological functional perspective. Similar conclusions have already been made upon analysis of other reports directed towards altering lignin amounts/compositions (see Anterola & Lewis, 2002).

The present study also had as its specific objectives to comprehensively establish the effects of AtCAD4/5 double mutation on lignification proper. Accordingly, various chemical degradation and chemical analyses procedures were developed for this purpose. The data so obtained, however, again underscored the progress made in terms of simply quantifying amounts of lignins (and other phenolics), as well as in determining inter-unit linkage frequencies, etc. That is, the approaches developed herein have now enabled applicants to much more accurately determine the amounts, as well as the nature of various inter-unit structures and inter-unit linkage frequencies, within the relatively small amounts of the poly-p-hydroxycinnamaldehyde polymer(s) being formed, i.e. by using criteria generally applied for characterization of all other (plant) natural products. Interestingly, it was established that the frequencies of the cleavable 8-O-4' linkages, leading to monomer release, within this poly-p-hydroxycinnamaldehyde corresponded closely to that observed for the equivalent amount of monolignol-derived lignin deposition. Moreover, evidence for the presence and nature of 8-5' linked substructures, previously described as nearly undetectable by Kim et al., 2003, in related CAD-deficient studies, are also summarized. As discussed below, the results are considered in terms of control over macromolecular lignin configuration, and of a very limited monomer degeneracy during (an ultimately aborted attempt of) template-guided polymerization.

Methods:

General experimental reagents/chemicals and equipment. All solvents used in this study, purchased from J. T. Baker (Mallinckrodt Baker Inc., Phillipsburg, N.J., USA), were of HPLC grade, whereas reagent grade N, O bis(trimethylsilyl) trifluoroacetamide (BSTFA), pyridine, nitrobenzene, ethanethiol, AcBr, DMSO-$d_6$, and cellulase (EC 3.2.1.4 from *Aspergillus niger,* 0.3 units/mg solid) were from Sigma-Aldrich (Milwaukee, Wis., USA). Grinding of *A. thaliana* plant stem material utilized a Fritsch planetary mill (Pulverisette) with agate bowls and balls (Gilson Company, Worthington, Ohio, USA). $^{1}H$ and $^{13}C$ NMR spectra were recorded on a Varian Inova 500 spectrometer (Varian Inc., Palo Alto, Calif., USA) at 325° K in DMSO-$d_6$ (500 μl) using for reference the residual solvent signal at 2.49 ppm for proton and 39.5 ppm for carbon. The light micrographs were recorded using an Olympus BH-2 light microscope equipped with a ProgRes C12plus digital camera (JENOPTIK, Jena, Germany). Nitrobenzene oxidations and thioacidolysis analyses were performed using an HP 6890 Series GC System (Agilent Technologies, Santa Clara, Calif., USA) equipped with a RESTEK-5Sil-MS (30 m×0.25 mm×0.25 μm) column (Restek US, Bellefonte, Pa., USA); silylated products were analyzed and quantified using an HP 5973 MS detector (EI mode, 70 eV). Acetyl bromide (AcBr) lignin analyses were carried out using a Perkin Elmer Lambda 20 spectrophotometer (Perkin Elmer Life and Analytical Sciences Inc., Boston, Mass., USA). Dynamic moduli of plants were measured on a dynamic mechanical analyzer, Tritec 2000 (Triton technology Ltd, UK).

Plant material and growth parameters. Seeds from cad-4, cad-5 double mutant lines were provided by Dr. A. Séguin (Natural Resources Canada, Sainte-Foy, Québec, Canada). Both wild type and CAD double mutant lines were grown in Washington State University greenhouses at 21 and 16° C. with a 15 h light/9 h dark cycle, a light intensity of ~150 mmol $m^{-2}$ $s^{-1}$ and a humidity range from 20 to 35%. Both WT and CAD double mutant lines were independently evaluated for their main (bolting) stem growth and development parameters (length and basal diameters), these being measured weekly from 3.5 weeks growth/development until 10 weeks using twenty randomly chosen plants/harvest sampling point.

Histochemistry. Histochemical analyses employed Wiesner and Mäule reagents for staining fresh hand cut stem cross-sections of WT and CAD double mutant lines at 4, 6 and 8 weeks growth/development (Patten et al., 2005). Light micrographs were recorded using an Olympus BH-2 photomicroscope.

Cell-wall residue (CWR) preparations. After removing leaves and secondary stems from the main "bolting" stems for each sample, the extractive-free cell wall residues (CWR) were prepared as previously described (Patten et al., 2005), i.e. by successive extraction of individual samples at room temperature for 12 h each with EtOH:toluene (1:1, v/v, 100 ml $g^{-1}$), EtOH (100 ml $g^{-1}$) and then twice with $H_2O$ (100 ml $g^{-1}$) prior to subsequent chemical degradative analyses.

Lignin enriched isolates (WT) and poly-p-hydroxycinnamaldehyde preparations. Extractive-free CWR's (~10 g) from WT and CAD double mutant lines (8 wks old) were individually subjected to a modified Björkman lignin isolation procedure as previously described (Jourdes et al., manuscript in preparation) to furnish a lignin-enriched isolate from WT (210 mg) and a poly-p-hydroxycinnamaldehyde enriched preparation from the CAD double mutant (160 mg); these isolates corresponded to ~10.1% and 14.2% of the estimated AcBr (UV absorbing) constituents present in the original CWR's.

WT lignin-enriched isolate: UV (dioxane) $\lambda_{max}$ (ε): 281 (15.75±0.35 L $g^{-1}$ $cm^{-1}$); for $^{13}C$ NMR spectra, see FIG. 30*a*.

CAD double mutant poly-p-hydroxycinnamaldehyde enriched isolate: UV (dioxane) $\lambda_{max}$ (ε): 325 (28.17±0.25 L $g^{-1}$ $cm^{-1}$); for $^{13}C$ NMR spectra, see FIG. 30*b*.

Lignin (WT) and poly-p-hydroxycinnamaldehyde enriched (cad-4 cad-5) isolates following cellulase digestion. Extractive-free CWR's (~8 g) from both WT and CAD double mutant lines were individually ground by ball-milling for 96 hr at 4° C., and then subjected to A. niger cellulase digestion prior to subsequent extraction as follows. The cellulase (~472 units) was first dissolved in NaOAc buffer (5 ml, 20 mM, pH 5.0), and centrifuged (7,200×g, 10 min) to remove insoluble impurities. The resulting supernatant was next added to each suspension of CWR (~8 g) in NaOAc buffer (45 ml, 20 mM, pH 5.0) and individually incubated for 48 h at 30° C.; the whole cellulase digestion procedure was then repeated (3 times) using fresh cellulase (~472 units) in NaOAc buffer. After a final digestion, the resulting suspensions were individually centrifuged (7,200×g, 10 min), with the insoluble residues remaining washed with distilled $H_2O$ (4×50 ml), then frozen at −80° C. and freeze-dried for 3 days to afford cellulase-digested CWR preparations (3.38 g for the CAD double mutant and 3.85 g for WT). The cellulase-digested CWR from WT was next subjected to the Björkman extraction procedure as described in Section 4.5 to furnish a cellulase digested lignin-enriched isolate (306.1 mg; 18.4% yield of estimated AcBr lignin content in CWR see Section 2.3.5.3). The cellulase-digested CWR from CAD double mutant was treated in the same manner to give a poly-p-hydroxycinnamaldehyde enriched extract (157.4 mg; 17.4% yield of estimated AcBr absorbing components solubilized from the CWR.)

WT derived lignin-enriched isolate following cellulase pretreatment: UV (dioxane) $\lambda_{max}$ (ε): 281 (15.75±0.35 L $g^{-1}$ $cm^{-1}$); for $^{13}C$ NMR spectra not shown (similar to FIG. 30*a* spectra).

CAD double mutant derived poly-p-hydroxycinnamaldehyde isolate following cellulase pretreatment: UV (dioxane) $\lambda_{max}$ (ε): 325 (28.17±0.25 L $g^{-1}$ $cm^{-1}$); for $^{13}C$ NMR spectra not shown (similar to FIG. 30*b* spectra).

Molecular weight distributions of lignin-enriched isolates. Molecular weight distributions (MWD's) of the lignin and poly-p-hydroxycinnamaldehyde isolates from WT and CAD double mutant lines were estimated by gel permeation chromatography (GPC) using a Sephadex G-100 column as previously described (Laskar et al., 2006).

NMR spectroscopic analyses of lignin-enriched isolates. NMR spectra of lignin and poly-p-hydroxycinnamaldehyde isolates (30 mg) were individually recorded as described in Section 4.1. For $^{13}C$ NMR, two-dimensional phase-sensitive gradient-selected HMQC and HMBC spectra were recorded using similar acquisition parameters as previously described (Laskar et al., 2006).

AcBr lignin/poly-p-hydroxycinnamaldehyde, alkaline nitrobenzene and thioacidolysis determinations. The lignin and poly-p-hydroxycinnamaldehyde contents of extractive-free CWR samples for each line were estimated by the AcBr method (Iiyama & Wallis, 1990; Blee et al., 2001) using recalculated AcBr lignin and poly-p-hydroxycinnamaldehyde extinction coefficients with monomeric compositions estimated by thioacidolysis. From previous studies, the AcBr extinction coefficients for H, G and S enriched lignins were estimated to be: 15.31 l $g^{-1}$ $cm^{-1}$ (H units); 18.61 l $g^{-1}$ $cm^{-1}$ (G units), 14.61 l $g^{-1}$ $cm^{-1}$ (S units) (Cardenas et al., manuscript submitted) and 24.83 l $g^{-1}$ $cm^{-1}$ for the poly-p-hydroxycinnamaldehyde component (see Section 2.3.5.3).

Monomeric compositions were estimated using both alkaline nitrobenzene oxidation (Iiyama & Lam, 1990) and thioacidolysis (Rolando et al., 1992; Blee et al., 2001) methods, with all products 84-89, 90-94 and 97-100 identified by comparison to calibration against authentic standards.

Chemical syntheses. The 8-O-4' linked p-hydroxycinnamaldehyde model compounds 95 and 96 were obtained in similar yield to that of Kim et al., 2000; 2002. These were individually subjected to thioacidolysis (Rolando et al., 1992; Blee et al., 2001) to individually furnish the indene derivatives 97-100 in comparable yields to that of Kim et al., 2000; 2002.

Dynamic mechanical analysis. Stems of both WT and the CAD double mutant at 6 and 7 weeks growth/development were tested in the tension mode using a TRITEC 2000 Dynamic Mechanical Analyzer. Three different stems with 3 replications of each were tested in each case. Measurements were carried out exactly as described in Patten et al., 2007.

Results:

Growth parameters and losses in dynamic modulus properties in cad-4 cad-5 (cad-c cad-d) "bolting" stem sections. Prior to investigating the nature of the phenolic materials deposited in stem tissue cell walls of *A. thaliana* WT (ecotype Wassilewskiia) and the corresponding CAD double mutant, the overall growth/development from germination until maturation/senescence onset of both lines was first compared. Concomitantly, estimations of the overall dynamic modulus properties of the resulting stems, and analysis of histochemical staining patterns using reagents typically used for lignin, were carried out for each line.

Figures 26A, 26B:
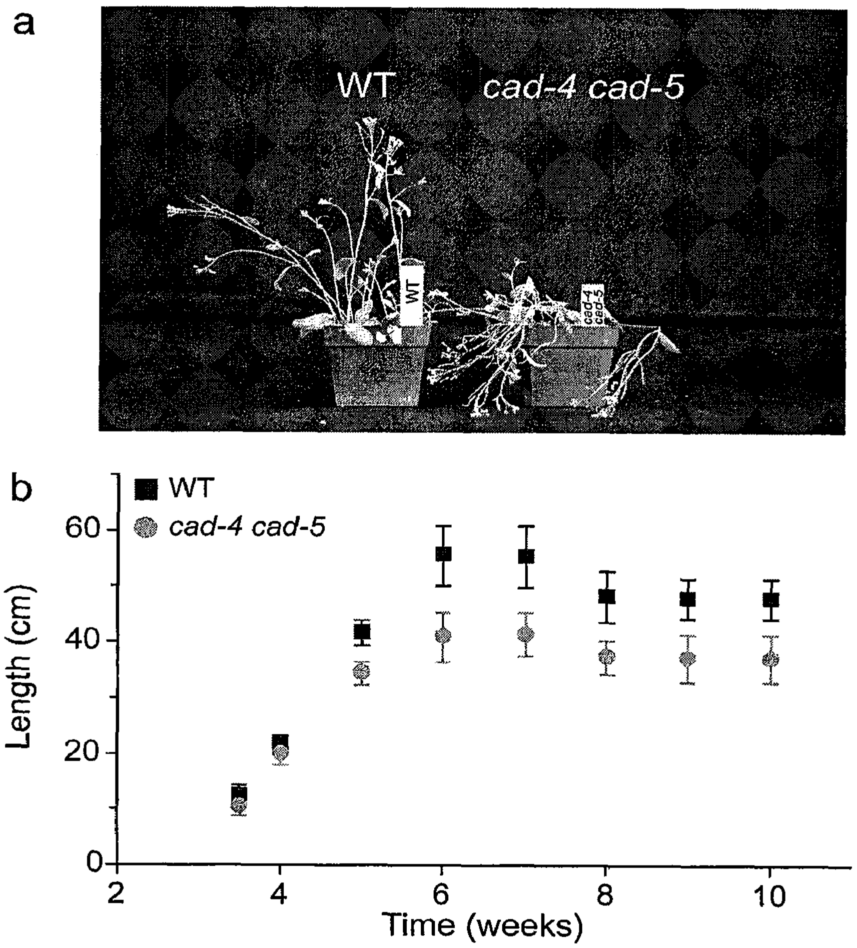

In terms of overall gross growth/developmental indices, no visible differences were noted between the WT and the double mutant lines at the rosette leaf developmental stage. In both cases, rosette sizes were similar with no observable differences in rosette leaf formation from germination until about 3 weeks growth/development (data not shown). The most striking visible phenotypical difference observed, however, between both lines was in the overall structural integrity of the inflorescence stem: at ~4 weeks until maturation, the stems of the double mutant became prostrate (FIG. 26*a*), in contrast to that of WT (Sibout et al., 2005). These data suggested a weakened vasculature apparatus for the CAD double mutant. Additionally, both stem lengths and diameters were consistently slightly smaller (~25% and ~15%) for the double mutant line when compared to WT (FIGS. 26*b* and *c*). In this regard, a reduction in stem length had also been noted for the CAD double mutant, albeit without either any specific quantification or indication of trend development (Sibout et al., 2005).

It was thus next useful to compare and contrast dynamic moduli properties of both WT and CAD double mutant lines in order to obtain some additional insight into possible structural integrity differences in the resulting tissues. Dynamic mechanical analyses (DMA) were therefore performed in the tension mode, where the storage tensile and loss moduli represent the elastic and viscous components of the complex modulus. The stems of both WT and the double mutant were compared at 6 and 7 weeks growth/development, using 3 different stems and 3 replications. The CAD double mutant line had a consistently lower tensile storage modulus (E'), approximately half ($7.1\times10^8$ Pa) than that of the WT line ($1.37\times10^9$ Pa) whereas the loss moduli (E") of both were very similar (FIG. 26*d*). To further establish differences in dynamic mechanical properties of both lines, the storage and loss moduli of stems, harvested at weeks 6 and 7, were compared at an 0.02% strain level using a paired-t-test (FIG. 26*e*).

Significant differences in storage moduli were again observed between both lines at weeks 6 (p value=0.036) and 7 (p value=0.014). Thus, the elastic component of dynamic modulus in tension is significantly reduced in the CAD double mutant, whereas the loss moduli for both are similar at weeks 6 (p value=0.951) and 7 (p value=0.241).

Histochemical analyses. Attention was next given to the histological detection of lignin/phenolics in the cell wall tissues of the developing stems of both WT and CAD double mutant lines. The two protocols utilized were phloroglucinol-HCl (for putative p-hydroxycinnamaldehyde end groups 14, 16 and 18), and the Mäule reaction for detection of syringyl (S) moieties (Patten et al., 2005). Plant lines were analyzed at 4, 6 and 8 weeks at the apex, middle and basal regions; for this report, however, only basal stem data are described (FIGS. 27 and 28). These analyses, when taken together, represent the early stages of "bolting" stem development (~3.5 weeks) until maturation/onset of senescence (~8 weeks).

For fresh hand-cut stem tissues of the WT line, in the absence of any histological stain for lignin, the guaiacyl (G)-rich xylem (x), as well as protoxylem (px) and interfascicular fibers (if), were readily discernible at all stages of growth/development. These were, however, not markedly different in color from the other cell/tissue types under the differential interference contrast (DIC) conditions used for visualization (FIGS. 27*a*, 27*c*, 27*e*, and 28*c*). For the CAD double mutant, on the other hand, as maturation proceeded there was a build-up of a distinct pigmentation in all lignifying elements, i.e. orange-brownish for x, versus reddish-orange for if (see FIGS. 27*b*, 27*d*, 27*f* and 28*a*).

Figures 28A, 28B, 28C, 28D:
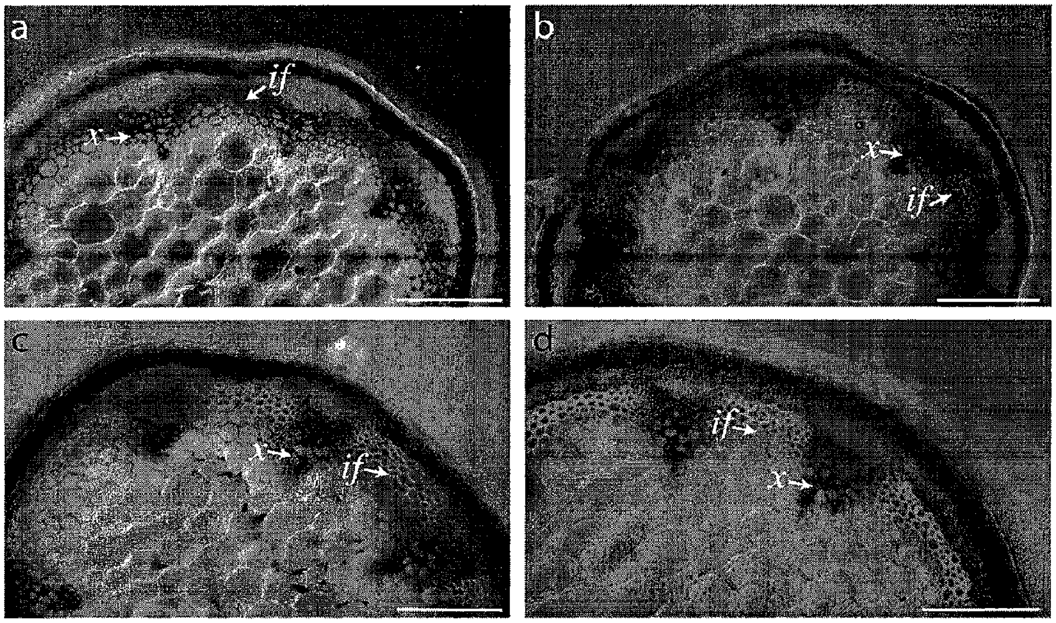
FIGS. 28A-D show, according to exemplary aspects of the present invention, effects of 0.5% HCl/MeOH treatment. Unstained cross-sections of 4 week old stems from CAD double mutant (a and b) and WT (c and d) lines; (a and c) are fresh stem cross-sections, whereas (b and d) are cross-sections following acidic MeOH (0.5% HCl) treatment. Abbreviations: if, interfascicular fibers; x, xylem. Scale bar: 200 μm.

This pigmentation was observed throughout all of the remaining phases of growth/development until maturation/senescence onset, as had been previously noted with various other CAD down-regulated lines (Halpin et al., 1994; Higuchi et al., 1994). The red coloration was, however, readily removed by treatment with acidic MeOH (containing 0.5% HCl, see FIGS. 28*a* versus 28*b*), as also observed for tobacco (Laskar et al., 2007); the corresponding treatment for WT is shown for comparison purposes (FIGS. 28*c* versus 28*d*).

Figures 27A, 27R:
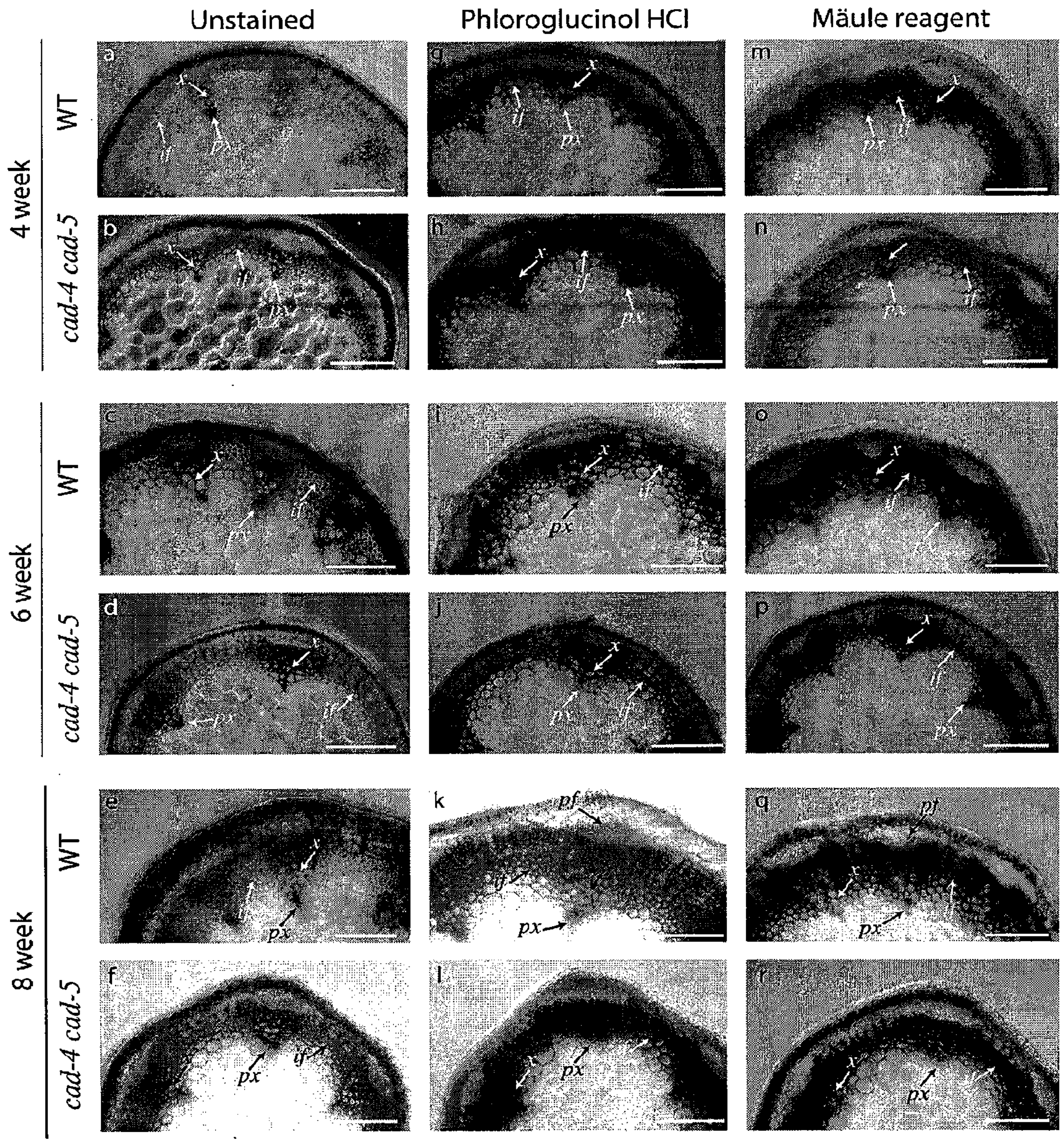
FIGS. 27*a-r* show, according to exemplary aspects of the present invention, histochemical detection of apparent lignin and phenolic deposition in WT and CAD double mutant lines at three different growth/developmental stages (4, 6 and 8 weeks). (*a* to *f*) Unstained cross-sections from WT (*a, c* and *e*) and from CAD double mutant (*b, d* and *f*) lines; (*g* to *l*) phloroglucinol-HCl staining method indicating lignified cell walls by red coloration in the cross-section for WT (*g, i* and *k*) and phenolics for the CAD double mutant (*h, j* and *l*) lines; (*m* to *r*) Mäule reagent staining indicating, by red coloration, the presence of syringyl (S) moieties in lignified cell walls for WT (*m, o* and *q*) and CAD double mutant (*n, p* and *r*) lines. Abbreviations: if, interfascicular fibers; pf, phloem fibers; px, primary xylem; x, xylem. Scale bar: 200 μm.

Next, for both WT and double mutant lines, phloroglucinol-HCl staining gave qualitatively similar positive results (for presumed p-hydroxycinnamaldehyde end groups) at all growth/developmental stages, i.e. from 4-8 weeks (FIGS. 27*g*-27*l*). However, the CAD double mutant apparently gave a somewhat darker red pigmentation compared to WT. The Mäule reagent, presumed to be syringyl (S) moiety-specific, also displayed extensive orange staining in the if regions for both the WT and the double mutant lines at 4, 6 and 8 weeks, but was largely absent in the xylem (x) and protoxylem (px) tissues (FIGS. 27*m*-27*r*) known to be G-rich (Patten et al., 2005). At maturation (~8 weeks), both staining methods indicated the presence of lignified phloem fibers (pf) in WT (FIGS. 27*k* and 27*q*), although these were not detected in the CAD double mutant under the same conditions (FIGS. 27*l* and 27*r*).

Characterization of cell-wall derived biopolymers from WT and cad-4 cad-5 double mutant lines. Attention was next given to applying/developing methodologies to extract the lignins from the WT cell-walls, as well as that of any biopolymeric phenolic material present in the CAD double mutant; for this purpose, plant stems were selected and harvested in each case at maturation (~8 weeks growth and development). Specifically, for each preparation, the determinations required, at the minimum, accurate and/or improved estimations of: extinction coefficients, molecular weight distributions (MWD's), assessment by $^1$H and $^{13}$C NMR spectroscopic analyses of the chemical nature of the biopolymeric substructures, as well as estimation of various inter-unit linkage frequencies (e.g. 8-O-4' bonds).

Phenolic biopolymer isolation protocols. Whole, extractive-free, stem tissues of both lines were thus individually subjected to two different isolation procedures, namely the modified Björkman protocol (Bjorkman, 1954; Jourdes et al., manuscipt in preparation) with or without an initial cellulase digestion step (see Methods). In this way, from WT stem tissue (10 g), the modified Björkman procedure alone afforded a lignin enriched isolate (210 mg) (so-called milled wood lignin, MWL), whereas with prior cellulase digestion a cellulase-liberated MWL isolate (382 mg) was obtained. In an analogous manner, the CAD double mutant stem tissues (10 g) gave 160 and 196 mg of isolates. Overall, the cellulase digestion step appears to be even more effective with WT tissues since the amounts of isolate increased by ~80%.

Figures 29A, 29B:
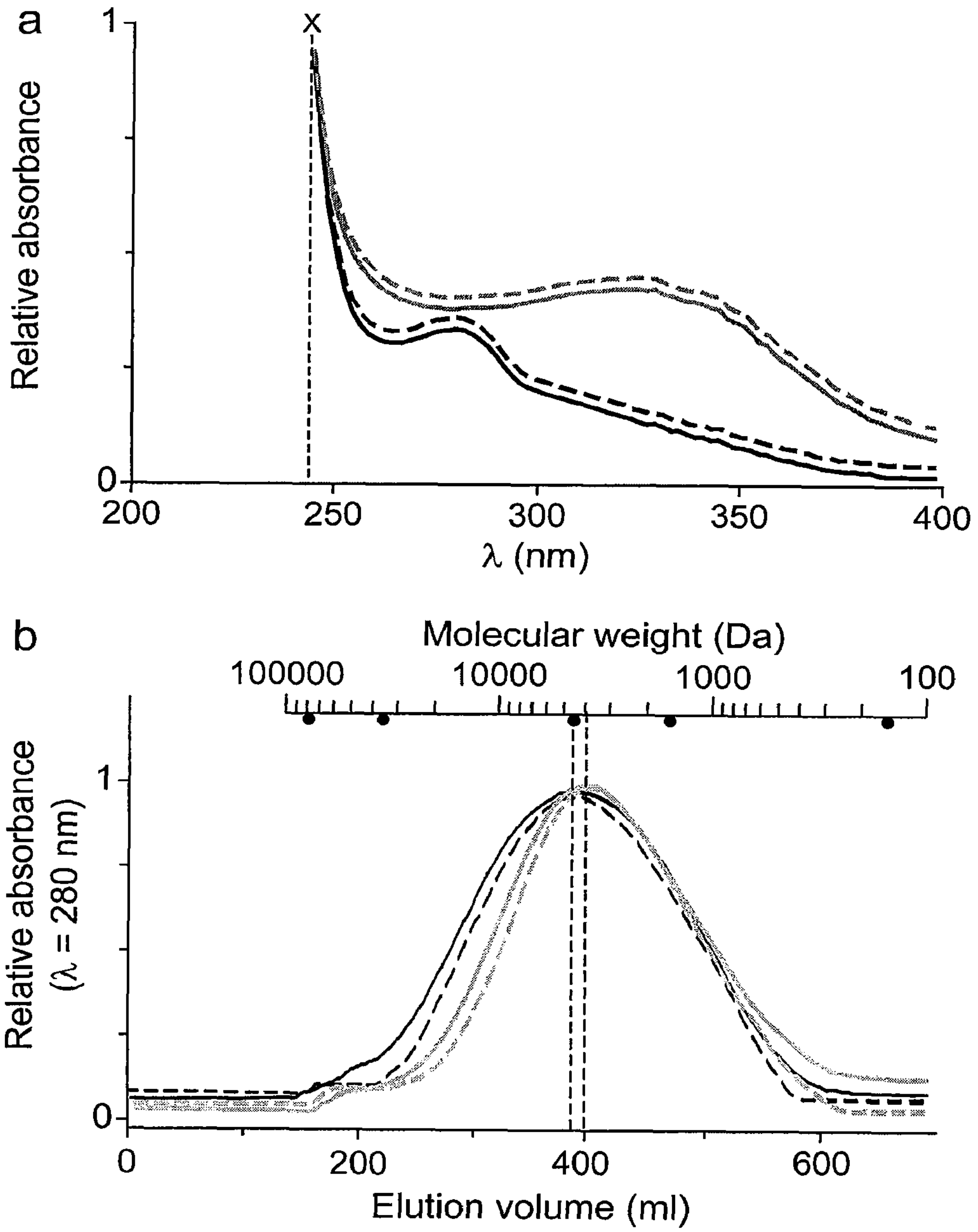
FIGS. 29A and B show, according to exemplary aspects of the present invention, UV spectra (a) and molecular weight distributions (b) of either lignin-enriched isolates from WT or poly-p-hydroxycinnamaldehyde enriched preparations from the CAD double mutant. Legend: dotted (----) and solid (—) black lines, WT lignin preparation with and without prior cellulase treatment; dotted (----) and solid (—) gray lines, CAD double mutant poly-p-hydroxycinnamaldehyde preparations with and without prior cellulase treatment; black circles represent sodium polystyrene sulfonate standards (~1, 430; 5,180; 29,000; 79,000) and coniferyl alcohol (3, $M_r$ 180) used for calibration. X=solvent (dioxane) UV cut-off.

Estimations of extinction coefficients in dioxane. The UV spectra of the lignin isolates from the WT line, with or without prior cellulase digestion, gave absorption maxima at $\lambda$=281 nm (estimated $\epsilon_{281}$=15.75±0.35 l $g^{-1}$ $cm^{-1}$) in dioxane, corresponding to a typical G/S lignin chromophore (FIG. 29*a*). By contrast, the IV spectra of the phenolic isolates obtained from the CAD double mutant were very different from that of the WT lignin isolates and exhibited a bathochromic shift to 325 nm with an estimated $\epsilon_{325}$=28.17±0.25 l $g^{-1}$ $cm^{-1}$.

Molecular weight distributions. The molecular weight distributions (MWD) of both WT and double mutant lignin-enriched isolates with and without prior cellulase treatment were next subjected to gel permeation chromatography (GPC), using a pre-calibrated Sephadex G-100 column (Laskar et al., 2006) eluted with 0.1 M Noah; the latter eluant has been employed in order to attempt to minimize associative effects in lignin-derived preparations (Dutta et al., 1989). All four samples had relatively broad MWD's with estimated molecular weights (Mw's) centered at ~4,600 Da for the two lignin-enriched isolates from WT, versus ~4,000 Da for the CAD double mutant preparations (FIG. 29*b*). Molecular weight averages were estimated following calibration of the Sephadex G-100 column with sodium polystyrene sulfonates (Mw's: ~1,430; 5,180; 29,000; 79,000) and coniferyl alcohol (3, $M_r$ 180), with polydispersity index values ($M_w$/$M_n$) calculated: ~2.1 for the WT lignin-enriched isolates and ~1.8 for the CAD double mutant preparations. As already noted for other WT lignin-derived isolates (Laskar et al., 2006), the polydispersity indices are considered to possibly reflect random cleavage during mechanical ball milling treatment (~4 days) rather than the actual molecular weight distributions of the phenolic materials present in situ.

NMR spectroscopic analyses. Various NMR spectroscopic analyses were next carried out in order to begin to compare the types of assignable interunit linkages/substructures present in the various polymeric isolates. A limitation of this approach, however, is that this methodology is currently not yet very applicable to either readily obtain lignin primary chain sequence data and/or to identify all structural entities present,. e.g. in the lignins. Nevertheless, the preparations obtained from WT and the CAD double mutant were individually subjected to NMR ($^1$H, $^{13}$C, 2 D HMQC and 2D HMBC) spectroscopic analyses (FIGS. 30*a-d* and 31*a-c*).

Lignin isolates from WT. The 1 D $^{13}$ C NMR spectra of the WT lignin-enriched isolates (FIG. 30*a*) were those of typical G/S lignins present in *Arabidopsis* as previously reported for WT ecotypes Landsberg erecta (Laskar et al., 2006) and Columbia (Marita et al., 1999); these are summarized below only as needed for comparative context. Thus, characteristic methoxyl group signals were readily observable at ~55.8 ppm, with the corresponding aromatic ring resonances assignable as before, i.e. ~102-107 and ~150-154 ppm for tertiary carbons-2/6 and quaternary carbons-3/5 in S aromatic units, with comparable G unit resonances at ~107-124 ppm and 145-154 ppm for tertiary aromatic carbons-2/5/6 and quaternary carbons-3/4, respectively. Signals for the quaternary carbon-1 for G units and carbons-1 and 4 for S units overlapped between 125 to 140 ppm.

2D HMQC analyses were used to examine the various oxygenated carbon resonances in the aliphatic region (50-90 ppm, FIG. 30*c*) (Lewis et al., 1987; Karhunen et al., 1995; Ralph et al., 2004 b; and Laskar et al., 2006). As before, the five expected (G/S) substructures were identified (FIG. 30*e*), namely: 8-O-4' aryl ether (substructure I), resinol-like (substructure II), phenylcoumaran (substructure III), dibenzodioxocin (substructure IV) and cinnamyl alcohol end groups (substructure V). All were assigned through their characteristic carbon-proton correlations ($\delta c/\delta_H$): i.e. 59.6/3.20 and 59.6/3.57 ($C_9/H_9$), 82.9/4.20 ($C_8/H_8$) and 70.8/4.68 ($C_7/H_7$) ppm for 8-O-4' aryl ether substructure I; 70.7/3.71 and 70.7/4.08 ($C_9/H_9$, $C_{9'}/H_{9'}$), 53.3/3.01 ($C_8/H_8$, $C_{8'}/H_{8'}$) and 84.6/4.59 ($C_7/H_7$, $C_{7'}/H_{7'}$) ppm for resinol-like substructure II; 62.6/3.69 and 62.6/3.32 ($C_9/H_9$), 52.6/3.38 ($C_8/H_8$) and 86.4/5.42 ($C_7/H_7$) ppm for phenylcoumaran substructure III; 61.3/4.05 and 61.3/3.95 ($C_9/H_9$), 85.7/4.09 ($C_8/H_8$) and 83.2/4.71 ($C_7/H_7$) ppm for dibenzodioxocin substructure IV, as well as 61.6/4.3 ($C_9/H_9$) ppm for cinnamyl alcohol end groups (V). Other inter-unit linkages, such as 8-1', diphenyl and/or diphenyl ether bonds were not definitively identified due to overlapping resonances. As noted before, this is a limitation of the techniques currently employed (Laskar et al., 2006).

Figures 30A, 30B, 30C, 30D, 30E:
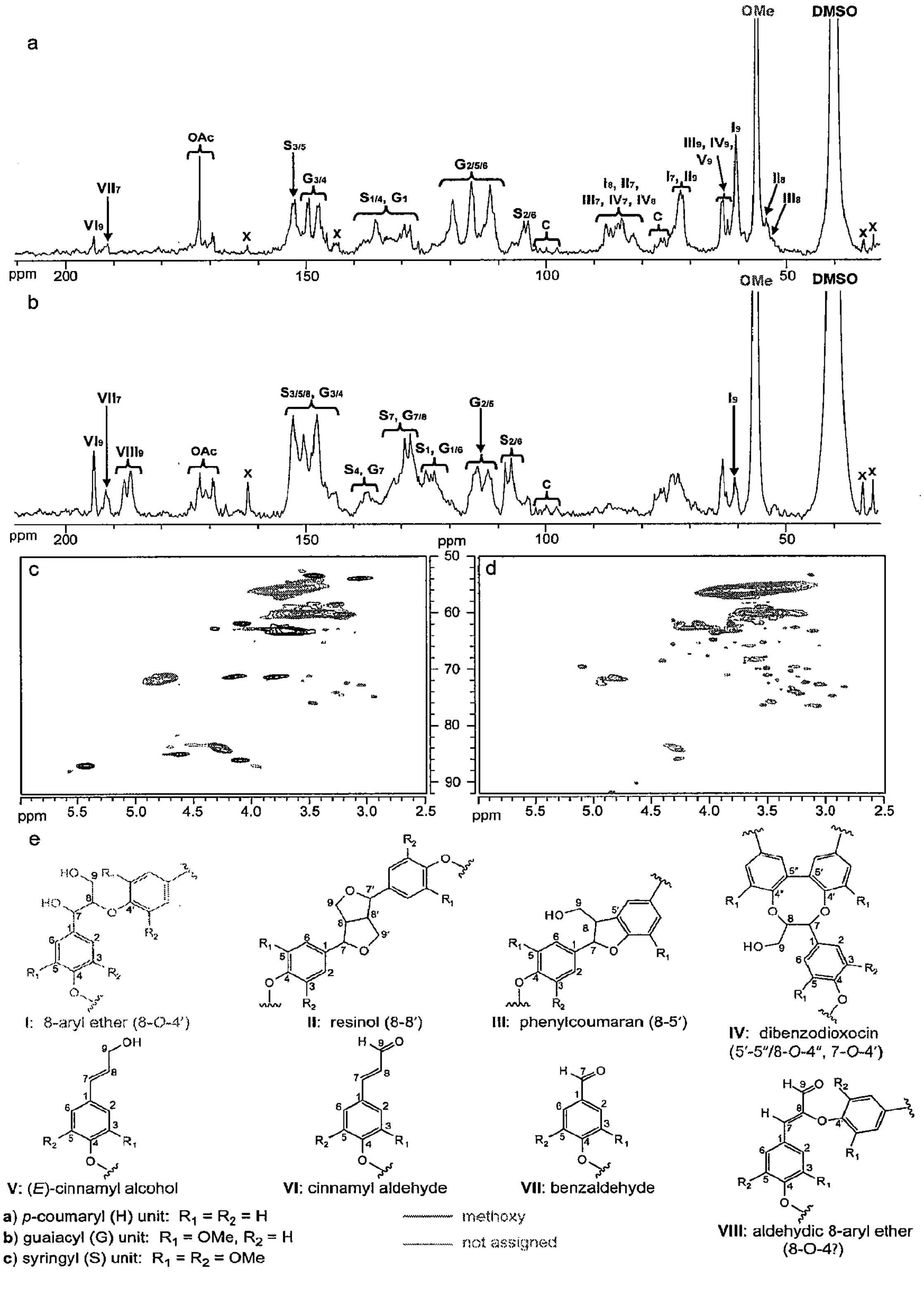
FIGS. 30A-E show, according to exemplary aspects of the present invention, NMR spectra of lignin-enriched isolates from WT and poly-p-hydroxycinnamaldehyde enriched isolates from CAD double mutant lines. a) 1D $^{13}$C-NMR spectrum of lignin-enriched isolates from WT, b) 1D $^{13}$C-NMR spectrum of poly-p-hydroxycinnamaldehyde enriched isolates from double mutant, c) 2D HMQC spectrum of oxygenated aliphatic region of lignin-enriched isolates from WT, d) 2D HMQC spectrum of oxygenated aliphatic region of poly-p-hydroxycinnamaldehyde enriched-isolates from double mutant, e) lignin substructures currently assignable by NMR spectroscopic analyses. For NMR spectroscopic peak assignments, the numbers I-VIII correspond to substructures I-VIII, whereas subscripts 1-9 correspond to carbons in specific substructures; a, b, c are used to designate the nature of the aromatic rings as p-hydroxyphenyl (H), guaiacyl (G) and syringyl (S) units.

As already also described (Laskar et al., 2006), minor aldehydic resonances were observed at 190.7 and 194.2 ppm (FIG. 30*a*) with these being assignable to cinnamyl aldehyde VI and benzaldehyde VII moieties (FIG. 30*e*). In particular, the 2D HMBC spectroscopic analysis gave clear correlations between the benzaldehydic carbon at ~190.7 ppm and two equivalent protons at ~7.18 ppm for carbons-2/6 in syringaldehyde moieties (═substructure VIIc). By contrast, no correlations were detected for either vanillin or p-hydroxybenzaldehyde substructures, i.e. VIIb or VIIa. For cinnamyl aldehyde VI like substructures, two different correlations between the aldehydic carbon at 194.2 ppm and the benzylic protons on carbon-7 at 7.57 ppm and 7.61 ppm were observed. In addition, the proton-7 at 7.57 ppm correlated with the two equivalent aromatic carbons 2/6 (106.3 ppm) in a sinapyl aldehydic moiety (═substructure VIc). In an analogous manner, the proton-7 at 7.61 ppm correlated with aromatic carbons-2/6 at 112.7/123.4 ppm which, in turn, corresponded to a coniferyl aldehyde moiety (═ substructure VIb). On the other hand, no correlations corresponding to a p-hydroxycinnamaldehyde moiety (═ substructure Via) were detected. According to the relative correlation intensities, substructure VIb was apparently more abundant than substructure VIc. The presence of these minor aldehydic substructures VIb, VIc and VIIc were reported previously (Laskar et al., 2006).

Further confirmation of substructures I to IV was made through 2D HMBC analyses. This established the presence of three-bond correlations between their carbon-7 (at ~70.8 ppm for I, ~84.6 ppm for II, ~86.4 ppm for III and at ~83.2 ppm for IV) with the aromatic protons of carbons-2/6 at ~6.8/6.9 ppm (G units) and ~6.6 ppm (S units), respectively. These substructures were apparently mainly present as G units (substructures I-IVb), and to a lesser extent S units (substructures I-IVc). However, as expected, the WT lignin-enriched isolates contained minor amounts of impurities that are generally observed in lignin preparations. These are marked by x and c in FIG. 30*a* (e.g. for carbohydrates (c) as indicated by resonances between 95-101 ppm (anomeric carbons) and 70-80 ppm, and also for glycerides esterified with acetyl groups (OAc, ~170 ppm)).

NMR spectroscopic analyses of the CAD double mutant isolates. Both isolates were subjected to NMR spectroscopic analyses ($^1H$, $^{13}C$, 2D HMQC and 2D HMBC) as described above and which established the presence of poly-p-hydroxycinnamaldehyde moieties (FIGS. 30*b*, 30*d* and 31*a-c*). As for the WT lignin isolates, intense signals at ~55.8 ppm characteristic of methoxyl groups attached to G/S aromatic nuclei were observed (FIG. 30*b*). However, the $^{13}C$ spectra of both isolates differed markedly from the WT lignin-enriched isolates, particularly in the oxygenated aliphatic regions: that is, monolignol-derived substructures II, III, IV and V could not be detected as such and the aromatic regions also displayed a quite distinct chemical shift profile, at least down to the noise level. Additionally, in the aldehydic region more intense resonances corresponding to aldehydic end group substructures VI and VII, as well as two new signals at 186.4 and 187.8 ppm provisionally assigned to substructure VIII were observed (FIGS. 30*b* and *e*). The $^{13}C$ spectrum of the poly-p-hydroxycinnamaldehyde also contains similar minor impurities (as marked by x and c in FIG. 30*b*) as previously observed for the WT isolate spectra (FIG. 30*a*).

Application of 2D HMQC spectroscopic analysis to the aliphatic $^{13}C$ regions (oxygenated carbon) resulted, however, only in detection of the monolignol derived 8-O-4' aryl ether substructure I. This was evident from small but characteristic correlations at 59.6/3.20 and 59.6/3.57 ($C_9/H_9$), 82.9/4.20 ($C_8/H_8$) and 70.8/4.68 ($C_7/H_7$) ppm (FIG. 30*d*). Once again, substructures II-V were not detected as above.

The main aldehyde-derived substructures present were next identified using 2D HMQC and 2D HMBC spectroscopic analyses, i.e. by examining specific correlations with those in the aldehydic carbon region (180-200 ppm) (FIG. 31). Overall, different types of substructures were identified according to the peaks detected in the HMBC spectra: cinnamaldehyde end groups (═ substructure VI), 8-O-4' aryl ether linked cinnamaldehydes (═ substructure VIII) and benzaldehydes (═ substructure VII); these substructures were all previously observed in CAD-downregulated tobacco (Kim et al., 2003; Laskar et al., 2007) as well as in a CAD-deficient pine mutant line (Kim et al., 2003).

Figures 31A, 31B, 31C, 31D:
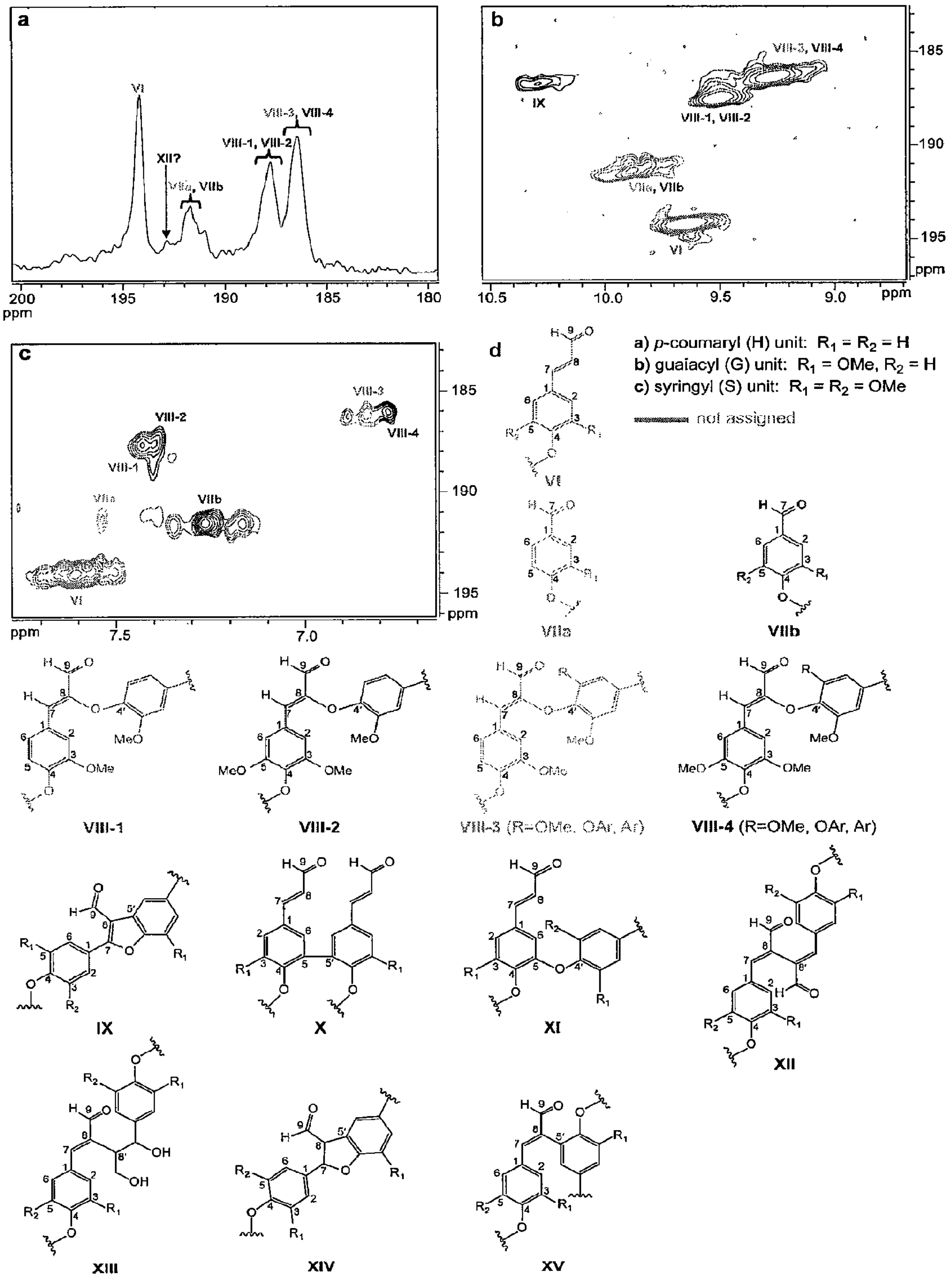
FIGS. 31A-D show, according to exemplary aspects of the present invention, NMR spectra of the aldehydic region of the poly-p-hydroxycinnamaldehyde enriched isolates from the CAD double mutant: a) 1D $^{13}$C-NMR spectrum, b) 2D HMQC spectrum, c) 2D HMBC spectrum, d) substructures currently assignable by NMR spectroscopic analyses. For NMR peak assignments, the numbers VI-XV correspond to substructures VI-XV, whereas subscripts a, b, c are used to designate the nature of the aromatic rings as p-hydroxyphenyl (H), guaiacyl (G) and syringyl (S) units.

The presence of cinnamaldehyde end groups was readily confirmed not only from the large resonance at 194.1 ppm in the $^{13}C$ spectra, but also from the intense correlations noted between aldehydic carbon-9 at 194.1 ppm and proton-9 at ~9.63 ppm in the HMQC spectra, as well as with proton-7 at ~7.61 ppm in the HMBC spectra (FIG. 31*a-c*). Designation of aromatic ring nuclei was next determined via analyses of long range correlations between proton-7 and carbon-2/6 at 112.7/123.4 ppm (G units, ═ substructure VIb) and at 106.3 ppm (S units, ═ substructure VIc). Note, however, that the correlation at 194.1/~7.61 ppm may also include other possible substructures possessing a similar aldehydic side-chain from carbons 7 to 9 e.g. substructures X and XI (Kim et al., 2003).

In an analogous manner, benzaldehydic substructures VII were detected through correlations in the 2D HMBC spectra between the aldehydic carbon-7 at ~190.7 ppm and the two aromatic protons-2/6 (FIG. 31*c*). Correlations were mainly observed between the benzaldehydic carbon at ~190.7 ppm and two equivalent protons-2/6 at ~7.26 ppm corresponding to a syringaldehydic moiety (═ substructure VIIc), whereas a much smaller correlation with protons-2/6 at ~7.54 ppm was indicative of a vanillin substructure (═VIIb).

The relatively large resonances at 186.4 ppm and 187.8 ppm in the $^{13}C$ spectra were next assigned to 8-O-4' styryl-O-aryl ether linkages (═ substructure VIII) (FIGS. 30*b* and 31*b*), depending on the nature of the aromatic ring connected to carbon 8 through ether linkages. The latter can be either in a G (═ substructure VIII-1 and VIII-2, see FIG. 31*d*), S and/or 5-substituted G (═ substructure VIII-3 and VIII-4) unit. The presence of the four 8-O-4' styryl-O-aryl ether substructures VIII-1 to VIII-4 was also evident from analysis of the HMBC spectra (FIG. 31*c*), with each identified through specific long range correlations between the aldehydic carbon-9 and proton-7 ($\delta c/\delta_H$), i.e. 187.8/7.46 for VIII-1, 187.8/7.40 for VIII-2, 186.4/6.83. for VIII-3 and 186.4/6.77 for VIII-4.

Of particular interest was the presence of substructure IX, containing a fully conjugated benzofuran skeleton (8-5') like substructure (FIG. 31*b* and 31*d*). This was identified by comparison of spectroscopic features for the somewhat analogous benzofuran aldehydic lignan 79 (so-called XH-14) isolated from *Salvia miltiorrhiza* Bunge (Danshen) (Yang et al., 1991), as well as with the benzofuran aldehyde 80 obtained by total synthesis (Moinuddin et al., unpublished results) (FIG. 32). The *Salvia* metabolite 79 had a specific correlation in the HMQC spectrum at 186.7/10.26 ppm between the aldehydic carbon-9 and the aldehydic proton-9, as did synthetic 800 which had a correlation at 186.5/10.33 ppm. Identical correlations were also observed in the poly-p-hydroxycinnamaldehyde isolates. Formation of substructure(s) IX presumably results from coupling of the corresponding aldehydes to initially generate expected substructures, such as XIV and XV. It is currently unknown, however, when during either plant growth/development and/or phenolic isolation re-aromatization occurs to give IX, as well as the significance of its formation.

To Applicants' knowledge, substructure IX was not previously reported in any CAD mutant line (Kim et al., 2003). However, by contrast, the 8-5' linked substructures XIV and XV (FIG. 31*d*) were readily detected in different synthetic dehydropolymerizates, these being generated by oxidative coupling of either coniferyl aldehyde (16) alone (Conners et al., 1970; Russell et al., 2000) or a mixture of coniferyl aldehyde (16) and coniferyl alcohol (21) (Kim et al., 2003). Yet, as mentioned above, these were not detected in the poly-p-hydroxycinnamaldehyde isolates obtained in this study. This is perhaps indicative of further differences between random coupling in vitro and that of the proteinaceous machinery in the plant cell walls controlling oxidative polymerization (see below).

The presence of an 8-8' cinnamaldehyde substructure (═ substructure XII) was also reported in lignin isolates from CAD-downregulated tobacco (Kim et al., 2003) as well as in different synthetic poly-p-hydroxycinnamaldehyde dehydropolymerizates (Conners et al., 1970; Russell et al., 2000). However, in applicants' hands, this substructure could not be unambiguously identified by NMR spectroscopic analysis in the poly-p-hydroxycinnamaldehyde isolates under the conditions employed. Although very tiny resonances in the $^{13}C$ spectrum at 192.5 ppm (FIG. 31*a*) were provisionally assignable to an 8-8' cinnamaldehyde substructure (═ substructure XII), there were no expected correlations in the 2D HMBC spectra to confirm its presence further, indicating that at best it was only present in very small amounts. A second 8-8' cinnamaldehyde substructure (═ substructure XIII), which was also reported as being present in a synthetic poly-p-hydroxycinnamaldehyde dehydropolymerizate formed from a mixture of 16 and 21 (Kim et al., 2003), was also not detected in the poly-p-hydroxycinnamaldehyde isolates from the CAD double mutant.

Finally, from the analyses of HMBC spectra of the poly-p-hydroxycinnamaldehyde isolates, various other correlations were observed but which could not yet be unambiguously assigned (FIG. 31*c*); these will be investigated further in future.

Figures 33A, 33B, 33C, 33D, 33E:
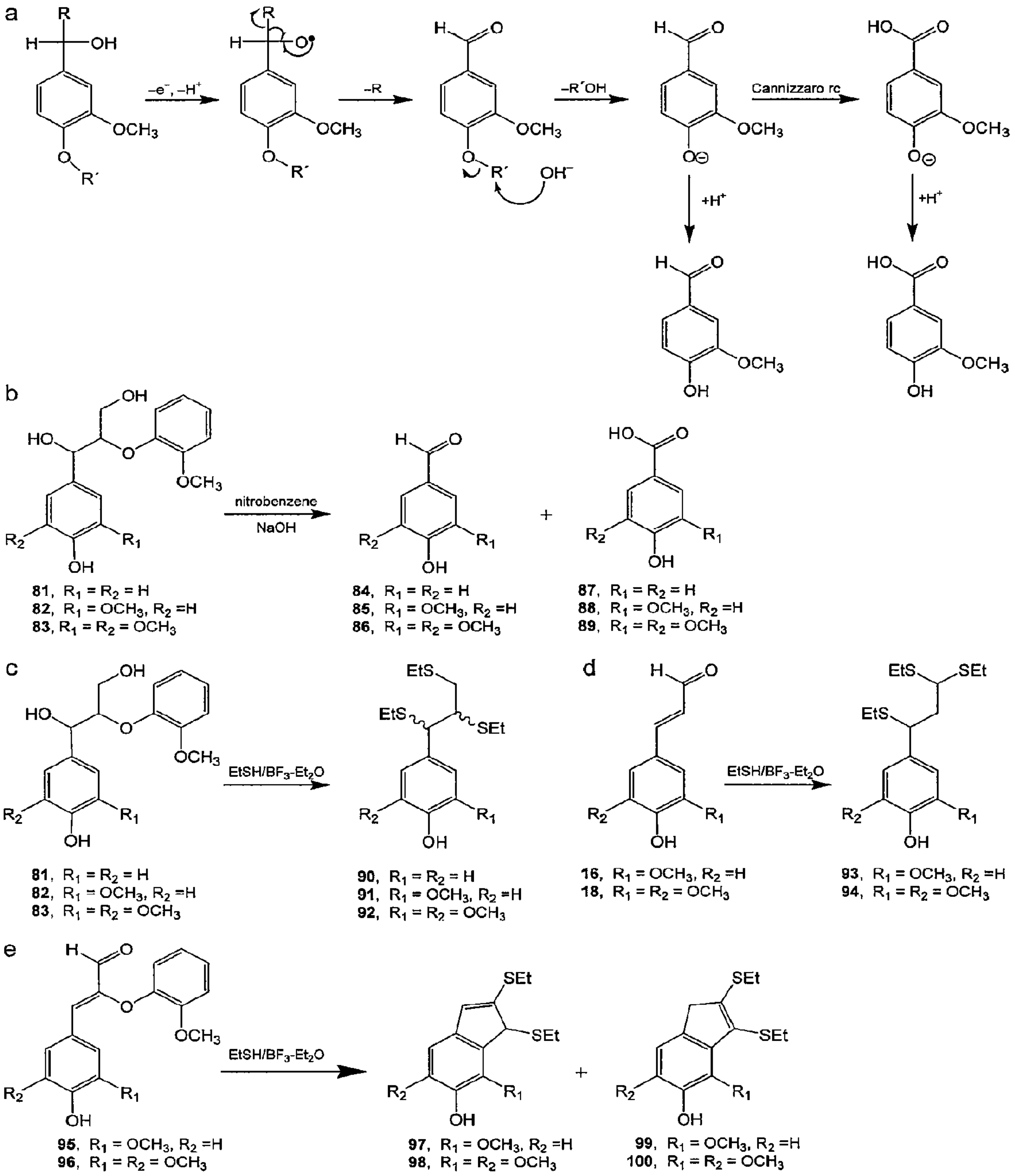
FIG. 33 shows, according to exemplary aspects of the present invention, nitrobenzene and thioacidolysis monomeric products from "lignin" model compounds and various "aldehydic" model compounds. a) Proposed mechanism for NBO lignin cleavage (Schultz & Templeton, 1986; Schultz et al., 1987). b) Products formed by alkaline nitrobenzene oxidation of 8-O-4' linked model compounds 81-83. c-e) Thioacidolysis products from 8-O-4' model compounds 81-831 (c), monomeric aldehydes 16 and 18 (d) and 8-O-4' linked p-hydroxycinnamaldehyde model compounds 95 and 96 (e).

Alkaline nitrobenzene oxidation (NBO)/thioacidolysis degradation/acetyl bromide analyses. Alkaline nitrobenzene oxidation (NBO) and thioacidolysis degradation procedures are currently routinely applied to the analysis of plant materials, due to their abilities to cleave various linkages in lignins, as well as that of related phenolics. For example, NBO oxidation of lignin "model" compounds 81-83 affords the various lignin-derived products 84-89 (FIG. 33*b*) (Schultz and Templeton, 1986; Schultz et al., 1987). For lignins, this procedure results in a homolytic oxidative fission of their 7-8 linkages, and ultimately cleavage of the 8-O-4' bonds as well (FIG. 33*a*) (Schultz and Templeton, 1986; Schultz et al., 1987). This method can, however, give overestimations if there are significant amounts of other non-lignin cell-wall bound p-hydroxycinnamic acids/aldehydes present (Anterola & Lewis, 2002). For thioacidolysis, the overall main monomeric monolignol-derived degradation products (90-92), obtained from lignins proper are depicted in FIG. 33*c;* their formation has also been studied using model compounds 81-83 containing 8-O-4' inter-unit linkages. For the lignins, both procedures are generally employed to estimate H:G:S ratios, as well as amounts of releasable products relative to lignin contents and/or cell wall residues (CWR). The acetyl bromide (AcBr) method, by contrast, solubilizes phenolic materials, such as lignin, and is often generally employed to estimate "lignin" contents from various plant sources.

Nitrobenzene oxidation. Alkaline nitrobenzene oxidations (NBO) of the four isolates from the WT and the CAD double mutant were thus next carried out. For both isolates from the WT line, the total amounts of H, G and S monomeric units released were ~1359±7.9 μmoles $g^{-1}$ (without cellulase pretreatment) and ~1214±28.5 μmoles $g^{-1}$ (with cellulase pretreatment), with H:G:S ratios of 1:85:14 and 1:87:12, respectively (TABLE 6). This in turn accounted for ~27 and 24% by weight of the lignin isolates assuming the products had originated from $C_6C_3$ moieties (FIG. 33*b*).

Treatment of the corresponding CAD double mutant isolates gave somewhat similar findings, in terms of total amounts of monomers released (~1274±10.5 and ~1197±11.9 μmoles $g^{-1}$), with overall recoveries of 26 and 24%. On the other hand, the H:G:S ratios differed significantly (1:68:31 and 1:69:30) from that of WT indicative of a significant increase in both amounts of S units released with a comparable decrease in G moieties. Taken together, the alkaline NBO degradation data for all four isolates indicated that there were roughly equimolar populations of cleavable/releasable monomers present.

Thioacidolysis. Treatment of the two lignin-derived isolates from the WT line gave ~1149±18.3 and ~1131±19.8 μmoles $g^{-1}$ of total thioacidolysis monomers, with H:G:S ratios of 1:83:16 and 1:82:17, respectively (TABLE 6). As noted, these were largely the monolignol-derived products 90-92 (FIG. 33*c*) and, to a much smaller extent, they also resulted from cleavage of tiny amounts of aldehydic end-groups in presumed 8-O-4' linkages isolated as compounds 93 and 94 (FIG. 33*d*). Taken together, however, the thioacidolysis products 90-94 released in both cases accounted for ~23% by weight of the lignin isolates. This product recovery data thus also corresponded reasonably closely with the values for the NBO analyses previously described above.

On the other hand, the amounts of monolignol-derived thioacidolytic cleavage products 90-92 (FIG. 33*d*) from the CAD double mutant phenolic isolates were only ~116±4.6 and 92±5.3 μmoles $g^{-1}$, with these values in both cases corresponding to ~10% of the phenolic isolates. Interestingly, the monolignol-derived moieties had H:G:S ratios of 1:83:16 and 1:82:17 (TABLE 6), which were comparable to the ratio obtained for the lignin in the WT lines.

In the previous preliminary analysis of the CAD double mutant (Sibout et al., 2005), it was reported that the various indene derivatives 97-100 could also be released following thioacidolysis, with these presumed to result from cleavage of 8-O-4' interunit linkages (FIG. 31*e*) derived from p-hydroxycinnamaldehyde 16 and 18 coupling. To investigate this possibility further, the corresponding model compounds 95 and 96 were synthesized and individually subjected to quantitative thioacidolysis for calibration purposes. In this way, the total amounts of indene derivatives 97-100, end-group aldehydes 93, 94 and monolignol derived products 90-92 released from the double mutant phenolic isolates were ~1050±15.1 and ~1041±18.5 μmoles $g^{-1}$ monomers, with H:G:S ratios of 1:72:27 and 1:71:28, respectively (TABLE 6). Thus, as also observed from the NBO analyses, the H:G:S ratios differed significantly from that of WT due to an increase in S units. Taken together, the thioacidolysis products 90-92 and 97-100 accounted for ~21-22% by weight of the poly-p-hydroxycinnamaldehyde isolates; these values were thus also in the same general range as those determined by the alkaline NBO degradation method.

TABLE 6

Estimations of lignin/poly-p-hydroxycinnamaldehydes contents and monomeric compositions.

| | | | WT (Wassilewskija) | | | |
|---|---|---|---|---|---|---|
| | | | CWR | CWR (cellulase) | Isolate | Isolate (cellulase) |
| AcBr lignin contents(% of CWR or isolate) | | | 20.8 ± 0.2 | 48.7 ± 0.3 | 98.5 ± 2.3 | 98.8 ± 2.2 |
| NBO | | H units (22, 25) | 4 ± 1.1 | 11 ± 3.8 | 6 ± 1.5 | 7 ± 1.7 |
| (μmoles $g^{-1}$ of | | G units (23, 26) | 261 ± 10.2 | 545 ± 13.2 | 1156 ± 8.3 | 1055 ± 28.4 |
| either CWR or | | S units (24, 27) | 65 ± 6.4 | 147 ± 5.7 | 197 ± 5.4 | 152 ± 8.9 |
| isolate) | | H + G + S units (22-27) | 330 ± 10.8 | 703 ± 13.2 | 1359 ± 7.9 | 1214 ± 28.5 |
| | | H:G:S | 1:79:20 | 1:78:21 | 1:85:14 | 1:87:12 |
| Thioacidolysis | 8-O-4' | H units (28) | 3 ± 0.2 | 2 ± 0.2 | 5 ± 0.1 | 6 ± 0.2 |
| (μmoles $g^{-1}$ of | monolignols | G units (29) | 244 ± 4.3 | 417 ± 6.6 | 930 ± 15.2 | 904 ± 17.1 |
| either CWR or | | S units (30) | 71 ± 3.9 | 93 ± 3.6 | 186 ± 10.8 | 194 ± 10.8 |

TABLE 6-continued

Estimations of lignin/poly-p-hydroxycinnamaldehydes contents and monomeric compositions.

| | | | | | | |
|---|---|---|---|---|---|---|
| isolate) | | H + G + S units (28-30) | 318 ± 6.9 | 512 ± 10.5 | 1121 ± 19.1 | 1104 ± 18.8 |
| | | H:G:S | 1:77:22 | 1:82:17 | 1:83:16 | 1:82:17 |
| | 8-O-4' | H units | nd | nd | nd | nd |
| | aldehydes | G units (35, 36) | nd | nd | tr | tr |
| | | S units (37, 38) | nd | nd | tr | tr |
| | | H + G + S units (35-38) | nd | nd | tr | tr |
| | | H:G:S | — | — | — | — |
| | End group | H units | nd | nd | nd | nd |
| | aldehydes | G units (31) | 13 ± 1.2 | 18 ± 1.8 | 24 ± 1.5 | 24 ± 1.9 |
| | | S units (32) | 2 ± 0.5 | 3 ± 0.4 | 4 ± 0.3 | 3 ± 0.7 |
| | | H + G + S units (31, 32) | 15 ± 1.1 | 21 ± 1.9 | 28 ± 1.2 | 27 ± 1.3 |
| | | H:G:S | 0:87:13 | 0:86:14 | 0:86:14 | 0:89:11 |
| | All units | H units | 3 ± 0.2 | 2 ± 0.2 | 5 ± 0.1 | 6 ± 0.2 |
| | | G units | 257 ± 6.2 | 435 ± 7.3 | 954 ± 15.8 | 928 ± 18.3 |
| | | S units | 73 ± 4.9 | 96 ± 4.7 | 190 ± 11.2 | 197 ± 11.2 |
| | | H + G + S units | 333 ± 9.3 | 533 ± 11.2 | 1149 ± 18.3 | 1131 ± 19.8 |
| | | H:G:S | 1:77:22 | 1:82:17 | 1:83:16 | 1:82:17 |
| | Ratio of all aldehyde/all units | | 0.04 | 0.04 | 0.02 | 0.02 |

| | | | CAD double mutant | | | |
|---|---|---|---|---|---|---|
| | | | CWR | CWR (cellulase) | Isolate | Isolate (cellulase) |
| AcBr lignin contents(% of CWR or isolate) | | | 11.3 ± 0.4 | 19.6 ± 0.4 | 99.1 ± 1.4 | 99.2 ± 1.8 |
| NBO | | H units (22, 25) | 2 ± 0.8 | 4 ± 0.7 | 6 ± 1.1 | 8 ± 0.9 |
| (μmoles $g^{-1}$ of | | G units (23, 26) | 76 ± 2.8 | 189 ± 3.5 | 868 ± 6.7 | 832 ± 7.9 |
| either CWR or | | S units (24, 27) | 38 ± 1.1 | 90 ± 5.7 | 400 ± 6.4 | 357 ± 7.4 |
| isolate) | | H + G + S units (22-27) | 116 ± 4.6 | 283 ± 9.8 | 1274 ± 10.5 | 1197 ± 11.9 |
| | | H:G:S | 1:66:33 | 1:67:32 | 1:68:31 | 1:69:30 |
| Thioacidolysis | 8-O-4' | H units (28) | 1 ± 0.4 | 1 ± 0.2 | 1 ± 0.1 | 1 ± 0.2 |
| (μmoles $g^{-1}$ of | monolignols | G units (29) | 10 ± 1.2 | 16 ± 1.8 | 98 ± 3.7 | 77 ± 4.8 |
| either CWR or | | S units (30) | 3 ± 0.5 | 4 ± 0.9 | 17 ± 1.1 | 14 ± 0.9 |
| isolate) | | H + G + S units (28-30) | 14 ± 1.5 | 21 ± 2.2 | 116 ± 4.6 | 92 ± 5.3 |
| | | H:G:S | 1:71:28 | 1:75:24 | 1:83:16 | 1:82:17 |
| | 8-O-4' | H units | nd | nd | nd | nd |
| | aldehydes | G units (35, 36) | 32 ± 1.5 | 79 ± 5.3 | 596 ± 10.3 | 569 ± 8.9 |
| | | S units (37, 38) | 16 ± 0.8 | 38 ± 4.3 | 256 ± 6.9 | 271 ± 8.2 |
| | | H + G + S units (35-38) | 48 ± 1.1 | 117 ± 10.6 | 852 ± 18.4 | 840 ± 17.1 |
| | | H:G:S | 0:67:33 | 0:68:32 | 0:70:30 | 0:68:32 |
| | End group | H units | nd | nd | nd | nd |
| | aldehydes | G units (31) | 17 ± 1.6 | 31 ± 2.1 | 68 ± 2.9 | 91 ± 3.8 |
| | | S units (32) | 3 ± 0.9 | 5 ± 0.8 | 14 ± 1.5 | 18 ± 1.2 |
| | | H + G + S units (31, 32) | 20 ± 3.6 | 36 ± 2.5 | 82 ± 3.2 | 109 ± 4.7 |
| | | H:G:S | 0:85:15 | 0:86:14 | 0:83:17 | 0:83:17 |
| | All units | H units | 1 ± 0.4 | 1 ± 0.2 | 1 ± 0.1 | 1 ± 0.2 |
| | | G units | 59 ± 2.1 | 126 ± 6.8 | 762 ± 10.5 | 746 ± 13.4 |
| | | S units | 22 ± 1.7 | 47 ± 5.1 | 287 ± 5.9 | 294 ± 11.8 |
| | | H + G + S units | 82 ± 4.1 | 174 ± 12.6 | 1050 ± 15.1 | 1041 ± 18.5 |
| | | H:G:S | 1:72:27 | 1:73:26 | 1:72:27 | 1:71:28 |
| | Ratio of all aldehyde/all units | | 0.83 | 0.88 | 0.89 | 0.91 |

nd: not detected; tr: traces; cellulase: cellulase pretreatment of plant tissue.

AcBr, NBO and thioacidolysis analyses were on either cell wall residues (CWR) or isolated lignins/poly-p-hydroxycinnamaldehydes from 8 week old WT and CAD double mutant plants. For each analysis, the values represent the mean ± standard error of two independent determinations measured in duplicate.

Acetyl bromide analyses. The acetyl bromide (AcBr) method is generically used by many researchers to estimate lignin contents in various plant cell wall residues (CWR). In this method, samples are treated with a reaction mixture consisting of 25% AcBr by volume in glacial acetic acid containing 4% of perchloric acid, with "lignin" estimations determined by measurement of the UV absorptivity (λ, 280 nm) of the corresponding solubilized material. An extinction coefficient of 20.09 l $g^{-1}$ $cm^{-1}$ (Iiyama & Wallis, 1988, 1990) has long been generically employed for such lignin estimations, but this does not take in the account differences in extinction coefficients of lignins with varying H, G and S compositions in different plant lines, and/or the presence of any other interfering chromophores. When applying this generic extinction coefficient to the analyses of the WT lignin enriched isolates, "lignin" contents of 84% were obtained, whereas with the CAD double mutant isolates, the values were in excess of >110%. The data obtained using the 20.09 l $g^{-1}$ $cm^{-1}$ extinction coefficient were thus considered as being potentially unreliable.

In order to attempt to more accurately determine the AcBr values for each isolate from the WT and the double mutant, the AcBr extinction coefficients were next individually determined (λ, 280 nm). This gave estimated values of $\epsilon_{280}$=17.85 l $g^{-1}$ $cm^{-1}$ for the WT lignin isolates, and $\epsilon_{280}$=23.61 l $g^{-1}$ $cm^{-1}$ for the CAD poly-p-hydroxycinnamaldehyde isolates.

As noted earlier, for both WT lignin isolates, the alkaline NBO and thioacidolysis procedures had given very similar estimated monomeric H:G:S ratios of 1:85:14 and 1:83:16. The AcBr extinction coefficient, based on these monomeric ratios, was then next theoretically calculated using the AcBr extinction coefficients previously obtained for purified H, G and S enriched lignin isolates, i.e. (H) 15.31, (G) 18.61 and (S) 14.61 l $g^{-1}$ $cm^{-1}$ (Cardenas et al., manuscript submitted).

In this way, an AcBr extinction coefficient of 17.98 l $g^{-1}$ $cm^{-1}$ was theoretically calculated according to the monomeric composition (obtained by thioacidolysis) of the WT lignin-enriched lignin isolates. This calculated value was thus in very good agreement (99.3%) with that experimentally determined. Using either of these extinction coefficient values, the estimated AcBr lignin contents for 8 week old (mature) WT stem tissue were ~20.8% for the cell wall residue (CWR) and ~48.7% for the cellulase degraded material as well as ~99% for the isolated lignin preparation (Table 1). [Note: we are aware that the ~99% lignin purity of the isolate is slightly over-estimated, since such preparations generally contain ~5-8% of non-lignin impurities, e.g. as noted in the NMR $^{13}C$ spectra (FIG. 30*a*)].

In an analogous manner, using the experimentally determined AcBr extinction coefficient of $\epsilon_{280}$=23.61 l $g^{-1}$ $cm^{-1}$ for the poly-p-hydroxycinnamaldehyde isolates together with that of the monomeric compositions estimated by thioacidolysis, it was also possible to theoretically calculate an AcBr extinction coefficient for the poly-aldehydic component alone, i.e. by subtracting the absorbance due to the H:G:S monolignol-derived units. As indicated above, based on the thioacidolysis data, the monolignol-derived moieties 28-30 and the aldehyde derived constituents 31, 32 and 35-38 were present in a ~9:1 ratio. This correction thus gave a theoretically calculated AcBr extinction coefficient of $\epsilon_{280}$=24.83 l $g^{-1}$ $cm^{-1}$ for the poly-p-hydroxycinnamaldehyde. Based on both extinction coefficients, the poly-p-hydroxycinnamaldehyde/lignin contents for the double mutant line were estimated as follows: ~11.3% in the extractive-free cell wall residue (CWR) of 8 week TABLE 6).

Lignin contents, releasable monomeric compositions and inter-unit linkage frequencies. The lignin and poly-p-hydroxycinnamaldehyde contents, as well as the monomeric compositions, of the extractive-free cell wall residues (CWR) from the WT and CAD double mutant lines were next estimated at different developmental stages, i.e. from 3.5 to 10 weeks (FIGS. 34*a-f*). For comparison purposes, the thioacidolysis and AcBr data obtained herein were also compared to data previously reported for various WT and other putative cad mutant *Arabidopsis* lines (FIG. 34*g*), with these being ostensibly harvested and analyzed at plant maturation (see Eudes et al., 2006, disscussed below) (Note that, in general, the H:G:S ratio and amounts in the CWR's of both WT and CAD double mutant lines had higher S contents than that of the lignin and poly-p-hydroxycinnamaldehyde isolates, indicative of hydrolytic changes occurring during the isolation protocols (TABLE 6)).

Figures 34A, 34B, 34C, 34D, 34E, 34F, 34G:
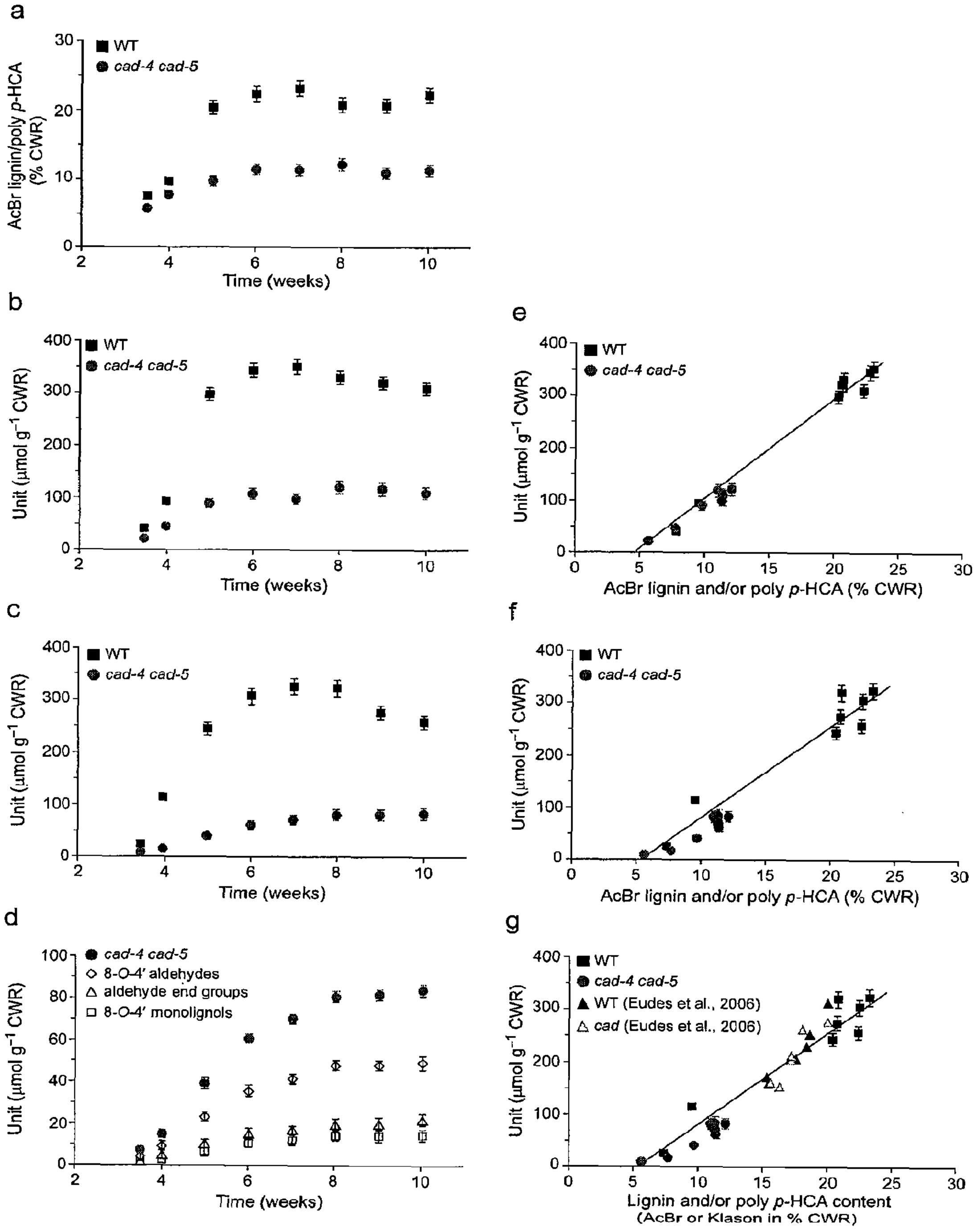
FIG. 34 shows, according to exemplary aspects of the present invention, correlation of estimated lignin/poly-p-hydroxycinnamaldehyde contents as a function of growth/developmental stage and/or monomer release. a) Estimated AcBr lignin and poly-p-hydroxycinnamaldehyde (poly-p-HCA) contents. Releasable monomeric derivatives by b) alkaline NBO and c, d) thioacidolysis. Correlation of changes in lignin/poly-p-hydroxycinnamaldehyde contents to releasable monomeric derivatives by e) alkaline NBO and f, g) thioacidolysis. For g) black squares and gray circles represent data obtained in this study, whereas black and gray triangles represent WT and various genes previously annotated as putative cad (At1g72680, At2g21730, At4g37970, At4g37980, At4g37990 and At4g39330) knockout mutants; none of these knockouts displayed any ostensible effects on overall lignification (data replotted from Eudes et al., 2006).

For the WT line in this study, lignin contents were again estimated using AcBr extinction coefficients calculated according to the thioacidolysis-derived monomeric compositions determined for each sample. The AcBr lignin contents thus increased rapidly during the stem "bolting" stage until reaching maximum levels close to maturation (>6 wks) (FIG. 34*a*) as previously reported for other WT *Arabidopsis* ecotypes, i.e. Landsberg erecta (Patten et al., 2005) and Columbia (Cardenas et al., manuscript submitted). The amounts of alkaline nitrobenzene oxidation (NBO) 22-27 (FIG. 34*b*) and thioacidolysis 28-32 (FIG. 34*c*) releasable monomers also followed the same trends, again increasing linearly with lignin deposition (FIGS. 34*e* and *f*). These trends were thus in good agreement with values previously obtained for *Arabidopsis* Landsberg and Columbia lines. Recoveries of degradation products 22-27 and 28-32, relative to estimated lignin contents, were ~24 to 27 (NBO) and ~23% (thioacidolysis).

In an analogous manner, the AcBr values from the CAD double mutant lines were obtained at the same sampling time points, with poly-p-hydroxycinnamaldehyde and lignin contents computed based on their relative aldehydic and monolignol contents and ratios (9:1), i.e. using $\epsilon_{280}$=24.83 l $g^{-1}$ $cm^{-1}$ for the estimated AcBr extinction coefficient of the poly-p-hydroxycinnamaldehyde component, and the theoretically calculated AcBr extinction coefficients (15.31 for H, 18.61 for G and 14.61 l $g^{-1}$ $cm^{-1}$ for S units) for the lignin (see Section 2.3.5.3). These data thus also established a progressive, albeit attenuated (relative to the WT line), increase in phenolic deposition which reached maximum values at ~6-8 weeks growth/development (FIG. 34*a*). For alkaline NBO analyses with the double mutant, the data so obtained showed a relatively rapid increase in monomer release from 3-6 weeks until reaching maximum values (FIG. 34*b*). However, in the CAD double mutant, there was only ~36% of the monomer amounts released relative to that from the WT lines at maturation, i.e. in accordance with the much lower poly-p-hydroxycinnamaldehyde/lignin contents. Based on the absorptivity values, the maximum levels of phenolics in the CAD double mutant CWR were ~11.3% or about half of the WT lignin content (~22.5% for WT).

Using degradative thioacidolysis analyses, the monomeric products released from the CAD double mutant CWR were now largely the indene derivatives 35-38 with minor amounts of end group aldehydes 31/32 and monolignol-derived 28-30 entities (FIG. 34*d*). Nevertheless, the data displayed the same overall trend as for the NBO analyses, i.e. an increase from 3-6 weeks until reaching a maximum value, with, in this case, overall amounts being ~27% of those from the WT lines (FIG. 34*c*). Recoveries of products 28-32 and 35-38, relative to the estimated poly-p-hydroxycinnamaldehyde and lignin contents, were estimated to be ~22% and thus similar to that for the WT line above.

Finally, the total amounts of products released by NBO and thioacidolysis degradative analyses for both the WT and the double mutant CWR's were plotted versus that of each AcBr lignin/AcBr phenolic content (FIGS. 34*e* and *f*).

Discussion of this Example 4

Evolutionary implications and technological limitations in lignin analyses. The generally accepted biochemical entry point into the monolignol/lignin pathway is the essential amino acid Phe, which during the course of vascular plant evolution from their aquatic forerunner beginnings (~430 million years ago) (Bolwell et al., 2001), was utilized as the carbon skeleton for a vast array of downstream phenylpropanoid pathway products. These downstream metabolic processes thus involved deamination, hydroxylation, methylation, and various reductive transformations, thereby affording the various monolignols 1, 3 and 5, and ultimately the lignins found in the ~350,000 distinct vascular plant species extant today (for a review see Lewis et al., 1999; Anterola and Lewis, 2002). Significantly, based on decades of lignin analyses using a very large number of vascular plant species (Sarkanen and Ludwig, 1971), it was already by then very well established that there was a very strong evolutionary pressure for lignin macromolecular configuration from the three monolignols 19, 21 and 23, as well as, to a lesser extent, from the closely related p-hydroxycinnamate monolignol ester derivatives in grasses (Lewis and Yamamoto, 1990). However, these studies gave no insight into how control over lignin macromolecular configuration was achieved.

Based on the above trends, it was thus quite unlikely that lignin macromolecular configuration, from either structural and/or physiological function perspectives, could be adequately duplicated and/or substituted through surrogate monomeric phenol replacement, i.e. such as had been reported earlier with the p-hydroxycinnamic acids 4-8, 2-methoxybenzaldehyde (76), feruloyl tyramine (78) derivatives and others including acetosyringone (77) (Ralph et al., 1997; 1998; 2004a; Boudet, 1998). Such reports, however, either gave no quantification data in support of these contentions and/or could not be confirmed in independent analyses (Anterola and Lewis, 2002; Laskar et al., 2006). The findings in this Example, which now demonstrate a very limited capacity for poly-p-hydroxycinnamaldehyde placement in the cell wall, thus shed incisive light as to why monolignol-derived lignification has evolved as such a potent selection force. That is, this study provides useful insight as to why lignin macromolecular configuration, in terms of being monolignol-derived, is very highly conserved thoughout the plant kingdom. More specifically, the *Arabidopsis* CAD double mutant described herein has now also provided an excellent opportunity to begin to comprehensively investigate macromolecular lignin assembly and the various effects on its disruption.

Overall gross growth/developmental trends and losses in biomechanical tissue properties: implications for commercial cultivars. The physiological effects of the CAD double mutation were very striking (FIG. 26*a*). While this resulted in a significant reduction in both "bolting" stem lengths and diameters (by 25 and ~15%) (FIGS. 26*b* and 26*c*), there was more importantly a significant loss in overall stem structural integrity properties (FIGS. 26*d* and 26*e*). That is, the storage and tensile loss moduli for the mutant "stem" tissues were greatly reduced (by ~50%) relative to that of the WT line, with the physiological consequences being that the mutant became essentially prostrate (FIG. 26*a*). It is not possible at this time to gauge from these analyses, however, the exact contribution of each of the various cell wall biopolymers (lignin, cellulose, hemicellulose, cell wall proteins) to the overall stem tissue mechanical properties. It is evident though that formation of only ~10% of the monolignol-derived lignin (relative to WT on a per lignin/poly-p-hydroxycinnamaldehyde weight basis) at maturation (TABLE 6), and the limited deposition of other phenolics i.e. the p-hydroxycinnamaldehydes 6-10 (discussed below), were insufficient to restore and/or duplicate the original WT stem material properties/structural integrity. Moreover, it was established by Applicants that both AtCAD4 and AtCAD5 were also expressed in various organs and cell types other than stem tissues (i.e. leaf trichomes, leaf hydathodes, leaf vasculature, various floral organs, siliques, root tissues and so forth); these findings thus suggest that their structural integrities will also be adversely affected.

From a physiological function perspective, it must also be considered that the plant lines analyzed herein were grown under highly favorable and controlled growth chamber/greenhouse conditions, which are unlikely to be duplicated in the wild. That is, the reductions in vascular tissue structural integrity observed herein may be less useful traits when such plant lines are subjected to the environment (wind, rain, snow, heat/cold, etc.). Furthermore, these lines may also be more prone/susceptible to pathogen attack, particularly since the vascular apparatus is often the main target. Moreover, with the current emphasis on reducing lignin contents in vascular plants, e.g. for improved bioethanol, wood, pulp and paper production, etc., it is clear that such effects may impact the potential for lignin biotechnological modification from a commercial cultivar standpoint. These are important aspects to evaluate when considering applications involving usage of large swaths of agricultural, forest or marginal lands to harbor such lignin modified crops.

The results obtained in this Example are also consistent with previous investigations using other CAD mutants and/or CAD down-regulated lines i.e. in terms of impaired/compromised structural integrity of stem tissues. For example, in maize, the main disadvantages of CAD mutations known for nearly 70 years—but currently largely overlooked by many researchers—have likely affected practical commercial considerations. The limitations reported have included lowering of grain/silage yield, increased lodging susceptibility, poor early season vigor, delayed flowering and delayed early season growth rates (Weller et al., 1985; Gentinetta et al., 1990). In addition, in loblolly pine, the CAD mutant (together with unknown mutations) displayed various growth/developmental and structural disadvantages (L. Pearson, Westvaco, personal communication) which to Applicants' knowledge has retarded commercial application at present. Furthermore, in poplar, CAD down-regulated lines displayed compromised biochemical properties indicative of vascular apparatus weakening (Huang et al., 1999). Similar conclusions were made with CAD downregulated tobacco, which resulted in reductions in longitudinal tensile modulus properties (Hepworth and Vincent, 1998). These reports thus underscore the practical considerations when considering potential commercial utilization, and thus relate to the level of vascular apparatus modification that can be achieved while maintaining acceptable structural properties.

The limited utility of histochemical analyses. The staining reactions observed when individually using phloroglucinol-HCl and the Mäule reagent were of limited utility. While the first reagent can react with p-hydroxycinnamaldehyde end groups 14-18, the procedure is not suitable for quantification. Moreover, the staining using phloroglucinol-HCl gave qualitatively similar results for both WT and CAD double mutant lines (FIG. 27*g-l*). A somewhat comparable situation existed for the Mäule reaction which also gave fairly similar levels of staining for both lines (FIGS. 27*m-r*), even though the double mutant had an increased S-level relative to WT.

Most striking was the red pigmentation in the CAD double mutant, this being readily removed by treatment with 0.5% HCl in MeOH as demonstrated earlier (Laskar et al., 2007), i.e. under similar conditions as for anthocyanin extraction (Andersen et al., 2004). This suggests that the small amounts of p-hydroxycinnamaldehydes 16 and 18, resulting in cell wall pigmentation, are not covalently linked, but are instead "misplaced" and adsorbed onto the cell wall, e.g. following apoptosis to generate the intense pigmentation observed. As noted by Laskar et al. (2007), the pigment co-elutes with the parent molecule, sinapyl aldehyde (10), when subjected to polyamide TLC purification.

Effects on carbon allocation and metabolic flux. A quite striking observation is that the overall phenolic content of the CAD double mutant was reduced by ~50% relative to WT, with the releasable monomers (through presumed 8-O-4' linkage cleavage) also being significantly reduced by ~63 and 73% for alkaline NBO and thioacidolysis (FIGS. 34*a-c*). These data thus clearly demonstrate that phenolic (biopolymer) carbon allocation to the cell walls was greatly attenuated. This is of interest given that previous metabolic flux analysis studies had indicated that CAD, under "normal" physiological conditions, had neither regulatory nor key roles in carbon allocation in the monolignol forming pathway (Anterola et al., 1999; 2002). This is in contrast to other assertions that CAD was a key enzyme (Baucher et al., 1996). Of course, any biochemical step becomes "rate-limiting," or "key", if essentially eliminated as has largely occurred with the CAD double mutant.

In general, CAD down-regulation in various plant species apparently had no deleterious effects on overall "lignin" contents in transgenic antisense/sense lines as determined by Klason, AcBr and thioglycollic acid (TGA) analyses (see Anterola and Lewis, 2002). However, all of the prior data obtained with tobacco (Halpin et al., 1994; Hibino et al., 1995; Yahiaoui et al., 1998), poplar (Baucher et al., 1996; Lapierre et al., 1999) and alfalfa (Baucher et al., 1998) had employed generic approaches for quantification (discussed in detail below in Section 3.5.1). Furthermore, in the Anterola and Lewis (2002) review, it was noted that there were most likely reductions in lignin contents proper when CAD down-regulation occurred, e.g. since overall biophysical/chemical properties of the tissues were deleteriously affected.

The data in this Example now establishes that additional factors influence carbon allocation to the pathway in the CAD double mutant, which may result from either: transcriptional regulation; substrate/product/pathway intermediate feedback inhibition and/or perception of a failure to obtain the needed cell wall biopolymeric properties. The main point of interest is that there was no compensatory replacement for macromolecular lignin configuration by seamless insertion of other non-lignin moieties (poly-p-hydroxycinnamaldehydes) or indeed of any other entities. By contrast, the limited deposition of the poly-p-hydroxycinnamaldehyde moieties was aborted at a very early stage of monomer cleavable 8-O-4' substructure formation (FIGS. 34*c* and *f*). This suggests that there is a regulatory "checkpoint" beyond which such processes, if futile, can not be sustained. Thus, taken together, this resulted in generation of rather structurally defective plants, whether from either a reduced carbon allocation and/or structural integrity perspective. These findings thus contrast with other reports that proposed seamless replacement of non-monolignol components (Ralph et al., 1997; 2004a). Specifically, the findings in this Example now place further emphasis on the importance of lignin structure, and that perfectly viable plants are not always produced upon monolignol pathway manipulation.

Lignins and Other Cell Wall (poly)phenolics: Evidence for Monomer Degeneracy During Template Polymerization:

Quantification of lignin amounts by Klason and acetyl bromide analyses: Current limitations and technological advances. This Example also brings to the forefront once again the serious technological challenges that continue to severely limit investigations in the lignin field, as well as that of related polyphenolic analyses, i.e. when routinely applying so-called "standard" techniques, such as generic Klason/AcBr/thioglycollic acid lignin determinations, and other degradation methodologies, e.g. thioacidolysis.

Of these, the two most widely utilized protocols for currently estimating gross lignin contents are the Klason and AcBr methods. The first method, while generally applicable to mature woody plant material, has long been known to have substantial limitations when generically applied to both herbaceous and immature woody tissues (discussed in (Anterola and Lewis, 2002, and references therein). Yet, it is still routinely applied. One example of its unreliability is that of the report of "lignin" contents in immature (approximately one-year old) poplar stems (*Populus tremula* x *Populus alba*), with these being as high as ~32% (Huntley et al., 2003), whereas other research groups analyzing 3 month and 2 year old poplar indicated that the levels were ~20% (Van Doorsselaere et al., 1995; Lapierre et al., 1999; Jouanin et al., 2000) Such values (~32%) fall well outside the ranges expected, since it is established that mature poplar wood tissues have lignin levels ~18-21% (Sarkanen and Hergert, 1971). If lignin determinations can be overestimated by up to nearly 80% as would appear from the Huntley et al. (2003) report, it is unlikely that such approaches are going to identify meaningful trends in lignin deposition/composition and assembly proper. Similar concerns about the unreliability of thioglycollic acid lignin determinations (Lee et al., 1997) have also been noted and critically evaluated (Anterola and Lewis, 2002).

The AcBr method has also been generically applied to numerous lignin determinations, using an extinction coefficient of $\epsilon_{280}$=20.09 l $g^{-1}$ $cm^{-1}$ (Iiyama and Wallis, 1990; Dence, 1992). This method, however, does not take into account the changes in extinction coefficients due to variations in lignin monomeric H, G and S compositions. As noted in this, and in a previous investigation using H, G and S enriched lignin isolates, the best current estimates of the actual extinction coefficients (λ, 280 nm) are (H) 15.31, (G) 18.61 and (S) 14.61 l $g^{-1}$ $cm^{-1}$ for each (Cardenas et al., manuscript submitted). Thus, taking the approach of estimating monomeric compositions at a particular stage of growth and development, it was possible in this Example to begin to make improved estimates of the actual lignin amounts, i.e. using the extinction coefficients and adjusting for monomeric compositions. (Applicants are, of course, cognizant that these values may be slightly revised upwards, since the methodologies currently in place to isolate lignins can result in ~5-8% of non-lignin impurities).

In the case of the poly-p-hydroxycinnamaldehyde enriched isolates, however, there was also an increase in overall absorbance at λ 280 nm due to the increased levels of the more highly conjugated p-hydroxycinnamaldehyde components. Hence, by using the experimentally determined values of $\epsilon_{280}$=24.83 l $g^{-1}$ $cm^{-1}$ for the poly-p-hydroxycinnamaldehyde and those above for the lignin component, the total (cell wall) phenolic contents for the CAD double mutant at 8 weeks old plants were estimated to be ~11.3% (=~50% of WT level).

Alkaline nitrobenzene oxidation/thioacidolysis analyses: evidence for monomer degeneracy during template polymerization? As described herein, the study of the cleavage and frequency of presumed 8-O-4' inter-unit linkages, leading to monomer release, was most instructive from several perspectives. First, in the WT line, there was a linear correspondence between monomer release and AcBr lignin content, with a very similar trend (albeit highly attenuated in overall amounts) noted for the releasable monomers (indene, p-hydroxycinnamaldehyde end-groups, monolignols) from the CAD double mutant (FIGS. 34*e* and *f*), assuming, of course, that cleavage of all monomeric releasable linkages are fully accounted for. In the latter case, these are derived from the styryl-O-aryl ethers (such as in substructure VIII-1-4, FIGS. 30*e* and 31*d*). Accordingly, the model compounds 95 and 96 (FIG. 33) were synthesized and then converted into authentic thioacidolysis products 97-100 for calibration purposes, with the assumption that the yields/recoveries obtained for the different reactions/isolation procedures reflected similar processes occurring during lignin and poly-p-hydroxycinnamaldehyde deconstruction.

This same approach was not taken in two other studies of the CAD double mutant (Sibout et al., 2005; Eudes et al., 2006), and only the monolignol-derived thioacidolysis products 90-91 were apparently used for calibration purposes. In any event, the indene derivatives 97-100 were estimated to apparently account for just ~0.12% of the CWR analyzed. By contrast, using the authentic standards in the study herein, the amounts of the indene products, etc., being formed were determined to be roughly an order of magnitude higher (~9 times) and which corresponded to ~16% of the poly-p-hydroxycinnamaldehyde isolates.

Secondly, as noted in our previous studies (Anterola and Lewis, 2002; Patten et al., 2005), the plots of amounts of cleavable monomer release versus either lignin or phenolic (poly-p-hydroxycinnamaldehyde/lignin) contents did not intercept at the origin of the X-axis for either plant line. That is, the abscissa was displaced away from the origin on the X-axis to a point roughly corresponding to either ca ~5% AcBr/lignin (WT) or ~5% AcBr phenolic (CAD double mutant) deposition (FIGS. 34*e-g*). Significantly, however, the detection of cleavable monomers for both WT and CAD double mutant lines occurred at apparently equivalent growth/developmental stages, i.e. suggesting that essentially similar assembly/deposition processes were being attempted to be duplicated.

This initial deposition stage of UV-absorbing material is often referred to as H-enriched "condensed" lignin, and is considered to contain non-cleavable carbon-carbon linkages (e.g. 3-3', 5-5') rather than cleavable (i.e. monomer releasable) 8-O-4' linkages. It is currently unknown, however, as to whether this "early" stage of presumed lignin deposition contains other 8-O-4' inter-unit linkages that do not release monomeric products upon cleavage. The intercept at ca ~5% AcBr/lignin (WT) or ~5% AcBr phenol, which represents the point of initial detection of (monomer cleavable) 8-O-4' linkages in both cases, gives no insight at present as to whether there is either a gradual or an abrupt structural demarcation between both early and later stages of lignin/(poly-p-hydroxycinnamaldehyde) deposition. Yet beyond this early stage and until macromolecular lignification configuration has either been completed and/or poly-p-hydroxycinnamaldehyde deposition is prematurely aborted, there was a clear linear correlation between (monomer cleavable) 8-O-4' inter-unit linkage frequency and lignin/phenolic contents in both cases. Furthermore, by subtracting the initial "5% AcBr lignin" amounts in the WT line, the cleavable subset of monomer releasable 8-O-4' inter-unit linkages in the later stages accounted for up to ~42 to 44% of the macromolecular lignin being laid down. In an analogous manner, by subtraction of the initial 5% AcBr phenolic content in the CAD double mutant line, the overall product recoveries at the point of termination of poly-p-hydroxycinnamaldehyde deposition were ~37 to 39%, i.e. in very good agreement with the WT value.

Thirdly, the data obtained indicated that the overall 8-O-4' inter-unit linkage frequencies were conserved in the CAD double mutant relative to that of the WT line, i.e. both lines gave equivalent amounts of releasable monomers per gram of estimated lignin/poly-p-hydroxycinnamaldehyde. Thus, these comparable 8-O-4' inter-unit linkage frequencies in both lines may suggest a very limited monomer degeneracy of p-hydroxycinnamaldehydes 14-18 for monolignol template polymerization. It is perhaps significant, however, that the CAD double mutant also retained the ability to form circa 10% of cleavable monolignol-derived moieties 90-92 relative to WT, which could be detected at each sampling point (FIG. 34*d*). One possibility to consider is that as primary (monolignol-derived) lignin chains are first laid down, these then provide a pre-formed lignin backbone for further template replication (Guan et al., 1997; Sarkanen, 1998). That is, the p-hydroxycinnamaldehyde moieties can be envisaged to partially replace the aligning/aligned monolignol 19, 21 and 23 (radicals) during subsequent template polymerization, e.g. on the lignin backbone (Chen and Sarkanen, 2003; Davin and Lewis, 2005). Alternatively, the p-hydroxycinnamaldehydes 14, 16 and 18 can participate in a proteinaceous guided assembly stage to a limited extent, thereby forming the primary chains for subsequent replication. Furthermore, because of the extended conjugation with the p-hydroxycinnamaldehydic end group, the proton at carbon-8 is more readily abstracted thereby affording the corresponding styryl-O-aryl ether products (8-O-4' inter-unit linkages, substructure VII-1-4, FIGS. 30*e* and 31*d*) rather than the typical 8-O-4' inter-unit linkages in substructure I (FIG. 30*e*). Yet, this process apparently can only continue up to about the equivalent of ~50% "lignin" deposition (relative to WT), which corresponds to ca 36% of monomer cleavable 8-O-4' inter-unit linkages in the lignins proper.

Interestingly, the poly-p-hydroxycinnamaldehyde-derived monomers released also had significantly higher levels of sinapyl aldehyde (18) derived moieties, relative to that in the WT line, although the reasons for this are as yet unknown.

Thus, whether aborting this process in the poly-p-hydroxycinnamaldehyde (CAD double mutant) reflects the organism's perception of the structural imperfections resulting from deficits in cell wall macromolecular lignin configuration proper and/or through some form of feedback inhibition/transcriptional control within the cells, cannot yet be gauged at this point. We interpret these data as most likely indicating, however, that the template polymerization process is a highly restricted attempt to use p-hydroxycinnamaldehydes to preserve native lignin configuration, i.e. which continues briefly until the failure/checkpoint level is reached. It is evident, however, that there is no seamless replacement of monolignol monomers 19, 21 and 23, and that the CAD double mutant has a significantly compromised structural integrity. Hence, this may simply reflect the organism attempting—in a limited way—to form a biopolymer with the same inter-unit lignin linkages as lignins proper, i.e. through limited monomer degeneracy during template chain replication as described above. On the other hand, the failure to complete this process, and the structural deficits introduced, again underscore the strong selection pressure that terrestrial vascular plants have evolved to afford lignins proper and not the structurally inferior poly-p-hydroxycinnamaldehydes noted herein.

Fourthly, recent studies by Eudes et al. (2006) examined various WT and knockout lines of other putative members of the AtCAD gene family i.e. AtCAD1-3 and AtCAD6-9 whose precise physiological roles still await to be determined (Kim et al., 2007). Interestingly, these researchers had reported that the various plant stem samples were considered to be analyzed at maturity. On the other hand, the Klason lignin values reported for the mature stems (see FIG. 10*g*, symbol black triangles for WT and gray triangles for cad mutants) had values ranging from 15.4 to 20.3%. When these data were next plotted herein against the amounts of monolignol releasable components for each line as above, together with our own data, the trends observed were in agreement with the observations made above. It appeared that the plant lines in the Eudes et al. (2006) study were thus harvested at varying stages of growth/development, with only a few at maturation. Nevertheless, at least for *Arabidopsis*, the Klason lignin determinations corresponded fairly closely to that of our modified AcBr lignin/polyphenol analyses. More importantly, it was quite striking that similar trends for all sets of data were evident for the monolignol-derived cleavable 8-O-4' inter-unit linkage frequencies when plotted in this manner (FIG. 34*g*), i.e. in terms of both displacement of the abscissa and in amounts of monolignol-derived moieties being released. These data thus again underscore the necessity in examining plant lines at various stages of growth and development, rather than the single point analyses that have generally become routine for many investigations in this field.

NMR spectroscopic analyses of the poly-p-hydroxycinnamaldehyde-enriched isolates and comparison to lignins proper. The application of NMR spectroscopy, as for the alkaline NBO and thioacidolysis degradation analyses, provided useful, albeit still incomplete, structural information for the isolates examined. This is because the current limitations of NMR spectroscopic analyses include the inability to readily probe lignin primary structure, as well as the inability to identify, detect and accurately quantify all of the various inter-unit linkages present; for example, there were various substructures tentatively identified in the poly-p-hydroxycinnamaldehyde isolates herein (unpublished observations) which await full synthetic verification.

Assuming, however, that there is some limited capacity for monomer degeneracy during template polymerization, then an attempted formation of the same inter-unit linkages and frequency as for macromolecular lignin configuration might be anticipated, i.e. to afford 8-O-4', 8-5' linkages and others—at least to the extent possible. That this has occurred was readily demonstrable, at least for the 8-O-4' inter-unit linkages which contained G-G, S-G, G-S (like) and S—S (like) bonds in amounts corresponding to those in lignins proper, and also presumably for the 8-5' inter-unit linkages as well. However, this continued only to a relatively earlier stage (~50%) of phenolic deposition when compared to that of lignification proper as described above.

Interestingly, various previous studies of both CAD down-regulated tobacco and pine, (Ralph et al., 1997; Chabannes et al., 2001) had reported that the 8-5' benzofuran linkages (≡ substructures IX) were absent (Kim et al., 2003). In the study herein, however, evidence for 8-5' linkage formation in the poly-p-hydroxycinnamaldehyde isolates was readily obtained (FIG. 31*e*, substructure IX). Indeed, such structural motifs had previously been noted in various lignans (e.g. compound 79) (Yang et al., 1991), and further verification of their presence in the poly-p-hydroxycinnamaldehyde isolates was also achieved by comparison of spectroscopic features with that of synthetic compound 80.

Applicants findings thus also substantially differ from that observed with the synthetic dehydropolymerizates obtained from coniferyl aldehyde (16) and coniferyl alcohol (21), whereby 8-5' linkages were readily detectable as substructures XIV and XV (Kim et al., 2003). The existence of the fully conjugated substructure IX in the poly-p-hydroxycinnamaldehyde isolates, and how they differ from the corresponding entities in synthetic dehydropolymerizates, may in future provide additional insight into how the true lignin-forming machinery is operative in planta. That is, this may also provide insights into the processes that are occurring leading to oxidation of the 7-8 double bond when the aldehydes 14, 16 and 18 are translocated into the cell wall(s), and the significance of same.

In further contrast to previous studies of CAD-downregulated plants (tobacco or pine) (Kim et al., 2003), as well as synthetic poly-p-hydroxycinnamaldehyde dehydropolymerizates (Connors et al., 1970; Russell et al., 2000), none of the 8-8' p-hydroxycinnamaldehyde substructures XII and XIII could unambiguously be identified in the poly-p-hydroxycinnamaldehyde isolates either. On the other hand, excluding their near absence under the conditions employed, several other putative aldehyde correlations were observed but which remain unassigned in the present study (FIG. 31*c*); these will be the subject of future investigations. Additionally, limitations in the application of the NMR spectroscopic analyses were such that the small levels of substructures II-V could not be detected, nor 8-1' diphenyl linkages, etc. (FIG. 30*d*).

Summary of this Example. As regards this particular investigation, there has been much discussion on the potential of modifying lignin contents and compositions for various purposes including optimizing: carbon sequestration; animal feed/forage digestibility; lumber properties and pulp/paper manufacture; plant material as a source of biofuels (including ethanol). It was thus instructive to comprehensively examine the *A. thaliana* (ecotype Wassilewskija) double mutant cad-4 cad-5 (cad-c cad-d) (Sibout et al., 2005) as regards effects on: plant growth and development, overall morphology, vascular apparatus integrity/biomechanical properties, disruption of lignification proper, as well as the chemical/physical properties of the predominantly poly-p-hydroxycinnamaldehyde formed in small amounts instead of lignin (described herein). Taken together, all of the findings above provide excellent insight as to why lignin formation involves monolignol, and not poly-p-hydroxycinnamaldehyde, polymerization. That is, lignin macromolecular configuration proper was disrupted through formation of the (non-monolignol) p-hydroxycinnamaldehydes with the resulting highly restricted attempt at template polymerization leading to premature termination of cell wall macromolecular assembly process(es). These findings further help explain why the 350,000 extant vascular plants form lignins from a very finite set of monolignol precursors to achieve the requisite structural/physiological properties. Moreover, it should be evident from this study that an understanding macromolecular lignin configuration (i.e. in terms of determination of lignin primary structures and the precise mode of biochemical formation) for each stage of its (their) deposition represents now urgent goal. The urgency for this is exemplified by the clear trends being noted in both lignin/phenol deposition and the conserved inter-unit frequencies in same. Finally, the findings place further restrictions on random (combinatorial chemistry) coupling, which are rationalized herein as a controlled template assembly with limited monomer degeneracy.

Literature References Relating to this Example:

Andersen, Ø. M., Fossen, T., Torskangerpoll, K., Fossen, A., Hauge, U., 2004. Anthocyanin from strawberry (*Fragaria ananassa*) with the novel aglycone, 5-carboxypyranopelargonidin. Phytochemistry 65, 405-410.

Anterola, A. M., van Rensburg, H., van Heerden, P. S., Davin, L. B., Lewis, N. G., 1999. Multi-site modulation of flux during monolignol formation in loblolly pine (*Pinus taeda*). Biochem. Biophys. Res. Commun. 261, 652-657.

Anterola, A. M., Jeon, J.-H., Davin, L. B., Lewis, N. G., 2002. Transcriptional control of monolignol biosynthesis in *Pinus taeda:* factors affecting monolignol ratios and carbon allocation in phenylpropanoid metabolism. J. Biol. Chem. 277, 18272-18280.

Anterola, A. M., Lewis, N. G., 2002. Trends in lignin modification: a comprehensive analysis of the effects of genetic manipulations/mutations on lignification and vascular integrity. Phytochemistry 61, 221-294.

Banoub, J. H., Delmas, M., 2003. Structural elucidation of the wheat straw lignin polymer by atmospheric pressure chemical ionization tandem mass spectrometry and matrix-assisted laser desorption/ionization time-of-flight mass spectrometry. J. Mass Spectrom. 38, 900-903.

Baucher, M., Chabbert, B., Pilate, G., Van Doorsselaere, J., Tollier, M.-T., Petit-Conil, M., Cornu, D., Monties, B., Van Montagu, M., Inze, D., Jouanin, L., Boerjan, W., 1996. Red xylem and higher lignin extractability by down-regulating a cinnamyl alcohol dehydrogenase in poplar. Plant Physiol. 112, 1479-1490.

Baucher, M., Monties, B., Van Montagu, M., Boerjan, W., 1998. Biosynthesis and genetic engineering of lignin. Crit. Rev. Plant Sci. 17, 125-197.

Björkman, A., 1954. Isolation of lignin from finely divided wood with neutral solvents. Nature 174, 1057-1058.

Blee, K., Choi, J. W., O'Connell, A. P., Jupe, S. C., Schuch, W., Lewis, N. G., Bolwell, G. P., 2001. Antisense and sense expression of cDNA coding for CYP73A15, a class II cinnamate-4-hydroxylase, leads to a delayed and reduced production of lignin in tobacco. Phytochemistry 57, 1159-1166.

Bolwell, G. P., Patten, A., Lewis, N. G., 2001. The Holy Grail of wood evolution—from wood anatomy to tissue-specific gene expression: to what extent do molecular studies of biosynthesis of cell wall biopolymers help the understanding of the evolution of woody species? Phytochemistry 57, 805-810.

Boudet, A. M., 1998. A new view of lignification. Trends Plant Sci. 3, 67-71.

Chabannes, M., Barakate, A., Lapierre, C., Marita, J. M., Ralph, J., Pean, M., Danoun, S., Halpin, C., Grima-Pettenati, J., Boudet, A. M., 2001. Strong decrease in lignin content without significant alteration of plant development is induced by simultaneous down-regulation of cinnamoyl CoA reductase (CCR) and cinnamyl alcohol dehydrogenase (CAD) in tobacco plants. Plant J. 28, 257-270.

Chen, Y.-r., Sarkanen, S., 2003. Macromolecular lignin replication: a mechanistic 0working hypothesis. Phytochemistry Rev. 2, 235-255.

Connors, W. J., Chen, C.-L., Pew, J. C., 1970. Enzymic dehydrogenation of the lignin model coniferaldehyde. J. Org. Chem. 35, 1920-1924.

Croteau, R., Kutchan, T. M., Lewis, N. G., 2000. Natural products (secondary metabolites). In: Buchanan, B. B., Gruissem, W., Jones, R. L. (Eds.), Biochemistry and Molecular Biology of Plants. American Society of Plant Physiologists, Rockville, Md., pp. 1250-1318.

Davin, L. B., Lewis, N. G., 2005. Lignin primary structures and dirigent sites. Curr. Opin. Biotechnol. 16, 407-415.

Dence, C. W., 1992. The determination of lignin. In: Lin, S. Y., Dence, C. W. (Eds.), Methods in Lignin Chemistry. Springer-Verlag, Berlin, pp. 33-61.

Dutta, S., Garver, T. M., Jr., Sarkanen, S., 1989. Modes of association between kraft lignin components. ACS Symp. Series 397, pp. 155-176.

Eudes, A., Pollet, B., Sibout, R., Do, C.-T., Seguin, A., Lapierre, C., Jouanin, L., 2006. Evidence for a role of AtCAD1 in lignification of elongating stems of *Arabidopsis thaliana*. Planta 225, 23-39.

Garver, T. M., Jr., Iwen, M. L., Sarkanen, S., 1989. The kinetics of macromolecular kraft lignin complex dissociation. Fifth International Symposium on Wood and Pulping Chemistry, TAPPI Proceedings, TAPPI Press, Atlanta, GA 1, 113-119.

Gentinetta, E., Bertolini, M., Rossi, I., Lorenzoni, C., Motto, M., 1990. Effect of brown midrib-3 mutant on forage quality and yield in maize. J. Genet. Breed. 44, 21-26.

Guan, S.-Y., Mlynár, J., Sarkanen, S., 1997. Dehydrogenative polymerization of coniferyl alcohol on macromolecular lignin templates. Phytochemistry 45, 911-918.

Halpin, C., Knight, M. E., Foxon, G. A., Campbell, M. M., Boudet, A. M., Boon, J. J., Chabbert, B., Tollier, M.-T., Schuch, W., 1994. Manipulation of lignin quality by down-regulation of cinnamyl alcohol dehydrogenase. Plant J. 6, 339-350.

Hepworth, D. G., Vincent, J. F. V., 1998. The mechanical properties of xylem tissue from tobacco plants (*Nicotiana tabacum* 'Samsun'). Ann. Bot. 81, 751-759.

Hibino, T., Takabe, K., Kawazu, T., Shibata, D., Higuchi, T., 1995. Increase of cinnamaldehyde groups in lignin of transgenic tobacco plants carrying an antisense gene for cinnamyl alcohol dehydrogenase. Biosci. Biotechnol. Biochem. 59, 929-931.

Higuchi, T., Ito, T., Umezawa, T., Hibino, T., Shibata, D., 1994. Red-brown color of lignified tissues of transgenic plants with antisense CAD gene: wine-red lignin from coniferyl aldehyde. J. Biotechnol. 37, 151-158.

Huang, X., Jeronimidis, G., Vincent, J. F. V., 1999. Mechanical properties of wood from transgenic poplar trees with modified lignification. The 2nd Symposium of Chinese Youth Scholars on Material Science and Technology 10, 1-9.

Huntley, S. K., Ellis, D., Gilbert, M., Chapple, C., Mansfield, S. D., 2003. Significant increases in pulping efficiency in C4H-F5H-transformed poplars: improved chemical savings and reduced environmental toxins. J. Agric. Food Chem. 51, 6178-6183.

Iiyama, K., Wallis, A. F. A., 1988. An improved acetyl bromide procedure for determining lignin in woods and wood pulps. Wood Sci. Technol. 22, 271-280.

Iiyama, K., Lam, T. B. T., 1990. Lignin in wheat internodes. Part 1: the reactivities of lignin units during alkaline nitrobenzene oxidation. J. Sci. Food Agric. 51, 481-491.

Iiyama, K., Wallis, A. F. A., 1990. Determination of lignin in herbaceous plants by an improved acetyl bromide procedure. J. Sci. Food Agric. 51, 145-161.

Jouanin, L., Goujon, T., de Nadaf, V., Martin, M.-T., Mila, I., Vallet, C., Pollet, B., Yoshinaga, A., Chabbert, B., Petit-Conil, M., Lapierre, C., 2000. Lignification in transgenic poplars with extremely reduced caffeic acid O-methyltransferase activity. Plant Physiol. 123, 1363-1373.

Karhunen, P., Rummakko, P., Sipila, J., Brunow, G., Kilpelainen, I., 1995. Dibenzodioxocins, a novel type of linkage in softwood lignins. Tetrahedron Lett. 36, 169-170.

Kim, H., Ralph, J., Yahiaoui, N., Pean, M., Boudet, A.-M., 2000. Cross-coupling of hydroxycinnamyl aldehydes into lignins. Org. Lett. 2, 2197-2200.

Kim, H., Ralph, J., Lu, F., Pilate, G., Leple, J.-C., Pollet, B., Lapierre, C., 2002. Identification of the structure and origin of thioacidolysis marker compounds for cinnamyl alcohol dehydrogenase deficiency in angiosperms. J. Biol. Chem. 277, 47412-47419.

Kim, H., Ralph, J., Lu, F., Ralph, S. A., Boudet, A.-M., MacKay, J. J., Sederoff, R. R., Ito, T., Kawai, S., Ohashi, H., Higuchi, T., 2003. NMR analysis of lignins in CAD-deficient plants. Part 1. Incorporation of hydroxycinnamaldehydes and hydroxybenzaldehydes into lignins. Org. Biomol. Chem. 1, 268-281.

Kim, S.-J., Kim, M.-R., Bedgar, D. L., Moinuddin, S. G. A., Cardenas, C. L., Davin, L. B., Kang, C., Lewis, N. G., 2004. Functional reclassification of the putative cinnamyl alcohol dehydrogenase multigene family in Arabidopsis. Proc. Natl. Acad. Sci., USA 101, 1455-1460.

Kim, S.-J., Kim, K.-W., Cho, M.-H., Franceschi, V. R., Davin, L. B., Lewis, N. G., 2007. Expression of cinnamyl alcohol dehydrogenases and their putative homologues during *Arabidopsis thaliana* growth and development: lessons for database annotations? Phytochemistry, (this issue).

Lapierre, C., Pollet, B., Petit-Conil, M., Toval, G., Romero, J., Pilate, G., Leplé, J.-C., Boerjan, W., Ferret, V., de Nada;, V., Jouanin, L., 1999. Structural alterations of lignins in transgenic poplars with depressed cinnamyl alcohol dehydrogenase or caffeic acid O-methyltransferase activity have an opposite impact on the efficiency of industrial kraft pulping. Plant Physiol. 119, 153-163.

Laskar, D. D., Jourdes, M., Patten, A. M., Helms, G. L., Davin, L. B., Lewis, N. G., 2006. The *Arabidopsis* cinnamoyl CoA reductase irx4 mutant has a delayed but coherent (normal) program of lignification. Plant J. 48, 674-686.

Laskar, D. D., Jourdes, M., Davin, L. B., Lewis, N. G., 2007. Cinnamyl alcohol dehydrogenase downregulation in tobacco: reassessment of red lignin. Phytochemistry, (in press).

Lee, D., Meyer, K., Chapple, C., Douglas, C. J., 1997. Antisense suppression of 4-coumarate: coenzyme A ligase activity in *Arabidopsis* leads to altered lignin subunit composition. Plant Cell 9, 1985-1998.

Lewis, N. G., Newman, J., Just, G., Ripmeister, J., 1987. Determination of bonding patterns of $^{13}C$ specifically enriched dehydrogenatively polymerized lignin in solution and solid state. Macromolecules 20, 1752-1756.

Lewis, N. G., Yamamoto, E., 1990. Lignin: occurrence, biogenesis and biodegradation. Annu. Rev. Plant Phys. Plant Mol. Biol. 41, 455-496.

Lewis, N. G., Davin, L. B., Sarkanen, S., 1999. The nature and function of lignins. In: Barton, Sir D. H. R., Nakanishi, K., Meth-Cohn, O. (Eds.), Comprehensive Natural Products Chemistry, vol. 3. Elsevier, Oxford, pp. 617-745.

Marita, J. M., Ralph, J., Hatfield, R. D., Chapple, C., 1999. NMR characterization of lignins in *Arabidopsis* altered in the activity of ferulate 5-hydroxylase. Proc. Natl. Acad. Sci., USA 96, 12328-12332.

Patten, A. M., Cardenas, C. L., Cochrane, F. C., Laskar, D. D., Bedgar, D. L., Davin, L. B., Lewis, N. G., 2005. Reassessment of effects on lignification and vascular development in the irx4 *Arabidopsis* mutant. Phytochemistry 66, 2092-2107.

Patten, A. M., Jourdes, M., Brown, E. E., Laborie, M.-P., Davin, L. B., Lewis, N. G., 2007. Reaction tissue formation and stem tensile modulus properties in wild type and p-coumarate-3-hydroxylase downregulated lines of alfalfa, *Medicago sativa* (Fabaceae). Am. J. Bot., (Manuscript in press).

Ralph, J., 1997. Recent advances in characterizing “non-traditional” lignins. 9th International Symposium on Wood and Pulping Chemistry 1, 5-11.

Ralph, J., MacKay, J. J., Hatfield, R. D., O’Malley, D. M., Whetten, R. W., Sederoff, R. R., 1997. Abnormal lignin in a loblolly pine mutant. Science 277, 235-239.

Ralph, J., Hatfield, R. D., Piquemal, J., Yahiaoui, N., Pean, M., Lapierre, C., Boudet, A. M., 1998. NMR characterization of altered lignins extracted from tobacco plants down-regulated for lignification enzymes cinnamyl-alcohol dehydrogenase and cinnamoyl-CoA reductase. Proc. Natl. Acad. Sci., USA 95, 12803-12808.

Ralph, J., Lundquist, K., Brunow, G., Lu, F., Kim, H., Schatz, P. F., Marita, J. M., Hatfield, R. D., Ralph, S. A., Christensen, J. H., Boerjan, W., 2004a. Lignins: natural polymers from oxidative coupling of 4-hydroxyphenylpropanoids. Phytochemistry Rev. 3, 29-60.

Ralph, S. A., Ralph, J., Landucci, L. L., 2004b. NMR database of lignin and cell wall model compounds. Available at URL dfrc.ars.usda.gov/software.html, accessed May 2005.

Rolando, C., Monties, B., Lapierre, C., 1992. Thioacidolysis. In: Lin, S. Y., Dence, C. W. (Eds.), Methods in Lignin Chemistry. Springer-Verlag, Berlin, pp. 334-349.

Russell, W. R., Provan, G. J., Burkitt, M. J., Chesson, A., 2000. Extent of incorporation of hydroxycinnamaldehydes into lignin in cinnamyl alcohol dehydrogenase-downregulated plants. J. Biotechnol. 79, 73-85.

Sarkanen, K. V., Hergert, H. L., 1971. Classification and distribution. In: Sarkanen, K. V., Ludwig, C. H. (Eds.). Wiley-Interscience, New York, N.Y., pp. 43-94.

Sarkanen, K. V., Ludwig, C. H., 1971. Lignins-Occurrence, Formation, Structure and Reactions. Wiley-Interscience, New York, N.Y.

Sarkanen, S., Teller, D. C., Stevens, C. R., McCarthy, J. L., 1984. Lignin. 20. Associative interactions between kraft lignin components. Macromolecules 17, 2588-2597.

Sarkanen, S., 1998. Template polymerization in lignin biosynthesis. In: Lewis, N. G., Sarkanen, S. (Eds.), Lignin and Lignan Biosynthesis, vol. 697. ACS Symposium Series, Washington, pp. 194-208.

Schultz, T. P., Templeton, M. C., 1986. Proposed mechanism for the nitrobenzene oxidation of lignin. Holzforschung 40, 93-97.

Schultz, T. P., Fischer, T. H., Dershem, S. M., 1987. Role of the p-hydroxyl group in the nitrobenzene oxidation of hydroxybenzyl alcohols. J. Org. Chem. 52, 279-281.

Sibout, R., Eudes, A., Mouille, G., Pollet, B., Lapierre, C., Jouanin, L., Séguin, A., 2005. CINNAMYL ALCOHOL DEHYDROGENASE-C and -D are the primary genes involved in lignin biosynthesis in the floral stem of *Arabidopsis*. Plant Cell 17, 2059-2076.

Van Doorsselaere, J., Baucher, M., Chognot, E., Chabbert, B., Tollier, M.-T., Petit-Conil, M., Leplé, J.-C., Pilate, G., Cornu, D., Monties, B., Van Montagu, M., Inzé, D., Boerjan, W., Jouanin, L., 1995. A novel lignin in poplar trees with a reduced caffeic acid/5-hydroxyferulic acid O-methyltransferase activity. Plant J. 8, 855-864.

Weller, R. F., Phipps, R. H., Cooper, A., 1985. The effect of the brown midrib-3 gene on the maturity and yield of forage maize. Grass and Forage Science 40, 335-339.

Yahiaoui, N., Marque, C., Myton, K. E., Negrel, J., Boudet, A. M., 1998. Impact of different levels of cinnamyl alcohol dehydrogenase down-regulation on lignins of transgenic tobacco plants. Planta 204, 8-15.

Yang, Z., Hon, P. M., Chui, K. Y., Xu, Z. L., Chang, H. M., Lee, C. M., Cui, Y. X., Wong, H. N. C., Poon, C. D., Fung, B. M., 1991. Naturally occurring benzofuran: isolation, structure elucidation. and total synthesis of 5-(3-hydroxypropyl)-7-methoxy-2-(3'-methoxy-4'-hydroxyphenyl)-3-benzo[b] furancarbaldehyde, a novel adenosine $A_1$ receptor ligand isolated from *Salvia miltiorrhiza* Bunge (Danshen). Tetrahedron Lett. 32, 2061-2064.

The invention claimed is:

1. A recombinant expression vector, comprising at least one nucleic acid sequence that encodes a polypeptide comprising the amino acid sequence of SEQ ID NO: 2, or a polypeptide comprising an amino acid sequence that is at least 99%, 98%, 97%, 96%, or 95% identical to SEQ ID NO: 2, the at least one nucleic acid sequence in operative association with transcriptional and translational regulatory regions or sequences suitable to provide for expression of the encoded polypeptide in a host cell, wherein the encoded polypeptide comprises a NADH-binding domain having a lysine residue corresponding to amino acid position 133 of SEQ ID NO: 2, and the encoded polypeptide converts p-coumaryl or coniferyl alcohol esters into chavicol, eugenol, or estragole.

2. A recombinant expression vector, comprising at least one nucleic acid sequence selected from the group consisting of SEQ ID NOS: 1, 3, 17, 19, and 21 wherein the nucleic acid sequence encodes a polypeptide comprising the amino acid sequence SEQ ID NO: 2, 4, 18, 20, or 22.

3. The recombinant expression vector of claim 1, wherein the host cell is a plant cell, yeast cell, bacterial cell, or insect cell.

4. The recombinant expression vector of claim 3, wherein the host cell is a plant cell.

5. A host cell, transformed with a recombinant expression vector comprising at least one nucleic acid sequence that encodes a polypeptide comprising the amino acid sequence of SEQ ID NO: 2, or a polypeptide comprising an amino acid sequence that is at least 99%, 98%, 97%, 96%, or 95% identical to SEQ ID NO: 2, the at least one nucleic acid sequence in operative association with transcriptional and translational regulatory regions or sequences suitable to provide for expression of the encoded polypeptide in the host cell, wherein the encoded polypeptide comprises a NADH-binding domain having a lysine residue corresponding to amino acid position 133 of SEQ ID NO: 2, and the encoded polypeptide converts p-coumaryl or coniferyl alcohol esters into chavicol, eugenol, or estragole.

6. The host cell of claim 5, wherein the host cell is a plant cell.

7. A host cell, comprising a first recombinant DNA construct and a second recombinant DNA construct, wherein the first recombinant DNA construct comprises a first DNA sequence encoding a polypeptide comprising the amino acid sequence SEQ ID NO: 2, or a polypeptide comprising an amino acid sequence that is at least 99%, 98%, 97%, 96%, or 95% identical to SEQ ID NO: 2, the first DNA sequence in operative association with transcriptional and translational regulatory regions or sequences suitable to provide for expression of the encoded polypeptide in the host cell, wherein the encoded polypeptide comprises a NADH-binding domain having a lysine residue corresponding to amino acid position 133 of SEQ ID NO: 2, and the encoded polypeptide converts p-coumaryl or coniferyl alcohol esters into chavicol, eugenol, or estragole, and wherein the second recombinant DNA construct comprises a second DNA sequence encoding an acyl transferase suitable for acylation on monolignols forming esters, the second DNA sequence in operative association with transcriptional and translational regulatory regions or sequences suitable to provide for expression of the encoded acyl transferase in the host cell.

8. The host cell of claim 7, wherein the host cell is a plant cell, and wherein the first and second recombinant DNA constructs are present as parts of a single recombinant DNA construct, or are present on separate recombinant DNA constructs.

9. The host cell of claim 7, wherein the host cell is a plant cell, yeast cell, bacterial cell, or insect cell.

10. The host cell of claim 9, wherein the host cell is a plant cell.

11. A plant having at least one cell transformed with the recombinant expression vector of claim 1.

12. A plant seed comprising at least one cell transformed with the recombinant expression vector of claim 1.

13. A method of making a re-engineered cultured cell or plant having a re-engineered biomass composition comprising introducing into a cultured cell or plant, a recombinant expression vector to provide for expression of a regiospecific reductase suitable to transfer a hydride to either the C-7position, or the C-9 position of at least one monolignol acyl ester or to a quinone methide derivative thereof, to provide at least one propenyl phenol derivative, wherein the recombinant expression vector comprises at least one nucleic acid sequence that encodes a polypeptide comprising an amino acid sequence selected from the group consisting of:

SEQ ID NO: 2;

a polypeptide comprising an amino acid sequence that is at least 99%, 98%, 97%, 96%, or 95% identical to SEQ ID NO:2, wherein the polypeptide comprises a NADH-binding domain having a lysine residue corresponding to amino acid position 133 of SEQ ID NO: 2, and the polypeptide converts p-coumaryl or coniferyl alcohol esters into chavicol, eugenol, or estragole; and

SEQ ID NO: 6, the at least one nucleic acid sequence in operative association with transcriptional and translational regulatory regions or sequences suitable to provide for expression of the encoded polypeptide in the cultured cell or plant, thereby making a re-engineered cultured cell or plant and thereby re-engineering the biomass composition of the re-engineered cultured cell or plant.

14. The method of claim 13, further comprising expression of at least one monolignol acyl transferase suitable for acylating at least one monolignol to form the at least one monolignol acyl ester.

15. The method of claim 14, wherein the monolignol acyl transferase is that of *Larrea tridentata*.

16. The method of claim 13, wherein the at least one monolignol acyl ester comprises p-coumaryl alcohol ester or coniferyl alcohol ester, and wherein the at least one propenyl phenol derivative comprises eugenol, chavicol, or estragole.

17. The method of claim 13, wherein the re-engineering of the biomass composition diverts monolignol carbon flow away from lignin biopolymer formation in the re-engineered cultured cell or plant.

18. The method of claim 13, wherein the re-engineering of the biomass composition converts monolignols into propenyl phenols in the re-engineered cultured cell or plant.

19. The method of claim 13, wherein the re-engineering of the biomass composition alters the amount or composition of lignins in the re-engineered cultured cell or plant.

20. The method of claim 19, wherein the altered amount or composition of lignins alters the dynamic modulus of the re-engineered cultured cell or plant relative to a control cell or plant.

21. The method of claim 20, wherein the amount of lignins is reduced and the dynamic modulus is reduced relative to a control cell or plant.

22. The method of claim 19, wherein the altered amount or composition of lignins alters the formation of reaction tissue in the re-engineered cultured cell or plant relative to a control cell or plant.

23. The method of claim 22, wherein the amount of lignins is reduced and the amount of reaction tissue is increased and/or the composition of reaction tissue is altered relative to a control cell or plant.

24. The method of claim 19, wherein the altered amount or composition of lignins alters the antimicrobial, analgesic, or plant defense properties of the re-engineered cultured cell or plant relative to a control cell or plant.

25. The method of claim 24, wherein the amount of lignins is reduced and the amount of antimicrobial, analgesic, or plant defense properties is increased relative to a control cell or plant.

26. The method of claim 19, wherein the altered amount or composition of lignins alters the flavor or fragrance properties of the re-engineered cultured cell or plant relative to a control cell or plant.

27. The method of claim 26, wherein the amount of lignins is reduced and alters the flavor or fragrance properties of the re-engineered cultured cell or plant relative to a control cell or plant.

28. The method of claim 13, further comprising isolating the at least one propenyl phenol derivative from the re-engineered cultured cell or plant to provide for at least one of: an isolated propenyl phenol derivative or biofuel; a propenyl phenol-depleted cell culture material; and a propenyl phenol-depleted plant material.

29. The method of claim 28, further comprising making, from the at least one isolated propenyl phenol derivative, at least one product selected from the group consisting of antibacterials, plant defense agents, analgesic agents, flavoring agents, polymer building blocks, and biofuels.

30. The method of claim 28, further comprising fermenting at least one of the propenyl phenol-depleted cell culture material and the propenyl phenol-depleted plant material.

31. The method of claim 30, wherein the fermenting comprises fermenting to produce ethanol.

32. The method of claim 28, further comprising producing wood, pulp, or paper products using at least one of the propenyl phenol-depleted cell culture material and the propenyl phenol-depleted plant material.

33. The method of claim 13, further comprising making, from the re-engineered cultured cell or plant, at least one product selected from the group consisting of antibacterials, plant defense agents, analgesic agents, flavoring agents, polymer building blocks, and biofuels.

34. The method of claim 13, further comprising fermenting the re-engineered cultured cell or plant.

35. The method of claim 34, wherein fermenting comprises fermenting to produce ethanol.

36. The method of claim 13, wherein the recombinant expression vector comprises at least one nucleic acid sequence that encodes a polypeptide comprising an amino acid sequence selected from the group consisting of SEQ ID NO:2, and a polypeptide sequence that is at least 99%, 98%, 97%, 96% or 95% identical to SEQ ID NO: 2, wherein the polypeptide comprises a NADH-binding domain having a lysine residue corresponding to amino acid position 133 of SEQ ID NO: 2, and the polypeptide converts p-coumaryl or coniferyl alcohol esters into chavicol, eugenol, or estragole.

* * * * *